(12) United States Patent
Zhang et al.

(10) Patent No.: US 9,550,768 B2
(45) Date of Patent: Jan. 24, 2017

(54) KINASE MODULATION AND INDICATIONS THEREFOR

(71) Applicant: PLEXXIKON INC., Berkeley, CA (US)

(72) Inventors: Chao Zhang, Moraga, CA (US); Gideon Bollag, Orinda, CA (US); Gaston Habets, Pleasant Hill, CA (US); Jiazhong Zhang, Foster City, CA (US); Prabha N. Ibrahim, Mountain View, CA (US); Guoxian Wu, Foster City, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 13/793,881

(22) Filed: Mar. 11, 2013

(65) Prior Publication Data

US 2013/0274259 A1   Oct. 17, 2013

Related U.S. Application Data

(63) Continuation-in-part of application No. PCT/US2012/038417, filed on May 17, 2012.

(60) Provisional application No. 61/487,249, filed on May 17, 2011, provisional application No. 61/522,652, filed on Aug. 11, 2011.

(51) Int. Cl.
| | | |
|---|---|---|
| *A61K 31/4439* | (2006.01) | |
| *C07D 471/04* | (2006.01) | |
| *A61K 45/06* | (2006.01) | |
| *A61K 31/444* | (2006.01) | |
| *A61K 31/506* | (2006.01) | |
| *A61K 31/5377* | (2006.01) | |

(52) U.S. Cl.
CPC ........... *C07D 471/04* (2013.01); *A61K 31/444* (2013.01); *A61K 31/4439* (2013.01); *A61K 31/506* (2013.01); *A61K 31/5377* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West et al. | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,863,288 B2 | 1/2011 | Ibrahim et al. | |
| 7,863,289 B2 | 1/2011 | Spevak et al. | |
| 7,872,018 B2 | 1/2011 | Ibrahim et al. | |
| 7,893,075 B2 * | 2/2011 | Zhang et al. | 514/275 |
| 7,947,708 B2 | 5/2011 | Ibrahim et al. | |
| 8,053,463 B2 | 11/2011 | Lin et al. | |
| 8,067,434 B2 | 11/2011 | Ibrahim et al. | |
| 8,110,576 B2 | 2/2012 | Ibrahim et al. | |
| 8,119,637 B2 | 2/2012 | Ibrahim et al. | |
| 8,129,404 B2 | 3/2012 | Ibrahim et al. | |
| 8,143,271 B2 | 3/2012 | Ibrahim et al. | |
| 8,153,641 B2 | 4/2012 | Ibrahim et al. | |
| 8,158,636 B2 | 4/2012 | Ibrahim et al. | |
| 8,198,273 B2 | 6/2012 | Ibrahim et al. | |
| 8,268,858 B2 | 9/2012 | Wu et al. | |
| 8,367,828 B2 | 2/2013 | Arnold et al. | |
| 8,404,700 B2 | 3/2013 | Ibrahim et al. | |
| 8,415,469 B2 | 4/2013 | Ibrahim et al. | |
| 8,461,169 B2 * | 6/2013 | Zhang et al. | 514/275 |
| 8,470,818 B2 | 6/2013 | Ibrahim et al. | |
| 8,642,606 B2 | 2/2014 | Ibrahim et al. | |
| 8,673,928 B2 | 3/2014 | Ibrahim et al. | |
| 8,722,702 B2 | 5/2014 | Zhang et al. | |
| 8,865,735 B2 | 10/2014 | Ibrahim et al. | |
| 8,901,301 B2 | 12/2014 | Ibrahim et al. | |
| 8,912,204 B2 | 12/2014 | Ibrahim et al. | |
| 2004/0142864 A1 | 7/2004 | Bremer et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0058339 A1 | 3/2006 | Ibrahim et al. | |

(Continued)

FOREIGN PATENT DOCUMENTS

| | | |
|---|---|---|
| CN | 102993199 | 3/2013 |
| WO | WO-97/49703 | 12/1997 |

(Continued)

OTHER PUBLICATIONS

Fan et. al., Bioorganic & Medicinal Chem. Letters, 1997, 7(24): 3107-3112.*
Zips et al. In vivo 2005, 19, 1-8.*
Sikora Current Science 2001, 81(5), 549-554.*
U.S. Appl. No. 14/602,119, filed Jan. 21, 2015, Ibrahim et al.
Calabresi, et al., "Section IX: Chemotherapy of neoplastic diseases," *Goodman & Gilman's The Pharmacological Basis of Therapeutics*, Tenth Edition, McGraw-Hill Medical Publishing Division, (2001), pp. 1381, 1383-1385 and 1388.

(Continued)

*Primary Examiner* — Svetlana M Ivanova
(74) *Attorney, Agent, or Firm* — Sheppard Mullin Richter & Hampton LLP

(57) ABSTRACT

Compounds, compositions and methods useful for treatment of Flt3-mediated diseases or conditions are provided herewith. Also provided herewith are methods for modulating the receptor protein tyrosine like kinase 3(Flt3).

6 Claims, 4 Drawing Sheets

(56) References Cited

U.S. PATENT DOCUMENTS

| | | |
|---|---|---|
| 2006/0135540 A1 | 6/2006 | Lin et al. |
| 2006/0160135 A1 | 7/2006 | Wang et al. |
| 2007/0032519 A1 | 2/2007 | Zhang et al. |
| 2007/0066641 A1 | 3/2007 | Ibrahim et al. |
| 2007/0072904 A1 | 3/2007 | Lin et al. |
| 2008/0221127 A1 | 9/2008 | Lin et al. |
| 2008/0234349 A1 | 9/2008 | Lin et al. |
| 2008/0249137 A1 | 10/2008 | Lin et al. |
| 2009/0076046 A1* | 3/2009 | Zhang et al. ............ 514/275 |
| 2010/0190777 A1 | 7/2010 | Wu et al. |
| 2010/0310659 A1 | 12/2010 | Desai et al. |
| 2011/0092538 A1 | 4/2011 | Spevak et al. |
| 2011/0112127 A1* | 5/2011 | Zhang et al. ............ 514/275 |
| 2011/0166174 A1 | 7/2011 | Zhang et al. |
| 2011/0183988 A1 | 7/2011 | Ibrahim et al. |
| 2011/0230482 A1 | 9/2011 | Zhang et al. |
| 2011/0263595 A1 | 10/2011 | Zhang et al. |
| 2012/0015966 A1 | 1/2012 | Lin et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0237531 A1 | 9/2013 | Wu et al. |
| 2013/0261117 A1 | 10/2013 | Ibrahim et al. |
| 2013/0303534 A1 | 11/2013 | Ibrahim et al. |
| 2014/0037617 A1 | 2/2014 | Bollag et al. |
| 2014/0038948 A1 | 2/2014 | Wu et al. |
| 2014/0045840 A1 | 2/2014 | Zhang et al. |
| 2014/0094611 A1 | 4/2014 | Ibrahim et al. |
| 2014/0128373 A1 | 5/2014 | Ibrahim et al. |
| 2014/0128390 A1 | 5/2014 | Lin et al. |
| 2014/0213554 A1 | 7/2014 | Wu et al. |
| 2014/0243365 A1 | 8/2014 | Zhang et al. |
| 2014/0288070 A1 | 9/2014 | Ibrahim et al. |
| 2014/0303121 A1 | 10/2014 | Zhang et al. |
| 2014/0303187 A1 | 10/2014 | Wu et al. |
| 2014/0357612 A1 | 12/2014 | Zhang et al. |
| 2015/0080372 A1 | 3/2015 | Ibrahim et al. |
| 2015/0133400 A1 | 5/2015 | Zhang et al. |
| 2015/0166547 A1 | 6/2015 | Ibrahim et al. |
| 2015/0183793 A1 | 7/2015 | Zhang et al. |
| 2015/0290205 A1 | 10/2015 | Ibrahim et al. |
| 2016/0168146 A1 | 6/2016 | Wu et al. |

FOREIGN PATENT DOCUMENTS

| | | |
|---|---|---|
| WO | WO-2005/062795 | 7/2005 |
| WO | WO-2006/009755 | 1/2006 |
| WO | WO-2006/009797 | 1/2006 |
| WO | WO-2006/015123 | 2/2006 |
| WO | WO-2007/002433 | 1/2007 |
| WO | WO-2007/013896 | 2/2007 |
| WO | WO-2007/106236 | 9/2007 |
| WO | WO-2008/064255 | 5/2008 |
| WO | WO 2008063888 A2 * | 5/2008 |
| WO | WO 2008064265 A2 * | 5/2008 |
| WO | WO 2010/111527 | 9/2010 |
| WO | WO 2010/129467 | 11/2010 |
| WO | WO-2011/057022 | 5/2011 |
| WO | WO-2011/133637 | 10/2011 |
| WO | WO-2012/158957 | 11/2012 |

OTHER PUBLICATIONS

*Cecil Textbook of Medicine* 20th Edition, J.C. Bennett & F. Plum, eds, W. B. Saunders Company, (1996), pp. 1005-1010.
Extended European Search Report for EP Application No. 12786188.8 dated Jan. 22, 2015 (7 pages).
Gura, "Cancer Models: Systems for Identifying New Drugs Are Often Faulty," *Science* (1997), pp. 1041-1042.
He, et al., "Gamma-secretase activating protein, a therapeutic target for Alzheimer's disease," *Nature*, (2010), 467(7311):95-98.
Heinrich et al., "Inhibition of KIT Tyrosine Kinase Activity: A Novel Molecular Approach to the Treatment of KIT-Positive Malignancies," Journal of Clinical Oncology, (2002), 20(6):1692-1703.
Holmes, et al., "Long-term effects of Aβ42 immunization in Alzheimer's disease: follow-up of a randomized, placebo-controlled phase I trial," *Lancet* (2008) 372:216-233.
International Preliminary Report on Patentability and Written Opinion for PCT/US2012/038417 dated Mar. 25, 2014 (8 pages).
International Search Report and Written Opinion for PCT/US2012/038417 dated Jul. 20, 2012 (11 pages).
International Search Report and Written Opinion for PCT/US2013/032835 dated Apr. 26, 2013 (12 pages).
International Preliminary Report on Patentability and Written Opinion for PCT/US2013/032835 dated Sep. 23, 2014 (8 pages).
Johnson et al., "Relationships between drug activity in NCI preclinical in vitro and in vivo models and early clinical trials," *British J. of Cancer*, (2001), 84(10):1424-1431.
Natali, et al., "Breast cancer is associated with loss of the c-kit oncogene product," *Int. J. Cancer*, (1992) 52:713-717.
Pearce et al, "Failure modes in anticancer drugs discovery and development," *Cancer Drug Design and Discovery Neidle*, Stephen, ed, Elsevier/Academic Press, (2008), pp. 424-435.
U.S. Appl. No. 14/798,167, filed Jul. 13, 2015, Ibrahim et al.
U.S. Appl. No. 14/637,303, filed Mar. 3, 2015, Lin et al.
U.S. Appl. No. 14/733,830, filed Jun. 8, 2015, Zhang et al.
U.S. Appl. No. 14/839,668, filed Aug. 28, 2015, Ibrahim.
U.S. Appl. No. 14/846,545, filed Sep. 4, 2015, Zhang et al.
Benjamin, et al., "Management of gastrointestinal stromal tumors in the imatinib era: selected case studies," The Oncologist (2006), 11(1):9-20.
Cassier, et al., "Efficacy of imatinib mesylate for the treatment of locally advanced and/or metastatic tenosynovial giant cell tumor/pigmented villonodular synovitis," Cancer (2012), 118(6);1649-1655.
Denardo, et al., "Leukocyte complexity predicts breast cancer survival and functionally regulates response to chemotherapy," Cancer Discovery, 1(1), 34 pages (e-published Apr. 3, 2011 as doi:10.1158/2159-8274).
Larson, "CML: Live long and prosper," Blood (2011), 118(17):4499-4500.
Nelson, "Novel agent shows 'dramatic' responses in PVNS," Medscape, May 15, 2014, available at http://www.medscape.com/viewarticle/825217.
Patwardhan, et al., "Sustained Inhibition of receptor tyrosine kinases and macrophage depletion by PLX3397 and rapamycin as a potential new approach for the treatment of MPNSTs," Clin. Cancer Res. (2014), 20(12); 1-13.
PLX3397 Phase 3 study for pigmented villonodular synovitis (PVNS) or giant cell tumor of the tendon sheath (GCT-TS) (ENLIVEN), 2015, available at https://clinicaltrials.gov/ct2/show/NCT02371369.
Prada, et al., "Neurofibroma-associated macrophages play roles in tumor growth and response to pharmacological inhibition," Acta Neuropathol. (2013), 125:159-168.
Ravi, et al., "Treatment of tenosynovial giant cell tumor and pigmented villonodular synovitis," Curr. Opin. Oncol. (2011), 23(4):361-366.
Robertson, et al., "Imatinib mesylate for plexiform neurofibromas in patients with neurofibromatosis type 1: a phase 2 trial," Lancet Oncol. (2012), 13(12):1218-1224.
Tap, et al., "A pilot study of PLX3397, a selective colony-stimulating factor 1 receptor (CSF1R) kinase inhibitor, in pigmented villonodular synovitis (PVNS)," J. Clin. Oncol. (2014), 32:5s.
Verspoor, et al., "Pigmented villonodular synovitis: current concepts about diagnosis and management," Future Oncol. (2013), 9(10):1515-1531.
U.S. Appl. No. 15/093,660, filed Apr. 7, 2016, Lin et al.
U.S. Appl. No. 15/147,781, filed May 5, 2016, Bollag et al.
U.S. Appl. No. 15/147,692, filed May 5, 2016, Ibrahim et al.
U.S. Appl. No. 15/147,709, filed May 5, 2016, Ibrahim et al.
U.S. Appl. No. 15/160,551, filed May 20, 2016, Ibrahim et al.
U.S. Appl. No. 15/161,103, filed May 20, 2016, Ibrahim.
U.S. Appl. No. 15/160,729, filed May 20, 2016, Ibrahim et al.
U.S. Appl. No. 15/221,474, filed Jul. 27, 2016, Holladay et al.
U.S. Appl. No. 15/048,851, filed Feb. 19, 2016, Wu et al.

(56) References Cited

OTHER PUBLICATIONS

Hitoshi Kiyoi, "FLT3 Inhibitors," *New Therapy*, (2010), 44(12):1405-1408.
Levis et al., "FLT3: It does matter in leuekemia," *Leukemia*, (2003), 17:1738-1752.

\* cited by examiner

KINASE MODULATION AND INDICATIONS THEREFOR

CROSS REFERENCE TO RELATED APPLICATIONS

This application is a continuation-in-part of PCT Application No. PCT/US2012/038417, filed on May 17, 2012, which application claims the benefit of U.S. Provisional Application Nos. 61/522,652 filed Aug. 8, 2011 and 61/487,249, filed on May 17, 2011, all of which are incorporated by reference in their entirety.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 039363-7304_SL.txt and is 15,147 bytes in size.

FIELD

This invention relates to ligands for FMS-like tyrosine kinase 3(Flt3), such as abnormally activated Flt3 kinase, and to methods for use thereof. The information provided is intended solely to assist the understanding of the reader. None of the information provided nor references cited is admitted to be prior art to the present invention. Each of the references cited is incorporated herein in its entirety and for any purpose.

BACKGROUND

FLT-3 (FMS-like tyrosine kinase 3) which is also known as FLK-2 (fetal liver kinase 2) and STK-I (stem cell kinase 1), is a class III RTK structurally related to PDGFR, and colony stimulating factor 1 (CSF1). These RTK contain five immunoglobulin-like domains in the extracellular region and an intracellular tyrosine kinase domain split in two by a specific hydrophilic insertion. The receptor tyrosine kinase Flt3 is expressed in hematopoietic precursor cells, and activation of Flt3 enhances colony-forming capacity of all hematopoietic lineages. Many different mutations of the Flt3 gene can result in the production of Flt3 protein with a kinase that is abnormally activated, and in such situations these mutant forms of Flt3 can cause malignant transformation of hematopoietic cells in vitro and in vivo. Internal tandem duplications (ITD) and/or insertions and, rarely, deletions in the FLT3-gene are implicated in 20-25% of all acute myeloid leukemias (AML). For example, insertion of several amino acids in the juxtamembrane region of Flt3, often referred to as internal tandem duplication mutations, cause malignant transformation of myeloid cells, and such mutations are present in about 25% of acute myeloid leukemia (AML) cases. The presence of these mutations is associated with decreased survival in AML. Mutations at other residues, such as F691 ("gatekeeper") and D835, have been detected in patients with AML. Point mutations have also been observed in the kinase domain of Flt3 in about 7% of AML cases. Other types of leukemia, such as chronic myelomonocytic leukemia (CMML) can also harbor activating mutations of Flt3. Thus Flt3 with activating mutations are an important target for several cancer types (Cancer Cell, (2007), 12:367-380; Blood, (2003), 101, 3164-317; Current Pharmaceutical Design (2005), 11:3449-3457).

SUMMARY

The present invention relates to methods of using compounds active on oncogenic Flt3 kinase or Flt3 mutant, such as abnormally activated Flt3 kinase. In one aspect, the present invention provides methods of using compounds of Formula I and all the sub formulas and compounds as described herein that can be used therapeutically and/or prophylactically involving modulation of a Flt3 kinase, such as an oncogenic Flt3 or Flt3 mutant. In one embodiment, the invention provides a method for treating a subject suffering from or at risk of an oncogenic Flt3 mediated disease or condition.

In some embodiments, provided herein is a method of treating Flt3 kinase mediated diseases or conditions in a subject, which comprises administering to the subject at risk or suffering from or having the diseases or conditions a therapeutically effective amount of a compound of Formula I having the following structure:

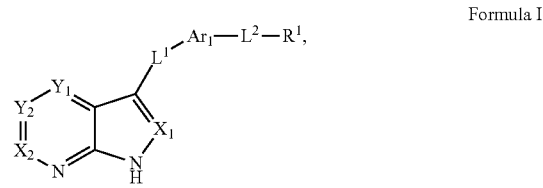

Formula I or a salt, prodrug, tautomer, or isomer thereof,
wherein:
$X_1$ is N or $CR^2$, $X_2$ is N or $CR^6$, $Y_1$ is N or $CR^4$, and $Y_2$ is N or $CR^5$, provided, however, that not more than one of $X_2$, $Y_1$ and $Y_2$ is N;

$L^1$ is selected from the group consisting of optionally substituted lower alkylene, —S—, —O—, —C(O)—, —C(S)—, —S(O)—, —S(O)$_2$—, and —NR$^7$—;

$L^2$ is selected from the group consisting of a bond, optionally substituted lower alkylene, -(alk)$_a$-S-(alk)$_b$-, -(alk)$_a$-O-(alk)$_b$-, -(alk)$_a$-OC(O)-(alk)$_b$-, -(alk)$_a$-C(O)O-(alk)$_b$-, -(alk)$_a$-OC(S)-(alk)$_b$-, -(alk)$_a$-C(S)O-(alk)$_b$-, -(alk)$_a$-C(O)-(alk)$_b$-, -(alk)$_a$-C(S)-(alk)$_b$-, -(alk)$_a$-C(O)NR$^9$-(alk)$_b$-, -(alk)$_a$-OC(O)NR$^9$-(alk)$_b$-, -(alk)$_a$-OC(S)NR$^9$-(alk)$_b$-, -(alk)$_a$-C(S)NR$^9$-(alk)$_b$-, -(alk)$_a$-S(O)-(alk)$_b$-, -(alk)$_a$-S(O)$_2$-(alk)$_b$-, -(alk)$_a$-S(O)$_2$NR$^9$-(alk)$_b$-, -(alk)$_a$-NR$^9$-(alk)$_b$-, -(alk)$_a$-NR$^9$C(O)-(alk)$_b$-, -(alk)$_a$-NR$^9$C(S)-(alk)$_b$-, -(alk)$_a$-NR$^9$C(O)NR$^9$-(alk)$_b$-, -(alk)$_a$-NR$^9$C(S)NR$^9$-(alk)$_b$-, -(alk)$_a$-NR$^9$C(O)O-(alk)$_b$-, -(alk)$_a$-NR$^9$C(S)O-(alk)$_b$-, -(alk)$_a$-NR$^9$S(O)$_2$-(alk)$_b$-, and -(alk)$_a$-NR$^9$S(O)$_2$NR$^9$-(alk)$_b$-, wherein alk is optionally substituted $C_{1-3}$ alkylene and a and b are independently 0 or 1;

$R^1$ is selected from the group consisting of optionally substituted lower alkyl, optionally substituted cycloalkyl, optionally substituted heterocycloalkyl, optionally substituted aryl, and optionally substituted heteroaryl;

$R^2$, $R^4$, $R^5$ and $R^6$ are independently selected from the group consisting of hydrogen, halogen, optionally substituted lower alkyl, optionally substituted lower alkenyl, optionally substituted lower alkynyl, optionally substituted cycloalkyl, optionally substituted heterocycloalkyl, optionally substituted aryl, optionally substituted heteroaryl, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —NR$^{10}$R$^{11}$, —NHR$^3$, —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, and —NR$^3$S(O)$_2$NR$^3$R$^3$;

Ar$_1$ is a 5 or 6 membered optionally substituted heteroarylene having the structure

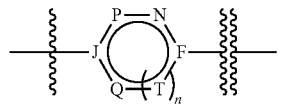

wherein

indicates the point of attachment of L$^1$ and

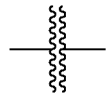

indicates the point of attachment of L$^2$, and wherein the indicated N is either =N— or —N=;

n is 0 or 1;

F and J are both C or one of F and J is C and the other of F and J is N;

P and Q are independently selected from CR, N, NR, O or S;

T is selected from CR or N;

wherein when n is 1, F and J are C, and P, T and Q are CR, or any one of P, T and Q is N and the other two of P, T and Q are CR, when n is 0 and F and J are both C, then one of P and Q are CR, N or NR and the other of P and Q is C, N, NR, O or S, provided both P and Q are not CR, when n is 0, one of F and J is N and the other of F and J is C, then one of P and Q is N and the other of P and Q is CR or both P and Q are CR, and R is hydrogen or an optional substituent as defined herein for optionally substituted heteroarylene that provides a stable compound;

R$^3$ at each occurrence is independently selected from the group consisting of optionally substituted lower alkyl, optionally substituted lower alkenyl, provided, however, that no alkene carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, or —NR$^3$S(O)$_2$NR$^3$R$^3$, optionally substituted lower alkynyl, provided, however, that no alkyne carbon thereof is bound to any —C(O)—, —C(S)—, —S(O)—, —S(O)$_2$—, —O—, —S—, or —N— of any of —OR$^3$, —SR$^3$, —C(O)R$^3$, —C(S)R$^3$, —S(O)R$^3$, —S(O)$_2$R$^3$, —C(O)OR$^3$, —C(S)OR$^3$, —C(O)NHR$^3$, —C(O)NR$^3$R$^3$, —C(S)NHR$^3$, —C(S)NR$^3$R$^3$, —S(O)$_2$NHR$^3$, —S(O)$_2$NR$^3$R$^3$, —NHR$^3$, —NHC(O)R$^3$, —NR$^3$C(O)R$^3$, —NHC(S)R$^3$, —NR$^3$C(S)R$^3$, —NHS(O)$_2$R$^3$, —NR$^3$S(O)$_2$R$^3$, —NHC(O)OR$^3$, —NR$^3$C(O)OH, —NR$^3$C(O)OR$^3$, —NHC(S)OR$^3$, —NR$^3$C(S)OH, —NR$^3$C(S)OR$^3$, —NHC(O)NHR$^3$, —NHC(O)NR$^3$R$^3$, —NR$^3$C(O)NH$_2$, —NR$^3$C(O)NHR$^3$, —NR$^3$C(O)NR$^3$R$^3$, —NHC(S)NHR$^3$, —NHC(S)NR$^3$R$^3$, —NR$^3$C(S)NH$_2$, —NR$^3$C(S)NHR$^3$, —NR$^3$C(S)NR$^3$R$^3$, —NHS(O)$_2$NHR$^3$, —NHS(O)$_2$NR$^3$R$^3$, —NR$^3$S(O)$_2$NH$_2$, —NR$^3$S(O)$_2$NHR$^3$, or —NR$^3$S(O)$_2$NR$^3$R$^3$, optionally substituted cycloalkyl, optionally substituted heterocycloalkyl, optionally substituted aryl, and optionally substituted heteroaryl;

R$^7$ is selected from the group consisting of hydrogen, optionally substituted lower alkyl, optionally substituted cycloalkyl, optionally substituted heterocycloalkyl, optionally substituted aryl, optionally substituted heteroaryl, —C(O)R$^8$, and —S(O)$_2$R$^8$;

R$^8$ is selected from the group consisting of optionally substituted lower alkyl, optionally substituted cycloalkyl, optionally substituted heterocycloalkyl, optionally substituted aryl and optionally substituted heteroaryl;

R$^9$ at each occurrence is independently selected from the group consisting of hydrogen, lower alkyl, and lower alkyl substituted with one or more substituents selected from the group consisting of fluoro, —OH, —NH$_2$, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR$^{12}$R$^{13}$, provided, however, that when R$^9$ is substituted lower alkyl, any substitution on the alkyl carbon bound to the —N— of NR$^9$— is fluoro;

R$^{10}$ and R$^{11}$ at each occurrence are independently selected from the group consisting of optionally substituted lower alkyl, optionally substituted lower alkenyl, provided, however, that no alkene carbon thereof is bound to the nitrogen of NR$^{10}$R$^{11}$, optionally substituted lower alkynyl, provided, however, that no alkyne carbon thereof is bound to the nitrogen of —NR$^{10}$R$^{11}$, optionally substituted cycloalkyl, optionally substituted heterocycloalkyl, optionally substituted aryl, and optionally substituted heteroaryl; or R$^{10}$ and R$^{11}$ together with the nitrogen to which they are attached form a monocyclic 5-7 membered optionally substituted heterocycloalkyl or a monocyclic 5 or 7 membered optionally substituted nitrogen containing heteroaryl; and $R^{12}$ and $R^{13}$ combine with the nitrogen to which they are attached to form a 5-7 membered heterocycloalkyl or 5-7 membered heterocycloalkyl substituted with one or more substituents selected from the group consisting of fluoro, —OH, —$NH_2$, lower alkyl, fluoro substituted lower alkyl, lower alkoxy, fluoro substituted lower alkoxy, lower alkylthio, and fluoro substituted lower alkylthio.

The Flt3 kinase can be an oncogenic Flt3 kinase or an Flt3 mutant having one or more mutations as described herein. In one embodiment, the Flt3 kinase is an Flt3 mutant encoded by an ITD mutation. In some embodiments, the invention provides a method of modulating an Flt3 kinase, which includes administering to a subject a compound of Formula I or any subformulas and any of the compounds as described herein. In certain embodiments, the invention provides a method for inhibiting an Flt3 kinase, which includes contacting the Flt3 kinase or a cell containing the Flt3 kinase with a compound of Formula I or any subformulas and any of the compounds as described herein.

In reference to Formula I, the core structure shown above with $X_1$, $X_2$, $Y_1$ and $Y_2$ as CH and with $L^1$-$Ar_1$-$L^2$-$R^1$ replaced with H is referred to as the "azaindole core." For that azaindole core, reference to ring atoms or ring positions is as shown in the following structure:

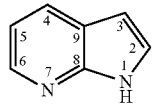

In one embodiment of the methods provided herein, compounds of Formula I have a structure selected from the following:

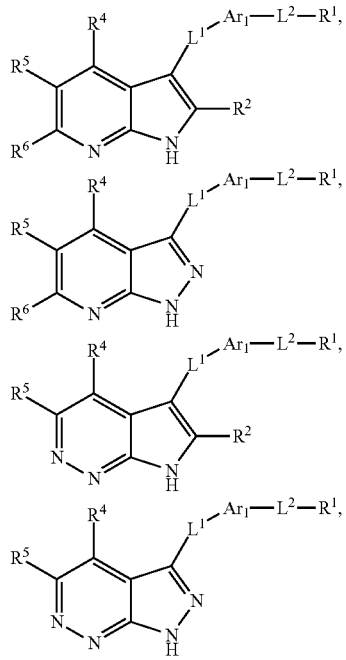

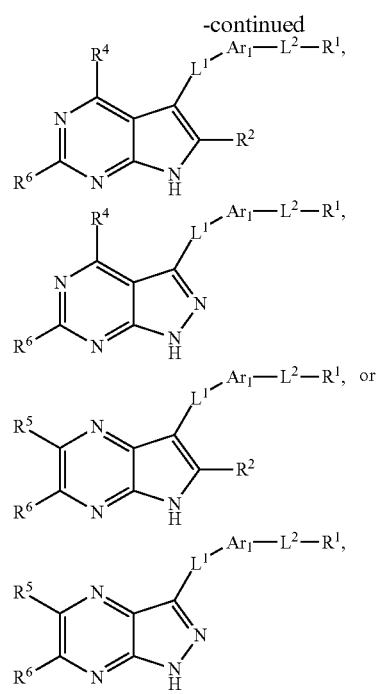

wherein $L^1$, $Ar_1$, $L^2$, $R^1$, $R^2$, $R^4$, $R^5$ and $R^6$ are as defined for Formula I.

In one embodiment of the methods provided herein, $X_1$ and $X_2$ in compounds of Formula I are N or CH. In another embodiment, $X_1$, $X_2$ and $Y_1$ are N or CH, where in a further embodiment, $Y_2$ is $CR^5$ and $R^5$ is other than hydrogen. In another embodiment, $X_1$, $X_2$ and $Y_2$ are N or CH, where in a further embodiment $Y_1$ is $CR^4$ and $R^4$ is other than hydrogen. In another embodiment, $X_1$, $X_2$ and $Y_1$ are CH, where in a further embodiment, $Y_2$ is $CR^5$ and $R^5$ is other than hydrogen. In another embodiment, $X_1$, $X_2$ and $Y_2$ are CH, where in a further embodiment $Y_1$ is $CR^4$ and $R^4$ is other than hydrogen.

In one embodiment of the methods provided herein, $X_1$, $X_2$, $Y_1$ and $Y_2$ in compounds of Formula I are independently $CR^2$, $CR^6$, $CR^4$ and $CR^5$ respectively, one of $R^4$ or $R^5$ is other than hydrogen, preferably where $R^2$ and $R^6$ are hydrogen. In one embodiment, wherein $X_1$, $X_2$, $Y_1$ and $Y_2$ are independently $CR^2$, $CR^6$, $CR^4$ and $CR^5$ respectively, $R^2$, $R^5$ and $R^6$ are hydrogen and $R^4$ is other than hydrogen. In one embodiment, wherein $X_1$, $X_2$, $Y_1$ and $Y_2$ are independently $CR^2$, $CR^6$, $CR^4$ and $CR^5$ respectively, $R^2$, $R^4$ and $R^6$ are hydrogen and $R^5$ is other than hydrogen.

In one embodiment of the methods provided herein, in compounds of Formula I, $X_1$ and $X_2$ are N or CH, preferably wherein both $X_1$ and $X_2$ are CH.

In one embodiment of the methods provided herein, in compounds of Formula I, $L^1$ is selected from the group consisting of S, O, lower alkylene, —C(O)—, —C(S)—, —S(O)—, —S(O)$_2$—, and —$NR^7$—, wherein lower alkylene is optionally substituted with fluoro, and wherein when $L^2$ is optionally substituted lower alkylene or comprises optionally substituted $C_{1-3}$ alkylene, the alkylene is optionally substituted with fluoro or lower alkyl. In one embodiment, $L^1$ is selected from the group consisting of —S—, —O—, —$CH_2$—, —$CF_2$—, —C(O)—, —C(S)—, —S(O)—, —S(O)$_2$—, and —NH—.

In one embodiment of the methods provided herein, in compounds of Formula I, $L^2$ is selected from the group consisting of a bond, optionally substituted lower alkylene, —O-(alk)$_b$-, —OC(O)-(alk)$_b$-, —C(O)O-(alk)$_b$-, —OC(S)-(alk)$_b$-, —C(S)O-(alk)$_b$-, —C(O)-(alk)$_b$-, —C(S)-(alk)$_b$-, —C(O)NR$^9$-(alk)$_b$-, —OC(O)NR$^9$-(alk)$_b$-, —OC(S)NR$^9$-(alk)$_b$-, —C(S)NR$^9$-(alk)$_b$-, —S(O)-(alk)$_b$-, —S(O)$_2$-(alk)$_b$-, —S(O)$_2$NR$^9$-(alk)$_b$-, —NR$^9$-(alk)$_b$-, —NR$^9$C(O)-(alk)$_b$-, —NR$^9$C(O)O-(alk)$_b$-, —NR$^9$C(S)-(alk)$_b$-, —NR$^9$C(S)O-(alk)$_b$-, —NR$^9$C(O)NR$^9$-(alk)$_b$-, —NR$^9$C(S)NR$^9$-(alk)$_b$-, —NR$^9$S(O)$_2$-(alk)$_b$-, and —NR$^9$S(O)$_2$NR$^9$-(alk)$_b$-.

Further to any of the above embodiments of the methods provided herein, in Formula I, when L$^1$ is substituted lower alkylene or when L$^2$ is substituted lower alkylene or comprises substituted C$_{1-3}$ alkylene, the alkylene is substituted with one or more, preferably 1, 2, or 3 substituents selected from the group consisting of fluoro, —OH, —NH$_2$, lower alkoxy, lower alkylthio, mono-alkylamino, di-alkylamino, and NR$^{12}$R$^{13}$, wherein the alkyl chain(s) of lower alkoxy, lower alkylthio, mono-alkylamino or di-alkylamino are optionally substituted with one or more, preferably 1, 2, or 3 substituents selected from the group consisting of fluoro, —OH, —NH$_2$, lower alkoxy, fluoro substituted lower alkoxy, lower alkylthio, fluoro substituted lower alkylthio, mono-alkylamino, di-alkylamino, or cycloalkylamino.

In one embodiment of the methods provided herein, in the compounds of Formula I, the variables P, J, Q, T, F, and n are selected to provide structures of Ar$_1$ selected from the group consisting of

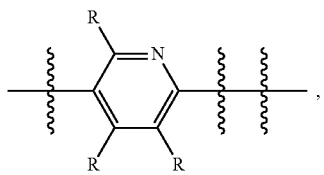

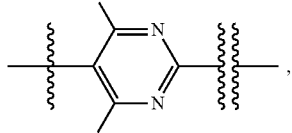

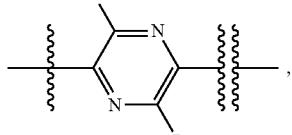

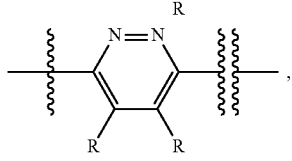

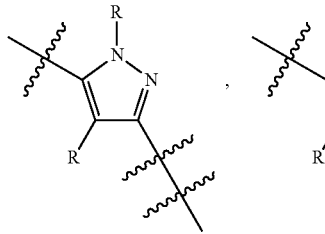

-continued

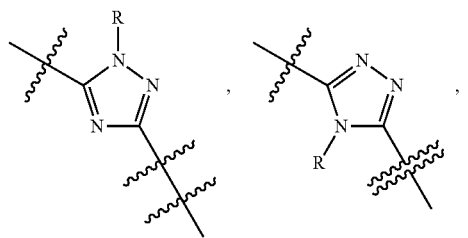

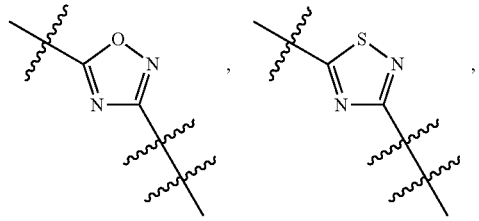

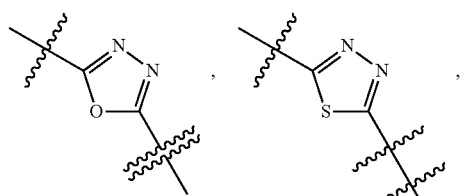

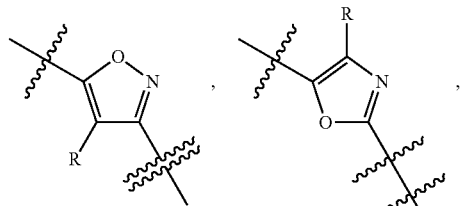

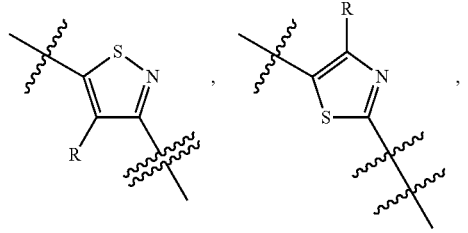

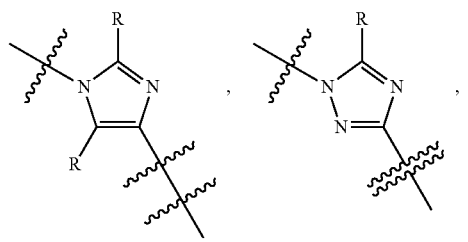

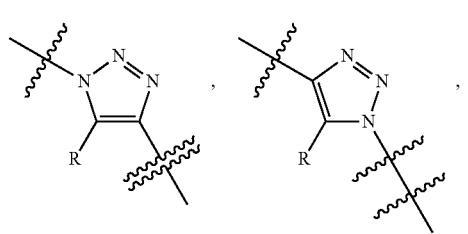

-continued

[two chemical structures with R group on pyrazole rings]
, and where each R is independently hydrogen or an optional substituent as defined herein for optionally substituted heteroaryl.

In one embodiment of the methods provided herein, a compound of Formula I has a structure according to the following sub-generic structure, Formula Ia,

[Formula Ia structure: 7-azaindole with $R^4$, $R^5$, $R^6$ substituents, $L^1$–$Ar_1$–$L^3$–$R^1$ at 3-position, $R^2$ at 2-position]

Formula Ia or a salt, prodrug, tautomer, or isomer thereof,
wherein $L^1$, $Ar_1$, $R^1$, $R^2$, $R^4$, $R^5$ and $R^6$ are as defined for Formula I;
$L^3$ is selected from the group consisting of a bond, optionally substituted lower alkylene, —O-(alk)$_b$-, —S-(alk)$_b$-, —NR$^{14}$-(alk)$_b$-, —C(O)-(alk)$_b$-, —C(S)-(alk)$_b$-, —S(O)-(alk)$_b$-, —S(O)$_2$-(alk)$_b$-, —NR$^{14}$C(O)-(alk)$_b$-, —C(O)NR$^{14}$-(alk)$_b$-, —S(O)$_2$NR$^{14}$—(alk)$_b$-, —NR$^{14}$S(O)$_2$-(alk)$_b$-, —NR$^{14}$C(O)NR$^{14}$—(alk)$_b$-, —NR$^{14}$C(S)NR$^{14}$-(alk)$_b$-, and —NR$^{14}$S(O)$_2$NR$^{14}$-(alk)$_b$-;
alk is optionally substituted $C_{1-3}$ alkylene;
b is 0 or 1; and
$R^{14}$ is hydrogen or lower alkyl.

In another embodiment of the methods provided herein, in compounds of Formula Ia, $R^2$, $R^5$ and $R^6$ are hydrogen, further wherein $R^4$ is other than hydrogen. In another embodiment, $R^2$, $R^4$ and $R^6$ are hydrogen, further wherein $R^5$ is other than hydrogen.

In particular embodiments of the methods provided herein, the compound of Formula I has a structure according to the following sub-generic structure, Formula Ib,

[Formula Ib structure with labels $R^{16}$, $R^{17}$, $R^{15}$, K, G, F, A, J, E, U, Z, V, W, M–$R^1$]

Formula Ib or a salt, prodrug, tautomer, or isomer thereof,
wherein:
V and W are independently selected from the group consisting of N and CH;
U and Z are independently selected from the group consisting of N and CR$^{18}$, provided, however, that not more than one of W, U and Z is N;
A is selected from the group consisting of —CR$^{19}$R$^{20}$—, —C(O)—, —C(S)—, —S—, —S(O)—, —S(O)$_2$—, —NR$^{21}$—, and —O—;
n is 0 or 1;
F and J are both C or one of F and J is C and the other of F and J is N;
E and K are selected from C, N, O or S;
G is selected from C or N;
   wherein
      when n is 1, F and J are C, and E, G and K are C, or any one of E, G and K is N and the other two of E, G and K are C, provided that when E, G or K is N, $R^{15}$, $R^{17}$ and $R^{16}$, respectively, are absent,
      when n is 0 and F and J are both C, then one of E and K is C or N and the other of E and K is C, N, O or S, provided both E and K are not C, and provided that when both E and K are N, one of $R^{15}$ and $R^{16}$ is absent, and provided that when one of E and K are N and the other is O or S, $R^{15}$ and $R^{16}$ are absent,
      when n is 0, one of F and J is N and the other of F and J is C, then one of E and K is N and the other of E and K is C, or both E and K are C, provided that when E is N, $R^{15}$ is absent and when K is N, $R^{16}$ is absent;
$R^1$ is selected from the group consisting of optionally substituted lower alkyl, optionally substituted cycloalkyl, optionally substituted heterocycloalkyl, optionally substituted aryl and optionally substituted heteroaryl;
$R^{15}$ is selected from the group consisting of hydrogen, optionally substituted lower alkyl, —OR$^{22}$, —SR$^{22}$ and halogen when E is C, is absent when E is O or S or when n=1 and E is N, and is absent or selected from the group consisting of hydrogen and optionally substituted lower alkyl when n=0 and E is N;
$R^{16}$ is selected from the group consisting of hydrogen, optionally substituted lower alkyl, —OR$^{22}$, —SR$^{22}$ and halogen when K is C, is absent when K is O or S or when n=1 and K is N, and is absent or selected from the group consisting of hydrogen and optionally substituted lower alkyl when n=0 and K is N;
$R^{17}$ is selected from the group consisting of hydrogen, optionally substituted lower alkyl, —OR$^{22}$, —SR$^{22}$ and halogen when G is C, or is absent when G is N;
$R^{18}$ is selected from the group consisting of hydrogen, halogen, optionally substituted lower alkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —NR$^{24}$R$^{25}$, —NHR$^{23}$, —OR$^{23}$, —SR$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NR$^{23}$S(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
M is selected from the group consisting of a bond, —(CR$^{19}$R$^{20}$)$_u$—, —(CR$^{19}$R$^{20}$)$_t$—C(O)—(CR$^{19}$R$^{20}$)$_s$—, —(CR$^{19}$R$^{20}$)$_t$—C(S)—(CR$^{19}$R$^{20}$)$_s$—, —(CR$^{19}$R$^{20}$)$_t$—C(O)O—(CR$^{19}$R$^{20}$)$_s$—, —(CR$^{19}$R$^{20}$)$_t$—C(S)O—(CR$^{19}$R$^{20}$)$_s$—, —(CR$^{19}$R$^{20}$)$_t$—C(O)

—NR²⁶—(CR¹⁹R²⁰)ₛ—,  —(CR¹⁹R²⁰)ₜ—C(S)NR²⁶—(CR¹⁹R²⁰)ₛ—,  —(CR¹⁹R²⁰)ₜ—S(O)—(CR¹⁹R²⁰)ₛ—,  —(CR¹⁹R²⁰)ₜ—S(O)₂—(CR¹⁹R²⁰)ₛ—,  —(CR¹⁹R²⁰)ₜ—S(O)₂NR²⁶—(CR¹⁹R²⁰)ₛ—,  —(CR¹⁹R²⁰)ₜ—C(O)—(CR¹⁹R²⁰)ₛ—,  —(CR¹⁹R²⁰)ₜ—C(S)—(CR¹⁹R²⁰)ₛ—,  —(CR¹⁹R²⁰)ₜ—C(O)NR²⁶—(CR¹⁹R²⁰)ₛ—,  —(CR¹⁹R²⁰)ₜ—OC(S)NR²⁶—(CR¹⁹R²⁰)ₛ—,  —(CR¹⁹R²⁰)ₜ—S—(CR¹⁹R²⁰)ₛ—,  —(CR¹⁹R²⁰)ₜ—NR²⁶—(CR¹⁹R²⁰)ₛ—,  —(CR¹⁹R²⁰)ₜ—NR²⁶C(O)—(CR¹⁹R²⁰)ₛ—,  —(CR¹⁹R²⁰)ₜ—NR²⁶C(S)—(CR¹⁹R²⁰)ₛ—,  —(CR¹⁹R²⁰)ₜ—NR²⁶C(O)O—(CR¹⁹R²⁰)ₛ—,  —(CR¹⁹R²⁰)ₜ—NR²⁶C(S)O—(CR¹⁹R²⁰)ₛ—,  —(CR¹⁹R²⁰)ₜ—NR²⁶C(O)NR²⁶—(CR¹⁹R²⁰)ₛ—,  —(CR¹⁹R²⁰)ₜ—NR²⁶C(S)NR²⁶—(CR¹⁹R²⁰)ₛ—,  —(CR¹⁹R²⁰)ₜ—NR²⁶S(O)₂—(CR¹⁹R²⁰)ₛ—, and —(CR¹⁹R²⁰)ₜ—NR²⁶S(O)₂NR²⁶—(CR¹⁹R²⁰)ₛ—;

wherein R¹⁹ and R²⁰ at each occurrence are independently selected from the group consisting of hydrogen, fluoro, —OH, —NH₂, lower alkyl, lower alkoxy, lower alkylthio, mono-alkylamino, di-alkylamino, and NR²⁷R²⁸, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH₂, lower alkoxy, fluoro substituted lower alkoxy, lower alkylthio, fluoro substituted lower alkylthio, mono-alkylamino, di-alkylamino, and cycloalkylamino; or any two of R¹⁹ and R²⁰ on the same or different carbons combine to form a 3-7 membered monocyclic cycloalkyl or 5-7 membered monocyclic heterocycloalkyl and any others of R¹⁹ and R²⁰ are independently selected from the group consisting of hydrogen, fluoro, —OH, —NH₂, lower alkyl, lower alkoxy, lower alkylthio, mono-alkylamino, di-alkylamino, and NR²⁷R²⁸, wherein the alkyl chain(s) of lower alkyl, lower alkoxy, lower alkylthio, mono-alkylamino, or di-alkylamino are optionally substituted with one or more substituents selected from the group consisting of fluoro, —OH, —NH₂, lower alkoxy, fluoro substituted lower alkoxy, lower alkylthio, fluoro substituted lower alkylthio, mono-alkylamino, di-alkylamino, and cycloalkylamino, and wherein the monocyclic cycloalkyl or monocyclic heterocycloalkyl are optionally substituted with one or more substituents selected from the group consisting of halogen, —OH, —NH₂, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino;

R²¹ and R²² at each occurrence are independently hydrogen or optionally substituted lower alkyl;

R²³ at each occurrence is independently selected from the group consisting of optionally substituted lower alkyl, optionally substituted lower alkenyl, provided, however, that no alkene carbon thereof is bound to any —C(O)—, —C(S)—, —S(O)₂—, —O—, —S—, or —N— of any of —NHR²³, —OR²³, —SR²³, —NHC(O)R²³, —NR²³C(O)R²³, —NHC(S)R²³, —NR²³C(S)R²³, —NHS(O)₂R²³, —NR²³S(O)₂R²³, —NHC(O)NHR²³, —NR²³C(O)NH₂, —NR²³C(O)NHR²³, —NHC(O)NR²³R²³, —NHC(S)NHR²³, —NR²³C(S)NH₂, —NR²³C(S)NHR²³, —NHC(S)NR²³R²³, —NHS(O)₂NHR²³, —NR²³S(O)₂NH₂, —NR²³S(O)₂NHR²³, —NHS(O)₂NR²³R²³, or —NR²³S(O)₂NR²³R²³, optionally substituted lower alkynyl, provided, however, that no alkyne carbon thereof is bound to any —C(O)—, —C(S)—, —S(O)—, —S(O)₂—, —O—, —S—, or —N— of any of —NHR²³, —OR²³, —SR²³, —NHC(O)R²³, —NR²³C(O)R²³, —NHC(S)R²³, —NR²³C(S)R²³, —NHS(O)₂R²³, —NHC(O)NHR²³, —NR²³C(O)NH₂, —NR²³C(O)NHR²³, —NHC(O)NR²³R²³, —NR²³C(O)NR²³R²³, —NHC(S)NHR²³, —NR²³C(S)NH₂, —NR²³C(S)NHR²³, —NHC(S)NR²³R²³, —NR²³C(S)NR²³R²³, —NHS(O)₂NHR²³, —NR²³S(O)₂NH₂, —NR²³S(O)₂NHR²³, —NHS(O)₂NR²³R²³, or —NR²³S(O)₂NR²³R²³, optionally substituted cycloalkyl, optionally substituted heterocycloalkyl, optionally substituted aryl, and optionally substituted heteroaryl;

R²⁴ and R²⁵ at each occurrence are independently selected from the group consisting of optionally substituted lower alkyl, optionally substituted lower alkenyl, provided, however, that no alkene carbon thereof is bound to the nitrogen of —NR²⁴R²⁵, optionally substituted lower alkynyl, provided, however, that no alkyne carbon thereof is bound to the nitrogen of —NR²⁴R²⁵, optionally substituted cycloalkyl, optionally substituted heterocycloalkyl, optionally substituted aryl, and optionally substituted heteroaryl; or R²⁴ and R²⁵ together with the nitrogen to which they are attached form a monocyclic 5-7 membered optionally substituted heterocycloalkyl or a monocyclic 5 or 7 membered optionally substituted nitrogen containing heteroaryl;

R²⁶ at each occurrence is independently selected from the group consisting of hydrogen, lower alkyl, and lower alkyl substituted with one or more substituents selected from the group consisting of fluoro, —OH, —NH₂, lower alkoxy, fluoro substituted lower alkoxy, lower alkylthio, fluoro substituted lower alkylthio, mono-alkylamino, fluoro substituted mono-alkylamino, di-alkylamino, fluoro substituted di-alkylamino, and —NR²⁷R²⁸, provided, however, that when R²⁶ is substituted lower alkyl, any substitution on the lower alkyl carbon bound to the —N— of —NR²⁶— is fluoro;

R²⁷ and R²⁸ combine with the nitrogen to which they are attached to form a 5-7 membered heterocycloalkyl or 5-7 membered heterocycloalkyl substituted with one or more substituents selected from the group consisting of fluoro, —OH, —NH₂, lower alkyl, fluoro substituted lower alkyl, lower alkoxy, fluoro substituted lower alkoxy, lower alkylthio, and fluoro substituted lower alkylthio;

u is 1-6;

t is 0-3; and s is 0-3;

provided that when V, W, U and Z are CH, n=1, E, F, G, J, and K are C, R¹⁵, R¹⁶ and R¹⁷ are H, A is —CH₂—, —CH(OH)—, or —C(O)—, and M is NHCH₂—, then R¹ is not phenyl, 4-trifluoromethyl-phenyl, 4-methoxy-phenyl, 4-chloro-phenyl, 4-fluoro-phenyl, 4-methyl-phenyl, 3-fluoro-phenyl or thiophen-2-yl, when V, W, U and Z are CH, n=1, E, F, G, J, and K are C, R¹⁵, R¹⁶ and R¹⁷ are H, and A is —CH₂—, then M-R¹ is not —NHCH₂CH(CH₃)₂, when V, W, and U are CH, n=1, E, F, G, J, and K are C, R¹⁵, R¹⁶ and R¹⁷ are H, A is —CH₂—, M-R¹ is —OCH₃, and Z is CR¹⁸, then R¹⁸ is not thiophen-3-yl, and when V, W, and U are CH, n=0, F, J, and K are C, E is N, $R^{15}$ is $CH_3$, $R^{16}$ is H, A is —C(O)—, M-$R^1$ is $CH(CH_3)_3$, and Z is $CR^{18}$, then $R^{18}$ is not 3-((E)-2-carboxy-vinyl)phenyl.

In one embodiment of the methods provided herein, in compounds of Formula Ib, the variables E, J, K, G, F, n, $R^{15}$, $R^{16}$ and $R^{17}$ are selected to provide structures selected from the group consisting of

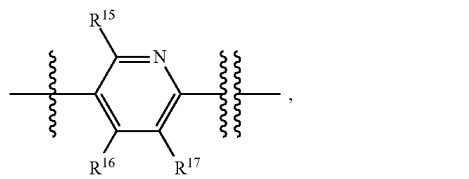,

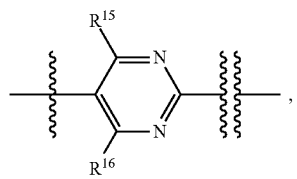,

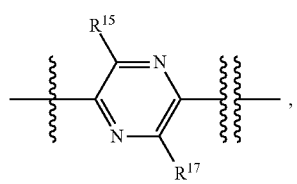,

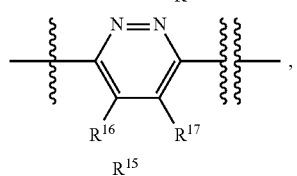,

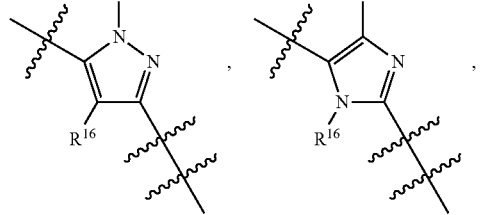,

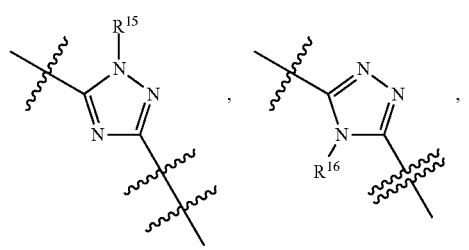,

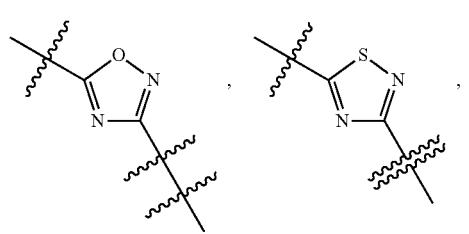

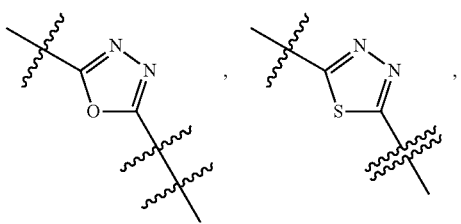,

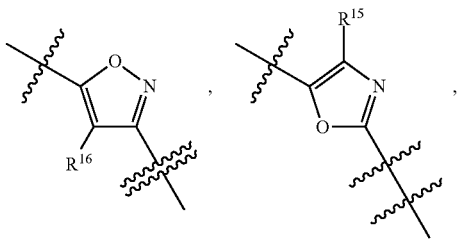,

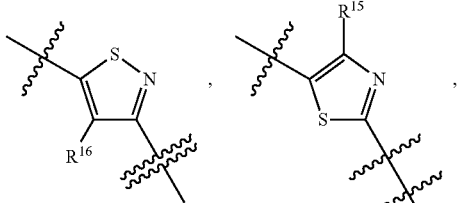,

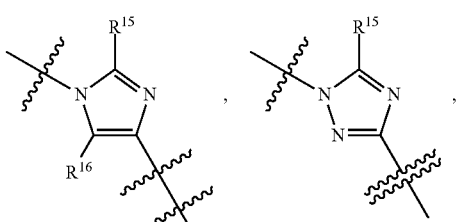,

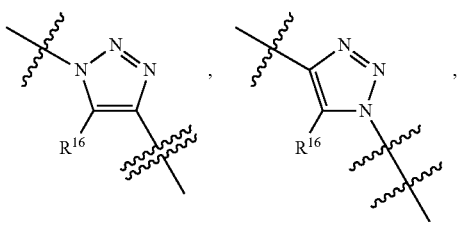,

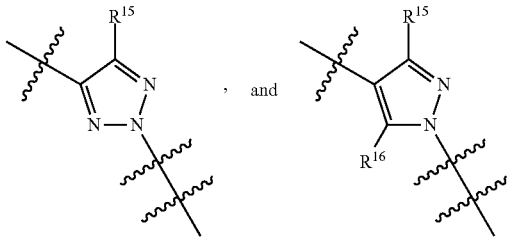, and wherein $R^{15}$, $R^{16}$ and $R^{17}$ are as defined for compounds of Formula Ib and wherein

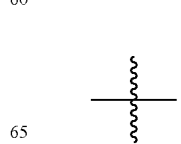

indicates the point of attachment of A and

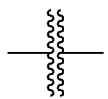

indicates the point of attachment of M.

In one embodiment of the methods provided herein, in compounds of Formula Ib, the variable M is selected from the group consisting of —O—$(CR^{19}R^{20})_s$—, —S—$(CR^{19}R^{20})_s$—, —OC(O)—$(CR^{19}R^{20})_s$—, —OC(S)$(CR^{19}R^{20})_s$—, —OC(O)$NR^{26}$—$(CR^{19}R^{20})_s$—, —OC(S)$NR^{26}$—$(CR^{19}R^{20})_s$—, —C(O)$NR^{26}$—$(CR^{19}R^{20})_s$—, —C(S)$NR^{26}$—$(CR^{19}R^{20})_s$—, —S(O)$_2NR^{26}$—$(CR^{19}R^{20})_s$—, —$NR^{26}$—$(CR^{19}R^{20})_s$—, —$NR^{26}$C(O)—$(CR^{19}R^{20})_s$—, —$NR^{26}$C(S)—$(CR)^{19}R^{20})_s$—, —$NR^{26}$C(O)O—$(CR^{19}R^{20})_s$—, —$NR^{26}$C(S)O—$(CR^{19}R^{20})_s$—, —$NR^{26}$C(O)$NR^{26}$—$(CR^{19}R^{20})_s$—, —$NR^{26}$C(S)$NR^{26}$—$(CR^{19}R^{20})_s$—, —$NR^{26}$S(O)$_2$—$(CR^{19}R^{20})_s$—, and —$NR^{26}$S(O)$_2NR^{26}$—$(CR^{19}R^{20})_s$—.

In one embodiment of the methods provided herein, in compounds of Formula Ib, the variable $R^{26}$ at each occurrence is independently selected from the group consisting of hydrogen, lower alkyl, and lower alkyl substituted with 1, 2, or 3 substituents selected from the group consisting of fluoro, —OH, —$NH_2$, alkoxy, lower alkylthio, mono-alkylamino, di-alkylamino and cycloalkylamino, provided that any substitution on the carbon that is bound to the nitrogen of —$NR^{26}$ is fluoro.

In one embodiment of the methods provided herein, in compounds of Formula Ib, the variable $R^1$ is selected from the group consisting of optionally substituted aryl and optionally substituted heteroaryl.

In one embodiment of the methods provided herein, in compounds of Formula Ib, the variable Z is N or CH, n is 1, E-$R^{15}$ is N or CH, K-$R^{16}$ is N or CH, and G-$R^{17}$ is N or CH, provided no more than one of E-$R^{15}$, K-$R^{16}$ and G-$R^{17}$ is N. In one embodiment, Z is N or CH, n is 1, and E-$R^{15}$, K-$R^{16}$ and G-$R^{17}$ are CH.

In one embodiment of the methods provided herein, in compounds of Formula Ib, the variables V, W and Z are CH, U is $CR^{18}$, n is 1, E-$R^{15}$ is N or CH, K-$R^{16}$ is N or CH, and G-$R^{17}$ is N or CH, provided no more than one of E-$R^{15}$, K-$R^{16}$ and G-$R^{17}$ is N. In another embodiment, V, W and Z are CH, U is $CR^{18}$, n is 1, and E-$R^{15}$, K-$R^{16}$ and G-$R^{17}$ are CH.

In one embodiment of the methods provided herein, in compounds of Formula Ib, the variable Z is N or CH, n is 1, E-$R^{15}$, K-$R^{16}$ and G-$R^{17}$ are CH, A is —$CH_2$—, M is $NHCH_2$—, further wherein $R^1$ is optionally substituted phenyl. In another embodiment, V, Z, U and W are CH, n is 1, E-$R^{15}$ is N or CH, K-$R^{16}$ is N or CH, and G-$R^{17}$ is N or CH, provided no more than one of E-$R^{15}$, K-$R^{16}$ and G-$R^{17}$ is N.

In one embodiment of the methods provided herein, in compounds of Formula Ib, the variable Z is N or CH, n is 1, E-$R^{15}$ is N or CH, K-$R^{16}$ is N or CH, and G-$R^{17}$ is N or CH, provided no more than one of E-$R^{15}$, K-$R^{16}$ and G-$R^{17}$ is N, and $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the methods provided herein, in compounds of Formula Ib, the variables V, Z, U and W are CH, n is 1, E-$R^{15}$, K-$R^{16}$ and G-$R^{17}$ are CH, A is —$CH_2$—, M is —$NHCH_2$—, and $R^1$ is optionally substituted phenyl, further wherein $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the methods provided herein, in compounds of Formula Ib, the variables V, W and Z are CH, U is $CR^{18}$, n is 1, E-$R^{15}$, K-$R^{16}$ and G-$R^{17}$ are CH, A is —$CH_2$—, M is —$NHCH_2$—, and $R^1$ is optionally substituted phenyl, further wherein $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the methods provided herein, in compounds of Formula Ib, when n is 1, and E, K and G are C, at least one of $R^{15}$, $R^{16}$ and $R^{17}$ is other than hydrogen. In another embodiment, n is 1, one of E, K, and G are N and the other two of E, K, and G are C and at least one of $R^{15}$, $R^{16}$ and $R^{17}$ is other than hydrogen. In another embodiment, n is 1, E, K and G are C, and at least one of $R^{15}$, $R^{16}$ and $R^{17}$ is other than hydrogen.

In one embodiment of the methods provided herein, in compounds of Formula Ib, n is 1, V and W are CH, U and Z are independently $CR^{18}$, one of E, K, and G are N and the other two of E, K, and G are C and at least one of $R^{15}$, $R^{16}$ and $R^{17}$ is other than hydrogen. In another embodiment, n is 1, V and W are CH, U and Z are independently $CR^{18}$, E, K and G are C, and at least one of $R^{15}$, $R^{16}$ and $R^{17}$ is other than hydrogen.

In one embodiment of the methods provided herein, in compounds of Formula Ib, n is 1, one of E, K, and G are N and the other two of E, K, and G are C, at least one of $R^{15}$, $R^{16}$ and $R^{17}$ is other than hydrogen, A is —$CH_2$—, M is —$NHCH_2$—, further wherein $R^1$ is optionally substituted phenyl. In another embodiment, n is 1, E, K, and G are C, at least one of $R^{15}$, $R^{16}$ and $R^{17}$ is other than hydrogen, A is —$CH_2$—, M is —$NHCH_2$—, further wherein $R^1$ is optionally substituted phenyl.

In one embodiment of the methods provided herein, in compounds of Formula Ib, n is 1, V, Z, U and W are CH, one of E, K, and G are N and the other two of E, K, and G are C and at least one of $R^{15}$, $R^{16}$ and $R^{17}$ is other than hydrogen. In another embodiment, V, Z, U and W are CH, E, K and G are C, and at least one of $R^{15}$, $R^{16}$ and $R^{17}$ is other than hydrogen.

In one embodiment of the methods provided herein, in compounds of Formula Ib, Z is $CR^{18}$, wherein $R^{18}$ is other than hydrogen, n is 1, E-$R^{15}$ is N or CH, K-$R^{16}$ is N or CH and G-$R^{17}$ is N or CH. In another embodiment, Z is $CR^{18}$, wherein $R^{18}$ is other than hydrogen, n is 1, and E-$R^{15}$, K-$R^{16}$ and G-$R^{17}$ are CH. In another embodiment, Z is $CR^{18}$, wherein $R^{18}$ is other than hydrogen, U is $CR^{18}$, V and W are CH, n is 1, and E-$R^{15}$, K-$R^{16}$ and G-$R^{17}$ are CH, further wherein U is CH.

In one embodiment of the methods provided herein, in compounds of Formula Ib, Z is $CR^{18}$, wherein $R^{18}$ is other than hydrogen, n is 1, E-$R^{15}$, K-$R^{16}$ and G-$R^{17}$ are CH, A is —$CH_2$—, M is —$NHCH_2$—, further wherein $R^1$ is optionally substituted phenyl. In a further embodiment, Z is $CR^{18}$, wherein $R^{18}$ is other than hydrogen, U is $CR^{18}$, V and W are CH, n is 1, E-$R^{15}$, K-$R^{16}$ and G-$R^{17}$ are CH, A is —$CH_2$—, M is —$NHCH_2$—, further wherein $R^1$ is optionally substituted phenyl. In a further embodiment, Z is $CR^{18}$, wherein $R^{18}$ is other than hydrogen, V, U and W are CH, n is 1, E-$R^{15}$, K-$R^{16}$ and G-$R^{17}$ are CH, A is —$CH_2$—, M is —$NHCH_2$—, further wherein $R^1$ is optionally substituted phenyl.

In one embodiment of the methods provided herein, in compounds of Formula Ib, U is $CR^{18}$, wherein $R^{18}$ is other than hydrogen, n is 1, E-$R^{15}$ is N or CH, K-$R^{16}$ is N or CH and G-$R^{17}$ is N or CH. In another embodiment, U is $CR^{18}$, wherein $R^{18}$ is other than hydrogen, n is 1, and E-$R^{15}$, K-$R^{16}$ and G-$R^{17}$ are CH. In another embodiment, U is $CR^{18}$, wherein $R^{18}$ is other than hydrogen, Z is $CR^{18}$, V and W are CH, n is 1, and E-$R^{15}$, K-$R^{16}$ and G-$R^{17}$ are CH, further wherein Z is CH.

In one embodiment of the methods provided herein, in compounds of Formula Ib, U is $CR^{18}$, wherein $R^{18}$ is other than hydrogen, n is 1, E-$R^{15}$, K-$R^{16}$ and G-$R^{17}$ are CH, A is —$CH_2$—, M is —$NHCH_2$—, further wherein $R^1$ is optionally substituted phenyl. In a further embodiment, U is $CR^{18}$, wherein $R^{18}$ is other than hydrogen, Z is $CR^{18}$, V and W are CH, n is 1, E-$R^{15}$, K-$R^{16}$ and G-$R^{17}$ are CH, A is —$CH_2$—, M is —$NHCH_2$—, further wherein $R^1$ is optionally substituted phenyl. In a further embodiment, U is $CR^{18}$, wherein $R^{18}$ is other than hydrogen, V, Z and W are CH, n is 1, E-$R^{15}$, K-$R^{16}$ and G-$R^{17}$ are CH, A is —$CH_2$—, M is —$NHCH_2$—, further wherein $R^1$ is optionally substituted phenyl.

In one embodiment of the methods provided herein, in compounds of Formula Ib, further to any of the above embodiments, $R^{15}$, $R^{16}$ and $R^{17}$ are independently selected from the group consisting of halogen, —OH, lower alkyl, fluoro substituted lower alkyl, lower alkoxy, and fluoro substituted lower alkoxy. Further to any of these embodiments $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In one embodiment of the methods provided herein, in compounds of Formula Ib, further to any of the above embodiments, $R^{18}$ is selected from the group consisting of halogen, —OH, optionally substituted lower alkyl and $OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl. Further to any of these embodiments, $R^1$ is phenyl optionally substituted with one or more substituents selected from the group consisting of halogen, —OH, —$NH_2$, —$NO_2$, —CN, optionally substituted lower alkyl and —$OR^{29}$, where $R^{29}$ is selected from the group consisting of optionally substituted lower alkyl, optionally substituted cycloalkyl, optionally substituted heterocycloalkyl, optionally substituted aryl and optionally substituted heteroaryl.

In another embodiment of methods provided herein, in compounds of Formula Ib, M is a bond and $R^1$ is other than thiophenyl.

In another embodiment of the methods provided herein, in compounds of Formula Ib, Z is N or $CR^{18}$ wherein $R^{18}$ is not hydrogen. Further to this embodiment, as allowed in the description of Formula Ib, E is $NR^{15}$ or $CR^{15}$, K is $NR^{16}$ or $CR^{16}$ and G is $CR^{17}$, or combinations thereof, wherein at least one of $R^{15}$, $R^{16}$ and $R^{17}$ is not hydrogen.

In one embodiment of the methods provided herein, a compound of Formula I has a structure according to the following sub-generic structure, Formula Ig,

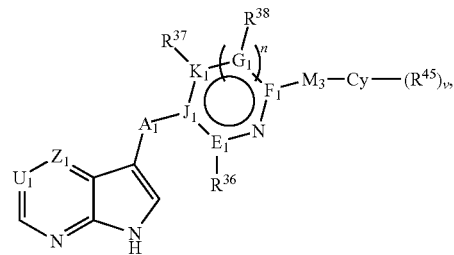

Formula Ig or a salt, prodrug, tautomer, or isomer thereof,
wherein:
  $Z_1$ is selected from the group consisting of N and $CR^{34}$;
  $U_1$ is selected from the group consisting of N and $CR^{35}$;
  $A_1$ is selected from the group consisting of —$CH_2$— and —C(O)—;
  $M_3$ is selected from the group consisting of a bond, —$NR^{39}$—, —S—, —O—, —$NR^{39}CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, and —$NR^{39}S(O)_2$—;
  n is 0 or 1;
  v is 0, 1, 2 or 3;
  $F_1$ and $J_1$ are both C or one of $F_1$ and $J_1$ is C and the other of $F_1$ and $J_1$ is N;
  $E_1$ and $K_1$ are independently selected from C, N, O or S;
  $G_1$ is selected from C or N;
    wherein
      when n is 1, $F_1$ and $J_1$ are C, and $E_1$, $G_1$ and $K_1$ are C, or any one of $E_1$, $G_1$ and $K_1$ is N and the other two of $E_1$, $G_1$ and $K_1$ are C, provided that when $E_1$, $G_1$ or $K_1$ is N, $R^{36}$, $R^{37}$ and $R^{38}$, respectively, are absent;
      when n is 0 and $F_1$ and $J_1$ are both C, then one of $E_1$ and $K_1$ is C or N and the other of $E_1$ and $K_1$ is C, N, O or S, provided both $E_1$ and $K_1$ are not C, and provided that when both $E_1$ and $K_1$ are N, one of $R^{36}$ and $R^{37}$ is absent, and provided that when one of $E_1$ and $K_1$ are N and the other is O or S, $R^{36}$ and $R^{37}$ are absent;
      when n is 0, one of $F_1$ and $J_1$ is N and the other of $F_1$ and $J_1$ is C, then one of $E_1$ and $K_1$ is N and the other of $E_1$ and $K_1$ is C, or both $E_1$ and $K_1$ are C, provided that when $E_1$ is N, $R^{36}$ is absent and when $K_1$ is N, $R^{37}$ is absent;
  Cy is selected from the group consisting of cycloalkyl, heterocycloalkyl, aryl and heteroaryl;
  $R^{34}$ and $R^{35}$ are independently selected from the group consisting of hydrogen, —$OR^{41}$, —$SR^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{34}$ or $R^{35}$, or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$ halogen, lower alkyl, fluoro substituted lower alkyl, and cycloalkylamino;

$R^{45}$ at each occurrence is independently selected from the group consisting of —OR$^{41}$, —SR$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{45}$, or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino;

$R^{36}$ is selected from the group consisting of hydrogen, halogen, lower alkyl, fluoro substituted lower alkyl, lower alkoxy, and fluoro substituted lower alkoxy when $E_1$ is C, is absent when $E_1$ is O or S or when n=1 and $E_1$ is N, and is absent or selected from the group consisting of hydrogen, lower alkyl, and fluoro substituted lower alkyl when n=0 and $E_1$ is N;

$R^{37}$ is selected from the group consisting of hydrogen, halogen, lower alkyl, fluoro substituted lower alkyl, lower alkoxy, and fluoro substituted lower alkoxy when $K_1$ is C, is absent when $K_1$ is O or S or when n=1 and $K_1$ is N, and is absent or selected from the group consisting of hydrogen, lower alkyl, and fluoro substituted lower alkyl when n=0 and $K_1$ is N;

$R^{38}$ is selected from the group consisting of hydrogen, halogen, lower alkyl, fluoro substituted lower alkyl, lower alkoxy, and fluoro substituted lower alkoxy when $G_1$ is C, or is absent when $G_1$ is N;

$R^{39}$ at each occurrence is independently hydrogen or lower alkyl;

$R^{40}$ is lower alkyl or fluoro substituted lower alkyl;

$R^{41}$ is selected from the group consisting of lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as $R^{41}$ or as substituents of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; and $R^{42}$ at each occurrence is independently selected from the group consisting of lower alkyl, heterocycloalkyl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, and heterocycloalkyl and heteroaryl are optionally substituted with one or more substituents selected from the group consisting of halogen, —CN, lower alkyl, fluoro substituted lower alkyl, lower alkoxy and fluoro substituted lower alkoxy.

In one embodiment of methods provided herein, in compounds of Formula Ig, n is 1, $G_1$ and $K_1$ are C, and E is N or C, preferably wherein E is C.

In one embodiment of the methods provided herein, in compounds of Formula Ig, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—.

In one embodiment of the methods provided herein, in compounds of Formula Ig, n is 1, $G_1$ and $K_1$ are C, and E is N or C, preferably wherein E is C, and $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—.

In one embodiment of the methods provided herein, in compounds of Formula Ig, each $R^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of the methods provided herein, in compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, and each $R^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1.

In one embodiment of the methods provided herein, in compounds of Formula Ig, $Z_1$ is CR$^{34}$, $U_1$ is CR$^{35}$, and $R^{34}$ and $R^{35}$ are both hydrogen. In one embodiment, $Z_1$ is CR$^{34}$, $U_1$ is CR$^{35}$, and $R^{34}$ and $R^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of $R^{34}$ and $R^{35}$ is hydrogen, and the other of $R^{34}$ and $R^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of the methods provided herein, in compounds of Formula Ig, each $R^{45}$ is independently selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, and $R^{34}$ and $R^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, both of $R^{34}$ and $R^{35}$ are hydrogen.

In one embodiment of the methods provided herein, in compounds of Formula Ig, each $R^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, one of $R^{34}$ and $R^{35}$ is hydrogen, and the other of $R^{34}$ and $R^{35}$ is selected from the group consisting of hydrogen, halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino.

In one embodiment of the methods provided herein, in compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, each $R^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$, $U_1$ is CR$^{35}$, and $R^{34}$ and $R^{35}$ are both hydrogen.

In one embodiment of the methods provided herein, in compounds of Formula Ig, n is 1, $G_1$ and $K_1$ are C, and E is N or C, preferably wherein E is C, $M_3$ is selected from the group consisting of —NR$^{39}$—, —O—, —NR$^{39}$CH$_2$—, —NR$^{39}$CH(R$^{40}$)—, —SCH$_2$—, —OCH$_2$—, —CH$_2$NR$^{39}$—, —NR$^{39}$C(O)—, and —NR$^{39}$S(O)$_2$—, preferably wherein $M_3$ is —NR$^{39}$CH$_2$—, —NR$^{39}$CH(R$^{40}$)—, —SCH$_2$—, —OCH$_2$—, or —CH$_2$NR$^{39}$—, each $R^{45}$ is selected from the group consisting of —OH, —NH$_2$, —CN, —NO$_2$, halogen, lower alkyl, fluoro substituted lower alkyl, lower alkoxy, fluoro substituted lower alkoxy, lower thioalkyl, fluoro substituted lower thioalkyl, mono-alkylamino, di-alkylamino and cycloalkylamino, preferably wherein v is 0, 1, or 2, also 0 or 1, $Z_1$ is CR$^{34}$ and $U_1$ is CR$^{35}$, and $R^{34}$ and $R^{35}$ are independently selected from the group consisting of hydrogen, —OR$^{41}$, halogen, lower alkyl, cycloalkyl, heterocycloalkyl, aryl and heteroaryl, wherein cycloalkyl, heterocycloalkyl, aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino. In a further embodiment, one of $R^{34}$ and $R^{35}$ is hydrogen, and the other of $R^{34}$ and $R^{35}$ is selected from the group consisting of halogen, lower alkyl, lower alkoxy, aryl and heteroaryl, wherein aryl and heteroaryl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino, and wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein the other of $R^{34}$ and $R^{35}$ is selected from the group consisting of halogen, lower alkyl, and lower alkoxy, wherein lower alkyl and lower alkoxy are optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, and cycloalkylamino, further wherein $R^{34}$ is hydrogen.

In one embodiment of the methods provided herein, a compound of Formula I has a structure according to the following sub-generic structure, Formula II,

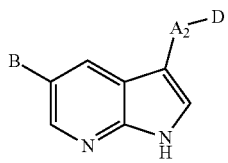

Formula II or a salt, prodrug, tautomer, or isomer thereof, wherein:

D has a structure selected from the group consisting of

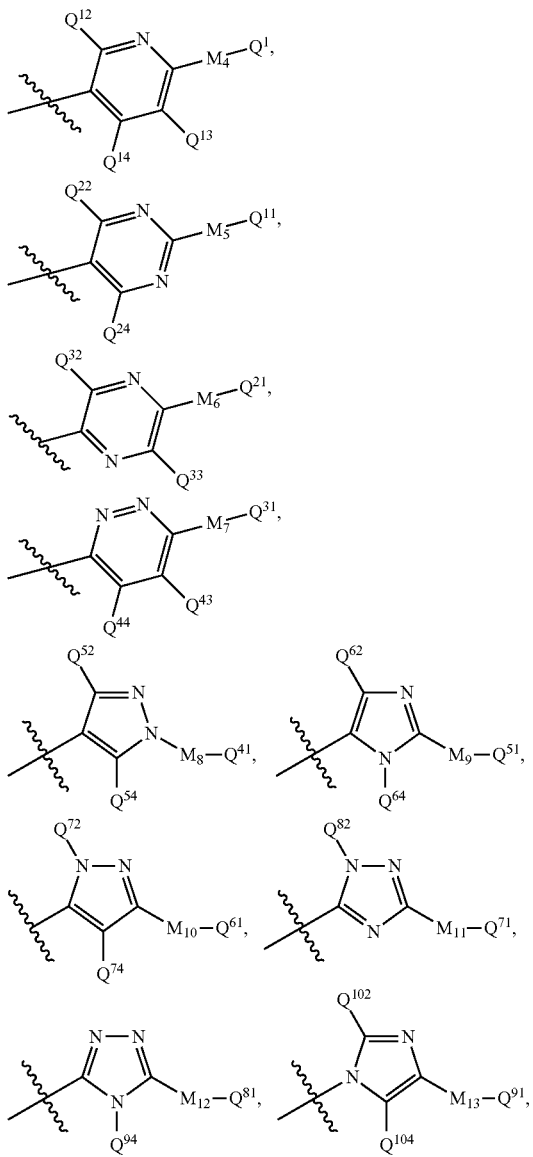

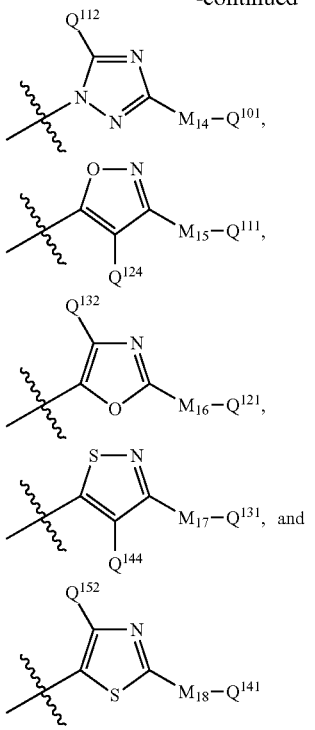

in which

indicates the attachment point of D to $A_2$ of Formula II;

$A_2$ is selected from the group consisting of —$CR^{19}R^{20}$—, —C(O)—, —C(S)—, —S—, —S(O)—, —S(O)$_2$—, —$NR^{21}$—, and —O—, provided, however, that when $A_2$ is $NR^{21}$, N is not bound to a nitrogen of D;

B is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$R^{23}$, —S(O)$_2R^{23}$ —C(O)$NR^{23}R^{23}$, —C(S)$NHR^{23}$, —C(S)$NR^{23}R^{23}$, —S(O)$_2NHR^{23}$, —S(O)$_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$— NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$;

$M_4$ is —$NR^{39}CH_2$—, —$NR^{39}CH(R^{40})$—, —$NR^{39}CH_2CH_2$—, or —$NR^{39}C(O)$—;

$M_5$, $M_6$, $M_7$, $M_9$, $M_{10}$, $M_{11}$, $M_{12}$, $M_{13}$, $M_{14}$, $M_{15}$ $M_{16}$, $M_{17}$ and $M_{18}$ are selected from the group consisting of a bond, —$(CR^{19}R^{20})_u$—, —$(CR^{19}R^{20})_t$—C(O)—$(CR^{19}R^{20})_s$—, —$(CR^{19}R^{20})_t$—C(S)—$(CR^{19}R^{20})_s$—, —(CR$^{19}$R$^{20}$)$_t$—C(O)O—(CR$^{19}$R$^{20}$)$_s$—, —(CR$^{19}$R$^{20}$)$_t$—C(S)O—(CR$^{19}$R$^{20}$)$_s$—, —(CR$^{19}$R$^{20}$)$_t$—C(O)NR$^{26}$—(CR$^{19}$R$^{20}$)$_s$—, —(CR$^{19}$R$^{20}$)$_t$—C(S)NR$^{26}$—(CR$^{19}$R$^{20}$)$_s$—, —(CR$^{19}$R$^{20}$)$_t$—S(O)—(CR$^{19}$R$^{20}$)$_s$—, —(CR$^{19}$R$^{20}$)$_t$—S(O)$_2$—(CR$^{19}$R$^{20}$)$_s$—, —(CR$^{19}$R$^{20}$)$_t$—S(O)$_2$NR$^{26}$—(CR$^{19}$R$^{20}$)$_s$—, —(CR$^{19}$R$^{20}$)$_t$—O—(CR$^{19}$R$^{20}$)$_s$—, —(CR$^{19}$R$^{20}$)$_t$—OC(O)—(CR$^{19}$R$^{20}$)$_s$—, —(CR$^{19}$R$^{20}$)$_t$—OC(S)—(CR$^{19}$R$^{20}$)$_s$—, —(CR$^{19}$R$^{20}$)$_t$—OC(O)NR$^{26}$—(CR$^{19}$R$^{20}$)$_s$—, —(CR$^{19}$R$^{20}$)$_t$—OC(S)NR$^{26}$—(CR$^{19}$R$^{20}$)$_s$—, —(CR$^{19}$R$^{20}$)$_t$—S—(CR$^{19}$R$^{20}$)$_s$—, —(CR$^{19}$R$^{20}$)$_t$—NR$^{26}$—(CR$^{19}$R$^{20}$)$_s$—, —(CR$^{19}$R$^{20}$)$_t$—NR$^{26}$C(O)—(CR$^{19}$R$^{20}$)$_s$—, —(CR$^{19}$R$^{20}$)$_t$—NR$^{26}$C(S)—(CR$^{19}$R$^{20}$)$_s$—, —(CR$^{19}$R$^{20}$)$_t$—NR$^{26}$C(O)O—(CR$^{19}$R$^{20}$)$_s$—, —(CR$^{19}$R$^{20}$)$_t$—NR$^{26}$C(S)O—(CR$^{19}$R$^{20}$)$_s$—, —(CR$^{19}$R$^{20}$)$_t$—NR$^{26}$C(O)NR$^{26}$—(CR$^{19}$R$^{20}$)$_s$—, —(CR$^{19}$R$^{20}$)$_t$—NR$^{26}$C(S)NR$^{26}$—(CR$^{19}$R$^{20}$)$_s$—, —(CR$^{19}$R$^{20}$)$_t$—NR$^{26}$S(O)$_2$—(CR$^{19}$R$^{20}$)$_s$—, and —(CR$^{19}$R$^{20}$)$_t$—NR$^{26}$S(O)$_2$NR$^{26}$—(CR$^{19}$R$^{20}$)$_s$—;

M$_8$ is selected from the group consisting of a bond, —(CR$^{19}$R$^{20}$)$_u$—, —(CR$^{19}$R$^{20}$)$_t$—C(O)—(CR$^{19}$R$^{20}$)$_s$—, —(CR$^{19}$R$^{20}$)$_t$—C(S)—(CR$^{19}$R$^{20}$)$_s$—, —(CR$^{19}$R$^{20}$)$_t$—C(O)O—(CR$^{19}$R$^{20}$)$_s$—, —(CR$^{19}$R$^{20}$)$_t$—C(S)O—(CR$^{19}$R$^{20}$)$_s$, —(CR$^{19}$R$^{20}$)$_t$—C(O)NR$^{26}$—(CR$^{19}$R$^{20}$)$_s$—, —(CR$^{19}$R$^{20}$)$_t$—C(S)NR$^{26}$—(CR$^{19}$R$^{20}$)$_s$—, —(CR$^{19}$R$^{20}$)$_t$—S(O)—(CR$^{19}$R$^{20}$)$_s$—, —(CR$^{19}$R$^{20}$)$_t$—S(O)$_2$—(CR$^{19}$R$^{20}$)$_s$—, —(CR$^{19}$R$^{20}$)$_t$—S(O)$_2$NR$^{26}$—(CR$^{19}$R$^{20}$)$_s$—, —(CR$^{19}$R$^{20}$)$_w$—O—(CR$^{19}$R$^{20}$)$_s$—, —(CR$^{19}$R$^{20}$)$_w$—OC(O)—(CR$^{19}$R$^{20}$)$_s$—, —(CR$^{19}$R$^{20}$)$_w$—OC(S)—(CR$^{19}$R$^{20}$)$_s$, —(CR$^{19}$R$^{20}$)$_w$—OC(O)NR$^{26}$—(CR$^{19}$R$^{20}$)$_s$—, —(CR$^{19}$R$^{20}$)$_w$—OC(S)NR$^{26}$—(CR$^{19}$R$^{20}$)$_s$—, —(CR$^{19}$R$^{20}$)$_w$—S—(CR$^{19}$R$^{20}$)$_s$—, —(CR$^{19}$R$^{20}$)$_w$—NR$^{26}$—(CR$^{19}$R$^{20}$)$_s$—, —(CR$^{19}$R$^{20}$)$_w$—NR$^{26}$C(O)—(CR$^{19}$R$^{20}$)$_s$—, —(CR$^{19}$R$^{20}$)$_w$—NR$^{26}$C(S)—(CR$^{19}$R$^{20}$)$_s$—, —(CR$^{19}$R$^{20}$)$_w$—NR$^{26}$C(O)O—(CR$^{19}$R$^{20}$)$_s$—, —(CR$^{19}$R$^{20}$)$_w$—NR$^{26}$C(S)O—(CR$^{19}$R$^{20}$)$_s$—, —(CR$^{19}$R$^{20}$)$_w$—NR$^{26}$C(O)NR$^{26}$—(CR$^{19}$R$^{20}$)$_s$—, —(CR$^{19}$R$^{20}$)$_w$—NR$^{26}$C(S)NR$^{26}$—(CR$^{19}$R$^{20}$)$_s$—, —(CR$^{19}$R$^{20}$)$_w$—NR$^{26}$S(O)$_2$—(CR$^{19}$R$^{20}$)$_s$—, and —(CR$^{19}$R$^{20}$)$_w$—NR$^{26}$S(O)$_2$NR$^{26}$—(CR$^{19}$R$^{20}$)$_s$—;

Q$^1$ is aryl or heteroaryl, wherein aryl or heteroaryl are optionally substituted with one or more substituents selected from the group consisting of halogen, lower alkyl, fluoro substituted lower alkyl, —NHS(O)$_2$R$^{43}$, —NHC(O)R$^{43}$, —NHR$^{43}$, —NR$^{43}$R$^{43}$, —OR$^{43}$, SR$^{43}$, S(O)R$^{43}$, and —S(O)$_2$R$^{43}$;

Q$^{11}$, Q$^{21}$, Q$^{31}$, Q$^{41}$, Q$^{51}$, Q$^{61}$, Q$^{71}$, Q$^{81}$, Q$^{91}$, Q$^{101}$, Q$^{111}$, Q$^{121}$, Q$^{131}$, and Q$^{141}$ are selected from the group consisting of optionally substituted lower alkyl, optionally substituted cycloalkyl, optionally substituted heterocycloalkyl, optionally substituted aryl and optionally substituted heteroaryl;

Q$^{12}$ is fluoro, chloro or —CF$_3$;

Q$^{13}$ and Q$^{14}$ are independently hydrogen, fluoro, chloro, lower alkyl, or fluoro substituted lower alkyl;

Q$^{22}$, Q$^{24}$, Q$^{32}$, Q$^{33}$, Q$^{43}$, Q$^{44}$, Q$^{52}$, Q$^{54}$, Q$^{102}$ and Q$^{104}$ are independently selected from the group consisting of hydrogen, halogen, lower alkyl, fluoro substituted lower alkyl, —NR$^{44}$R$^{44}$, —OR$^{44}$, and —SR$^{44}$, provided, however, that at least one of Q$^{22}$ and Q$^{24}$, at least one of Q$^{32}$ and Q$^{33}$, at least one of Q$^{43}$ and Q$^{44}$, at least one of Q$^{52}$ and Q$^{54}$, and at least one of Q$^{102}$ and Q$^{104}$ is hydrogen, fluoro, chloro, lower alkyl or fluoro substituted lower alkyl;

Q$^{62}$, Q$^{74}$, Q$^{112}$, Q$^{124}$, Q$^{132}$, Q$^{144}$, and Q$^{152}$ are hydrogen, fluoro, chloro, lower alkyl, fluoro substituted lower alkyl, —NR$^{44}$R$^{44}$, —OR$^{44}$, or —SR$^{44}$;

Q$^{64}$, Q$^{72}$, Q$^{82}$, and Q$^{94}$ are hydrogen, lower alkyl or fluoro substituted lower alkyl;

R$^{43}$ at each occurrence is independently optionally substituted lower alkyl, optionally substituted cycloalkyl, optionally substituted heterocycloalkyl, optionally substituted aryl or optionally substituted heteroaryl;

R$^{39}$ and R$^{40}$ are as defined for Formula Ig;

each R$^{44}$ is independently hydrogen, lower alkyl or fluoro substituted lower alkyl;

w is 1, 2, or 3; and

R$^{19}$, R$^{20}$, R$^{21}$, R$^{23}$, R$^{24}$, R$^{25}$, R$^{26}$, s, t and u are as defined for Formula Ib.

In certain embodiments of the methods provided herein, e.g., the compound is not

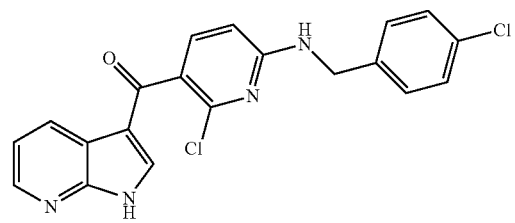

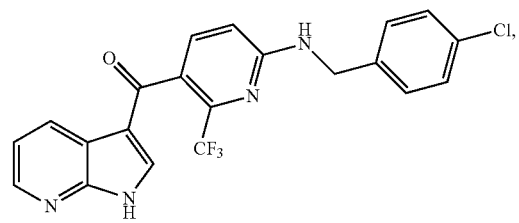

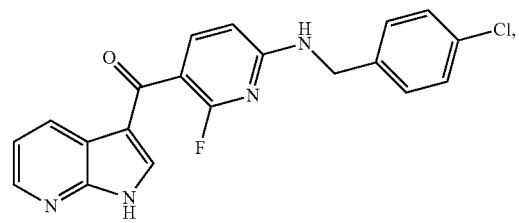

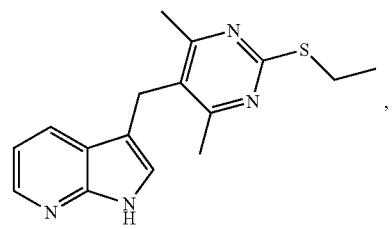

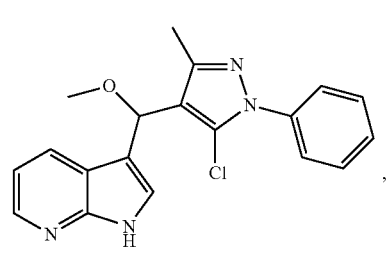

-continued
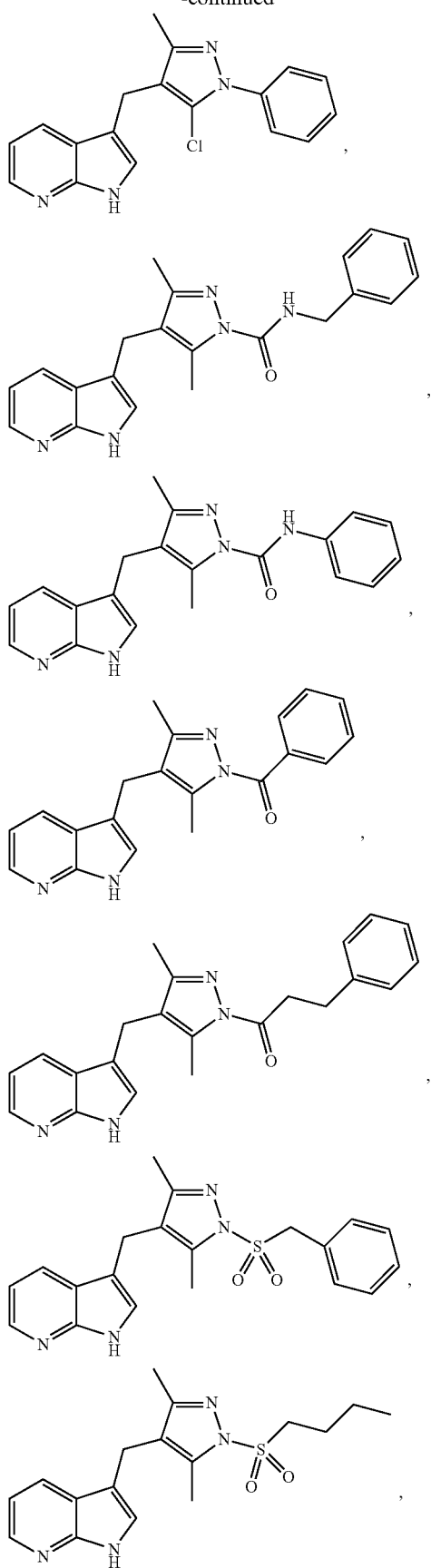
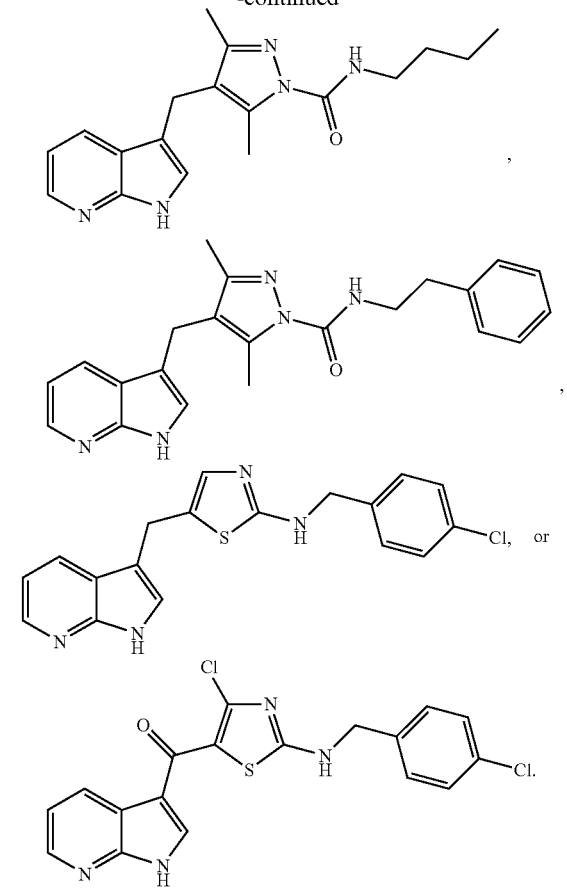
In one embodiment of the methods provided herein, in compounds of Formula II,
D has a structure selected from the group consisting of
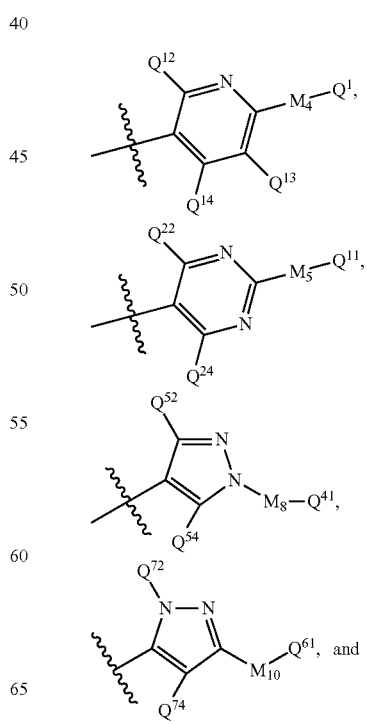

-continued

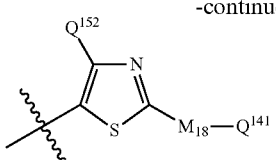

in which

indicates the attachment point of D to $A_2$ of Formula II;

$A_2$ is selected from the group consisting of —$CR^{19}R^{20}$—, —C(O)—, —C(S)—, —S—, —S(O)—, —S(O)$_2$—, —$NR^{21}$—, and —O—, provided, however, that when $A_2$ is $NR^{21}$, N is not bound to a nitrogen of D, preferably $A_2$ is —$CH_2$— or —C(O)—;

B is selected from the group consisting of hydrogen, —CN, —$OR^{41}$, —$SR^{41}$, —$NHR^{41}$, —$NR^{41}R^{41}$, —$NR^{39}C(O)R^{41}$, —$NR^{39}S(O)_2R^{41}$, —$C(O)NR^{39}R^{41}$, $C(O)R^{41}$, $S(O)_2NR^{39}R^{41}$, —$S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as B, or as substituents of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino;

$M_4$ is —$NR^{39}CH_2$—, —$NR^{39}CH(R^{40})$—, —$NR^{39}CH_2CH_2$—, or —$NR^{39}C(O)$—, preferably —$NHCH_2$— or —NHC(O)—;

$M_5$, $M_{10}$, and $M_{18}$ are selected from the group consisting of a bond, —$(CR^{19}R^{20})_u$—, —$(CR^{19}R^{20})_t$—C(O)—$(CR^{19}R^{20})_s$—, —$(CR^{19}R^{20})_t$—C(S)—$(CR^{19}R^{20})_s$—, —$(CR^{19}R^{20})_t$—C(O)O—$(CR^{19}R^{20})_s$—, —$(CR^{19}R^{20})_t$—C(S)O—$(CR^{19}R^{20})_s$—, —$(CR^{19}R^{20})_t$—C(O)$NR^{26}$—$(CR^{19}R^{20})_s$—, —$(CR^{19}R^{20})_t$—C(S)$NR^{26}$—$(CR^{19}R^{20})_s$—, —$(CR^{19}R^{20})_t$—S(O)—$(CR^{19}R^{20})_s$—, —$(CR^{19}R^{20})_t$—S(O)$_2$—$(CR^{19}R^{20})_s$—, —$(CR^{19}R^{20})_t$—S(O)$_2NR^{26}$—$(CR^{19}R^{20})_s$—, —$(CR^{19}R^{20})_t$—O—$(CR^{19}R^{20})_s$—, —$(CR^{19}R^{20})_t$—OC(O)—$(CR^{19}R^{20})_s$—, —$(CR^{19}R^{20})_t$—OC(S)—$(CR^{19}R^{20})_s$, —$(CR^{19}R^{20})_t$—OC(O)$NR^{26}$—$(CR^{19}R^{20})_s$—, —$(CR^{19}R^{20})_t$—OC(S)$NR^{26}$—$(CR^{19}R^{20})_s$—, —$(CR^{19}R^{20})_t$—S—$(CR^{19}R^{20})_s$—, —$(CR^{19}R^{20})_t$—$NR^{26}$—$(CR^{19}R^{20})_s$—, —$(CR^{19}R^{20})_t$—$NR^{26}$C(O)—$(CR^{19}R^{20})_s$—, —$(CR^{19}R^{20})_t$—$NR^{26}$C(S)—$(CR^{19}R^{20})_s$—, —$(CR^{19}R^{20})_t$—$NR^{26}$C(O)O—$(CR)^{19}R^{20})_s$—, —$(CR^{19}R^{20})_t$—$NR^{26}$C(S)O—$(CR^{19}R^{20})_s$—, —$(CR^{19}R^{20})_t$—$NR^{26}$C(O)$NR^{26}$—$(CR^{19}R^{20})_s$—, —$(CR^{19}R^{20})_t$—$NR^{26}$C(S)$NR^{26}$—$(CR^{19}R^{20})_s$—, —$(CR^{19}R^{20})_t$—$NR^{26}$S(O)$_2$—$(CR^{19}R^{20})_s$—, and —$(CR^{19}R^{20})_t$—$NR^{26}$S(O)$_2NR^{26}$—$(CR^{19}R^{20})_s$—, preferably a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —C(O)$NR^{39}$—, —$S(O)_2NR^{39}$—, —$CH_2NR^{39}$—, —$CH(R^{40})NR^{39}$—, —$NR^{39}C(O)$—, or —$NR^{39}S(O)_2$—, more preferably —$NR^{39}CH_2$—, —$NR^{39}CH(R^{40})$— or —$NR^{39}C(O)$—, more preferably —$NHCH_2$—, —$NHCH(CH_3)$— or —NHC(O)—;

$M_8$ is selected from the group consisting of a bond, —$(CR^{19}R^{20})_u$—, —$(CR^{19}R^{20})_t$—C(O)—$(CR^{19}R^{20})_s$—, —$(CR^{19}R^{20})_t$—C(S)—$(CR^{19}R^{20})_s$—, —$(CR^{19}R^{20})_t$—C(O)O—$(CR^{19}R^{20})_s$—, —$(CR^{19}R^{20})_t$—C(S)O—$(CR^{19}R^{20})_s$—, —$(CR^{19}R^{20})_t$—C(O)$NR^{26}$—$(CR^{19}R^{20})_s$—, —$(CR^{19}R^{20})_t$—C(S)$NR^{26}$—$(CR^{19}R^{20})_s$—, —$(CR^{19}R^{20})_t$—S(O)—$(CR^{19}R^{20})_s$—, —$(CR^{19}R^{20})_t$—S(O)$_2$—$(CR^{19}R^{20})_s$—, —$(CR^{19}R^{20})_t$—S(O)$_2NR^{26}$—$(CR^{19}R^{20})_s$—, —$(CR^{19}R^{20})_w$—O—$(CR^{19}R^{20})_s$—, —$(CR^{19}R^{20})_w$—OC(O)—$(CR^{19}R^{20})_s$—, —$(CR^{19}R^{20})_w$—OC(S)—$(CR^{19}R^{20})_s$—, —$(CR^{19}R^{20})_w$—OC(O)$NR^{26}$—$(CR^{19}R^{20})_s$—, —$(CR^{19}R^{20})_w$—OC(S)$NR^{26}$—$(CR^{19}R^{20})_s$—, —$(CR^{19}R^{20})_w$—S—$(CR^{19}R^{20})_s$—, —$(CR^{19}R^{20})_w$—$NR^{26}$—$(CR^{19}R^{20})_s$—, —$(CR^{19}R^{20})_w$—$NR^{26}$C(O)—$(CR^{19}R^{20})_s$—, —$(CR^{19}R^{20})_w$—$NR^{26}$C(S)—$(CR^{19}R^{20})_s$—, —$(CR^{19}R^{20})_w$—$NR^{26}$C(O)O—$(CR^{19}R^{20})_s$—, —$(CR^{19}R^{20})_w$—$NR^{26}$C(S)O—$(CR^{19}R^{20})_s$—, —$(CR^{19}R^{20})_w$—$NR^{26}$C(O)$NR^{26}$—$(CR^{19}R^{20})_s$—, —$(CR^{19}R^{20})_w$—$NR^{26}$C(S)$NR^{26}$—$(CR^{19}R^{20})_s$—, —$(CR^{19}R^{20})_w$—$NR^{26}$S(O)$_2$—$(CR^{19}R^{20})_s$—, and —$(CR^{19}R^{20})_w$—$NR^{26}$S(O)$_2NR^{26}$—$(CR^{19}R^{20})_s$—, preferably a bond, —$CH_2$—, —$CH_2C(O)$—, —$S(O)_2$—, —$S(O)_2CH_2$—, —$S(O)_2CH(CH_3)$—, —$S(O)_2CH_2CH_2$—, —$S(O)_2NR^{39}$—, —$S(O)_2NR^{39}CH_2$—, —$S(O)_2NR^{39}CH(CH_3)$—, —$S(O)_2NR^{39}CH_2CH_2$—, —C(O)—, —C(O)$CH_2$—, —C(O)$CH(CH_3)$—, —C(O)$CH_2CH_2$—, —C(O)$NR^{39}$—, —C(O)$NR^{39}CH_2$—, —C(O)$NR^{39}CH(CH_3)$—, and —C(O)$NR^{39}CH_2CH_2$—, more preferably —C(O)$NR^{39}CH_2$—, —C(O)$NR^{39}CH(R^{40})$— or —C(O)$NR^{39}CH_2CH_2$—, more preferably —C(O)$NHCH_2$—, —C(O)$NHCH(CH_3)$— or —C(O)$NHCH_2CH_2$—;

$Q^1$, $Q^{11}$, $Q^{41}$, $Q^{61}$, and $Q^{141}$ are aryl or heteroaryl, wherein aryl or heteroaryl are optionally substituted with one or more substituents selected from the group consisting of, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, and wherein cycloalkyl, heterocycloalkyl, aryl, and heteroaryl as a substituent of $Q^1$, $Q^{11}$, $Q^{41}$, $Q^{61}$, or $Q^{141}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino, preferably $Q^1$, $Q^{11}$, $Q^{41}$, $Q^{61}$, and $Q^{141}$ are aryl or heteroaryl, wherein aryl or heteroaryl are optionally substituted with one or more halogen, lower alkyl, fluoro substituted lower alkyl, —$NHS(O)_2R^{41}$, —$NHC(O)R^{41}$, —$NHR^{41}$, —$NR^{41}R^{41}$, —$OR^{41}$ or —$S(O)_2R^{41}$;

$Q^{12}$ is fluoro, chloro or —$CF_3$;

$Q^{13}$ and $Q^{14}$ are independently hydrogen, fluoro, chloro, lower alkyl, or fluoro substituted lower alkyl;

$Q^{22}, Q^{24}, Q^{52}$ and $Q^{54}$ are independently selected from the group consisting of hydrogen, halogen, lower alkyl, fluoro substituted lower alkyl, —$NR^{44}R^{44}$, —$OR^{44}$, and —$SR^{44}$, provided, however, that at least one of $Q^{22}$ and $Q^{24}$ and at least one of $Q^{52}$ and $Q^{54}$ is hydrogen, fluoro, chloro, lower alkyl or fluoro substituted lower alkyl;

$Q^{74}$ and $Q^{152}$ are hydrogen, fluoro, chloro, lower alkyl, fluoro substituted lower alkyl, —$NR^{44}R^{44}$, —$OR^{44}$, or —$SR^{44}$;

$Q^{72}$ is hydrogen, lower alkyl or fluoro substituted lower alkyl;

$R^{39}$, $R^{40}$ and $R^{41}$ are as defined for Formula Ig;

each $R^{44}$ is independently hydrogen, lower alkyl or fluoro substituted lower alkyl; and $R^{19}, R^{20}, R^{21}, R^2$, s, t and u are as defined for Formula Ib.

In one embodiment of the methods provided herein, a compound of Formula II has a structure according to the following sub-generic structure, Formula IIa,

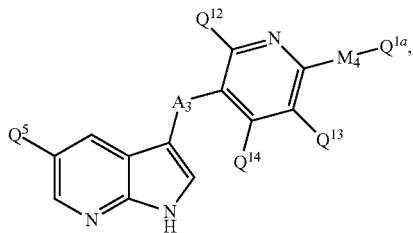

Formula IIa or a salt, prodrug, tautomer, or isomer thereof, wherein:

$A_3$ is —$CH_2$— or —C(O)—;

$Q^{1a}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$;

$Q^5$ is hydrogen, —$OR^{43}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{43}$, —$NR^{43}R^{43}$, —$OR^{43}$ and —$S(O)_2R^{43}$; and $M_4$, $Q^{12}$, $Q^{13}$, $Q^{14}$, $R^{41}$, and $R^{43}$ are as defined for Formula II.

In certain embodiments of the methods provided herein, the compound is not

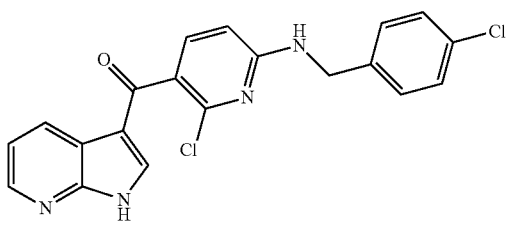

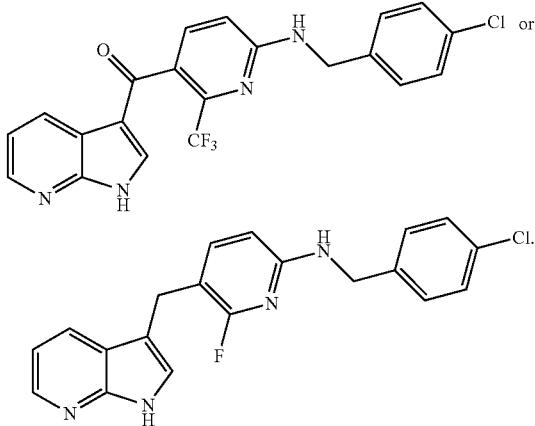

In one embodiment of the methods provided herein, in compounds of Formula IIa, $A_3$ is —$CH_2$— and $M_4$ is —$NHCH_2$—. In one embodiment $A_3$ is —C(O)— and $M_4$ is —$NHCH_2$—. In one embodiment $A_3$ is —C(O)— and $M_4$ is —NHC(O)—. In one embodiment $A_3$ is —$CH_2$— and $M_4$ is —NHC(O)—.

In one embodiment of the methods provided herein, in compounds of Formula IIa, $A_3$ is —$CH_2$—, $M_4$ is —$NHCH_2$—, $Q^5$ is —$OR^{43}$, —CN, $C_{1-3}$ alkyl, fluoro substituted $C_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —$NHR^{43}$, —$NR^{43}R^{43}$, —$OR^{43}$ and —$S(O)_2R^{43}$, and $Q^{13}$ and $Q^{14}$ are hydrogen.

In one embodiment of the methods provided herein, in compounds of Formula IIa, $A_3$ is —C(O)—, $M_4$ is —$NHCH_2$—, $Q^5$ is —$OR^{43}$, —CN, $C_{1-3}$ alkyl, fluoro substituted $C_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —$NHR^{43}$, —$NR^{43}R^{43}$, —$OR^{43}$ and —$S(O)_2R^{43}$, and $Q^{13}$ and $Q^{14}$ are hydrogen.

In one embodiment of the methods provided herein, in compounds of Formula IIa, $A_3$ is —C(O)—, $M_4$ is —NHC(O)—, $Q^5$ is —$OR^{43}$, —CN, $C_{1-3}$ alkyl, fluoro substituted $C_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —$NHR^{43}$, —$NR^{43}R^{43}$, —$OR^{43}$ and —$S(O)_2R^{43}$, and $Q^{13}$ and $Q^{14}$ are hydrogen.

In one embodiment of the methods provided herein, in compounds of Formula IIa, $A_3$ is —$CH_2$—, $M_4$ is —NHC(O)—, $Q^5$ is —$OR^{43}$, —CN, $C_{1-3}$ alkyl, fluoro substituted $C_{1-3}$ alkyl, fluoro, chloro, aryl or heteroaryl, wherein aryl or heteroaryl are optionally substituted with one or more substituents selected from the group consisting of halogen, lower alkyl, fluoro substituted lower alkyl, —$NHR^{43}$, —$NR^{43}R^{43}$, —$OR^{43}$ and —$S(O)_2R^{43}$, and $Q^{13}$ and $Q^{14}$ are hydrogen.

In one embodiment of the methods provided herein, in compounds of Formula IIa, $A_3$ is —$CH_2$— or —C(O)—; $Q^{1a}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$;

$Q^5$ is hydrogen, —CN, —OR$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$ and —OR$^{41}$; M$_4$ is —NR$^{39}$CH$_2$—, —NR$^{39}$CH(R$^{40}$)—, —NR$^{39}$CH$_2$CH$_2$—, or —NR$^{39}$C(O)—; Q$^{12}$ is fluoro, chloro or —CF$_3$; and Q$^{13}$ and Q$^{14}$ are independently hydrogen, fluoro, chloro, lower alkyl, or fluoro substituted lower alkyl, wherein R$^{41}$ is as defined for Formula II.

In one embodiment, further to any of the embodiments of the methods provided herein, in Formula IIa above, R$^{43}$ is R$^{41}$ as defined for Formula Ig. In one embodiment, further to any of the embodiments of the methods provided herein, in Formula IIa above, R$^{43}$ is R$^{42}$ as defined for Formula Ig.

In one embodiment, further to any of the embodiments of the methods provided herein, in Formula IIa above, Q$^{1a}$ is phenyl or pyridinyl, wherein phenyl or pyridinyl are substituted with 1 or 2 substituents selected from the group consisting of fluoro, chloro, methyl, methoxy, trifluoromethyl, difluoromethoxy and trifluoromethoxy; A$_3$ is —CH$_2$—; M$_4$ is —NHCH$_2$—; and Q$^5$ is CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy. In one embodiment, further to any of the embodiments of Formula IIa above, Q$^{1a}$ is phenyl mono substituted with chloro, preferably at the 4-position; A$_3$ is —CH$_2$—; M$_4$ is —NHCH$_2$—; and Q$^5$ is —CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy. In one embodiment, further to any of the embodiments of Formula IIa, Q$^{1a}$ is pyridin-3-yl monosubstituted with methyl, methoxy, trifluoromethyl, difluoromethoxy or trifluoromethoxy, preferably at the 6-position; A$_3$ is —CH$_2$—; M$_4$ is —NHCH$_2$—; Q$^5$ is —CN, fluoro, chloro, methyl, trifluoromethyl, methoxy, difluoromethoxy, trifluoromethoxy, aryl or heteroaryl, wherein aryl or heteroaryl are optionally substituted with one or more halogen, lower alkyl, fluoro substituted lower alkyl, lower alkoxy, or fluoro substituted lower alkoxy.

In one embodiment of the methods provided herein, in compounds of Formula IIa, A$_3$ is —CH$_2$—; M$_4$ is —NHCH$_2$—; Q$^{1a}$ is phenyl or pyridinyl, wherein phenyl or pyridinyl are substituted with 1 or 2 substituents selected from the group consisting of fluoro, chloro, methyl, methoxy, trifluoromethyl, difluoromethoxy and trifluoromethoxy; Q$^5$ is hydrogen, fluoro, chloro, methyl, methoxy, trifluoromethyl, trifluoromethoxy, —CN, or 1-methyl-1H-pyrazole-4-yl; Q$^{12}$ is fluoro or chloro; and Q$^{13}$ and Q$^{14}$ are hydrogen. In one embodiment, A$_3$ is —CH$_2$—; M$_4$ is —NHCH$_2$—; Q$^{1a}$ is phenyl mono substituted with chloro, preferably at the 4-position, Q$^5$ is hydrogen, chloro, methyl, methoxy, or CN; Q$^{12}$ is fluoro or chloro; and Q$^{13}$ and Q$^{14}$ are hydrogen. In one embodiment, A$_3$ is —CH$_2$—; M$_4$ is —NHCH$_2$—; Q$^{1a}$ is pyridin-3-yl monosubstituted with methyl, methoxy, trifluoromethyl, difluoromethoxy or trifluoromethoxy, preferably at the 6-position; Q$^5$ is hydrogen, chloro, methyl, methoxy, —CN, or 1-methyl-1H-pyrazole-4-yl; Q$^{12}$ is fluoro or chloro; and Q$^{13}$ and Q$^{14}$ are hydrogen.

In one embodiment of the methods provided herein, wherein the compound of Formula IIa is a compound selected from Table 1 below.

TABLE 1

(4-Chloro-benzyl)-[5-(5-chloro-1H-pyrrolo[2,3-b]pyridin-3-ylmethyl)-6-fluoro-pyridin-2-yl]-amine (P-0132),
(4-Chloro-benzyl)-[6-chloro-5-(1H-pyrrolo[2,3-b]pyridin-3-ylmethyl)-pyridin-2-yl]-amine (P-0161),
[6-Chloro-5-(1H-pyrrolo[2,3-b]pyridin-3-ylmethyl)-pyridin-2-yl]-(6-trifluoromethyl-pyridin-3-ylmethyl)-amine (P-0174),
[6-Chloro-5-(5-chloro-1H-pyrrolo[2,3-b]pyridin-3-ylmethyl)-pyridin-2-yl]-(6-trifluoromethyl-pyridin-3-ylmethyl)-amine (P-0176),
{6-Chloro-5-[5-(1-methyl-1H-pyrazol-4-yl)-1H-pyrrolo[2,3-b]pyridin-3-ylmethyl]-pyridin-2-yl}-(6-trifluoromethyl-pyridin-3-ylmethyl)-amine (P-0179),
[5-(5-Chloro-1H-pyrrolo[2,3-b]pyridin-3-ylmethyl)-6-fluoro-pyridin-2-yl]-(6-trifluoromethyl-pyridin-3-ylmethyl)-amine (P-0186),
[6-Fluoro-5-(5-methoxy-1H-pyrrolo[2,3-b]pyridin-3-ylmethyl)-pyridin-2-yl]-(6-trifluoromethyl-pyridin-3-ylmethyl)-amine (P-0187),
[6-Fluoro-5-(1H-pyrrolo[2,3-b]pyridin-3-ylmethyl)-pyridin-2-yl]-(6-trifluoromethyl-pyridin-3-ylmethyl)-amine (P-0188),
3-{2-Chloro-6-[(6-trifluoromethyl-pyridin-3-ylmethyl)-amino]-pyridin-3-ylmethyl}-1H-pyrrolo[2,3-b]pyridine-5-carbonitrile (P-0232),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0233),
[6-Chloro-5-(5-methyl-1H-pyrrolo[2,3-b]pyridin-3-ylmethyl)-pyridin-2-yl]-(6-trifluoromethyl-pyridin-3-ylmethyl)-amine (P-0234),
[6-Fluoro-5-(1H-pyrrolo[2,3-b]pyridin-3-ylmethyl)-pyridin-2-yl]-(6-methoxy-pyridin-3-ylmethyl)-amine (P-0378),
[5-(5-Chloro-1H-pyrrolo[2,3-b]pyridin-3-ylmethyl)-6-fluoro-pyridin-2-yl]-(6-methoxy-pyridin-3-ylmethyl)-amine (P-0379),
(5-Fluoro-pyridin-3-ylmethyl)-[6-fluoro-5-(1H-pyrrolo[2,3-b]pyridin-3-ylmethyl)-pyridin-2-yl]-amine (P-0414),
3-{2-Fluoro-6-[(5-fluoro-pyridin-3-ylmethyl)-amino]-pyridin-3-ylmethyl}-1H-pyrrolo[2,3-b]pyridine-5-carbonitrile (P-0415) and
3-[6-(4-Chloro-benzylamino)-2-fluoro-pyridin-3-ylmethyl]-1H-pyrrolo[2,3-b]pyridine-5-carbonitrile (P-0432),
all salts, prodrugs, tautomers, or isomers thereof In certain instances, the Flt3 kinase is a Flt3 mutant encoded by an ITD mutation. In some embodiments, the disease is AML.

In one embodiment of the methods provided herein, a compound of Formula II has a structure according to the following sub-generic structure, Formula IIb,

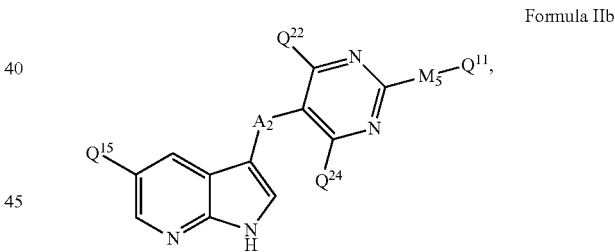

Formula IIb or a salt, prodrug, tautomer, or isomer thereof, wherein:
A$_2$ is selected from the group consisting of —CR$^{19}$R$^{20}$—, —C(O)—, —C(S)—, —S—, —S(O)—, —S(O)$_2$—, —NR$^{21}$—, and —O—;
Q$^{15}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$, —NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$; M$_5$, Q$^{11}$, Q$^{22}$ and Q$^{24}$ are as defined for Formula II; and R$^{19}$, R$^{20}$, R$^{21}$, R$^{23}$, R$^{24}$, and R$^{25}$ are as defined for Formula Ib.

In certain embodiments of the methods provided herein, the compound is not

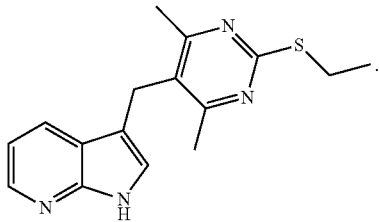 [SMILES: CCSc1nc(C)c(Cc2c[nH]c3ncccc23)c(C)n1]

In one embodiment of the methods provided herein, in compounds of Formula IIb, M$_5$ is —(CR$^{19}$R$^{20}$)$_t$—, —NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or NR$^{39}$C(O)—, wherein R$^{39}$ is hydrogen or lower alkyl and R$^{40}$ is lower alkyl or fluoro substituted lower alkyl. In one embodiment, A$_2$ is —CR$^{19}$R$^{20}$— or —C(O)—, preferably —CH$_2$— or —C(O)—. In one embodiment, Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and Q$^{15}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, Q$^{22}$ and Q$^{24}$ are independently hydrogen, fluoro, chloro, or —CF$_3$, preferably Q$^{22}$ and Q$^{24}$ are hydrogen.

In one embodiment of the methods provided herein, in compounds of Formula IIb, M$_5$ is —(CR$^{19}$R$^{20}$)$_t$—NR$^{26}$—(CR$^{19}$R$^{20}$)$_s$— or —(CR$^{19}$R$^{20}$)$_t$—NR$^{26}$—C(O)—(CR$^{19}$R$^{20}$)$_s$—, preferably —NR$^{26}$—(CR$^{19}$R$^{20}$)$_s$— or, —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, and A$_2$ is —CR$^{19}$R$^{20}$— or —C(O)—, preferably —CH$_2$— or —C(O)—. In one embodiment, M$_5$ is —(CR$^{19}$R$^{20}$)$_t$—NR$^{26}$—(CR$^{19}$R$^{20}$)$_s$— or —(CR$^{19}$R$^{20}$)$_t$—NR$^{26}$—C(O)—(CR$^{19}$R$^{20}$)$_s$—, preferably —NR$^{26}$—(CR$^{19}$R$^{20}$)$_s$— or, —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; A$_2$ is —CR$^{19}$R$^{20}$— or —C(O)—, preferably —CH$_2$— or —C(O)—; Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{15}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_5$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; A$_2$ is —CR$^{19}$R$^{20}$— or —C(O)—, preferably —CH$_2$— or —C(O)—; Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{15}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{22}$ and Q$^{24}$ are independently hydrogen, fluoro, chloro, or —CF$_3$, preferably Q$^{22}$ and Q$^{24}$ are hydrogen.

In one embodiment of the methods provided herein, in compounds of Formula IIb, M$_5$ is —NR$^{39}$CH$_2$—, —NR$^{39}$CH(R$^{40}$)—, —NR$^{39}$CH$_2$CH$_2$—, or —NR$^{39}$C(O)—; A$_2$ is —CH$_2$— or —C(O)—, preferably —CH$_2$—; Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{15}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{22}$ and Q$^{24}$ are independently hydrogen, fluoro, chloro, lower alkyl, or fluoro substituted lower alkyl, preferably hydrogen, fluoro, chloro, or —CF$_3$, more preferably both Q$^{22}$ and Q$^{24}$ are hydrogen, wherein R$^{41}$ is as defined for Formula Ig.

In one embodiment of the methods provided herein, in compounds of Formula IIb, A$_2$ is —CH$_2$— or —C(O)—, preferably —CH$_2$—; Q$^{11}$ is cycloalkyl, heterocycloalkyl, aryl or heteroaryl, wherein cycloalkyl, heterocycloalkyl, aryl or heteroaryl are optionally substituted with one or more substituents selected from the group consisting of —OR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{11}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{15}$ is hydrogen, —CN, —OR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl NHR$^{41}$, —NR$^{41}$R$^{41}$, and —OR$^{41}$; M$_5$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{22}$, and Q$^{24}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{22}$ and Q$^{24}$ is hydrogen, fluoro, chloro, lower alkyl or fluoro substituted lower alkyl, wherein R$^{39}$, R$^{40}$, R$^{41}$, and R$^{42}$ are as defined for Formula Ig, and R$^{44}$ is as defined for Formula II.

In one embodiment of the methods provided herein, in compounds of Formula IIb, A$_2$ is —CH$_2$—; Q$^{11}$ is aryl or heteroaryl, wherein aryl or heteroaryl are optionally substituted with one or more substituents selected from the group consisting of fluoro, chloro, lower alkyl, fluoro substituted lower alkyl, lower alkoxy, fluoro substituted lower alkoxy, di-alkylamino, and heterocycloalkyl; Q$^{15}$ is hydrogen, —CN, fluoro, chloro, lower alkyl, fluoro substituted lower alkyl, lower alkoxy, or fluoro substituted lower alkoxy; M$_5$ is —NR$^{39}$CH$_2$—, —NR$^{39}$CH$_2$CH$_2$—, or —NR$^{39}$CH(R$^{40}$)—; and Q$^{22}$ and Q$^{24}$ are independently hydrogen, halogen, lower alkyl, fluoro substituted lower alkyl, lower alkoxy, or fluoro substituted lower alkoxy, provided, however, that at least one of Q$^{22}$ and Q$^{24}$ is hydrogen, fluoro, chloro, lower alkyl or fluoro substituted lower alkyl.

In one embodiment, further to any of the embodiments of the methods provided herein, which includes Formula IIb above, each occurrence of R$^{41}$ is R$^{42}$ as defined for Formula Ig.

In one embodiment of the methods provided herein, in compounds of Formula IIb, M$_5$ is —NHCH$_2$CH$_2$—, —NHCH$_2$—, —N(CH$_3$)CH$_2$—, or —NHCH(CH$_3$)—, preferably —NHCH$_2$—; A$_2$ is —CH$_2$—; Q$^{11}$ is cycloalkyl, heterocycloalkyl, phenyl or heteroaryl, wherein phenyl or heteroaryl are optionally substituted with 1 or 2 substituents selected from the group consisting of halogen, lower alkyl, fluoro substituted lower alkyl, lower alkoxy, fluoro substituted lower alkoxy, di-alkylamino, and heterocycloalkyl; Q$^{15}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, lower alkoxy, and fluoro substituted lower alkoxy; and Q$^{22}$ and Q$^{24}$ are independently hydrogen, fluoro, chloro, lower alkyl, or fluoro substituted lower alkyl, preferably hydrogen, fluoro, chloro, or —CF$_3$, more preferably both Q$^{22}$ and Q$^{24}$ are hydrogen.

In one embodiment of the methods provided herein, in compounds of Formula IIb, M$_5$ is —NHCH$_2$—; A$_2$ is —CH$_2$—; Q$^{11}$ is phenyl substituted with 1 or 2 substituents selected from the group consisting of fluoro, chloro, methyl, fluoro substituted methyl, methoxy, and fluoro substituted methoxy; Q$^{15}$ is hydrogen, —CN, fluoro, chloro, lower alkyl, fluoro substituted lower alkyl, lower alkoxy, fluoro substituted lower alkoxy, preferably hydrogen or chloro; and Q$^{22}$ and Q$^{24}$ are hydrogen.

In one embodiment of the methods provided herein, wherein the compound of Formula IIb is a compound selected from the group consisting of:

(4-Chloro-benzyl)-[5-(5-chloro-1H-pyrrolo[2,3-b]pyridin-3-ylmethyl)-pyrimidin-2-yl]-amine (P-0260),
[5-(5-Chloro-1H-pyrrolo[2,3-b]pyridin-3-ylmethyl)-pyrimidin-2-yl]-(2,6-difluoro-benzyl)-amine (P-0261),
[5-(5-Chloro-1H-pyrrolo[2,3-b]pyridin-3-ylmethyl)-pyrimidin-2-yl]-(2-trifluoromethyl-benzyl)-amine (P-0262),
(2-Chloro-benzyl)-[5-(5-chloro-1-pyrrolo[2,3-b]pyridin-3-ylmethyl)-pyrimidin-2-yl]-amine (P-0263),
[5-(5-Chloro-1H-pyrrolo[2,3-b]pyridin-3-ylmethyl)-pyrimidin-2-yl]-(2-fluoro-benzyl)-amine (P-0264),
[5-(5-Chloro-1H-pyrrolo[2,3-b]pyridin-3-ylmethyl)-pyrimidin-2-yl]-(2,4-difluoro-benzyl)-amine (P-0265),
[5-(5-Chloro-1H-pyrrolo[2,3-b]pyridin-3-ylmethyl)-pyrimidin-2-yl]-(4-trifluoromethyl-benzyl)-amine (P-0266),
[5-(5-Chloro-1H-pyrrolo[2,3-b]pyridin-3-ylmethyl)-pyrimidin-2-yl]-(2,5-difluoro-benzyl)-amine (P-0267),
[5-(5-Chloro-1H-pyrrolo[2,3-b]pyridin-3-ylmethyl)-pyrimidin-2-yl]-(3-trifluoromethyl-benzyl)-amine (P-0268),
[5-(5-Chloro-1H-pyrrolo[2,3-b]pyridin-3-ylmethyl)-pyrimidin-2-yl]-(2-fluoro-5-trifluoromethyl-benzyl)-amine (P-0289),
(2-Fluoro-5-trifluoromethyl-benzyl)-[5-(1H-pyrrolo[2,3-b]pyridin-3-ylmethyl)-pyrimidin-2-yl]-amine (P-0291),
(2,5-Difluoro-benzyl)-[5-(1H-pyrrolo[2,3-b]pyridin-3-ylmethyl)-pyrimidin-2-yl]-amine (P-0292),
(2-Chloro-5-trifluoromethyl-benzyl)-[5-(1H-pyrrolo[2,3-b]pyridin-3-ylmethyl)-pyrimidin-2-yl]-amine (P-0293),
(3-Fluoro-5-trifluoromethyl-benzyl)-[5-(1H-pyrrolo[2,3-b]pyridin-3-ylmethyl)-pyrimidin-2-yl]-amine (P-0294),
(3,5-Difluoro-benzyl)-[5-(1H-pyrrolo[2,3-b]pyridin-3-ylmethyl)-pyrimidin-2-yl]-amine (P-0295),
(2-Fluoro-benzyl)-[5-(1H-pyrrolo[2,3-b]pyridin-3-ylmethyl)-pyrimidin-2-yl]-amine (P-0300),
(2-Chloro-benzyl)-[5-(1H-pyrrolo[2,3-b]pyridin-3-ylmethyl)-pyrimidin-2-yl]-amine (P-0301),
[5-(1H-Pyrrolo[2,3-b]pyridin-3-ylmethyl)-pyrimidin-2-yl]-(2-trifluoromethyl-benzyl)-amine (P-0302),
[5-(1H-Pyrrolo[2,3-b]pyridin-3-ylmethyl)-pyrimidin-2-yl]-(2-trifluoromethoxy-benzyl)-amine (P-0303),
(5-Chloro-2-fluoro-benzyl)-[5-(1H-pyrrolo[2,3-b]pyridin-3-ylmethyl)-pyrimidin-2-yl]-amine (P-0304),
(2,4-Dichloro-benzyl)-[5-(1H-pyrrolo[2,3-b]pyridin-3-ylmethyl)-pyrimidin-2-yl]-amine (P-0305),
(2,4-Difluoro-benzyl)-[5-(1H-pyrrolo[2,3-b]pyridin-3-ylmethyl)-pyrimidin-2-yl]-amine (P-0306),
(4-Chloro-benzyl)-[5-(1H-pyrrolo[2,3-b]pyridin-3-ylmethyl)-pyrimidin-2-yl]-amine (P-0307),
[5-(1H-Pyrrolo[2,3-b]pyridin-3-ylmethyl)-pyrimidin-2-yl]-(4-trifluoromethyl-benzyl)-amine (P-0308),
(2-Fluoro-3-trifluoromethyl-benzyl)-[5-(1H-pyrrolo[2,3-b]pyridin-3-ylmethyl)-pyrimidin-2-yl]-amine (P-0309),
(2,5-Dichloro-benzyl)-[5-(1H-pyrrolo[2,3-b]pyridin-3-ylmethyl)-pyrimidin-2-yl]-amine (P-0310),
(3-Chloro-2-fluoro-benzyl)-[5-(1H-pyrrolo[2,3-b]pyridin-3-ylmethyl)-pyrimidin-2-yl]-amine (P-0311),
(2-Difluoromethoxy-benzyl)-[5-(1H-pyrrolo[2,3-b]pyridin-3-ylmethyl)-pyrimidin-2-yl]-amine (P-0312),
(2,3-Dichloro-benzyl)-[5-(1H-pyrrolo[2,3-b]pyridin-3-ylmethyl)-pyrimidin-2-yl]-amine (P-0313),
(4-Chloro-2-fluoro-benzyl)-[5-(1H-pyrrolo[2,3-b]pyridin-3-ylmethyl)-pyrimidin-2-yl]-amine (P-0314),
(5-Fluoro-2-trifluoromethyl-benzyl)-[5-(1H-pyrrolo[2,3-b]pyridin-3-ylmethyl)-pyrimidin-2-yl]-amine (P-0315), (2-Chloro-4-fluoro-benzyl)-[5-(1H-pyrrolo[2,3-b]pyridin-3-ylmethyl)-pyrimidin-2-yl]-amine (P-0316),
(5-Chloro-2-methyl-benzyl)-[5-(1-pyrrolo[2,3-b]pyridin-3-ylmethyl)-pyrimidin-2-yl]-amine (P-0317),
(5-Fluoro-2-methyl-benzyl)-[5-(1H-pyrrolo[2,3-b]pyridin-3-ylmethyl)-pyrimidin-2-yl]-amine (P-0318),
(2-Fluoro-4-trifluoromethyl-benzyl)-[5-(1H-pyrrolo[2,3-b]pyridin-3-ylmethyl)-pyrimidin-2-yl]-amine (P-0319),
(4-Fluoro-2-trifluoromethyl-benzyl)-[5-(1H-pyrrolo[2,3-b]pyridin-3-ylmethyl)-pyrimidin-2-yl]-amine (P-0320),
[5-(5-Chloro-1H-pyrrolo[2,3-b]pyridin-3-ylmethyl)-pyrimidin-2-yl]-(2-difluoromethoxy-benzyl)-amine (P-0390),
[5-(5-Chloro-1H-pyrrolo[2,3-b]pyridin-3-ylmethyl)-pyrimidin-2-yl]-(5-fluoro-2-trifluoromethyl-benzyl)-amine (P-0391),
(3-Chloro-2-fluoro-benzyl)-[5-(5-chloro-1H-pyrrolo[2,3-b]pyridin-3-ylmethyl)-pyrimidin-2-yl]-amine (P-0392),
[5-(5-Chloro-1H-pyrrolo[2,3-b]pyridin-3-ylmethyl)-pyrimidin-2-yl]-(2-fluoro-3-trifluoromethyl-benzyl)-amine (P-0393),
[5-(5-Chloro-1H-pyrrolo[2,3-b]pyridin-3-ylmethyl)-pyrimidin-2-yl]-(2-fluoro-4-trifluoromethyl-benzyl)-amine (P-0394),
[5-(5-Chloro-1H-pyrrolo[2,3-b]pyridin-3-ylmethyl)-pyrimidin-2-yl]-(2,3-difluoro-benzyl)-amine (P-0395),
(2-Chloro-4-fluoro-benzyl)-[5-(5-chloro-1H-pyrrolo[2,3-b]pyridin-3-ylmethyl)-pyrimidin-2-yl]-amine (P-0396),
[5-(5-Chloro-1H-pyrrolo[2,3-b]pyridin-3-ylmethyl)-pyrimidin-2-yl]-(2-trifluoromethoxy-benzyl)-amine (P-0402),
(2-Chloro-5-fluoro-benzyl)-[5-(1H-pyrrolo[2,3-b]pyridin-3-ylmethyl)-pyrimidin-2-yl]-amine (P-0407),
(2-Chloro-5-fluoro-benzyl)-[5-(5-chloro-1H-pyrrolo[2,3-b]pyridin-3-ylmethyl)-pyrimidin-2-yl]-amine (P-0408),
[5-(5-Chloro-1H-pyrrolo[2,3-b]pyridin-3-ylmethyl)-pyrimidin-2-yl]-pyridin-4-ylmethyl-amine (P-0416),
[5-(5-Chloro-1H-pyrrolo[2,3-b]pyridin-3-ylmethyl)-pyrimidin-2-yl]-(2-pyrrolidin-1-yl-ethyl)-amine (P-0417),
Benzyl-[5-(5-chloro-1H-pyrrolo[2,3-b]pyridin-3-ylmethyl)-pyrimidin-2-yl]-amine (P-0418),
Benzyl-[5-(5-chloro-1H-pyrrolo[2,3-b]pyridin-3-ylmethyl)-pyrimidin-2-yl]-methyl-amine (P-0419),
[5-(5-Chloro-1H-pyrrolo[2,3-b]pyridin-3-ylmethyl)-pyrimidin-2-yl]-(4-trifluoromethoxy-benzyl)-amine (P-0420),
(3-Chloro-benzyl)-[5-(5-chloro-1H-pyrrolo[2,3-b]pyridin-3-ylmethyl)-pyrimidin-2-yl]-amine (P-0421),
[5-(5-Chloro-1H-pyrrolo[2,3-b]pyridin-3-ylmethyl)-pyrimidin-2-yl]-pyridin-3-ylmethyl-amine (P-0422),
[5-(5-Chloro-1H-pyrrolo[2,3-b]pyridin-3-ylmethyl)-pyrimidin-2-yl]-(4-fluoro-benzyl)-amine (P-0423),
(3-Chloro-benzyl)-[5-(5-chloro-1H-pyrrolo[2,3-b]pyridin-3-ylmethyl)-pyrimidin-2-yl]-methyl-amine (P-0424),
[5-(5-Chloro-1H-pyrrolo[2,3-b]pyridin-3-ylmethyl)-pyrimidin-2-yl]-(3,5-difluoro-benzyl)-amine (P-0425),
[5-(5-Chloro-1H-pyrrolo[2,3-b]pyridin-3-ylmethyl)-pyrimidin-2-yl]-[1-(2-fluoro-phenyl)-ethyl]-amine (P-0426),
[1-(4-Chloro-phenyl)-ethyl]-[5-(5-chloro-1H-pyrrolo[2,3-b]pyridin-3-ylmethyl)-pyrimidin-2-yl]-amine (P-0427),
[5-(5-Chloro-1H-pyrrolo[2,3-b]pyridin-3-ylmethyl)-pyrimidin-2-yl]-[(S)-1-(4-fluoro-phenyl)-ethyl]-amine (P-0428),
[5-(5-Chloro-1H-pyrrolo[2,3-b]pyridin-3-ylmethyl)-pyrimidin-2-yl]-(6-trifluoromethyl-pyridin-3-ylmethyl)-amine (P-0429),
(2-Chloro-benzyl)-[5-(5-chloro-1H-pyrrolo[2,3-b]pyridin-3-ylmethyl)-pyrimidin-2-yl]-methyl-amine (P-0430),
[5-(5-Chloro-1H-pyrrolo[2,3-b]pyridin-3-ylmethyl)-pyrimidin-2-yl]-(2-methyl-benzyl)-amine (P-0431),
[5-(5-Chloro-1H-pyrrolo[2,3-b]pyridin-3-ylmethyl)-pyrimidin-2-yl]-(2-methoxy-benzyl)-amine (P-0433),
[5-(5-Chloro-1H-pyrrolo[2,3-b]pyridin-3-ylmethyl)-pyrimidin-2-yl]-(2-morpholin-4-yl-ethyl)-amine (P-0434),
[5-(5-Chloro-1H-pyrrolo[2,3-b]pyridin-3-ylmethyl)-pyrimidin-2-yl]-cyclohexylmethyl-amine (P-0435),
[5-(5-Chloro-1H-pyrrolo[2,3-b]pyridin-3-ylmethyl)-pyrimidin-2-yl]-pyridin-2-ylmethyl-amine (P-0436),
[2-(4-Chloro-phenyl)-ethyl]-[5-(5-chloro-1H-pyrrolo[2,3-b]pyridin-3-ylmethyl)-pyrimidin-2-yl]-amine (P-0437),
[5-(5-Chloro-1H-pyrrolo[2,3-b]pyridin-3-ylmethyl)-pyrimidin-2-yl]-(4-difluoromethoxy-benzyl)-amine (P-0438),
[5-(5-Chloro-1H-pyrrolo[2,3-b]pyridin-3-ylmethyl)-pyrimidin-2-yl]-(4-methoxy-benzyl)-amine (P-0439),
[5-(5-Chloro-1H-pyrrolo[2,3-b]pyridin-3-ylmethyl)-pyrimidin-2-yl]-(4-methyl-benzyl)-amine (P-0440),
[5-(5-Chloro-1H-pyrrolo[2,3-b]pyridin-3-ylmethyl)-pyrimidin-2-yl]-(2-methoxy-ethyl)-amine (P-0441),
[5-(5-Chloro-1H-pyrrolo[2,3-b]pyridin-3-ylmethyl)-pyrimidin-2-yl]-(3-fluoro-benzyl)-amine (P-0442),
(3-Chloro-4-fluoro-benzyl)-[5-(5-chloro-1H-pyrrolo[2,3-b]pyridin-3-ylmethyl)-pyrimidin-2-yl]-amine (P-0443),
[5-(5-Chloro-1H-pyrrolo[2,3-b]pyridin-3-ylmethyl)-pyrimidin-2-yl]-(2-ethoxy-benzyl)-amine (P-0444),
[5-(5-Chloro-1H-pyrrolo[2,3-b]pyridin-3-ylmethyl)-pyrimidin-2-yl]-(4-morpholin-4-yl-benzyl)-amine (P-0445),
[5-(5-Chloro-1H-pyrrolo[2,3-b]pyridin-3-ylmethyl)-pyrimidin-2-yl]-(3-difluoromethoxy-benzyl)-amine (P-0446),
(4-Chloro-3-fluoro-benzyl)-[5-(5-chloro-1H-pyrrolo[2,3-b]pyridin-3-ylmethyl)-pyrimidin-2-yl]-amine (P-0447),
[5-(5-Chloro-1H-pyrrolo[2,3-b]pyridin-3-ylmethyl)-pyrimidin-2-yl]-[1-(3-fluoro-phenyl)-ethyl]-amine (P-0448), and
[5-(5-Chloro-1H-pyrrolo[2,3-b]pyridin-3-ylmethyl)-pyrimidin-2-yl]-(2-dimethylamino-benzyl)-amine (P-0449), or
all salts, prodrugs, tautomers, or isomers thereof.

In one embodiment of the methods provided herein, a compound of Formula II has a structure according to the following sub-generic structure, Formula IIc,

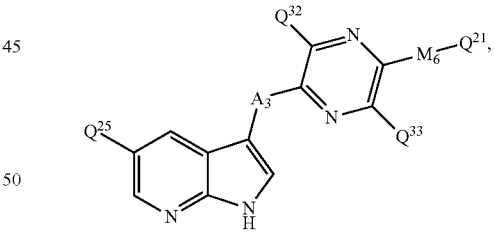

Formula IIc or a salt, prodrug, tautomer, or isomer thereof,
wherein:
$A_4$ is selected from the group consisting of —$CR^{19}R^{20}$—, —C(O)—, —C(S)—, —S—, —S(O)—, —$S(O)_2$—, —$NR^{21}$—, and —O—;
$Q^{25}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$—S(O)$R^{23}$, —S(O)$_2R^{23}$, —C(O)$NHR^{23}$, —C(O)$NR^{23}R^{23}$, —C(S)

NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_6$, Q$^{21}$, Q$^{32}$ and Q$^{33}$ are as defined for Formula II; and R$^{19}$, R$^{20}$, R$^{21}$, R$^{23}$, R$^{24}$, and R$^{25}$ are as defined for Formula Ib.

In one embodiment of the methods provided herein, in compounds of Formula IIc, M$_6$ is —(CR$^{19}$R$^{20}$)$_t$—NR$^{26}$—CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, wherein R$^{39}$ is hydrogen or lower alkyl and R$^{40}$ is lower alkyl or fluoro substituted lower alkyl. In one embodiment, A$_4$ is —CR$^{19}$R$^{20}$— or —C(O)—, preferably —CH$_2$— or —C(O)—. In one embodiment, Q$^{21}$ is aryl or heteroaryl, wherein aryl or heteroaryl are optionally substituted with one or more substituted selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and Q$^{25}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, Q$^{32}$ and Q$^{33}$ are independently hydrogen, fluoro, chloro, or —CF$_3$.

In one embodiment of the methods provided herein, in compounds of Formula IIc, M$_6$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or, —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, and A$_4$ is —CR$^{19}$R$^{20}$— or —C(O)—, preferably —CH$_2$— or —C(O)—. In one embodiment, M$_5$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; A$_4$ is —CR$^{19}$R$^{20}$— or —C(O)—, preferably —CH$_2$— or —C(O)—; Q$^{21}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{25}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_6$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$— preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; A$_4$ is —CR$^{19}$R$^{20}$— or —C(O)—, preferably —CH$_2$— or —C(O)—; Q$^{21}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{25}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{32}$ and Q$^{33}$ are independently hydrogen, fluoro, chloro, or —CF$_3$.

In one embodiment of the methods provided herein, in compounds of Formula IIc, M$_6$ is —NR$^{39}$CH$_2$—, —NR$^{39}$CH(R$^{40}$)— or —NR$^{39}$C(O)—, preferably —NHCH$_2$—; A$_4$ is —CH$_2$— or —C(O)—, preferably —CH$_2$—; Q$^{21}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{25}$ is hydrogen, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{32}$ and Q$^{33}$ are independently hydrogen, fluoro, chloro, lower alkyl, or fluoro substituted lower alkyl, preferably Q$^{32}$ and Q$^{33}$ are independently hydrogen fluoro, chloro, or —CF$_3$, wherein R$^{41}$ is as defined for Formula Ig.

In one embodiment of the methods provided herein, in compounds of Formula IIc, A$_4$ is —CH$_2$— or —C(O)—, preferably —CH$_2$—; Q$^{21}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{21}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{25}$ is hydrogen, —CN, —OR$^{41}$, —SR$^{41}$, —S(O)R$^{41}$, —S(O)$_2$R$^{41}$, —NHR$^{4}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_6$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{32}$ and Q$^{33}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{32}$ and Q$^{33}$ is hydrogen, fluoro, chloro, lower alkyl or fluoro substituted lower alkyl, wherein $R^{39}$, $R^{40}$, $R^{41}$, $R^{42}$, and $R^{44}$ are as defined for Formula II.

In one embodiment of the methods provided herein, in compounds of Formula IIc, $A_4$ is —CH$_2$—; $Q^{21}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{25}$ is hydrogen, —CN, fluoro, chloro, lower alkyl, fluoro substituted lower alkyl, lower alkoxy, or fluoro substituted lower alkoxy; $M_6$ is —NR$^{39}$CH$_2$—, —NR$^{39}$CH$_2$CH$_2$—, or —NR$^{39}$CH(R$^{40}$)—; and $Q^{32}$ and $Q^{33}$ are independently hydrogen, halogen, lower alkyl, fluoro substituted lower alkyl, lower alkoxy, or fluoro substituted lower alkoxy, provided, however, that at least one of $Q^{32}$ and $Q^{33}$ is hydrogen, fluoro, chloro, lower alkyl or fluoro substituted lower alkyl.

In one embodiment, further to any of the embodiments of the methods provided herein, which includes Formula IIc above, each occurrence of $R^{41}$ is $R^{42}$ as defined for Formula Ig.

In one embodiment of the methods provided herein, a compound of Formula II has a structure according to the following sub-generic structure, Formula IId,

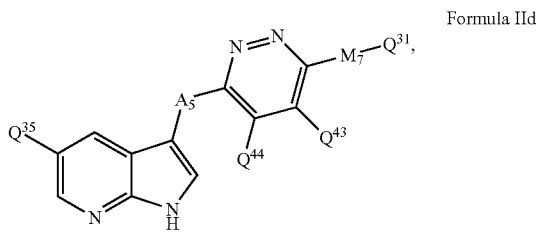

Formula IId or a salt, prodrug, tautomer, or isomer thereof,
wherein:
$A_5$ is selected from the group consisting of —CR$^{19}$R$^{20}$—, —C(O)—, —C(S)—, —S—, —S(O)—, —S(O)$_2$—, —NR$^{21}$—, and —O—;
$Q^{35}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$—S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
$M_7$, $Q^{31}$, $Q^{43}$ and $Q^{44}$ are as defined for Formula II; and $R^{19}$, $R^{20}$, $R^{21}$, $R^{23}$, $R^{24}$, and $R^{25}$ are as defined for Formula Ib.

In one embodiment of the methods provided herein, in compounds of Formula IId, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$, preferably —NR$^{26}$—(CR$^{19}$R$^{20}$)$_s$— or, —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, wherein $R^{39}$ is hydrogen or lower alkyl and $R^{40}$ is lower alkyl or fluoro substituted lower alkyl. In one embodiment, $A_5$ is —CR$^{19}$R$^{20}$— or —C(O)—, preferably —CH$_2$— or —C(O)—. In one embodiment, $Q^{31}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{35}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{43}$ and $Q^{44}$ are independently hydrogen, fluoro, chloro, or —CF$_3$.

In one embodiment of the methods provided herein, in compounds of Formula IId, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or, —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—, and $A_5$ is —CR$^{19}$R$^{20}$— or —C(O)—, preferably —CH$_2$— or —C(O)—. In one embodiment, $M_7$ is —(CR$^{19}$R$^{20}$)$_t$—NR$^{26}$—(CR$^{19}$R$^{20}$)$_s$— or —(CR$^{19}$R$^{20}$)$_t$—NR$^{26}$—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CH$_2$—, —NR$^{39}$CH(R$^{40}$)— or —NR$^{39}$C(O)—; $A_5$ is —CR$^{19}$R$^{20}$— or —C(O)—, preferably —CH$_2$— or —C(O)—; $Q^{31}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; $Q^{35}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{43}$ and $Q^{44}$ are independently hydrogen, fluoro, chloro, or —CF$_3$.

In one embodiment of the methods provided herein, in compounds of Formula IId, $M_7$ is —NR$^{39}$CH$_2$—, —NR$^{39}$CH(R$^{40}$)— or —NR$^{39}$C(O)—, preferably —NHCH$_2$—; $A_5$ is —CH$_2$— or —C(O)—, preferably —CH$_2$—; $Q^{31}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{35}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{43}$ and Q$^{44}$ are independently hydrogen, fluoro, chloro, lower alkyl, or fluoro substituted lower alkyl, preferably Q$^{43}$ and Q$^{44}$ are independently hydrogen, fluoro, chloro, or —CF$_3$, wherein R$^{41}$ is as defined for Formula Ig.

In one embodiment of the methods provided herein, in compounds of Formula IId, A$_5$ is —CH$_2$— or —C(O)—, preferably —CH$_2$—; Q$^{31}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{31}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{35}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_7$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and Q$^{43}$ and Q$^{44}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{43}$ and Q$^{44}$ is hydrogen, fluoro, chloro, lower alkyl or fluoro substituted lower alkyl, wherein R$^{39}$, R$^{40}$, R$^{41}$, R$^{42}$, and R$^{44}$ are as defined for Formula II.

In one embodiment of the methods provided herein, in compounds of Formula IId, A$_5$ is —CH$_2$—; Q$^{31}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{35}$ is hydrogen, —CN, fluoro, chloro, lower alkyl, fluoro substituted lower alkyl, lower alkoxy, or fluoro substituted lower alkoxy; M$_7$ is —NR$^{39}$CH$_2$—, —NR$^{39}$CH$_2$CH$_2$—, or —NR$^{39}$CH(R$^{40}$)—; and Q$^{43}$ and Q$^{44}$ are independently hydrogen, halogen, lower alkyl, fluoro substituted lower alkyl, lower alkoxy, or fluoro substituted lower alkoxy, provided, however, that at least one of Q$^{43}$ and Q$^{44}$ is hydrogen, fluoro, chloro, lower alkyl or fluoro substituted lower alkyl.

In one embodiment, further to any of the embodiments of the methods provided herein, which includes Formula IId above, each occurrence of R$^{41}$ is R$^{42}$ as defined for Formula Ig.

In one embodiment of the methods provided herein, a compound of Formula II has a structure according to the following sub-generic structure, Formula IIe;

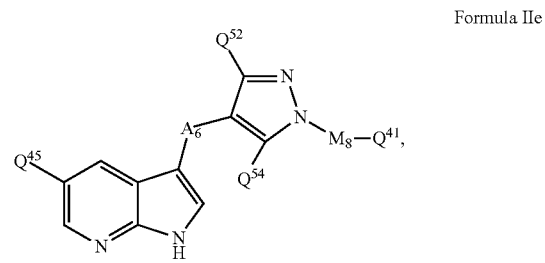

Formula IIe or a salt, prodrug, tautomer, or isomer thereof, wherein:
A$_6$ is selected from the group consisting of —CR$^{19}$R$^{20}$—, —C(O)—, —C(S)—, —S—, —S(O)—, —S(O)$_2$—, —NR$^{21}$—, and —O—;
Q$^{45}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$ —C(O)NR$^{23}$R$^{23}$, —C(S)NHR$^{23}$, —C(S)NR$^{23}$R$^{23}$, —S(O)NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
M$_8$, Q$^{41}$, Q$^{52}$ and Q$^{54}$ are as defined in Formula II; and R$^{19}$, R$^{20}$, R$^{21}$, R$^{23}$, R$^{24}$, and R$^{25}$ are as defined for Formula Ib.

In certain embodiments of the methods provided herein, the compound is not

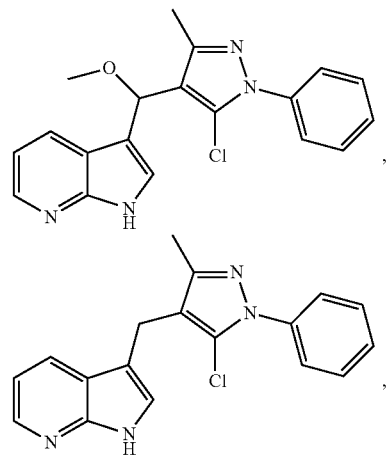

-continued

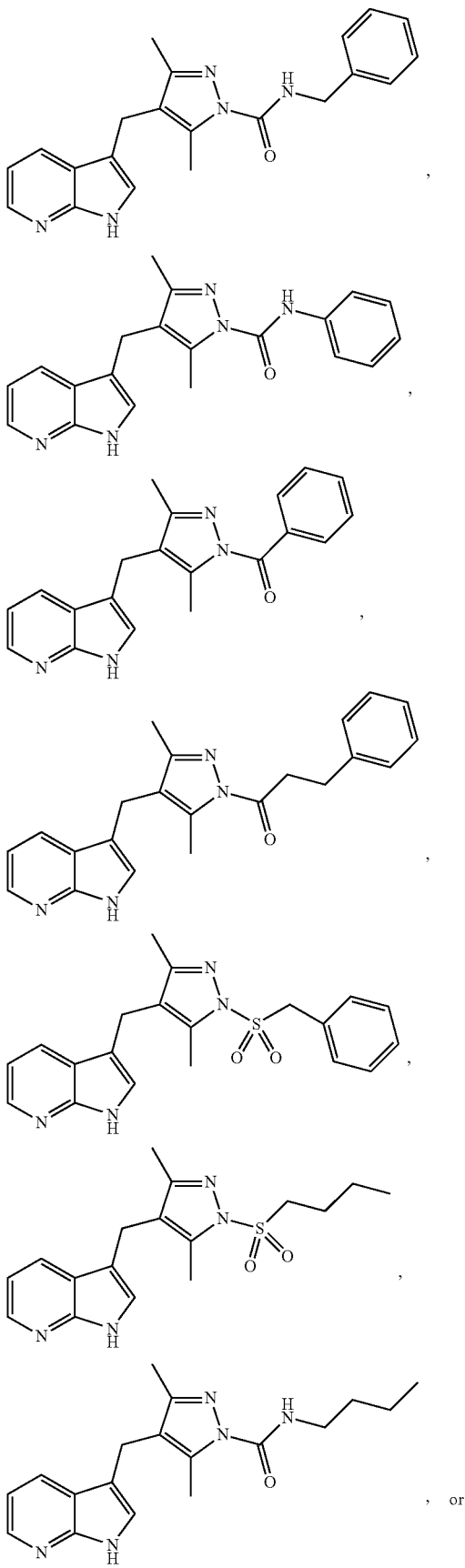
,

-continued

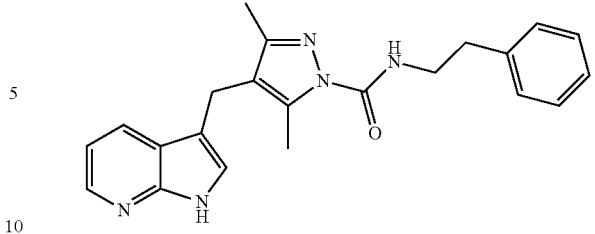
.

In one embodiment of the methods provided herein, in compounds of Formula IIe, $M_8$ is —$(CR^{19}R^{20})_t$—C(O)NR$^{26}$—$(CR^{19}R^{20})_s$—, preferably —C(O)NR$^{26}$—$(CR^{19}R^{20})_s$—, more preferably —C(O)NR$^{39}$—CR$^{80}$R$^{80}$— or C(O)NR$^{39}$—$(CR^{80}R^{80})_2$—, wherein R$^{39}$ is hydrogen or lower alkyl and R$^{80}$ is hydrogen, lower alkyl or fluoro substituted lower alkyl, preferably hydrogen. In one embodiment, $A_6$ is —CR$^{19}$R$^{20}$— or —C(O)—, preferably —CH$_2$— or —C(O)—. In one embodiment, $Q^{41}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{45}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{52}$ and $Q^{54}$ are independently hydrogen, fluoro, chloro, methyl, or —CF$_3$.

In one embodiment of the methods provided herein, in compounds of Formula IIe, $M_8$ is —$(CR^{19}R^{20})_t$—C(O)NR$^{26}$—$(CR^{19}R^{20})_s$—, preferably —C(O)NR$^{26}$—$(CR^{19}R^{20})_s$—, more preferably —C(O)NR$^{39}$—CR$^{80}$R$^{80}$— or —C(O)NR$^{39}$—$(CR^{80}R^{80})_2$—, and $A_6$ is —CR$^{19}$R$^{20}$— or —C(O)—, preferably —CH$_2$— or —C(O)—. In one embodiment, $M_8$ is —$(CR^{19}R^{20})_t$—C(O)NR$^{26}$—$(CR^{19}R^{20})_s$—, preferably —C(O)NR$^{26}$—$(CR^{19}R^{20})_s$—, more preferably —C(O)NR$^{39}$—CR$^{80}$R$^{80}$— or —C(O)NR$^{39}$—$(CR^{80}R^{80})_2$—; $A_6$ is —CR$^{19}$R$^{20}$— or —C(O)—, preferably —CH$_2$— or —C(O)—; $Q^{41}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{45}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, $M_8$ is —$(CR^{19}R^{20})_t$—C(O)NR$^{26}$—$(CR^{19}R^{20})_s$—, preferably —C(O)NR$^{26}$—$(CR^{19}R^{20})_s$—, more preferably —C(O)NR$^{39}$—CR$^{80}$R$^{80}$— or —C(O)NR$^{39}$—$(CR^{80}R^{80})_2$—; $A_6$ is —CR$^{19}$R$^{20}$— or —C(O)—, preferably —CH$_2$— or —C(O)—; $Q^{41}$ is aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; $Q^{45}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkoxy, —NHR$^{23}$, —NR$^{23}$R$^{23}$, —OR$^{23}$ and —S(O)$_2$R$^{23}$; and Q$^{52}$ and Q$^{54}$ are independently hydrogen, fluoro, chloro, methyl, or —CF$_3$.

In one embodiment of the methods provided herein, in compounds of Formula IIe, M$_8$ is —C(O)NR$^{39}$—CH$_2$—, —C(O)NR$^{39}$CH(CH$_3$)—, or —C(O)NR$^{39}$—(CH$_2$)$_2$—; A$_6$ is —CH$_2$— or —C(O)—, preferably —CH$_2$—; Q$^{41}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{45}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and Q$^{52}$ and Q$^{54}$ are independently hydrogen, fluoro, chloro, lower alkyl, or fluoro substituted lower alkyl, preferably Q$^{52}$ and Q$^{54}$ are independently fluoro, chloro, methyl, or —CF$_3$, wherein R$^{41}$ is as defined in Formula Ig.

In one embodiment of the methods provided herein, in compounds of Formula IIe, A$_6$ is —CH$_2$— or —C(O)—, preferably —CH$_2$—; Q$^{41}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{41}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, NR$^{39}$S(O)$_2$R$^{42}$, —S(O)$_2$R$^{42}$, halogen, lower alkyl, fluoro substituted lower alkyl, and cycloalkylamino; Q$^{45}$ is hydrogen, —CN, —SR$^{41}$, —S(O)R$^{41}$, —S(O)$_2$R$^{41}$, —NR$^{41}$R$^{41}$, —NR$^{39}$C(O) R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_8$ is —C(O)NR$^{39}$CH$_2$—, —C(O)NR$^{39}$CH(R$^{40}$)—, or —C(O)NR$^{39}$CH$_2$CH$_2$—; and Q$^{52}$ and Q$^{54}$ are independently hydrogen, halogen, lower alkyl, fluoro substituted lower alkyl, —NR$^{44}$R$^{44}$, —OR$^{44}$, or —SR$^{44}$, provided, however, that at least one of Q$^{52}$ and Q$^{54}$ is hydrogen, fluoro, chloro, lower alkyl or fluoro substituted lower alkyl, wherein R$^{39}$, R$^{40}$, R$^{41}$, R$^{42}$ and R$^{44}$ are as defined for Formula II.

In one embodiment of the methods provided herein, in compounds of Formula IIe, A$_6$ is —CH$_2$—; Q$^{41}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{45}$ is hydrogen, —CN, fluoro, chloro, lower alkyl, fluoro substituted lower alkyl, lower alkoxy, or fluoro substituted lower alkoxy; M$_8$ is —C(O)NR$^{39}$CH$_2$—, —C(O)NR$^{39}$CH(R$^{40}$)—, or —C(O)NR$^{39}$CH$_2$CH$_2$—; and Q$^{52}$ and Q$^{54}$ are independently hydrogen, halogen, lower alkyl, fluoro substituted lower alkyl, lower alkoxy, or fluoro substituted lower alkoxy, provided, however, that at least one of Q$^{52}$ and Q$^{54}$ is hydrogen, fluoro, chloro, lower alkyl or fluoro substituted lower alkyl.

In one embodiment, further to any of the embodiments of the methods provided herein, which includes Formula IIe above, each occurrence of R$^{41}$ is R$^{42}$ as defined for Formula Ig.

In one embodiment of the methods provided herein, in compounds of Formula IIe, M$_8$ is —C(O)NHCH$_2$—, —C(O)NH—CH(CH$_3$)— or —C(O)NH—(CH$_2$)$_2$—; A$_6$ is —CH$_2$— or —C(O)—, preferably —CH$_2$—; Q$^{41}$ is aryl or heteroaryl, wherein aryl or heteroaryl are optionally substituted with 1 or 2 substituents selected from the group consisting of fluoro, chloro, methyl, fluoro substituted methyl, methoxy, and fluoro substituted methoxy; Q$^{45}$ is hydrogen, —CN, fluoro, chloro, lower alkyl, fluoro substituted lower alkyl, lower alkoxy, or fluoro substituted lower alkoxy, preferably hydrogen or chloro; and Q$^{52}$ and Q$^{54}$ are independently hydrogen, fluoro, chloro, lower alkyl, or fluoro substituted lower alkyl, preferably Q$^{52}$ and Q$^{54}$ are methyl.

In one embodiment of the methods provided herein, wherein the compound of Formula IIe is a compound is selected from the group consisting of:

3-(1-Benzyl-3,5-dimethyl-1H-pyrazol-4-ylmethyl)-1H-pyrrolo[2,3-b]pyridine (P-0133), 2-[3,5-Dimethyl-4-(1H-pyrrolo[2,3-b]pyridin-3-ylmethyl)-pyrazol-1-yl]-1-phenyl-ethanone (P-0134), 3,5-Dimethyl-4-(1H-pyrrolo[2,3-b]pyridin-3-ylmethyl)-pyrazole-1-carboxylic acid 4-methoxy-benzylamide (P-0135), 3,5-Dimethyl-4-(1H-pyrrolo[2,3-b]pyridin-3-ylmethyl)-pyrazole-1-carboxylic acid 2-chloro-benzylamide (P-0136), 3,5-Dimethyl-4-(1H-pyrrolo[2,3-b]pyridin-3-ylmethyl)-pyrazole-1-carboxylic acid 2-fluoro-benzylamide (P-0137), 3-[3,5-Dimethyl-1-(5-trifluoromethyl-furan-2-ylmethyl)-1H-pyrazol-4-ylmethyl]-1H-pyrrolo[2,3-b]pyridine (P-0138), 3-[3,5-Dimethyl-1-(5-methyl-isoxazol-3-ylmethyl)-1H-pyrazol-4-ylmethyl]-1H-pyrrolo[2,3-b]pyridine (P-0139), 3,5-Dimethyl-4-(1H-pyrrolo[2,3-b]pyridin-3-ylmethyl)-pyrazole-1-carboxylic acid 4-chloro-benzylamide (P-0140), 3,5-Dimethyl-4-(1H-pyrrolo[2,3-b]pyridin-3-ylmethyl)-pyrazole-1-carboxylic acid [2-(4-methoxy-phenyl)-ethyl]-amide (P-0141), 3,5-Dimethyl-4-(1H-pyrrolo[2,3-b]pyridin-3-ylmethyl)-pyrazole-1-carboxylic acid 3-methoxy-benzylamide (P-0142), 3-{3,5-Dimethyl-1-[4-methyl-2-(4-trifluoromethyl-phenyl)-thiazol-5-ylmethyl]-1H-pyrazol-4-ylmethyl}-1H-pyrrolo[2,3-b]pyridine (P-0143), 3-[3,5-Dimethyl-1-(4-methyl-2-phenyl-thiazol-5-ylmethyl)-1H-pyrazol-4-ylmethyl]-1H-pyrrolo[2,3-b]pyridine (P-0144), 3,5-Dimethyl-4-(1H-pyrrolo[2,3-b]pyridin-3-ylmethyl)-pyrazole-1-carboxylic acid 2-methoxy-benzylamide (P-0145), 3,5-Dimethyl-4-(1H-pyrrolo[2,3-b]pyridin-3-ylmethyl)-pyrazole-1-carboxylic acid [2-(2,4-dichloro-phenyl)-ethyl]-amide (P-0146), 3,5-Dimethyl-4-(1H-pyrrolo[2,3-b]pyridin-3-ylmethyl)-pyrazole-1-carboxylic acid [2-(4-fluoro-phenyl)-ethyl]-amide (P-0147), 3,5-Dimethyl-4-(1H-pyrrolo[2,3-b]pyridin-3-ylmethyl)-pyrazole-1-carboxylic acid [2-(2-fluoro-phenyl)-ethyl]-amide (P-0148), 3,5-Dimethyl-4-(1H-pyrrolo[2,3-b]pyridin-3-ylmethyl)-pyrazole-1-carboxylic acid ((S)-1-phenyl-ethyl)-amide (P-0149), 3,5-Dimethyl-4-(1H-pyrrolo[2,3-b]pyridin-3-ylmethyl)-pyrazole-1-carboxylic acid 3-fluoro-benzylamide (P-0150), 3,5-Dimethyl-4-(1H-pyrrolo[2,3-b]pyridin-3-ylmethyl)-pyrazole-1-carboxylic acid 4-fluoro-benzylamide (P-0151), 3,5-Dimethyl-4-(1H-pyrrolo[2,3-b]pyridin-3-ylmethyl)-pyrazole-1-carboxylic acid 4-methyl-benzylamide (P-0152), 3,5-Dimethyl-4-(1H-pyrrolo[2,3-b]pyridin-3-ylmethyl)-pyrazole-1-carboxylic acid 2-methyl-benzylamide (P-0153), 4-(5-Chloro-1H-pyrrolo[2,3-b]pyridin-3-ylmethyl)-3,5-dimethyl-pyrazole-1-carboxylic acid [2-(4-fluoro-phenyl)-ethyl]-amide (P-0157), 4-(5-Chloro-1H-pyrrolo[2,3-b]pyridin-3-ylmethyl)-3,5-dimethyl-pyrazole-1-carboxylic acid 4-fluoro-benzylamide (P-0158), 4-(5-Chloro-1H-pyrrolo[2,3-b]pyridin-3-ylmethyl)-3,5-dimethyl-pyrazole-1-carboxylic acid 4-chloro-benzylamide (P-0159) and 4-(5-Chloro-1H-pyrrolo[2,3-b]pyridin-3-ylmethyl)-3,5-dimethyl-pyrazole-1-carboxylic acid [(S)-1-(4-fluoro-phenyl)-ethyl]-amide (P-0160) or all salts, prodrugs, tautomers, or isomers thereof.

In one embodiment of the methods provided herein, a compound of Formula II has a structure according to the following sub-generic structure, Formula IIf,

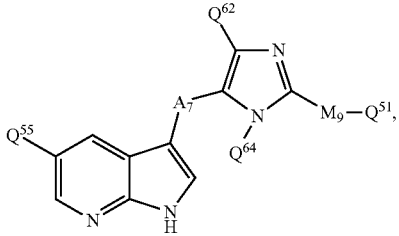

Formula IIf or a salt, prodrug, tautomer, or isomer thereof,
wherein:
$A_7$, is selected from the group consisting of —$CR^{19}R^{20}$—, —C(O)—, —C(S)—, —S—, —S(O)—, —S(O)$_2$—, —$NR^{21}$—, and —O—;

$Q^{55}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —S(O)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$_2NHR^{23}$, —S(O)$_2NR^{23}R^{23}$, —NHC(O)$R^{23}$, —$NR^{23}C(O)R^{23}$, —NHC(S)$R^{23}$, —$NR^{23}C(S)R^{23}$, —NHS(O)$_2R^{23}$—NHC(O)$NHR^{23}$, —$NR^{23}C(O)NH_2$, —$NR^{23}C(O)NHR^{23}$, —NHC(O)$NR^{23}R^{23}$, —$NR^{23}C(O)NR^{23}R^{23}$, —NHC(S)$NHR^{23}$, —$NR^{23}C(S)NH_2$, —$NR^{23}C(S)NHR^{23}$, —NHC(S)$NR^{23}R^{23}$, —$NR^{23}C(S)NR^{23}R^{23}$, —NHS(O)$_2NHR^{23}$, —$NR^{23}S(O)_2NH_2$, —$NR^{23}S(O)_2NHR^{23}$, —NHS(O)$_2NR^{23}R^{23}$, and —$NR^{23}S(O)_2NR^{23}R^{23}$;

$M_9$, $Q^{51}$, $Q^{62}$, and $Q^{64}$ are as defined for Formula II; and $R^{19}$, $R^{20}$, $R^{21}$, $R^{23}$, $R^{24}$, and $R^{25}$ are as defined for Formula Ib.

In one embodiment of the methods provided herein, in compounds of Formula IIf, $M_9$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_7$ is —$CR^{19}R^{20}$— or —C(O)—, preferably —$CH_2$— or —C(O)—. In one embodiment, $Q^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$ and $Q^{55}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. Further to any of the above embodiments, $Q^{62}$ is hydrogen, fluoro, chloro, lower alkyl or fluoro substituted lower alkyl.

In one embodiment of the methods provided herein, in compounds of Formula IIf, $M_9$ is —$(CR^{19}R^{20})_t$—$NR^{26}$—$CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—, and $A_7$ is —$CR^{19}R^{20}$— or —C(O)—, preferably —$CH_2$— or —C(O)—. In one embodiment, $M_9$ is —$(CR^{19}R^{20})_t$—$NR^{26}$—$CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR(CR^{80}R^{80})_2$—; $A_7$ is —$CR^{19}R^{20}$— or —C(O)—, preferably —$CH_2$— or —C(O)—; $Q^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{55}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. In one embodiment, $M_9$ is —$(CR^{19}R^{20})_s$— or —$NR^{26}C(O)$—$(CR^{19}R^{20})_s$—, more —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$—, —$NR^{39}(CR^{80}R^{80})_2$—; $A_7$ is —$CR^{19}R^{20}$— or —C(O)—, preferably —$CH_2$— or —C(O)—; $Q^{51}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{55}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{62}$ is hydrogen, fluoro, chloro, lower alkyl or fluoro substituted lower alkyl.

In one embodiment of the methods provided herein, in compounds of Formula IIf, M$_9$ is —NR$^{39}$CH$_2$— or —NR$^{39}$—(CH$_2$)$_2$—; A$_7$ is —CH$_2$— or —C(O)—, preferably —CH$_2$—; Q$^{51}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{55}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and Q$^{62}$ is hydrogen, fluoro, chloro, lower alkyl or fluoro substituted lower alkyl, wherein R$^{41}$ is as defined in Formula Ig.

In one embodiment of the methods provided herein, in compounds of Formula IIf, A$_7$ is —CH$_2$— or —C(O)—, preferably —CH$_2$—; Q$^{51}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{51}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{55}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_9$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; Q$^{62}$ is hydrogen, fluoro, chloro, lower alkyl, fluoro substituted lower alkyl, —NR$^{44}$R$^{44}$, —OR$^{44}$, or —SR$^{44}$; and Q$^{64}$ is hydrogen, lower alkyl, or fluoro substituted lower alkyl, wherein R$^{39}$, R$^{40}$, R$^{41}$, R$^{42}$ and R$^{44}$ are as defined for Formula II.

In one embodiment of the methods provided herein, in compounds of Formula IIf, A$_7$ is —CH$_2$—; Q$^{51}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{55}$ is hydrogen, —CN, fluoro, chloro, lower alkyl, fluoro substituted lower alkyl, lower alkoxy, or fluoro substituted lower alkoxy; M$_9$ is —NR$^{39}$CH$_2$—, —NR$^{39}$CH$_2$CH$_2$—, or —NR$^{39}$CH(R$^{40}$)—; Q$^{62}$ is hydrogen, fluoro, chloro, lower alkyl, fluoro substituted lower alkyl, lower alkoxy, or fluoro substituted lower alkoxy; and Q$^{64}$ is hydrogen, lower alkyl, or fluoro substituted lower alkyl.

In one embodiment, further to any of the embodiments the methods provided herein, which includes Formula IIf above, each occurrence of R$^{41}$ is R$^{42}$ as defined for Formula Ig.

In one embodiment of the methods provided herein, a compound of Formula II has a structure according to the following sub-generic structure, Formula IIg,

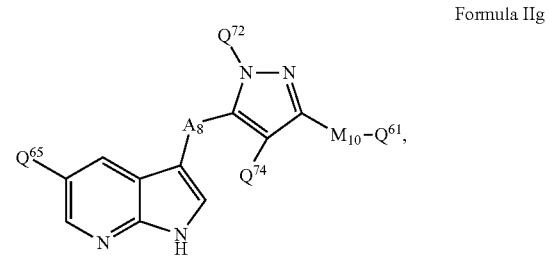

Formula IIg or a salt, prodrug, tautomer, or isomer thereof,
wherein:
A$_8$ is selected from the group consisting of —CR$^{19}$R$^{20}$—, —C(O)—, —C(S)—, —S—, —S(O)—, —S(O)$_2$—, —NR$^{21}$—, and —O—;

Q$^{65}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$—S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_{10}$, Q$^{61}$, Q$^{72}$, Q$^{74}$ are as defined for Formula II; and R$^{19}$, R$^{20}$, R$^{21}$, R$^{23}$, R$^{24}$, and R$^{25}$, R$^{26}$ are as defined for Formula Ib.

In one embodiment of compounds of Formula IIg, M$_{10}$ is —(CR$^{19}$R$^{20}$)$_t$—NR$^{26}$—CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$—, or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, A$_8$ is —CR$^{19}$R$^{20}$— or —C(O)—, preferably —CH$_2$— or —C(O)—. In one embodiment, Q$^{61}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{65}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{74}$ is hydrogen, fluoro, chloro, lower alkyl or fluoro substituted lower alkyl.

In one embodiment of the methods provided herein, in compounds of Formula IIg, $M_{10}$ is —$(CR^{19}R^{20})_t$—$NR^{26}$—$CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —NR$(CR^{80}R^{80})_2$—, and $A_8$ is —$CR^{19}R^{20}$— or —C(O)—, preferably —$CH_2$— or —C(O)—. In one embodiment, $M_{10}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_8$ is —$CR^{19}R^{20}$— or —C(O)—, preferably —$CH_2$— or —C(O)—; $Q^{61}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{65}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. In one embodiment, $M_{10}$ is —$(CR^{19}R^{20})_t$—$NR^{26}$—$(CR^{19}R^{20})_s$— or —$(CR^{19}R^{20})_t$—$NR^{26}C(O)$—$(CR^{19}R^{20})_s$—, preferably —$NR^{26}$—$(CR^{19}R^{20})_s$— or —$NR^{26}C(O)$—$(CR^{19}R^{20})_s$—, more preferably —$NR^{39}CR^{80}R^{80}$— or —$NR^{39}(CR^{80}R^{80})_2$—; $A_8$ is —$CR^{19}R^{20}$— or —C(O)—, preferably —$CH_2$— or —C(O)—; $Q^{61}$ is optionally substituted lower alkyl, aryl or heteroaryl, wherein aryl or heteroaryl are optionally substituted with one or more substituents selected from the group consisting of halogen, -lower alkyl, fluoro substituted lower alkyl, —$NHR^{23}$, —$NR^{23}R^{23}$, —$OR^{23}$ and $S(O)_2R^{23}$; $Q^{65}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl —$NHR^{23}$, —$NR^{23}R^{23}$, —$OR^{23}$, and —$S(O)_2R^{23}$; and $Q^{74}$ is hydrogen, fluoro, chloro, lower alkyl or fluoro substituted lower alkyl.

In one embodiment of the methods provided herein, in compounds of Formula IIg, $M_{10}$ is —$NR^{39}CH_2$— or —$NR^{39}$—$(CH_2)_2$—; $A_8$ is —$CH_2$— or —C(O)—, preferably —$CH_2$—; $Q^{61}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; $Q^{65}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$—$OR^{41}$ and —$S(O)_2R^{41}$; and $Q^{74}$ is hydrogen, fluoro, chloro, lower alkyl or fluoro substituted lower alkyl, wherein $R^{41}$ is as defined for Formula Ig.

In one embodiment of the methods provided herein, in compounds of Formula IIg, $A_8$ is —$CH_2$— or —C(O)—, preferably —$CH_2$—; $Q^{61}$ is aryl or heteroaryl, wherein aryl or heteroaryl are optionally substituted with one or more substituents selected from the group consisting of —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{61}$, or as a substituent of lower alkyl are optionally substituted with one or more substituents selected from the group consisting of —OH, —$NH_2$, —CN, —$NO_2$, —$S(O)_2NH_2$, —$C(O)NH_2$, —$OR^{42}$, —$SR^{42}$, —$NHR^{42}$, —$NR^{42}R^{42}$, —$NR^{39}C(O)R^{42}$, —$NR^{39}S(O)_2R^{42}$, —$S(O)_2R^{42}$, halogen, lower alkyl, fluoro substituted lower alkyl, and cycloalkylamino; $Q^{65}$ is hydrogen, —CN, —$OR^{41}$, —$SR^{41}$, —$S(O)R^{41}$, —$S(O)_2R^{41}$, —$NHR^{41}$, —$NR^{41}R^{41}$, —$NR^{39}C(O)R^{41}$, —$NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, and —$OR^{41}$; $M_{10}$ is a bond, —$NR^{39}$—, —S—, —O—, —$NR^{39}CH_2$—, —$NR^{39}CH_2CH_2$—, —$NR^{39}CH(R^{40})$—, —$SCH_2$—, —$OCH_2$—, —$C(O)NR^{39}$—, —$S(O)_2NR^{39}$—, —$CH_2NR^{39}$—, —$CH(R^{40})NR^{39}$—, —$NR^{39}C(O)$—, or —$NR^{39}S(O)_2$—; $Q^{74}$ is hydrogen, fluoro, chloro, lower alkyl, fluoro substituted lower alkyl, —$NR^{44}R^{44}$, —$OR^{44}$, or —$SR^{44}$; and $Q^{72}$ is hydrogen, lower alkyl, or fluoro substituted lower alkyl, wherein $R^{39}$, $R^{40}$, $R^{41}$, $R^{42}$ and $R^{44}$ are as defined for Formula II.

In one embodiment of the methods provided herein, in compounds of Formula IIg, $A_8$ is —$CH_2$—; $Q^{61}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{65}$ is hydrogen, —CN, fluoro, chloro, lower alkyl, fluoro substituted lower alkyl, lower alkoxy, or fluoro substituted lower alkoxy; $M_{10}$ is —$NR^{39}CH_2$—, —$NR^{39}CH_2CH_2$—, or —$NR^{39}CH(R^{40})$—; $Q^{74}$ is hydrogen, fluoro, chloro, lower alkyl, fluoro substituted lower alkyl, lower alkoxy, or fluoro substituted lower alkoxy; and $Q^{72}$ is hydrogen, lower alkyl, or fluoro substituted lower alkyl.

In one embodiment, further to any of the embodiments of the methods provided herein, in Formula IIg above, each occurrence of $R^{41}$ is $R^{42}$ as defined for Formula Ig.

In one embodiment of the methods provided herein, in compounds of Formula IIg, $M_{10}$ is —$NHCH_2$—, $A_8$ is —$CH_2$—, $Q^{61}$ is phenyl optionally substituted with 1 or 2 substituents selected from the group consisting of fluoro, chloro, methyl, trifluoromethyl, methoxy, difluoromethoxy, or trifluoromethoxy, $Q^{65}$ is hydrogen, fluoro, —CN, or 1-methyl-pyrazol-4-yl, $Q^{72}$ is lower alkyl or fluoro substituted lower alkyl, and $Q^{74}$ is hydrogen, fluoro, chloro, lower alkyl, or fluoro substituted lower alkyl. In one embodiment, $M_{10}$ is —NHCH$_2$—, $A_8$ is —CH$_2$—, $Q^{61}$ is 4-fluoro-phenyl, $Q^{65}$ is hydrogen, chloro, —CN, or 1-methyl-pyrazol-4-yl, $Q^{72}$ is methyl or ethyl and $Q^{74}$ is hydrogen or chloro.

In one embodiment of the methods provided herein, the compound of Formula IIg is selected from the group consisting of:

[1-Ethyl-5-(1H-pyrrolo[2,3-b]pyridin-3-ylmethyl)-1H-pyrazol-3-yl]-(4-fluoro-benzyl)-amine (P-0165), (4-Fluoro-benzyl)-[1-methyl-5-(1H-pyrrolo[2,3-b]pyridin-3-ylmethyl)-1H-pyrazol-3-yl]-amine (P-0169),

[5-(5-Chloro-1H-pyrrolo[2,3-b]pyridin-3-ylmethyl)-1-methyl-1H-pyrazol-3-yl]-(4-fluoro-benzyl)-amine (P-0170), (4-Fluoro-benzyl)-{1-methyl-5-[5-(1-methyl-1H-pyrazol-4-yl)-1H-pyrrolo[2,3-b]pyridin-3-ylmethyl]-1H-pyrazol-3-yl}-amine (P-0180), (5-Chloro-1H-pyrrolo[2,3-b]pyridin-3-yl)-[2-ethyl-5-(4-fluoro-benzylamino)-2H-pyrazol-3-yl]-methanone (P-0184),

[5-(5-Chloro-1H-pyrrolo[2,3-b]pyridin-3-ylmethyl)-1-ethyl-1H-pyrazol-3-yl]-(4-fluoro-benzyl)-amine (P-0185), 3-[5-(4-Fluoro-benzylamino)-2-methyl-2H-pyrazol-3-ylmethyl]-1H-pyrrolo[2,3-b]pyridine-5-carbonitrile (P-0191), (3-Chloro-benzyl)-[5-(5-chloro-1H-pyrrolo[2,3-b]pyridin-3-ylmethyl)-1-methyl-1H-pyrazol-3-yl]-amine (P-0410),

[5-(5-Chloro-1H-pyrrolo[2,3-b]pyridin-3-ylmethyl)-1-methyl-1H-pyrazol-3-yl]-(2,5-difluoro-benzyl)-amine (P-0411) and

[5-(5-Chloro-1H-pyrrolo[2,3-b]pyridin-3-ylmethyl)-1-methyl-1H-pyrazol-3-yl]-(2-fluoro-benzyl)-amine (P-0413), or all salts, prodrugs, tautomers, or isomers thereof.

In one embodiment of the methods provided herein, a compound of Formula II has a structure according to the following sub-generic structure, Formula IIh,

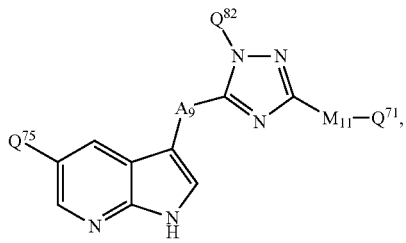

Formula IIh or a salt, prodrug, tautomer, or isomer thereof, wherein:

$A_9$ is selected from the group consisting of —CR$^{19}$R$^{20}$—, —C(O)—, —C(S)—, —S—, —S(O)—, —S(O)$_2$—, —NR$^{21}$—, and —O—;

$Q^{75}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$—C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

$M_{11}$, $Q^{71}$, and $Q^{82}$ are as defined for Formula II; and $R^{19}$, $R^{20}$, $R^{21}$, $R^{23}$, $R^{24}$, and $R^{25}$ are as defined for Formula Ib.

In one embodiment of the methods provided herein, in compounds of Formula IIh, $M_{11}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, $A_9$ is —CR$^{19}$R$^{20}$— or —C(O)—, preferably —CH$_2$— or —C(O)—. In one embodiment, $Q^{71}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$; —OR$^{23}$ and —S(O)$_2$R$^{23}$ and $Q^{75}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$; —OR$^{23}$ and —S(O)$_2$R$^{23}$.

In one embodiment of the methods provided herein, in compounds of Formula IIh, $M_{11}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and $A_9$ is —CR$^{19}$R$^{20}$— or —C(O)—, preferably —CH$_2$— or —C(O)—. In one embodiment, $M_{11}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; $A_9$ is —CR$^{19}$R$^{20}$— or —C(O)—, preferably —CH$_2$— or —C(O)—; $Q^{71}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{75}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$.

In one embodiment of the methods provided herein, in compounds of Formula IIh, $M_{11}$ is —NR$^{39}$CH$_2$— or —NR$^{39}$—(CH$_2$)$_2$—; $A_9$ is —CH$_2$— or —C(O)—, preferably —CH$_2$—; $Q^{71}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$—, —OR$^{41}$ and —S(O)$_2$R$^{41}$; Q$^{75}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$, wherein R$^{41}$ is as defined for Formula Ig.

In one embodiment of the methods provided herein, in compounds of Formula IIh, A$_9$ is —CH$_2$— or —C(O)—, preferably —CH$_2$—; Q$^{71}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$—NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{71}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{75}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_{11}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$—, —CH$_2$NR$^{39}$—, —CH(R$^{40}$)NR$^{39}$—, —NR$^{39}$C(O)—, or —NR$^{39}$S(O)$_2$—; and Q$^{82}$ is hydrogen, lower alkyl, or fluoro substituted lower alkyl, wherein R$^{39}$, R$^{40}$, R$^{41}$, R$^{42}$ and R$^{44}$ are as defined for Formula II.

In one embodiment of the methods provided herein, in compounds of Formula IIh, A$_9$ is —CH$_2$—; Q$^{71}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{75}$ is hydrogen, —CN, fluoro, chloro, lower alkyl, fluoro substituted lower alkyl, lower alkoxy, or fluoro substituted lower alkoxy; M$_{11}$ is —NR$^{39}$CH$_2$—, —NR$^{39}$CH$_2$CH$_2$—, or —NR$^{39}$CH(R$^{40}$)—; and Q$^{82}$ is hydrogen, lower alkyl, or fluoro substituted lower alkyl.

In one embodiment, further to any of the embodiments of the methods provided herein, in Formula IIh above, each occurrence of R$^{41}$ is R$^{42}$ as defined for Formula Ig.

In one embodiment of the methods provided herein, a compound of Formula II has a structure according to the following sub-generic structure, Formula IIi,

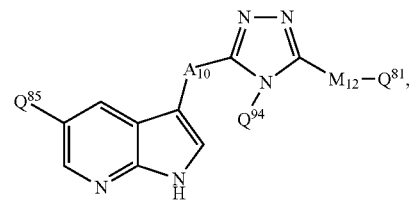

Formula IIi or a salt, prodrug, tautomer, or isomer thereof,
wherein:
A$_{10}$ is selected from the group consisting of —CR$^{19}$R$^{20}$—, —C(O)—, —C(S)—, —S—, —S(O)—, —S(O)$_2$—, —NR$^{21}$—, and —O—;
Q$^{85}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)NHR$^{23}$—NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
M$_{12}$, Q$^{81}$, and Q$^{94}$ are as defined for Formula II; and
R$^{19}$, R$^{20}$, R$^{21}$, R$^{23}$, R$^{24}$, and R$^{25}$ are as defined for Formula Ib.

In one embodiment of the methods provided herein, in compounds of Formula IIi, M$_{12}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, A$_{10}$ is —CR$^{19}$R$^{20}$— or —C(O)—, preferably —CH$_2$— or —C(O)—. In one embodiment, Q$^{81}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and Q$^{85}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$.

In one embodiment of the methods provided herein, in compounds of Formula IIi, M$_{12}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and A$_{10}$ is —CR$^{19}$R$^{20}$— or —C(O)—, preferably —CH$_2$— or —C(O)—. In one embodiment, $M_{12}$ is $-(CR^{19}R^{20})_t-NR^{26}-(CR^{19}R^{20})_s-$ or $-(CR^{19}R^{20})_t-NR^{26}C(O)-(CR^{19}R^{20})_s-$ preferably $-NR^{26}-(CR^{19}R^{20})_s-$ or $-NR^{26}C(O)-(CR^{19}R^{20})_s-$, more preferably $-NR^{39}CR^{80}R^{80}-$ or $-NR^{39}(CR^{80}R^{80})_s-$; $A_{10}$ is $-CR^{19}R^{20}-$ or $-C(O)-$, preferably $-CH_2-$ or $-C(O)-$; $Q^{81}$ is optionally substituted lower alkyl, aryl or heteroaryl, wherein aryl or heteroaryl are optionally substituted with one or more substituents selected from the group consisting of halogen, lower alkyl, fluoro substituted lower alkyl, $-NHR^{23}$, $-NR^{23}R^{23}$, $-OR^{23}$ and $-S(O)_2R^{23}$; and $Q^{85}$ is hydrogen, $-OR^{23}$, $-CN$, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, $-NHR^{23}$, $-NR^{23}R^{23}$, $-OR^{23}$ and $-S(O)_2R^{23}$.

In one embodiment of the methods provided herein, in compounds of Formula IIi, $M_{12}$ is $-NR^{39}CH_2-$ or $-NR^{39}-(CH_2)_2-$; $A_{10}$ is $-CH_2-$ or $-C(O)-$, preferably $-CH_2-$; $Q^{81}$ is aryl or heteroaryl, wherein aryl or heteroaryl are optionally substituted with one or more substituents selected from the group consisting of halogen, lower alkyl, fluoro substituted lower alkyl, $-NHR^{41}$, $-NR^{41}R^{41}$, $-OR^{41}$ and $-S(O)_2R^{41}$; $Q^{85}$ is hydrogen, $-CN$, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, $-NHR^{41}$, $-NR^{41}R^{41}$, $-OR^{41}$ and $-S(O)_2R^{41}$, wherein $R^{41}$ is as defined for Formula Ig.

In one embodiment of the methods provided herein, in compounds of Formula IIi, $A_{10}$ is $-CH_2-$ or $-C(O)-$, preferably $-CH_2-$; $Q^{81}$ is aryl or heteroaryl, wherein aryl or heteroaryl are optionally substituted with one or more substituents selected from the group consisting of $-OR^{41}$, $-SR^{41}$, $-S(O)R^{41}$, $-S(O)_2R^{41}$, $-NHR^{41}$, $-NR^{41}R^{41}$, $-NR^{39}C(O)R^{41}$, $-NR^{39}S(O)_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{81}$, or as a substituent of lower alkyl are optionally substituted with one or more substituents selected from the group consisting of $-OH$, $-NH_2$, $-CN$, $-NO_2$, $-S(O)_2NH_2$, $-C(O)NH_2$, $-OR^{42}$, $-SR^{42}$, $-NHR^{42}$, $-NR^{42}R^{42}$, $-NR^{39}C(O)R^{42}$, $NR^{39}S(O)_2R^{42}$, $-S(O)_2R^{42}$, halogen, lower alkyl, fluoro substituted lower alkyl, and cycloalkylamino; $Q^{85}$ is hydrogen, $-CN$, $-OR^{41}$, $-SR^{41}$, $-S(O)R^{41}$, $-S(O)_2R^{41}$, $-NHR^{41}$, $-NR^{41}R^{41}$, $-NR^{39}C(O)R^{41}$, $-NR^{39}S(O)_2R^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, $-NHR^{41}$, $-NR^{41}R^{41}$, and $-OR^{41}$; $M_{12}$ is a bond, $-NR^{39}-$, $-S-$, $-O-$, $-NR^{39}CH_2-$, $-NR^{39}CH_2CH_2-$, $-NR^{39}CH(R^{40})-$, $-SCH_2-$, $-OCH_2-$, $-C(O)NR^{39}-$, $-S(O)_2NR^{39}-$, $-CH_2NR^{39}-$, $-CH(R^{40})NR^{39}-$, $-NR^{39}C(O)-$, or $-NR^{39}S(O)_2-$; and $Q^{94}$ is hydrogen, lower alkyl, or fluoro substituted lower alkyl, wherein $R^{39}$, $R^{40}$, $R^{41}$, $R^{42}$ and $R^{44}$ are as defined for Formula II.

In one embodiment of the methods provided herein, in compounds of Formula IIi, $A_{10}$ is $-CH_2-$; $Q^{81}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{85}$ is hydrogen, $-CN$, fluoro, chloro, lower alkyl, fluoro substituted lower alkyl, lower alkoxy, or fluoro substituted lower alkoxy; $M_{12}$ is $-NR^{39}CH_2-$, $-NR^{39}CH_2CH_2-$, or $-NR^{39}CH(R^{40})-$; and $Q^{94}$ is hydrogen, lower alkyl, or fluoro substituted lower alkyl.

In one embodiment, further to any of the embodiments of the methods provided herein, in Formula IIi above, each occurrence of $R^{41}$ is $R^{42}$ as defined for Formula Ig.

In one embodiment of the methods provided herein, a compound of Formula II has a structure according to the following sub-generic structure, Formula IIj,

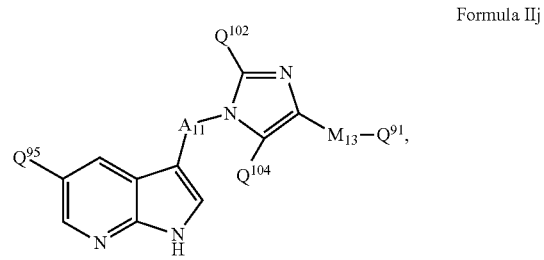

Formula IIj or a salt, prodrug, tautomer, or isomer thereof,
wherein:
$A_{11}$ is selected from the group consisting of $-CR^{19}R^{20}-$, $-C(O)-$, $-C(S)-$, $-S(O)-$, and $-S(O)_2-$;

$Q^{95}$ is selected from the group consisting of hydrogen, halogen, optionally substituted lower alkyl, optionally substituted cycloalkyl, optionally substituted heterocycloalkyl, optionally substituted aryl, optionally substituted heteroaryl, $-OH$, $-NH_2$, $-NO_2$, $-CN$, $-NHC(O)NH_2$, $-NHC(S)NH_2$, $-NHS(O)_2NH_2$, $-C(O)NH_2$, $-C(S)NH_2$, $-S(O)_2NH_2$, $-NR^{24}R^{25}$, $-NHR^{23}$, $-OR^{23}$, $-SR^{23}$, $-C(O)R^{23}$, $-S(O)R^{23}$, $-S(O)_2R^{23}$, $-C(O)NHR^{23}$, $-C(O)NR^{23}R^{23}$, $-C(S)NHR^{23}$, $-C(S)NR^{23}R^{23}$, $-S(O)_2NHR^{23}$, $-S(O)_2NR^{23}R^{23}$, $-NHC(O)R^{23}$, $-NR^{23}C(O)R^{23}$, $-NHC(S)R^{23}$, $-NR^{23}C(S)R^{23}$, $-NHS(O)_2R^{23}-$NHC(O)NHR^{23}$, $-NR^{23}C(O)NH_2$, $-NR^{23}C(O)NHR^{23}$, $-NHC(O)NR^{23}R^{23}$, $-NR^{23}C(O)NR^{23}R^{23}$, $-NHC(S)NHR^{23}$, $-NR^{23}C(S)NH_2$, $-NR^{23}C(S)NHR^{23}$, $-NHC(S)NR^{23}R^{23}$, $-NR^{23}C(S)NR^{23}R^{23}$, $-NHS(O)_2NHR^{23}$, $-NR^{23}S(O)_2NH_2$, $-NR^{23}S(O)_2NHR^{23}$, $-NHS(O)_2NR^{23}R^{23}$, and $-NR^{23}S(O)_2NR^{23}R^{23}$;

$M_{13}$, $Q^{91}$, $Q^{102}$ and $Q^{104}$ are as defined for Formula II; and $R^{19}$, $R^{20}$, $R^{23}$, $R^{24}$, and $R^{25}$ are as defined for Formula Ib.

In one embodiment of the methods provided herein, in compounds of Formula IIj, $M_{13}$ is $-(CR^{19}R^{20})_t-NR^{26}-CR^{19}R^{20})_s-$ or $-(CR^{19}R^{20})_t-NR^{26}C(O)-(CR^{19}R^{20})_s-$, preferably $-NR^{26}-(CR^{19}R^{20})_s-$ or $-NR^{26}C(O)-(CR^{19}R^{20})_s-$, more preferably $-NR^{39}CR^{80}R^{80}-$ or $-NR^{39}(CR^{80}R^{80})_2-$, wherein $R^{39}$ is hydrogen or lower alkyl and $R^{80}$ is hydrogen, lower alkyl or fluoro substituted lower alkyl, preferably hydrogen. In one embodiment, $A_{11}$ is $-CR^{19}R^{20}-$ or $-C(O)-$, preferably $-CH_2-$ or —C(O)—. In one embodiment, $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{95}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{102}$ and $Q^{104}$ are independently hydrogen, fluoro, chloro, methyl, or —CF$_3$.

In one embodiment of the methods provided herein, in compounds of Formula IIj, $M_{13}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or, —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and $A_{11}$ is —CR$^{19}$R$^{20}$— or —C(O)—, preferably —CH$_2$— or —C(O)—. In one embodiment, $M_{13}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; $A_{11}$ is —CR$^{19}$R$^{20}$— or —C(O)—, preferably —CH$_2$— or —C(O)—; $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{95}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, $M_{13}$ is —(CR$^{19}$R$^{20}$)$_t$—NR$^{26}$—CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— is —NR$^{39}$(CR$^{80}$R$^{80}$)$_2$—; $A_{11}$ is —CR$^{19}$R$^{20}$— or —C(O)—, preferably —CH$_2$— or —C(O)—; $Q^{91}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; $Q^{95}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{102}$ and $Q^{104}$ are independently hydrogen, fluoro, chloro, methyl, or —CF$_3$.

In one embodiment of the methods provided herein, in compounds of Formula IIj, $M_{13}$ is —NR$^{39}$CH$_2$— or —NR$^{39}$—(CH$_2$)$_2$—; $A_{11}$ is —CH$_2$— or —C(O)—, preferably —CH$_2$—; $Q^{91}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; $Q^{95}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and $Q^{102}$ and $Q^{104}$ are independently hydrogen, fluoro, chloro, lower alkyl, or fluoro substituted lower alkyl, preferably $Q^{102}$ and $Q^{104}$ are independently hydrogen, fluoro, chloro, methyl, or —CF$_3$, wherein R$^{41}$ is as defined for Formula Ig.

In one embodiment of the methods provided herein, in compounds of Formula IIj, $A_{11}$ is —CH$_2$— or —C(O)—, preferably —CH$_2$—; $Q^{91}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{91}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{95}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_{13}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$—, —CH$_2$NR$^{39}$—, —CH(R$^{40}$)NR$^{39}$—, —NR$^{39}$C(O)—, or —NR$^{39}$S(O)$_2$—; and $Q^{102}$ and $Q^{104}$ are independently hydrogen, halogen, lower alkyl, fluoro substituted lower alkyl, —NR$^{44}$R$^{44}$, —OR$^{44}$, or —SR$^{44}$, provided, however, that at least one of $Q^{102}$ and R$^{104}$ is hydrogen, fluoro, chloro, lower alkyl or fluoro substituted lower alkyl, wherein R$^{39}$, R$^{40}$, R$^{41}$, R$^{42}$ and R$^{44}$ are as defined for Formula II.

In one embodiment of the methods provided herein, in compounds of Formula IIj, $A_{11}$ is —CH$_2$—; $Q^{91}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{95}$ is hydrogen, —CN, fluoro, chloro, lower alkyl, fluoro substituted lower alkyl, lower alkoxy, or fluoro substituted lower alkoxy; $M_{13}$ is —NR$^{39}$CH$_2$—, —NR$^{39}$CH$_2$CH$_2$—, or —NR$^{39}$CH(R$^4$)—; and $Q^{102}$ and $Q^{104}$ are independently hydrogen, halogen, lower alkyl, fluoro substituted lower alkyl, lower alkoxy, or fluoro substituted lower alkoxy, provided, however, that at least one of $Q^{102}$ and $Q^{104}$ is hydrogen, fluoro, chloro, lower alkyl or fluoro substituted lower alkyl.

In one embodiment, further to any of the embodiments of the methods provided herein, in Formula IIj above, each occurrence of R$^{41}$ is R$^{42}$ as defined for Formula Ig.

In one embodiment of the methods provided herein, a compound of Formula II has a structure according to the following sub-generic structure, Formula IIk,

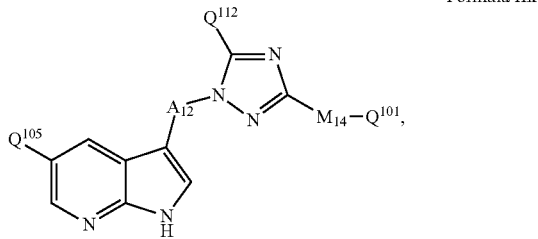

Formula IIk or a salt, prodrug, tautomer, or isomer thereof,
wherein:
$A_{12}$ is selected from the group consisting of —$CR^{19}R^{20}$, —C(O)—, —C(S)—, —S(O)—, and —$S(O)_2$—;
$Q^{105}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^{23}$, —C(O)$R^{23}$, —C(S)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$_2NHR^{23}$, —S(O)$_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$—NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$;
$M_{14}$, $Q^{101}$, and $Q^{112}$ are as defined for Formula II; and
$R^{19}$, $R^{20}$, $R^{23}$, $R^{24}$, and $R^{25}$ are as defined for Formula Ib.

In one embodiment of the methods provided herein, in compounds of Formula IIk, $M_{14}$ is —$(CR^{19}R^{20})_t$—$NR^{26}$—$CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{12}$ is —$CR^{19}R^{20}$— or —C(O)—, preferably —$CH_2$— or —C(O)—. In one embodiment, $Q^{101}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$ and $Q^{105}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$. Further to any of the above embodiments, $Q^{112}$ is hydrogen, fluoro, chloro, lower alkyl or fluoro substituted lower alkyl.

In one embodiment of the methods provided herein, in compounds of Formula IIk, $M_{14}$ is —$(CR^{19}R^{20})_t$—$NR^{26}$—$CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or, —$NR^{26}$C(O)—$(CR^{19}R^{20})_s$—, more preferably —$NR^{39}CR^{80}R^{80}$— or —$NR^{39}(CR^{80}R^{80})_2$—, and $A_{12}$ is —$CR^{19}R^{20}$— or —C(O)—, preferably —$CH_2$— or —C(O)—. In one embodiment, $M_{14}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—; $A_{12}$ is —$CR^{19}R^{20}$— or —C(O)—, preferably —$CH_2$— or —C(O)—; $Q^{101}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; $Q^{105}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —$S(O)_2R^{23}$; and $Q^{112}$ is hydrogen, fluoro, chloro, lower alkyl or fluoro substituted lower alkyl.

In one embodiment of the methods provided herein, in compounds of Formula IIk, $M_{14}$ is —$NR^{39}CH_2$— or —$NR^{39}$—$(CH_2)_2$—; $A_{12}$ is —$CH_2$— or —C(O)—, preferably —$CH_2$—; $Q^{101}$ is aryl or heteroaryl, wherein aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; $Q^{105}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —$S(O)_2R^{41}$; and $Q^{112}$ is hydrogen, fluoro, chloro, lower alkyl or fluoro substituted lower alkyl, wherein $R^{41}$ is as defined for Formula Ig.

In one embodiment of the methods provided herein, in compounds of Formula IIk, $A_{12}$ is —$CH_2$— or —C(O)—, preferably —$CH_2$—; $Q^{101}$ is aryl or heteroaryl, wherein aryl or heteroaryl are optionally substituted with one or more substituents selected from the group consisting of —$OR^{41}$, —$SR^{41}$, —S(O)$R^{41}$, —S(O)$_2R^{41}$, —$NHR^{41}$, —$NR^{41}R^{41}$, —$NR^{39}$C(O)$R^{41}$, —$NR^{39}$S(O)$_2R^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{101}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{105}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_{14}$ is a bond, —NR$^{39}$—, —S—, —O—, —NR$^{39}$CH$_2$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$—, —CH$_2$NR$^{39}$—, —CH(R$^{40}$)NR$^{39}$—, —NR$^{39}$C(O)—, or —NR$^{39}$S(O)$_2$—; and $Q^{112}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of the methods provided herein, in compounds of Formula IIk, $A_{12}$ is —CH$_2$—; $Q^{101}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{105}$ is hydrogen, —CN, fluoro, chloro, lower alkyl, fluoro substituted lower alkyl, lower alkoxy, or fluoro substituted lower alkoxy; $M_{14}$ is —NR$^{39}$CH$_2$—, —NR$^{39}$CH$_2$CH$_2$—, or —NR$^{39}$CH(R$^{40}$)—; and $Q^{112}$ is hydrogen, fluoro, chloro, lower alkyl, fluoro substituted lower alkyl, lower alkoxy, or fluoro substituted lower alkoxy.

In one embodiment, further to any of the embodiments of the methods provided herein, in Formula IIk above, each occurrence of R$^{41}$ is R$^{42}$ as defined for Formula Ig.

In one embodiment of the methods provided herein, a compound of Formula II has a structure according to the following sub-generic structure, Formula IIm, Formula IIm

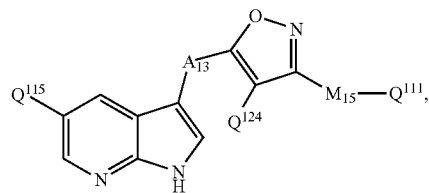

or a salt, prodrug, tautomer, or isomer thereof, wherein:
$A_{13}$ is selected from the group consisting of —CR$^{19}$R$^{20}$—, —C(O)—, —C(S)—, —S—, —S(O)—, —S(O)$_2$—, —NR$^{21}$—, and —O—;
$Q^{115}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$ —S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$— NHC(O)NHR$^{23}$, NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;
$M_{15}$, $Q^{111}$, and $Q^{124}$ are as defined for Formula II; and
R$^{19}$, R$^{20}$, R$^{21}$, R$^{23}$, R$^{24}$, and R$^{25}$ are as defined for Formula Ib.

In one embodiment of the methods provided herein, in compounds of Formula IIm, $M_{15}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, $A_{13}$ is —CR$^{19}$R$^{20}$— or —C(O)—, preferably —CH$_2$— or —C(O)—. In one embodiment, $Q^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{115}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{124}$ is hydrogen, fluoro, chloro, lower alkyl or fluoro substituted lower alkyl.

In one embodiment of the methods provided herein, in compounds of Formula IIm, $M_{15}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$— preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and $A_{13}$ is —CR$^{19}$R$^{20}$— or —C(O)—, preferably —CH$_2$— or —C(O)—. In one embodiment, $M_{15}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$, more preferably —NR$^{39}$CR$^{80}$R$^{80}$— or —NR$^{39}$(CR$^{80}$R$^{80}$)$_2$—; $A_{13}$ is —CR$^{19}$R$^{20}$— or —C(O)—, preferably —CH$_2$— or —C(O)—; $Q^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{115}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, M$_{15}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; A$_{13}$ is —CR$^{19}$R$^{20}$— or —C(O)—, preferably —CH$_2$— or —C(O)—; Q$^{111}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; Q$^{115}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{124}$ is hydrogen, fluoro, chloro, lower alkyl or fluoro substituted lower alkyl.

In one embodiment of the methods provided herein, in compounds of Formula IIm, M$_{15}$ is —NR$^{39}$CH$_2$— or —NR$^{39}$—(CH$_2$)$_2$—; A$_{13}$ is —CH$_2$— or —C(O)—, preferably —CH$_2$—; Q$^{111}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{115}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{42}$, —NR$^{42}$R$^{42}$, —OR$^{42}$ and —S(O)$_2$R$^{42}$; and Q$^{124}$ is hydrogen, fluoro, chloro, lower alkyl or fluoro substituted lower alkyl, wherein R$^{41}$ is as defined for Formula Ig.

In one embodiment of the methods provided herein, in compounds of Formula IIm, A$_{13}$ is —CH$_2$— or —C(O)—, preferably —CH$_2$—; Q$^{111}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{111}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{115}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_{15}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH(R$^{40}$NR$^{39}$—, —NR$^{39}$C(O)—, or —NR$^{39}$S(O)$_2$—; and Q$^{124}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of the methods provided herein, in compounds of Formula IIm, A$_{13}$ is —CH$_2$—; Q$^{111}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{115}$ is hydrogen, —CN, fluoro, chloro, lower alkyl, fluoro substituted lower alkyl, lower alkoxy, or fluoro substituted lower alkoxy; M$_{15}$ is —NR$^{39}$CH$_2$—, —NR$^{39}$CH$_2$CH$_2$—, or —NR$^{39}$CH(R$^{40}$)—; and Q$^{124}$ is hydrogen, fluoro, chloro, lower alkyl, fluoro substituted lower alkyl, lower alkoxy, or fluoro substituted lower alkoxy.

In one embodiment, further to any of the embodiments of the methods provided herein, in Formula IIm above, each occurrence of R$^{41}$ is R$^{42}$ as defined for Formula Ig.

In one embodiment of the methods provided herein, a compound of Formula II has a structure according to the following sub-generic structure, Formula IIn,

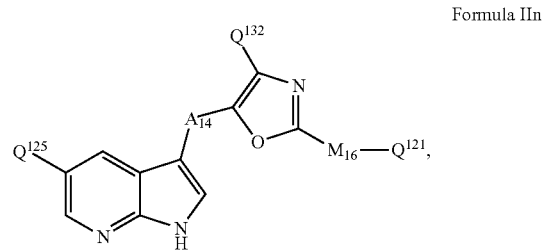

Formula IIn or a salt, prodrug, tautomer, or isomer thereof, wherein:

A$_{14}$ is selected from the group consisting of —CR$^{19}$R$^{20}$—, —C(O)—, —C(S)—, —S—, —S(O)—, —S(O)$_2$—, —NR$^{21}$—, and —O—;

Q$^{125}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$, —C(S)R$^{23}$, —S(O)R$^{23}$, —S(O)$_2$R$^{23}$—C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_{16}$, Q$^{121}$, and Q$^{132}$ are as defined for Formula II; and R$^{19}$, R$^{20}$, R$^{21}$, R$^{23}$, R$^{24}$, and R$^{25}$ are as defined for Formula Ib.

In one embodiment of the methods provided herein, in compounds of Formula IIn, M$_{16}$ is —(CR$^{19}$R$^{20}$)$_t$—NR$^{26}$—

$(CR^{19}R^{20})_s$— or —$(CR^{19}R^{20})_t$—NR$^{26}$C(O)—$(CR^{19}R^{20})_s$—, preferably —NR$^{26}$—$(CR^{19}R^{20})_s$— or —NR$^{26}$C(O)—$(CR^{19}R^{20})_s$—, more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, $A_{14}$ is —CR$^{19}$R$^{20}$— or —C(O)—, preferably —CH$_2$— or —C(O)—. In one embodiment, $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$ and $Q^{125}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, $Q^{132}$ is hydrogen, fluoro, chloro, lower alkyl or fluoro substituted lower alkyl.

In one embodiment of the methods provided herein, in compounds of Formula IIn, $M_{16}$ is —$(CR^{19}R^{20})_t$—NR$^{26}$—$(CR^{19}R^{20})_s$— or —$(CR^{19}R^{20})_t$—NR$^{26}$C(O)—$(CR^{19}R^{20})_s$— preferably —NR$^{26}$—$(CR^{19}R^{20})_s$— or —NR$^{26}$C(O)—$(CR^{19}R^{20})_s$—, more preferably —NR$^{39}$CR$^{80}$R$^{80}$— or —NR$^{39}$(CR$^{80}$R$^{80}$)$_2$—, and $A_{14}$ is an —CR$^{19}$R$^{20}$— or —C(O)—, preferably —CH$_2$— or —C(O)—. In one embodiment, $M_{16}$ is —$(CR^{19}R^{20})_t$—NR$^{26}$—$(CR^{19}R^{20})_s$— or —$(CR^{19}R^{20})_t$—NR$^{26}$C(O)—$(CR^{19}R^{20})_s$—, preferably —NR$^{26}$—$(CR^{19}R^{20})_s$— or —NR$^{26}$C(O)—$(CR^{19}R^{20})_s$—, more preferably —NR$^{39}$CR$^{80}$R$^{80}$— or —NR$^{39}$(CR$^{80}$R$^{80}$)$_2$—, and $A_{14}$ is —CR$^{19}$R$^{20}$— or —C(O)—, preferably —CH$_2$— or —C(O)—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{125}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. In one embodiment, $M_{16}$ is —$(CR^{19}R^{201})_t$—NR$^{26}$—$(CR^{19}R^{20})_s$— or —$(CR^{19}R^{20})_t$—NR$^{26}$C(O)—$(CR^{19}R^{20})_s$—, preferably —NR$^{26}$—$(CR^{19}R^{20})_s$— or —NR$^{26}$C(O)—$(CR^{19}R^{20})_s$—, more preferably —NR$^{39}$CR$^{80}$R$^{80}$— or —NR$^{39}$(CR$^{80}$OR$^{80}$)$_2$—; $A_{14}$ is —CR$^{19}$R$^{20}$— or —C(O)—, preferably —CH$_2$— or —C(O)—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl —NHR$^{23}$, —NR$^{23}$R$^{23}$, —OR$^{23}$, and —S(O)$_2$R$^{23}$; $Q^{125}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and $Q^{132}$ is hydrogen, fluoro, chloro, lower alkyl or fluoro substituted lower alkyl.

In one embodiment of the methods provided herein, in compounds of Formula IIn, $M_{16}$ is —NR$^{39}$CH$_2$— or —NR$^{39}$—(CH$_2$)$_2$—; $A_{14}$ is —CH$_2$— or —C(O)—, preferably —CH$_2$—; $Q^{121}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{42}$, —NR$^{42}$R$^{42}$, —OR$^{42}$ and —S(O)$_2$R$^{42}$; $Q^{125}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and $Q^{132}$ is hydrogen, fluoro, chloro, lower alkyl or fluoro substituted lower alkyl, wherein R$^{41}$ is as defined for Formula Ig.

In one embodiment of the methods provided herein, in compounds of Formula IIn, $A_{14}$ is —CH$_2$— or —C(O)—, preferably —CH$_2$—; $Q^{121}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of $Q^{121}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; $Q^{125}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; $M_{16}$ is a bond, —NR$^{39}$—, —S—, —O—, —NR$^{39}$CH$_2$—, —NR$^{39}$CH$_2$CH$_2$—, —NR$^{39}$CH(R$^{40}$)—, SCH$_2$—, —OCH$_2$—, —C(O)NR$^{39}$—, —S(O)$_2$NR$^{39}$—, —CH$_2$NR$^{39}$—, —CH(R$^{40}$)NR$^{39}$—, —NR$^{39}$C(O)—, or —NR$^{39}$S(O)$_2$—; and $Q^{132}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of the methods provided herein, in compounds of Formula IIn, $A_{14}$ is —CH$_2$—; $Q^{121}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; $Q^{125}$ is hydrogen, —CN, fluoro, chloro, lower alkyl, fluoro substituted lower alkyl, lower alkoxy, or fluoro substituted lower alkoxy; $M_{16}$ is —NR$^{39}$CH$_2$—, —NR$^{39}$CH$_2$CH$_2$—, or —NR$^{39}$CH(R$^{40}$)—; and $Q^{132}$ is hydrogen, fluoro, chloro, lower alkyl, fluoro substituted lower alkyl, lower alkoxy, or fluoro substituted lower alkoxy.

In one embodiment, further to any of the embodiments of the methods provided herein, in Formula IIn above, each occurrence of $R^{41}$ is $R^{42}$ as defined for Formula Ig.

In one embodiment of the methods provided herein, a compound of Formula II has a structure according to the following sub-generic structure, Formula IIo,

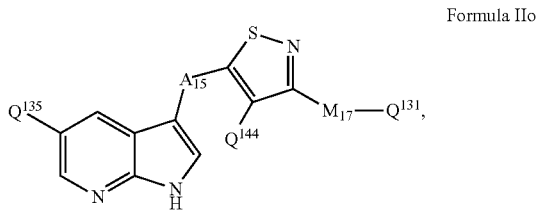

Formula IIo or a salt, prodrug, tautomer, or isomer thereof, wherein:

$A_{15}$ is selected from the group consisting of —$CR^{19}R^{20}$—, —C(O)—, —C(S)—, —S—, —S(O)—, —S(O)$_2$—, —$NR^{21}$—, and —O—;

$Q^{135}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —$NH_2$, —$NO_2$, —CN, —NHC(O)$NH_2$, —NHC(S)$NH_2$, —NHS(O)$_2NH_2$, —C(O)$NH_2$, —C(S)$NH_2$, —S(O)$_2NH_2$, —$NR^{24}R^{25}$, —$NHR^{23}$, —$OR^{23}$, —$SR^2$, —C(O)$R^{23}$ —S(O)$R^{23}$, —S(O)$_2R^{23}$, —C(O)$NHR^{23}$, —C(O)$NR^{23}R^{23}$, —C(S)$NHR^{23}$, —C(S)$NR^{23}R^{23}$, —S(O)$_2NHR^{23}$, —S(O)$_2NR^{23}R^{23}$, —NHC(O)$R^{23}$, —$NR^{23}$C(O)$R^{23}$, —NHC(S)$R^{23}$, —$NR^{23}$C(S)$R^{23}$, —NHS(O)$_2R^{23}$— NHC(O)$NHR^{23}$, —$NR^{23}$C(O)$NH_2$, —$NR^{23}$C(O)$NHR^{23}$, —NHC(O)$NR^{23}R^{23}$, —$NR^{23}$C(O)$NR^{23}R^{23}$, —NHC(S)$NHR^{23}$, —$NR^{23}$C(S)$NH_2$, —$NR^{23}$C(S)$NHR^{23}$, —NHC(S)$NR^{23}R^{23}$, —$NR^{23}$C(S)$NR^{23}R^{23}$, —NHS(O)$_2NHR^{23}$, —$NR^{23}$S(O)$_2NH_2$, —$NR^{23}$S(O)$_2NHR^{23}$, —NHS(O)$_2NR^{23}R^{23}$, and —$NR^{23}$S(O)$_2NR^{23}R^{23}$;

$M_{17}$, $Q^{131}$, and $Q^{144}$ are as defined for Formula II; and $R^{19}$, $R^{20}$, $R^{21}$, $R^{23}$, $R^{24}$ and $R^{25}$ are as defined for Formula Ib.

In one embodiment of the methods provided herein, in compounds of Formula IIo, $M_{17}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$— or —$NR^{39}(CR^{80}R^{80})_2$—, wherein $R^{39}$ is hydrogen or lower alkyl and $R^{80}$ is hydrogen, lower alkyl or fluoro substituted lower alkyl, preferably hydrogen. In one embodiment, $A_{15}$ is —$CR^{19}R^{20}$— or —C(O)—, preferably —$CH_2$— or —C(O)—. In one embodiment, $Q^{131}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$ and $Q^{135}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$. Further to any of the above embodiments, $Q^{144}$ is hydrogen, fluoro, chloro, lower alkyl, or fluoro substituted lower alkyl.

In one embodiment of the methods provided herein, in compounds of Formula IIo, $M_{17}$ is —$(CR^{19}R^{20})_t$—$NR^{26}$—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$—, —$NR^{39}(CR^{80}R^{80})_2$—, and $A_{15}$ is —$CR^{19}R^{20}$— or —C(O)—, preferably —$CH_2$— or —C(O)—. In one embodiment, $M_{17}$ is —$(CR^{19}R^{20})_t$—$NR^{26}$C(O)—$(CR^{19}R^{20})_s$— or —$(CR^{19}R^{20})_t$—$NR^{26}$C(O)—$(CR^{19}R^{20})_s$—, preferably —$NR^{26}$—$(CR^{19}R^{20})_s$— or —$NR^{26}$C(O)—$(CR^{19}R^{20})_s$—, more preferably —$NR^{39}CR^{80}R^{80}$—, —$NR^{39}(CR^{80}R^{80})_2$—; $A_{15}$ is —$CR^{19}R^{20}$ or —C(O)—, preferably —$CH_2$— or —C(O)—; $Q^{131}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{135}$ is hydrogen, —$OR^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{23}$, —$NR^{23}R^{23}$, —$OR^{23}$ and —S(O)$_2R^{23}$; and $Q^{144}$ is hydrogen, fluoro, chloro, lower alkyl, or fluoro substituted lower alkyl.

In one embodiment of the methods provided herein, in compounds of Formula IIo, $M_{17}$ is —$NR^{39}CH_2$— or —$NR^{39}$—$(CH_2)_2$—; $A_{15}$ is —$CH_2$— or —C(O)—, preferably —$CH_2$—; $Q^{131}$ is aryl or heteroaryl, wherein aryl or heteroaryl are optionally substituted with one or more substituents selected from the group consisting of halogen, lower alkyl, fluoro substituted lower alkyl, —$NHR^{42}$, —$NR^{42}R^{42}$, —$OR^{42}$ and —S(O)$_2R^{42}$; $Q^{135}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —$NHR^{41}$, —$NR^{41}R^{41}$, —$OR^{41}$ and —S(O)$_2R^{41}$; and $Q^{144}$ is hydrogen, fluoro, chloro, lower alkyl, or fluoro substituted lower alkyl, wherein $R^{41}$ is as defined for Formula Ig.

In one embodiment of the methods provided herein, in compounds of Formula IIo, $A_{15}$ is —$CH_2$— or —C(O)—, preferably —$CH_2$—; $Q^{131}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{131}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$; —NR$^{39}$C(O)R$^{42}$; —NR$^{39}$S(O)$_2$R$^{42}$, —S(O)$_2$R$^{42}$, halogen, lower alkyl, fluoro substituted lower alkyl, and cycloalkylamino; Q$^{135}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$; —OR$^{41}$; and M$_{15}$ is a bond, —NR$^{39}$—, —S—, —O—, —NR$^{39}$CH$_2$—, —NR$^{39}$CH$_2$CH$_2$—, —NR$^{39}$CH(R$^{40}$)—, —SCH$_2$—, —OCH$_2$—, —C(O)NR$^{39}$—, —S(O)$_2$NR$^{39}$—, —CH$_2$NR$^{39}$—, —CH$_2$(R$^{40}$)NR$^{39}$—, —NR$^{39}$C(O)—, or —NR$^{39}$S(O)$_2$—; and Q$^{144}$ is hydrogen, fluoro, chloro, lower alkyl, fluoro substituted lower alkyl, —NR$^{44}$R$^{44}$; —OR$^{44}$, or —SR$^{44}$, wherein R$^{39}$, R$^{40}$, R$^{41}$, R$^{42}$ and R$^{44}$ are as defined for Formula II.

In one embodiment of the methods provided herein, in compounds of Formula IIo, A$_{15}$ is —CH$_2$—; Q$^{131}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{135}$ is hydrogen, —CN, fluoro, chloro, lower alkyl, fluoro substituted lower alkyl, lower alkoxy, or fluoro substituted lower alkyl; M$_{15}$ is —NR$^{39}$CH$_2$—, —NR$^{39}$CH$_2$CH$_2$—, or —NR$^{39}$CH(R$^{40}$)—; and Q$^{144}$ is hydrogen, fluoro, chloro, lower alkyl, fluoro substituted lower alkyl, lower alkoxy, or fluoro substituted lower alkoxy.

In one embodiment, further to any of the embodiments of the methods provided herein, in Formula IIo above, each occurrence of R$^{41}$ is R$^{42}$ as defined for Formula Ig.

In one embodiment of the methods provided herein, a compound of Formula II has a structure according to the following sub-generic structure, Formula IIp,

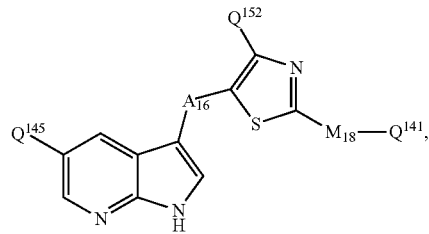

Formula IIp or a salt, prodrug, tautomer, or isomer thereof, wherein:

A$_{16}$ is selected from the group consisting of —CR$^{19}$R$^{20}$—, —C(O)—, —C(S)—, —S—, —S(O)—, —S(O)$_2$—, —NR$^{21}$—, and —O—;

Q$^{145}$ is selected from the group consisting of hydrogen, halogen, optionally substituted lower alkyl, optionally substituted cycloalkyl, optionally substituted heterocycloalkyl, optionally substituted aryl, optionally substituted heteroaryl, —OH, —NH$_2$, —NO$_2$, —CN, —NHC(O)NH$_2$, —NHC(S)NH$_2$, —NHS(O)$_2$NH$_2$, —C(O)NH$_2$, —C(S)NH$_2$, —S(O)$_2$NH$_2$, —NR$^{24}$R$^{25}$, —NHR$^{23}$, —OR$^{23}$, —SR$^{23}$, —C(O)R$^{23}$—S(O)R$^{23}$, —S(O)$_2$R$^{23}$, —C(O)NHR$^{23}$, —C(O)NR$^{23}$R$^{23}$, —C(S)NHR$^{23}$, —C(S)NR$^{23}$R$^{23}$, —S(O)$_2$NHR$^{23}$, —S(O)$_2$NR$^{23}$R$^{23}$, —NHC(O)R$^{23}$, —NR$^{23}$C(O)R$^{23}$, —NHC(S)R$^{23}$, —NR$^{23}$C(S)R$^{23}$, —NHS(O)$_2$R$^{23}$—NHC(O)NHR$^{23}$, —NR$^{23}$C(O)NH$_2$, —NR$^{23}$C(O)NHR$^{23}$, —NHC(O)NR$^{23}$R$^{23}$, —NR$^{23}$C(O)NR$^{23}$R$^{23}$, —NHC(S)NHR$^{23}$, —NR$^{23}$C(S)NH$_2$, —NR$^{23}$C(S)NHR$^{23}$, —NHC(S)NR$^{23}$R$^{23}$, —NR$^{23}$C(S)NR$^{23}$R$^{23}$, —NHS(O)$_2$NHR$^{23}$, —NR$^{23}$S(O)$_2$NH$_2$, —NR$^{23}$S(O)$_2$NHR$^{23}$, —NHS(O)$_2$NR$^{23}$R$^{23}$, and —NR$^{23}$S(O)$_2$NR$^{23}$R$^{23}$;

M$_{18}$, Q$^{141}$, and Q$^{152}$ are as defined for Formula II; and R$^{19}$, R$^{20}$, R$^{21}$, R$^{23}$, R$^{24}$, and R$^{25}$ are as defined for Formula Ib.

In certain embodiments of the methods provided herein, the compound is not

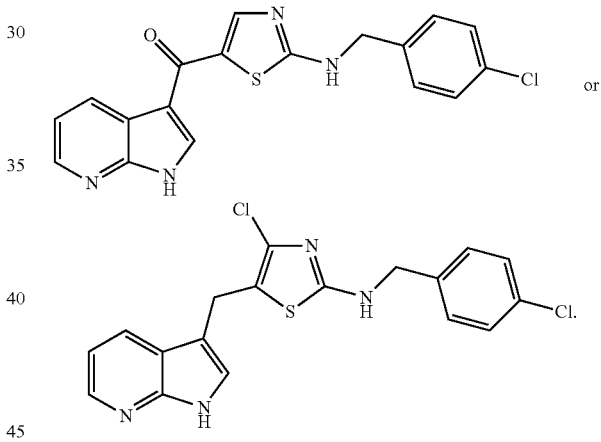

In one embodiment of the methods provided herein, in compounds of Formula IIp, M$_{18}$ is —(CR$^{19}$R$^{20}$)$_t$—NR$^{26}$—(CR$^{19}$R$^{20}$)$_s$ or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—; more preferably —NR$^{39}$CR$^{80}$R$^{80}$— or —NR$^{39}$(CR$^{80}$R$^{80}$)$_2$—, wherein R$^{39}$ is hydrogen or lower alkyl and R$^{80}$ is hydrogen, lower alkyl or fluoro substituted lower alkyl, preferably hydrogen. In one embodiment, A$_{16}$ is —CR$^{19}$R$^{20}$— or —C(O)—, preferably —CH$_2$— or —C(O)—. In one embodiment, Q$^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$; —OR$^{23}$ and —S(O)$_2$R$^{23}$ and Q$^{145}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$. Further to any of the above embodiments, Q$^{152}$ is hydrogen, fluoro, chloro, lower alkyl, or fluoro substituted lower alkyl.

In one embodiment of the methods provided herein, in compounds of Formula IIp, M$_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—, and A$_{16}$ is —CR$^{19}$R$^{20}$— or —C(O)—, preferably —CH$_2$— or —C(O)—. In one embodiment, M$_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; A$_{16}$ is —CR$^{19}$R$^{20}$— or —C(O)—, preferably —CH$_2$— or —C(O)—; Q$^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{145}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$; —OR$^{23}$ and —S(O)$_2$R$^{23}$. In one embodiment, M$_{18}$ is —(CR$^{19}$R$^{20}$)$_t$—NR$^{26}$—(CR$^{19}$R$^{20}$)$_s$— or —(CR$^{19}$R$^{20}$)$_t$—NR$^{26}$C(O)—(CR$^{19}$R$^{20}$)$_s$—, preferably —NR$^{26}$—(CR$^{19}$R$^{20}$)$_s$— or —NR$^{26}$C(O)—(CR$^{19}$R$^{20}$)$_s$—, more preferably —NR$^{39}$CR$^{80}$R$^{80}$— or —NR$^{39}$(CR$^{80}$R$^{80}$)$_2$—; or A$_{16}$ is —CR$^{19}$R$^{20}$— or —C(O)—, preferably —CH$_2$— or C(O)—; Q$^{141}$ is optionally substituted lower alkyl, aryl or heteroaryl, wherein aryl or heteroaryl are optionally substituted with one or more substituents selected from the group consisting of halogen, lower alkyl, fluoro substituted lower alkyl —NHR$^{23}$, —NR$^{23}$R$^{23}$, —OR$^{23}$, and —S(O)$_2$R$^{23}$; Q$^{145}$ is hydrogen, —OR$^{23}$, —CN, fluoro, chloro, lower alkyl, fluoro substituted lower alkyl, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{23}$, —NR$^{23}$R$^{23}$, —OR$^{23}$ and —S(O)$_2$R$^{23}$; and Q$^{152}$ is hydrogen, fluoro, chloro, lower alkyl, or fluoro substituted lower alkyl.

In one embodiment of the methods provided herein, in compounds of Formula IIp, M$_{18}$ is —NR$^{39}$CH$_2$— or —NR$^{39}$—(CH$_2$)$_2$—; A$_{16}$ is —CH$_2$— or —C(O)—, preferably —CH$_2$—; Q$^{141}$ is aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; Q$^{145}$ is hydrogen, —CN, fluoro, chloro, lower alkyl, fluoro substituted lower alkyl, lower alkoxy, fluoro substituted lower alkoxy, cycloalkyl, heterocycloalkyl, aryl or heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$; and Q$^{152}$ is hydrogen, fluoro, chloro, lower alkyl, or fluoro substituted lower alkyl, wherein R$^{41}$ is as defined for Formula Ig.

In one embodiment of the methods provided herein, in compounds of Formula IIp, A$_{16}$ is —CH$_2$— or —C(O)—, preferably —CH$_2$—; Q$^{141}$ is aryl or heteroaryl, wherein aryl or heteroaryl are optionally substituted with one or more substituents selected from the group consisting of —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, halogen, lower alkyl, cycloalkyl, heterocycloalkyl, aryl and heteroaryl, wherein lower alkyl is optionally substituted with one or more substituents selected from the group consisting of fluoro, lower alkoxy, fluoro substituted lower alkoxy, lower alkylthio, fluoro substituted lower alkylthio, mono-alkylamino, di-alkylamino, cycloalkyl, heterocycloalkyl, aryl, and heteroaryl, wherein cycloalkyl, heterocycloalkyl, aryl, and heteroaryl as a substituent of Q$^{141}$, or as a substituent of lower alkyl are optionally substituted with one or more substituents selected from the group consisting of —OH, —NH$_2$, —CN, —NO$_2$, —S(O)$_2$NH$_2$, —C(O)NH$_2$, —OR$^{42}$, —SR$^{42}$, —NHR$^{42}$, —NR$^{42}$R$^{42}$, —NR$^{39}$C(O)R$^{42}$, —NR$^{39}$S(O)$_2$R$^{42}$, —S(O)$_2$R$^{42}$, halogen, lower alkyl, fluoro substituted lower alkyl, and cycloalkylamino; Q$^{145}$ is hydrogen, —CN, —OR$^{41}$, —SR$^{41}$, —S(O)R$^{41}$, —S(O)$_2$R$^{41}$, —NHR$^{41}$, —NR$^{41}$R$^{41}$, —NR$^{39}$C(O)R$^{41}$, —NR$^{39}$S(O)$_2$R$^{41}$, fluoro, chloro, lower alkyl, fluoro substituted lower alkyl, aryl or heteroaryl, wherein aryl or heteroaryl are optionally substituted with one or more substituents selected from the group consisting of halogen, lower alkyl, fluoro substituted lower alkyl, —NHR$^{41}$, —NR$^{41}$R$^{41}$, and —OR$^{41}$; M$_{18}$ is a bond, —NR$^{39}$—, —S—, —O—, —NR$^{39}$CH$_2$—, —NR$^{39}$CH$_2$CH$_2$—, —NR$^{39}$CH(R$^{40}$)—, SCH$_2$—, —OCH$_2$—, —C(O)NR$^{39}$—, —S(O)$_2$—, —CH$_2$NR$^{39}$—, —CH(R$^{40}$)NR$^{39}$—, —NR$^{39}$C(O)—, or —NR$^{39}$S(O)$_2$—; and Q$^{152}$ is hydrogen, fluoro, chloro, lower alkyl, fluoro substituted lower alkyl, —NR$^{44}$R$^{44}$, —OR$^{44}$, or —SR$^{44}$, wherein R$^{39}$, R$^{40}$, R$^{41}$, R$^{42}$ and R$^{44}$ are as defined for Formula II.

In one embodiment of the methods provided herein, in compounds of Formula IIp, A$_{16}$ is —CH$_2$—; Q$^{141}$ is aryl or heteroaryl, wherein aryl or heteroaryl are optionally substituted with one or more substituents selected from the group consisting of fluoro, chloro, lower alkyl, fluoro substituted lower alkyl, lower alkoxy, and fluoro substituted lower alkoxy; Q$^{145}$ is hydrogen, —CN, fluoro, chloro, lower alkyl, fluoro substituted lower alkyl, lower alkoxy, or fluoro substituted lower alkoxy; M$_{18}$ is —NR$^{39}$CH$_2$—, —NR$^{39}$CH$_2$CH$_2$—, or —NR$^{39}$CH(R$^{40}$)—; and Q$^{152}$ is hydrogen, fluoro, chloro, lower alkyl, fluoro substituted lower alkyl, lower alkoxy, or fluoro substituted lower alkoxy.

In one embodiment, further to any of the embodiments of the methods provided herein, in Formula IIp above, each occurrence of R$^{41}$ is R$^{42}$ as defined for Formula Ig.

In one embodiment of the methods provided herein, in compounds of Formula IIp, M$_{18}$ is —NH—CH$_2$— or —NH—(CH$_2$)$_2$—, preferably —NH—CH$_2$—; A$_{16}$ is —CH$_2$— or —C(O)—, preferably —CH$_2$—; Q$^{141}$ is aryl or heteroaryl, wherein aryl or heteroaryl are optionally substituted with 1 or 2 substituents selected from the group consisting of fluoro, chloro, lower alkyl, fluoro substituted lower alkyl, lower alkoxy, fluoro substituted lower alkoxy, and heterocycloalkyl; Q$^{145}$ is hydrogen, —CN, fluoro, chloro, lower alkyl, fluoro substituted lower alkyl, lower alkoxy, or fluoro substituted lower alkoxy, preferably hydrogen, —CN, or chloro; and Q$^{152}$ is hydrogen, fluoro, chloro, lower alkyl, or fluoro substituted lower alkyl, preferably hydrogen or chloro, more preferably chloro.

In one embodiment of the methods provided herein, the compound of Formula Ih is selected from the group consisting of

[4-Chloro-5-(1H-pyrrolo[2,3-b]pyridin-3-ylmethyl)-thiazol-2-yl]-(4-fluoro-benzyl)-amine (P-0156),
[4-Ethyl-5-(1H-pyrrolo[2,3-b]pyridin-3-ylmethyl)-thiazol-2-yl]-(4-fluoro-benzyl)-amine (P-0162),
(4-Fluoro-benzyl)-[4-methyl-5-(1H-pyrrolo[2,3-b]pyridin-3-ylmethyl)-thiazol-2-yl]-amine (P-0163),
[4-Chloro-5-(1H-pyrrolo[2,3-b]pyridin-3-ylmethyl)-thiazol-2-yl]-pyridin-3-ylmethyl-amine (P-0164),
[4-Chloro-5-(1H-pyrrolo[2,3-b]pyridin-3-ylmethyl)-thiazol-2-yl]-pyridin-2-ylmethyl-amine (P-0167),
[4-Chloro-5-(1H-pyrrolo[2,3-b]pyridin-3-ylmethyl)-thiazol-2-yl]-pyridin-4-ylmethyl-amine (P-0168),
[4-Chloro-5-(1H-pyrrolo[2,3-b]pyridin-3-ylmethyl)-thiazol-2-yl]-(6-methyl-pyridin-2-ylmethyl)-amine (P-0171),
[4-Chloro-5-(1H-pyrrolo[2,3-b]pyridin-3-ylmethyl)-thiazol-2-yl]-(1,5-dimethyl-1H-pyrazol-3-ylmethyl)-amine (P-0172),
[4-Chloro-5-(1H-pyrrolo[2,3-b]pyridin-3-ylmethyl)-thiazol-2-yl]-(6-trifluoromethyl-pyridin-3-ylmethyl)-amine (P-0173),
[4-Chloro-5-(1H-pyrrolo[2,3-b]pyridin-3-ylmethyl)-thiazol-2-yl]-(2,5-dimethyl-2H-pyrazol-3-ylmethyl)-amine (P-0175),
[2-(4-Fluoro-benzylamino)-thiazol-5-yl]-(1H-pyrrolo[2,3-b]pyridin-3-yl)-methanone (P-0177),
{2-[(4-Chloro-benzyl)-methyl-amino]-thiazol-5-yl}-(1H-pyrrolo[2,3-b]pyridin-3-yl)-methanone (P-0178),
[4-Chloro-5-(5-chloro-1H-pyrrolo[2,3-b]pyridin-3-ylmethyl)-thiazol-2-yl]-thiazol-2-ylmethyl-amine (P-0189),
[4-Chloro-5-(5-chloro-1H-pyrrolo[2,3-b]pyridin-3-ylmethyl)-thiazol-2-yl]-(6-methoxy-pyridin-3-ylmethyl)-amine (P-0190),
Benzyl-[4-chloro-5-(5-chloro-1H-pyrrolo[2,3-b]pyridin-3-ylmethyl)-thiazol-2-yl]-amine (P-0192),
[4-Chloro-5-(5-chloro-1H-pyrrolo[2,3-b]pyridin-3-ylmethyl)-thiazol-2-yl]-(3-methoxy-benzyl)-amine (P-0193),
(4-Chloro-benzyl)-[4-chloro-5-(5-chloro-1H-pyrrolo[2,3-b]pyridin-3-ylmethyl)-thiazol-2-yl]-amine (P-0194),
[4-Chloro-5-(5-chloro-1H-pyrrolo[2,3-b]pyridin-3-ylmethyl)-thiazol-2-yl]-(4-fluoro-benzyl)-amine (P-0195),
[4-Chloro-5-(5-chloro-1H-pyrrolo[2,3-b]pyridin-3-ylmethyl)-thiazol-2-yl]-(2,4-dimethyl-thiazol-5-ylmethyl)-amine (P-0196),
[4-Chloro-5-(5-chloro-1H-pyrrolo[2,3-b]pyridin-3-ylmethyl)-thiazol-2-yl]-(2-ethyl-5-methyl-3H-imidazol-4-ylmethyl)-amine (P-0197),
[4-Chloro-5-(5-chloro-1H-pyrrolo[2,3-b]pyridin-3-ylmethyl)-thiazol-2-yl]-(2-ethyl-2H-pyrazol-3-ylmethyl)-amine (P-0198),
[4-Chloro-5-(5-chloro-1H-pyrrolo[2,3-b]pyridin-3-ylmethyl)-thiazol-2-yl]-(6-methoxy-pyridin-2-ylmethyl)-amine (P-0199),
[4-Chloro-5-(5-chloro-1H-pyrrolo[2,3-b]pyridin-3-ylmethyl)-thiazol-2-yl]-(3-fluoro-pyridin-4-ylmethyl)-amine (P-0200),
[4-Chloro-5-(5-chloro-1H-pyrrolo[2,3-b]pyridin-3-ylmethyl)-thiazol-2-yl]-(2-methyl-thiazol-4-ylmethyl)-amine (P-0201),
[4-Chloro-5-(5-chloro-1H-pyrrolo[2,3-b]pyridin-3-ylmethyl)-thiazol-2-yl]-(4-methyl-thiazol-5-ylmethyl)-amine (P-0202),
[4-Chloro-5-(5-chloro-1H-pyrrolo[2,3-b]pyridin-3-ylmethyl)-thiazol-2-yl]-(5-chloro-pyridin-2-ylmethyl)-amine (P-0203),
[4-Chloro-5-(1H-pyrrolo[2,3-b]pyridin-3-ylmethyl)-thiazol-2-yl]-(2,4-dimethyl-thiazol-5-ylmethyl)-amine (P-0204),
[4-Chloro-5-(1H-pyrrolo[2,3-b]pyridin-3-ylmethyl)-thiazol-2-yl]-(2-ethyl-5-methyl-3H-imidazol-4-ylmethyl)-amine (P-0205),
[4-Chloro-5-(1H-pyrrolo[2,3-b]pyridin-3-ylmethyl)-thiazol-2-yl]-(5-fluoro-pyridin-2-ylmethyl)-amine (P-0206),
[4-Chloro-5-(1H-pyrrolo[2,3-b]pyridin-3-ylmethyl)-thiazol-2-yl]-(5-methoxy-pyridin-3-ylmethyl)-amine (P-0207),
[4-Chloro-5-(1H-pyrrolo[2,3-b]pyridin-3-ylmethyl)-thiazol-2-yl]-(4,5-dimethyl-thiophen-2-ylmethyl)-amine (P-0208),
[4-Chloro-5-(1H-pyrrolo[2,3-b]pyridin-3-ylmethyl)-thiazol-2-yl]-(2,5-dimethyl-thiophen-3-ylmethyl)-amine (P-0209),
[4-Chloro-5-(5-chloro-1H-pyrrolo[2,3-b]pyridin-3-ylmethyl)-thiazol-2-yl]-(5-fluoro-pyridin-3-ylmethyl)-amine (P-0231),
[4-Chloro-5-(5-chloro-1H-pyrrolo[2,3-b]pyridin-3-ylmethyl)-thiazol-2-yl]-pyridin-3-ylmethyl-amine (P-0236),
[4-Chloro-5-(5-chloro-1H-pyrrolo[2,3-b]pyridin-3-ylmethyl)-thiazol-2-yl]-pyridin-4-ylmethyl-amine (P-0237),
[4-Chloro-5-(5-chloro-1H-pyrrolo[2,3-b]pyridin-3-ylmethyl)-thiazol-2-yl]-(3-chloro-pyridin-4-ylmethyl)-amine (P-0238),
[4-Chloro-5-(5-chloro-1H-pyrrolo[2,3-b]pyridin-3-ylmethyl)-thiazol-2-yl]-(1-ethyl-1H-pyrazol-4-ylmethyl)-amine (P-0239),
[4-Chloro-5-(5-chloro-1H-pyrrolo[2,3-b]pyridin-3-ylmethyl)-thiazol-2-yl]-(5-fluoro-pyridin-2-ylmethyl)-amine (P-0240),
[4-Chloro-5-(5-chloro-1H-pyrrolo[2,3-b]pyridin-3-ylmethyl)-thiazol-2-yl]-(5-methoxy-pyridin-3-ylmethyl)-amine (P-0241),
[4-Chloro-5-(5-chloro-1H-pyrrolo[2,3-b]pyridin-3-ylmethyl)-thiazol-2-yl]-(6-trifluoromethyl-pyridin-3-ylmethyl)-amine (P-0242),
[4-Chloro-5-(5-chloro-1H-pyrrolo[2,3-b]pyridin-3-ylmethyl)-thiazol-2-yl]-(2-chloro-6-fluoro-benzyl)-amine (P-0243),
[4-Chloro-5-(5-chloro-1H-pyrrolo[2,3-b]pyridin-3-ylmethyl)-thiazol-2-yl]-phenethyl-amine (P-0244),
[4-Chloro-5-(5-chloro-1H-pyrrolo[2,3-b]pyridin-3-ylmethyl)-thiazol-2-yl]-(2,4-difluoro-benzyl)-amine (P-0245),
[4-Chloro-5-(5-chloro-1H-pyrrolo[2,3-b]pyridin-3-ylmethyl)-thiazol-2-yl]-(2-fluoro-benzyl)-amine (P-0246),
[4-Chloro-5-(5-chloro-1H-pyrrolo[2,3-b]pyridin-3-ylmethyl)-thiazol-2-yl]-(2-methoxy-pyridin-3-ylmethyl)-amine (P-0247),
(2-Chloro-benzyl)-[4-chloro-5-(5-chloro-1H-pyrrolo[2,3-b]pyridin-3-ylmethyl)-thiazol-2-yl]-amine (P-0248),
[4-Chloro-5-(5-chloro-1H-pyrrolo[2,3-b]pyridin-3-ylmethyl)-thiazol-2-yl]-(2-methyl-benzyl)-amine (P-0249),
[4-Chloro-5-(5-chloro-1H-pyrrolo[2,3-b]pyridin-3-ylmethyl)-thiazol-2-yl]-(2-chloro-4-fluoro-benzyl)-amine (P-0250),
[4-Chloro-5-(5-chloro-1H-pyrrolo[2,3-b]pyridin-3-ylmethyl)-thiazol-2-yl]-(3-fluoro-pyridin-2-ylmethyl)-amine (P-0251),
[4-Chloro-5-(5-chloro-1H-pyrrolo[2,3-b]pyridin-3-ylmethyl)-thiazol-2-yl]-(6-morpholin-4-yl-pyridin-2-ylmethyl)-amine (P-0252),

[4-Chloro-5-(5-chloro-1H-pyrrolo[2,3-b]pyridin-3-ylmethyl)-thiazol-2-yl]-(3,5-dichloro-pyridin-4-ylmethyl)-amine (P-0253),

[4-Chloro-5-(5-chloro-1H-pyrrolo[2,3-b]pyridin-3-ylmethyl)-thiazol-2-yl]-(2-trifluoromethyl-benzyl)-amine (P-0254),

[4-Chloro-5-(5-chloro-1H-pyrrolo[2,3-b]pyridin-3-ylmethyl)-thiazol-2-yl]-(6-methyl-pyridin-2-ylmethyl)-amine (P-0255) and

[5-(5-Chloro-1H-pyrrolo[2,3-b]pyridin-3-ylmethyl)-thiazol-2-yl]-(4-fluoro-benzyl)-amine (P-0290), or all salts, prodrugs, tautomers, or isomers thereof.

In one embodiment of the methods provided herein, a compound of Formula I has a structure according to the following sub-generic structure, Formula III,

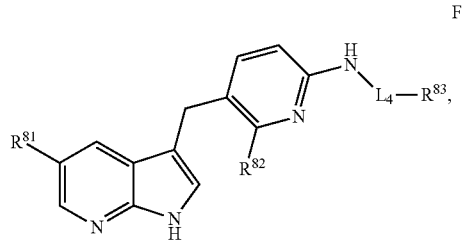

Formula III all salts, prodrugs, tautomers, or isomers thereof, wherein:

$L_4$ is —CH$_2$—, —CH$_2$CH$_2$—, —CH(R$^{40}$)—, —C(O)—, or —C(O)NH—;

$R^{81}$ is selected from the group consisting of hydrogen, —OR$^{41}$, —CN, fluoro, chloro, lower alkyl, fluoro substituted lower alkyl, cycloalkyl, heterocycloalkyl, aryl and heteroaryl, wherein cycloalkyl, heterocycloalkyl, aryl or heteroaryl are optionally substituted with one or more substituents selected from the group consisting of halogen, lower alkyl, fluoro substituted lower alkyl, —NHR$^{41}$, —NR$^{41}$R$^{41}$, —OR$^{41}$ and —S(O)$_2$R$^{41}$;

$R^{82}$ is selected from the group consisting of hydrogen, C$_{1-3}$ alkyl, fluoro substituted C$_{2-3}$alkyl, OH, C$_{1-3}$ alkoxy, and fluoro substituted C$_{1-3}$ alkoxy;

$R^{83}$ is heterocycloalkyl, heteroaryl, or

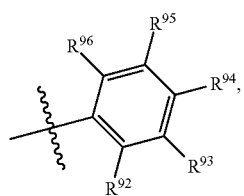

in which

indicates the attachment point of $R^{83}$ to $L_4$ of Formula III, wherein heterocycloalkyl or heteroaryl are optionally substituted with one or more substituents selected from the group consisting of halogen, lower alkyl, fluoro substituted lower alkyl, cycloalkylamino, —NHR$^{41}$, —NR$^{41}$R$^{41}$, —OR$^{41}$ and —S(O)$_2$R$^{41}$;

$R^{92}$, $R^{93}$, $R^{94}$, $R^{95}$, and $R^{96}$ are independently selected from the group consisting of hydrogen, halogen, lower alkyl, fluoro substituted lower alkyl, cycloalkylamino, —NHS(O)$_2$R$^{41}$, —NHC(O)R$^{41}$, —NHR$^{41}$, —NR$^{41}$R$^{41}$, —OR$^{41}$ and —S(O)$_2$R$^{41}$; and $R^{40}$ and $R^{41}$ are as defined for Formula Ig.

In certain embodiments of the methods provided herein, the compound is not

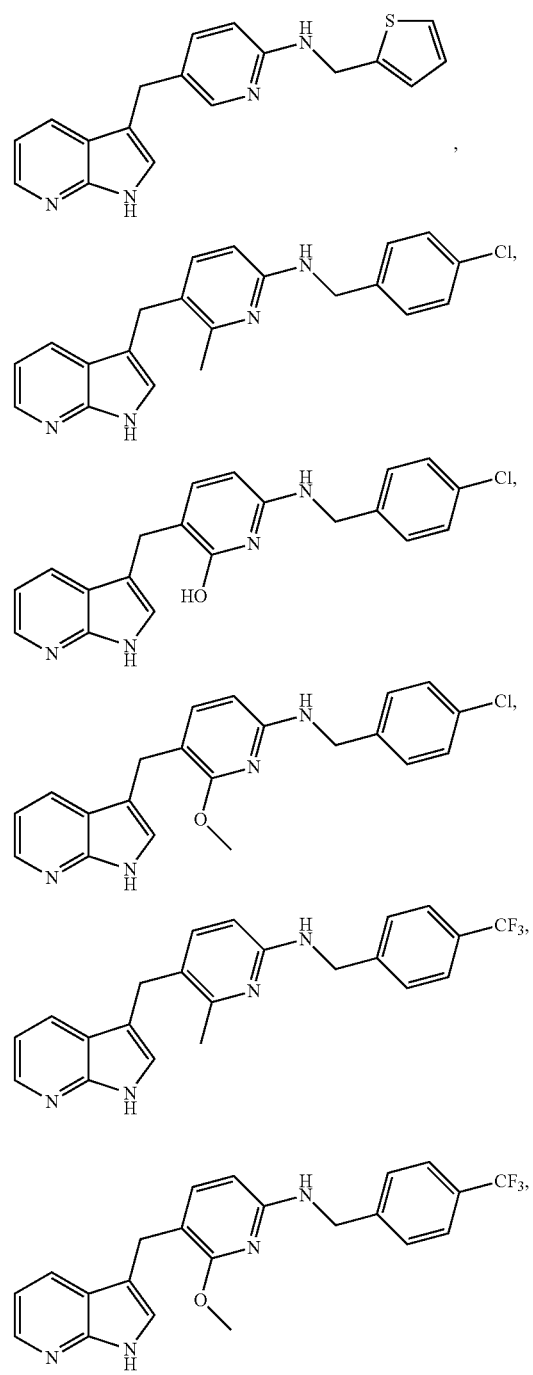

-continued
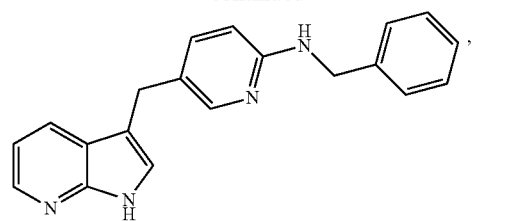
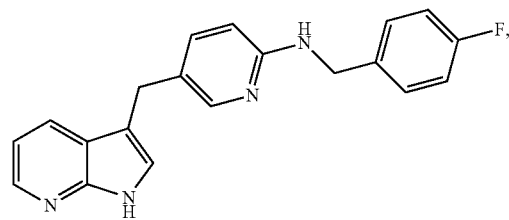
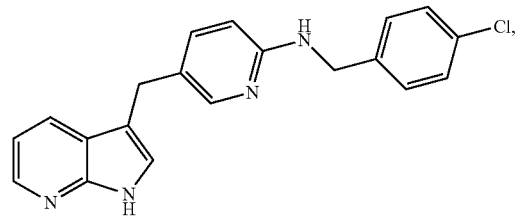
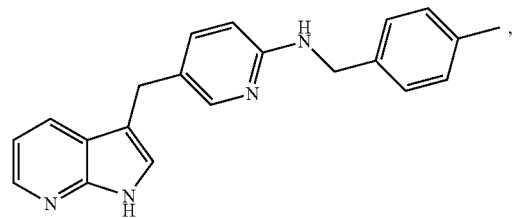
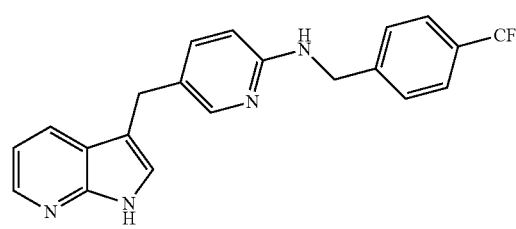
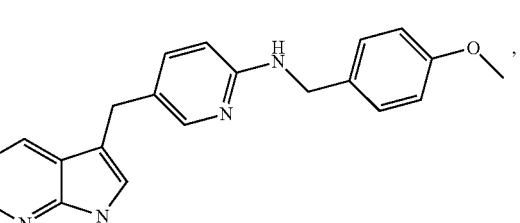
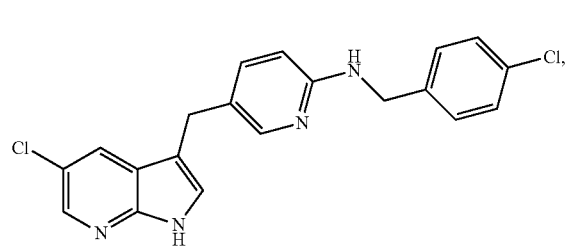
-continued
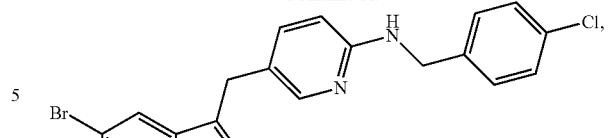
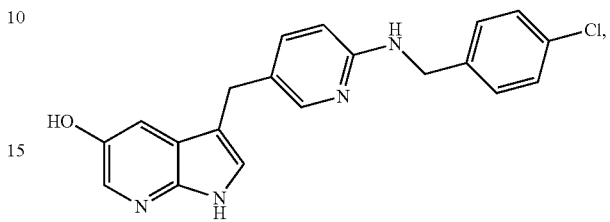
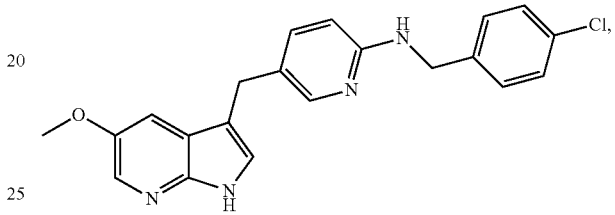
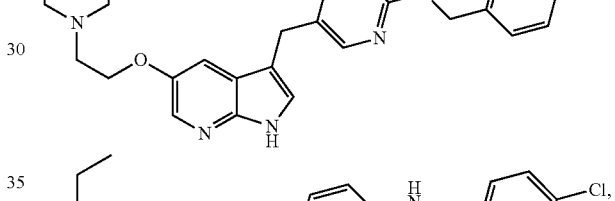
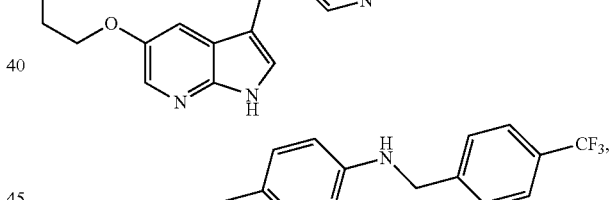
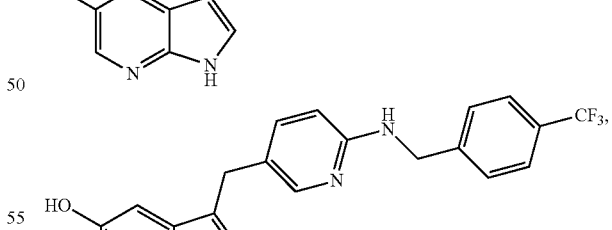
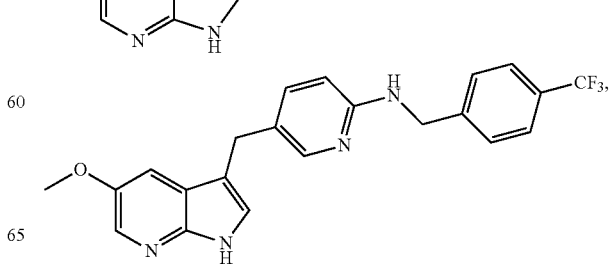

—CH(CH$_3$)— or —C(O)—, R$^{81}$ is hydrogen, fluoro, chloro, —CN, lower alkyl, fluoro substituted lower alkyl, lower alkoxy, or fluoro substituted lower alkoxy, R$^{82}$ is hydrogen, R$^{83}$ is wherein R$^{92}$, R$^{93}$, R$^{94}$, R$^{95}$, and R$^{96}$ are independently hydrogen, fluoro, chloro, lower alkyl, fluoro substituted lower alkyl, lower alkoxy, or fluoro substituted lower alkoxy, provided, however, that when R$^{94}$ is fluoro, chloro, lower alkyl, fluoro substituted lower alkyl, lower alkoxy, or fluoro substituted lower alkoxy, at least one of R$^{92}$, R$^{93}$, R$^{95}$, and R$^{96}$ is fluoro, chloro, lower alkyl, fluoro substituted lower alkyl, lower alkoxy, or fluoro substituted lower alkoxy.

In one embodiment of the methods provided herein, in compounds of Formula III, L$_4$ is —CH$_2$—, —CH$_2$CH$_2$—, —CH(CH$_3$)— or —C(O)—, R$^{81}$ is hydrogen, fluoro, chloro, —CN, methyl, or methoxy, preferably hydrogen, chloro, —CN, or methyl, R$^{82}$ is hydrogen, R$^{83}$ is wherein R$^{92}$, R$^{93}$, R$^{94}$, R$^{95}$, and R$^{96}$ are independently hydrogen, fluoro, chloro, methyl, ethyl, trifluoromethyl, methoxy, ethoxy, difluoromethoxy or trifluoromethoxy, preferably hydrogen, chloro, methyl, trifluoromethyl, methoxy, ethoxy, or trifluoromethoxy, provided, however, that when R$^{94}$ is fluoro, chloro, methyl, ethyl, trifluoromethyl, methoxy, ethoxy, difluoromethoxy or trifluoromethoxy, at least one of R$^{92}$, R$^{93}$, R$^{95}$, and R$^{96}$ is fluoro, chloro, methyl, ethyl, trifluoromethyl, methoxy, ethoxy, difluoromethoxy or trifluoromethoxy.

In one embodiment of the methods provided herein, in compounds of Formula III, L$_4$ is —CH$_2$—, R$^{81}$ is fluoro, chloro, —CN, methyl, or methoxy, preferably chloro, —CN, or methyl, R$^{82}$ is hydrogen, R$^{83}$ is wherein R$^{94}$ is hydrogen and R$^{92}$, R$^{93}$, R$^{95}$, and R$^{96}$ are independently hydrogen, fluoro, chloro, methyl, trifluoromethyl, methoxy, ethoxy, difluoromethoxy or trifluoromethoxy.

In one embodiment of the methods provided herein, in compounds of Formula III, L$_4$ is —CH$_2$—, —CH$_2$CH$_2$—, In one embodiment of the methods provided herein, in compounds of Formula III, $L_4$ is —$CH_2$—, —$CH_2CH_2$—, —C(O)—, or —CH($CH_3$)—, preferably —$CH_2$— or —C(O)—, $R^{81}$ is hydrogen, fluoro, $R^{82}$ is hydrogen, $R^{83}$ is

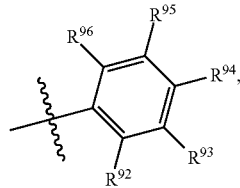

wherein $R^{92}$ is fluoro, chloro, methyl, ethyl, trifluoromethyl, methoxy, ethoxy, difluoromethoxy, or trifluoromethoxy, preferably fluoro, chloro, methyl, or trifluoromethyl, and $R^{93}$, $R^{94}$, $R^{95}$, and $R^{96}$ are independently hydrogen, fluoro, chloro, methyl, trifluoromethyl, methoxy, difluoromethoxy, or trifluoromethoxy, preferably hydrogen or fluoro. In one embodiment, $L_4$ is —$CH_2$—, —C(O)—, or —CH($CH_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, and $R^{93}$, $R^{94}$, $R^{95}$, and $R^{96}$ are hydrogen. In one embodiment, $L_4$ is —$CH_2$—, —C(O)—, or —CH($CH_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, $R^{94}$, $R^{95}$, and $R^{96}$ are hydrogen, and $R^{93}$ is fluoro, chloro, methyl, ethyl, trifluoromethyl, methoxy, ethoxy, difluoromethoxy, or trifluoromethoxy, preferably fluoro, chloro, trifluoromethyl or methoxy, more preferably fluoro. In one embodiment, $L_4$ is —$CH_2$—, —C(O)—, or —CH($CH_3$)—, $R^{81}$ is hydrogen, $R^{82}$ is hydrogen, $R^{92}$ is fluoro, chloro, methyl, ethyl, trifluoromethyl, methoxy, ethoxy, difluoromethoxy, or trifluoromethoxy, preferably fluoro, methyl, or trifluoromethyl, $R^{93}$, $R^{95}$, and $R^{96}$ are hydrogen, and $R^{94}$ is fluoro, chloro, methyl, ethyl, trifluoromethyl, methoxy, ethoxy, difluoromethoxy, or trifluoromethoxy, preferably fluoro, chloro, methyl or trifluoromethyl, more preferably fluoro. In one embodiment, $L_4$ is —$CH_2CH_2$— or —C(O)—, $R^{81}$ is hydrogen, $R^{82}$ is hydrogen, $R^{92}$, $R^{95}$, and $R^{96}$ are hydrogen, $R^{93}$ is hydrogen, fluoro, chloro, methyl, ethyl, trifluoromethyl, methoxy, ethoxy, difluoromethoxy, or trifluoromethoxy, preferably hydrogen, fluoro, chloro, methyl, trifluoromethyl, methoxy, or trifluoromethoxy, more preferably fluoro, chloro, trifluoromethyl or methoxy, and $R^{94}$ is hydrogen, fluoro, or chloro, provided, however, that when $L_4$ is —C(O)— and $R^{94}$ is fluoro or chloro, $R^{93}$ is not hydrogen. In one embodiment, $L_4$ is —$CH_2CH_2$—, $R^{81}$ is hydrogen, $R^{82}$ is hydrogen $R^{92}$, $R^{94}$, $R^{95}$, and $R^{96}$ are hydrogen $R^{93}$, and R is hydrogen, fluoro, chloro, methy, ethyl, trifluoromethyl, methoxy, ethoxy, difluoromethoxy, or trifluoromethoxy, preferably hydrogen or fluoro. In one embodiment, $L_4$ is —C(O)—, $R^{81}$ is hydrogen, $R^{82}$ is hydrogen, $R^{92}$, $R^{95}$, and $R^{96}$ are hydrogen, $R^{93}$ is fluoro, chloro, methyl, ethyl, trifluoromethyl, methoxy, ethoxy, difluoromethoxy, or trifluoromethoxy, preferably fluoro, chloro, trifluoromethyl or methoxy, and $R^{94}$ is hydrogen, fluoro, or chloro.

In one embodiment of the methods provided herein, in compounds of Formula III, $R^{83}$ is pyrrolidine, morpholine, pyridine, pyrimidine, pyrazine, pyrazole, isoxazole, imidazol, or benzimidazole, wherein $R^{83}$ is optionally substituted with one or more substituents independently selected from the group consisting of halogen, lower alkyl, fluoro substituted lower alkyl, cycloalkylamino, —$NHR^{41}$, —$NR^{41}R^{41}$, —$OR^{41}$ and —$S(O)_2R^{41}$, preferably wherein $R^{83}$ is optionally substituted with 1 or 2 substituents independently selected from fluoro, chloro, lower alkyl, fluoro substituted lower alkyl, lower alkoxy, fluoro substituted lower alkoxy, or cycloalkylamino, more preferably fluoro, chloro, methyl, trifluoromethyl, methoxy or morpholine.

In one embodiment of the methods provided herein, in compounds of Formula III, $L_4$ is —$CH_2$—, —$CH_2CH_2$—, —CH($CH_3$)— or —C(O)—, preferably —$CH_2$—, —$CH_2CH_2$—, or —C(O)—, $R^{81}$ is hydrogen, fluoro, chloro, —CN, lower alkyl, fluoro substituted lower alkyl, lower alkoxy, or fluoro substituted lower alkoxy, preferably hydrogen, chloro, methyl or —CN, $R^{82}$ is hydrogen, and $R^{83}$ is pyrrolidine, morpholine, pyridine, pyrimidine, pyrazine, pyrazole, isoxazole, imidazole, or benzimidazole, wherein $R^{83}$ is optionally substituted with 1 or 2 substituents independently selected from fluoro, chloro, lower alkyl, fluoro substituted lower alkyl, lower alkoxy, fluoro substituted lower alkoxy, or cycloalkylamino, preferably fluoro, chloro, methyl, trifluoromethyl, methoxy or morpholine.

In one embodiment of the methods provided herein, in compounds of Formula III, $L_4$ is —$CH_2$ or —C(O)—. In another embodiment of the methods provided herein, in compounds of Formula III, $R^{81}$ is selected from the group consisting of hydrogen, —CN, fluoro, chloro, lower alkyl, fluoro substituted lower alkyl, lower alkoxy, and fluoro substituted lower alkoxy. In yet another embodiment of the methods provided herein, in compounds of Formula III, $R^{82}$ is hydrogen. In still another embodiment of the methods provided herein, in compounds of Formula III, $R^{83}$ is nitrogen containing heteroaryl, wherein nitrogen containing heteroaryl is optionally substituted with one or two substituents selected from the group consisting of halogen, lower alkyl, fluoro substituted lower alkyl, cycloalkylamino, —$NHR^{41}$, —$NR^{41}R^{41}$, —$OR^{41}$ and —$S(O)_2R^{41}$. In another embodiment of the methods provided herein, in compounds of Formula III, $R^{41}$ at each occurrence is lower alkyl or cycloalkyl, wherein lower alkyl is optionally substituted with one or more fluoro.

In some embodiments of the methods provided herein, in compounds of Formula III, $L_4$ is —$CH_2$ or —C(O)—; $R^{81}$ is selected from the group consisting of hydrogen, —CN, fluoro, chloro, lower alkyl, fluoro substituted lower alkyl, lower alkoxy, and fluoro substituted lower alkoxy; $R^{82}$ is hydrogen; $R^{83}$ is, nitrogen containing heteroaryl, wherein nitrogen containing heteroaryl is optionally substituted with one or two substituents selected from the group consisting of halogen, lower alkyl, fluoro substituted lower alkyl, cycloalkylamino, —$NHR^{41}$, —$NR^{41}R^{41}$, —$OR^{41}$ and —$S(O)_2R^{41}$; and $R^{41}$ at each occurrence is lower alkyl or cycloalkyl, wherein lower alkyl is optionally substituted with one or more fluoro.

In one embodiment of the methods provided herein, in compounds of Formula III, the compound is selected from the group consisting of:
Pyridin-3-ylmethyl-[5-(1H-pyrrolo[2,3-b]pyridin-3-ylmethyl)-pyridin-2-yl]-amine (P-0094),
(5-Methyl-isoxazol-3-ylmethyl)-[5-(1H-pyrrolo[2,3-b]pyridin-3-ylmethyl)-pyridin-2-yl]-amine (P-0095),
(2-Pyrrolidin-1-yl-ethyl)-[5-(1H-pyrrolo[2,3-b]pyridin-3-ylmethyl)-pyridin-2-yl]-amine (P-0096),
[1-(4-Methanesulfonyl-phenyl)-ethyl]-[5-(1H-pyrrolo[2,3-b]pyridin-3-ylmethyl)-pyridin-2-yl]-amine (P-0097),
(2-Morpholin-4-yl-ethyl)-[5-(1H-pyrrolo[2,3-b]pyridin-3-ylmethyl)-pyridin-2-yl]-amine (P-0099), 3,4-Dichloro-N-[5-(1H-pyrrolo[2,3-b]pyridin-3-ylmethyl)-pyridin-2-yl]-benzamide (P-0100),
2-Chloro-4-fluoro-N-[5-(1H-pyrrolo[2,3-b]pyridin-3-ylmethyl)-pyridin-2-yl]-benzamide (P-0101),
2,5-Dimethyl-2H-pyrazole-3-carboxylic acid [5-(1H-pyrrolo[2,3-b]pyridin-3-ylmethyl)-pyridin-2-yl]-amide (P-0102),
Thiophene-2-carboxylic acid [5-(1H-pyrrolo[2,3-b]pyridin-3-ylmethyl)-pyridin-2-yl]-amide (P-0103),
2-Methoxy-N-[5-(1H-pyrrolo[2,3-b]pyridin-3-ylmethyl)-pyridin-2-yl]-isonicotinamide (P-0104),
N-[5-(1H-Pyrrolo[2,3-b]pyridin-3-ylmethyl)-pyridin-2-yl]-isonicotinamide (P-0105),
Pyrazine-2-carboxylic acid [5-(1H-pyrrolo[2,3-b]pyridin-3-ylmethyl)-pyridin-2-yl]-amide (P-0106),
Pyridine-2-carboxylic acid [5-(1H-pyrrolo[2,3-b]pyridin-3-ylmethyl)-pyridin-2-yl]-amide (P-0107),
6-Methyl-N-[5-(1H-pyrrolo[2,3-b]pyridin-3-ylmethyl)-pyridin-2-yl]-nicotinamide (P-0108),
4-Fluoro-3-methyl-N-[5-(1H-pyrrolo[2,3-b]pyridin-3-ylmethyl)-pyridin-2-yl]-benzamide (P-0109),
5-Methyl-pyrazine-2-carboxylic acid [5-(1H-pyrrolo[2,3-b]pyridin-3-ylmethyl)-pyridin-2-yl]-amide (P-0110),
3-Chloro-N-[5-(1H-pyrrolo[2,3-b]pyridin-3-ylmethyl)-pyridin-2-yl]-benzamide (P-0111),
4-Fluoro-N-[5-(1H-pyrrolo[2,3-b]pyridin-3-ylmethyl)-pyridin-2-yl]-3-trifluoromethyl-benzamide (P-0112),
N-[5-(1H-Pyrrolo[2,3-b]pyridin-3-ylmethyl)-pyridin-2-yl]-3-trifluoromethoxy-benzamide (P-0113),
N-[5-(1H-Pyrrolo[2,3-b]pyridin-3-ylmethyl)-pyridin-2-yl]-3-trifluoromethyl-benzamide (P-0114),
3-Chloro-4-fluoro-N-[5-(1H-pyrrolo[2,3-b]pyridin-3-ylmethyl)-pyridin-2-yl]-benzamide (P-0115),
3,4-Difluoro-N-[5-(1H-pyrrolo[2,3-b]pyridin-3-ylmethyl)-pyridin-2-yl]-benzamide (P-0116),
2-Chloro-N-[5-(1H-pyrrolo[2,3-b]pyridin-3-ylmethyl)-pyridin-2-yl]-benzamide (P-0117),
5-Fluoro-2-methyl-N-[5-(1H-pyrrolo[2,3-b]pyridin-3-ylmethyl)-pyridin-2-yl]-benzamide (P-0118),
2-Fluoro-N-[5-(1H-pyrrolo[2,3-b]pyridin-3-ylmethyl)-pyridin-2-yl]-benzamide (P-0119),
3-Methoxy-N-[5-(1H-pyrrolo[2,3-b]pyridin-3-ylmethyl)-pyridin-2-yl]-benzamide (P-0120),
3-Fluoro-N-[5-(1H-pyrrolo[2,3-b]pyridin-3-ylmethyl)-pyridin-2-yl]-benzamide (P-0121),
3-Methyl-N-[5-(1H-pyrrolo[2,3-b]pyridin-3-ylmethyl)-pyridin-2-yl]-benzamide (P-0122),
2-Chloro-N-[5-(1H-pyrrolo[2,3-b]pyridin-3-ylmethyl)-pyridin-2-yl]-isonicotinamide (P-0123),
((R)-1-Phenyl-ethyl)-[5-(1H-pyrrolo[2,3-b]pyridin-3-ylmethyl)-pyridin-2-yl]-amine (P-0125),
(3-Morpholin-4-yl-benzyl)-[5-(1H-pyrrolo[2,3-b]pyridin-3-ylmethyl)-pyridin-2-yl]-amine (P-0126),
[1-(2-Fluoro-phenyl)-ethyl]-[5-(1H-pyrrolo[2,3-b]pyridin-3-ylmethyl)-pyridin-2-yl]-amine (P-0127),
[2-(3-Fluoro-phenyl)-ethyl]-[5-(1H-pyrrolo[2,3-b]pyridin-3-ylmethyl)-pyridin-2-yl]-amine (P-0128),
(3-Chloro-benzyl)-[5-(1H-pyrrolo[2,3-b]pyridin-3-ylmethyl)-pyridin-2-yl]-amine (P-0129),
(1-Methyl-1H-imidazol-4-ylmethyl)-[5-(1H-pyrrolo[2,3-b]pyridin-3-ylmethyl)-pyridin-2-yl]-amine (P-0130),
(1,5-Dimethyl-1H-pyrazol-3-ylmethyl)-[5-(1H-pyrrolo[2,3-b]pyridin-3-ylmethyl)-pyridin-2-yl]-amine (P-0131),
[5-(5-Chloro-1H-pyrrolo[2,3-b]pyridin-3-ylmethyl)-pyridin-2-yl]-(6-trifluoromethyl-pyridin-3-ylmethyl)-amine (P-0181),
[5-(1H-Pyrrolo[2,3-b]pyridin-3-ylmethyl)-pyridin-2-yl]-(6-trifluoromethyl-pyridin-3-ylmethyl)-amine (P-0182),
(3-Chloro-pyridin-4-ylmethyl)-[5-(1H-pyrrolo[2,3-b]pyridin-3-ylmethyl)-pyridin-2-yl]-amine (P-0183),
(2-Chloro-6-fluoro-benzyl)-[5-(1H-pyrrolo[2,3-b]pyridin-3-ylmethyl)-pyridin-2-yl]-amine (P-0210),
Phenethyl-[5-(1H-pyrrolo[2,3-b]pyridin-3-ylmethyl)-pyridin-2-yl]-amine (P-0211),
(2,4-Difluoro-benzyl)-[5-(1H-pyrrolo[2,3-b]pyridin-3-ylmethyl)-pyridin-2-yl]-amine (P-0212),
(2-Fluoro-benzyl)-[5-(1H-pyrrolo[2,3-b]pyridin-3-ylmethyl)-pyridin-2-yl]-amine (P-0213),
(3-Bromo-pyridin-4-ylmethyl)-[5-(1H-pyrrolo[2,3-b]pyridin-3-ylmethyl)-pyridin-2-yl]-amine (P-0214),
(2-Methoxy-pyridin-3-ylmethyl)-[5-(1H-pyrrolo[2,3-b]pyridin-3-ylmethyl)-pyridin-2-yl]-amine (P-0215),
(2-Chloro-benzyl)-[5-(1H-pyrrolo[2,3-b]pyridin-3-ylmethyl)-pyridin-2-yl]-amine (P-0216),
(2-Methyl-benzyl)-[5-(1H-pyrrolo[2,3-b]pyridin-3-ylmethyl)-pyridin-2-yl]-amine (P-0217),
(1-Methyl-1H-benzoimidazol-2-ylmethyl)-[5-(1H-pyrrolo[2,3-b]pyridin-3-ylmethyl)-pyridin-2-yl]-amine (P-0218),
(6-Methoxy-pyridin-3-ylmethyl)-[5-(1H-pyrrolo[2,3-b]pyridin-3-ylmethyl)-pyridin-2-yl]-amine (P-0219),
(1H-Benzoimidazol-2-ylmethyl)-[5-(1H-pyrrolo[2,3-b]pyridin-3-ylmethyl)-pyridin-2-yl]-amine (P-0220),
(2-Chloro-4-fluoro-benzyl)-[5-(1H-pyrrolo[2,3-b]pyridin-3-ylmethyl)-pyridin-2-yl]-amine (P-0221),
(5-Methoxy-pyridin-3-ylmethyl)-[5-(1H-pyrrolo[2,3-b]pyridin-3-ylmethyl)-pyridin-2-yl]-amine (P-0222),
(3-Fluoro-pyridin-4-ylmethyl)-[5-(1H-pyrrolo[2,3-b]pyridin-3-ylmethyl)-pyridin-2-yl]-amine (P-0223),
(6-Methoxy-pyridin-2-ylmethyl)-[5-(1H-pyrrolo[2,3-b]pyridin-3-ylmethyl)-pyridin-2-yl]-amine (P-0224),
(4-Fluoro-2-trifluoromethyl-benzyl)-[5-(1H-pyrrolo[2,3-b]pyridin-3-ylmethyl)-pyridin-2-yl]-amine (P-0225),
[5-(1H-Pyrrolo[2,3-b]pyridin-3-ylmethyl)-pyridin-2-yl]-(2-trifluoromethyl-benzyl)-amine (P-0226),
(3,5-Dichloro-pyridin-4-ylmethyl)-[5-(1H-pyrrolo[2,3-b]pyridin-3-ylmethyl)-pyridin-2-yl]-amine (P-0227),
(6-Morpholin-4-yl-pyridin-2-ylmethyl)-[5-(1H-pyrrolo[2,3-b]pyridin-3-ylmethyl)-pyridin-2-yl]-amine (P-0228),
(3-Fluoro-pyridin-2-ylmethyl)-[5-(1H-pyrrolo[2,3-b]pyridin-3-ylmethyl)-pyridin-2-yl]-amine (P-0229),
(5-Fluoro-pyridin-3-ylmethyl)-[5-(1H-pyrrolo[2,3-b]pyridin-3-ylmethyl)-pyridin-2-yl]-amine (P-0230),
(3-Chloro-pyridin-4-ylmethyl)-[5-(5-chloro-1H-pyrrolo[2,3-b]pyridin-3-ylmethyl)-pyridin-2-yl]-amine (P-0235),
3-{6-[(3-Chloro-pyridin-4-ylmethyl)-amino]-pyridin-3-ylmethyl}-1H-pyrrolo[2,3-b]pyridine-5-carbonitrile (P-0256),
3-[6-(4-Chloro-benzylamino)-pyridin-3-ylmethyl]-1H-pyrrolo[2,3-b]pyridine-5-carbonitrile (P-0257),
Propane-1-sulfonic acid (2,4-difluoro-3-{[5-(1H-pyrrolo[2,3-b]pyridin-3-ylmethyl)-pyridin-2-ylamino]-methyl}-phenyl)-amide (P-0258),
Propane-1-sulfonic acid (3-{[5-(5-chloro-1H-pyrrolo[2,3-b]pyridin-3-ylmethyl)-pyridin-2-ylamino]-methyl}-2,4-difluoro-phenyl)-amide (P-0259),
3-[6-(4-Trifluoromethyl-benzylamino)-pyridin-3-ylmethyl]-1H-pyrrolo[2,3-b]pyridine-5-carbonitrile (P-0269),
[5-(5-Chloro-1H-pyrrolo[2,3-b]pyridin-3-ylmethyl)-pyridin-2-yl]-(2-fluoro-benzyl)-amine (P-0270),
3-[6-(2-Fluoro-benzylamino)-pyridin-3-ylmethyl]-1H-pyrrolo[2,3-b]pyridine-5-carbonitrile (P-0271), (2-Fluoro-benzyl)-[5-(5-methyl-1H-pyrrolo[2,3-b]pyridin-3-ylmethyl)-pyridin-2-yl]-amine (P-0272),
3-{6-[(6-Trifluoromethyl-pyridin-3-ylmethyl)-amino]-pyridin-3-ylmethyl}-1H-pyrrolo[2,3-b]pyridine-5-carbonitrile (P-0273),
3-[6-(2-Trifluoromethyl-benzylamino)-pyridin-3-ylmethyl]-1H-pyrrolo[2,3-b]pyridine-5-carbonitrile (P-0274),
[5-(5-Chloro-1H-pyrrolo[2,3-b]pyridin-3-ylmethyl)-pyridin-2-yl]-(2-trifluoromethyl-benzyl)-amine (P-0275),
[5-(5-Methyl-1H-pyrrolo[2,3-b]pyridin-3-ylmethyl)-pyridin-2-yl]42-trifluoromethyl-benzyl)-amine (P-0276),
3-[6-(2,6-Difluoro-benzylamino)-pyridin-3-ylmethyl]-1H-pyrrolo[2,3-b]pyridine-5-carbonitrile (P-0277),
[5-(5-Chloro-1H-pyrrolo[2,3-b]pyridin-3-ylmethyl)-pyridin-2-yl]-(2,6-difluoro-benzyl)-amine (P-0278),
(2-Chloro-benzyl)-[5-(5-methyl-1H-pyrrolo[2,3-b]pyridin-3-ylmethyl)-pyridin-2-yl]-amine (P-0279),
(2-Chloro-benzyl)-[5-(5-chloro-1H-pyrrolo[2,3-b]pyridin-3-ylmethyl)-pyridin-2-yl]-amine (P-0280),
3-[6-(2-Chloro-benzylamino)-pyridin-3-ylmethyl]-1H-pyrrolo[2,3-b]pyridine-5-carbonitrite (P-0281),
(6-Methoxy-pyridin-3-ylmethyl)-[5-(5-methyl-1H-pyrrolo[2,3-b]pyridin-3-ylmethyl)-pyridin-2-yl]-amine (P-0282),
[5-(5-Chloro-1H-pyrrolo[2,3-b]pyridin-3-ylmethyl)-pyridin-2-yl]-(6-methoxy-pyridin-3-ylmethyl)-amine (P-0283),
3-{6-[(6-Methoxy-pyridin-3-ylmethyl)-amino]-pyridin-3-ylmethyl}-1H-pyrrolo[2,3-b]pyridine-5-carbonitrile (P-0284),
(2-Methoxy-pyridin-3-ylmethyl)-[5-(5-methyl-1H-pyrrolo[2,3-b]pyridin-3-ylmethyl)-pyridin-2-yl]amine (P-0285),
[5-(5-Chloro-1H-pyrrolo[2,3-b]pyridin-3-ylmethyl)-pyridin-2-yl]-(2-methoxy-pyridin-3-ylmethyl)-amine (P-0286),
3-{6-[(2-Methoxy-pyridin-3-ylmethyl)-amino]-pyridin-3-ylmethyl}-1H-pyrrolo[2,3-b]pyridine-5-carbonitrile (P-0287),
(2-Ethoxy-benzyl)-[5-(1H-pyrrolo[2,3-b]pyridin-3-ylmethyl)-pyridin-2-yl]-amine (P-0288),
(2,5-Difluoro-benzyl)-[5-(1H-pyrrolo[2,3-b]pyridin-3-ylmethyl)-pyridin-2-yl]-amine (P-0296),
(2,5-Difluoro-benzyl)-[5-(5-methyl-1H-pyrrolo[2,3-b]pyridin-3-ylmethyl)-pyridin-2-yl]-amine (P-0297),
[5-(5-Chloro-1H-pyrrolo[2,3-b]pyridin-3-ylmethyl)-pyridin-2-yl]-(2,5-difluoro-benzyl)-amine (P-0298),
3-[6-(2,5-Difluoro-benzylamino)-pyridin-3-ylmethyl]-1H-pyrrolo[2,3-b]pyridine-5-carbonitrile (P-0299),
3-[6-(2-Trifluoromethoxy-benzylamino)-pyridin-3-ylmethyl]-1H-pyrrolo[2,3-b]pyridine-5-carbonitrile (P-0321),
[5-(1H-Pyrrolo[2,3-b]pyridin-3-ylmethyl)-pyridin-2-yl]-(2-trifluoromethoxy-benzyl)-amine (P-0322),
3-[6-(2-Ethoxy-benzylamino)-pyridin-3-ylmethyl]-1H-pyrrolo[2,3-b]pyridine-5-carbonitrile (P-0323),
[5-(5-Chloro-1H-pyrrolo[2,3-b]pyridin-3-ylmethyl)-pyridin-2-yl]-(5-fluoro-pyridin-3-ylmethyl)-amine (P-0324),
[5-(5-Fluoro-1H-pyrrolo[2,3-b]pyridin-3-ylmethyl)-pyridin-2-yl]-(2-trifluoromethyl-benzyl)-amine (P-0325),
[5-(5-Methoxy-1H-pyrrolo[2,3-b]pyridin-3-ylmethyl)-pyridin-2-yl]-(2-trifluoromethyl-benzyl)-amine (P-0326),
(2-Chloro-benzyl)-[5-(5-fluoro-1-pyrrolo[2,3-b]pyridin-3-ylmethyl)-pyridin-2-yl]-amine (P-0327),
(2-Chloro-benzyl)-[5-(5-methoxy-1-pyrrolo[2,3-b]pyridin-3-ylmethyl)-pyridin-2-yl]-amine (P-0328),
(2,5-Difluoro-benzyl)-[5-(5-fluoro-1H-pyrrolo[2,3-b]pyridin-3-ylmethyl)-pyridin-2-yl]-amine (P-0329),
(2,5-Difluoro-benzyl)-[5-(5-methoxy-1H-pyrrolo[2,3-b]pyridin-3-ylmethyl)-pyridin-2-yl]-amine (P-0330),
[5-(5-Fluoro-1H-pyrrolo[2,3-b]pyridin-3-ylmethyl)-pyridin-2-yl]-(6-methoxy-pyridin-3-ylmethyl)-amine (P-0331),
(6-Methoxy-pyridin-3-ylmethyl)-[5-(5-methoxy-1H-pyrrolo[2,3-b]pyridin-3-ylmethyl)-pyridin-2-yl]-amine (P-0332),
(2,6-Difluoro-benzyl)-[5-(5-fluoro-1H-pyrrolo[2,3-b]pyridin-3-ylmethyl)-pyridin-2-yl]-amine (P-0333),
(2,6-Difluoro-benzyl)-[5-(5-methoxy-1H-pyrrolo[2,3-b]pyridin-3-ylmethyl)-pyridin-2-yl]-amine (P-0334),
(2-Methoxy-benzyl)-[5-(1H-pyrrolo[2,3-b]pyridin-3-ylmethyl)-pyridin-2-yl]-amine (P-0336),
3-[6-(2-Methoxy-benzylamino)-pyridin-3-ylmethyl]-1H-pyrrolo[2,3-b]pyridine-5-carbonitrile (P-0337),
[5-(5-Chloro-1H-pyrrolo[2,3-b]pyridin-3-ylmethyl)-pyridin-2-yl]-(2-difluoromethoxy-benzyl)-amine (P-0338),
3-[6-(2-Difluoromethoxy-benzylamino)-pyridin-3-ylmethyl]-1H-pyrrolo[2,3-b]pyridine-5-carbonitrile (P-0339),
(2,6-Difluoro-benzyl)-[5-(1H-pyrrolo[2,3-b]pyridin-3-ylmethyl)-pyridin-2-yl]-amine (P-0340),
(2,6-Difluoro-benzyl)-[5-(5-methyl-1H-pyrrolo[2,3-b]pyridin-3-ylmethyl)-pyridin-2-yl]-amine (P-0341),
(2,4-Dichloro-benzyl)-[5-(1H-pyrrolo[2,3-b]pyridin-3-ylmethyl)-pyridin-2-yl]-amine (P-0342),
(3-Fluoro-benzyl)-[5-(1H-pyrrolo[2,3-b]pyridin-3-ylmethyl)-pyridin-2-yl]-amine (P-0343),
(2-Fluoro-4-trifluoromethyl-benzyl)-[5-(1H-pyrrolo[2,3-b]pyridin-3-ylmethyl)-pyridin-2-yl]-amine (P-0344),
(4-Chloro-2-fluoro-benzyl)-[5-(1H-pyrrolo[2,3-b]pyridin-3-ylmethyl)-pyridin-2-yl]-amine (P-0345),
(3-Fluoro-5-trifluoromethyl-benzyl)-[5-(1H-pyrrolo[2,3-b]pyridin-3-ylmethyl)-pyridin-2-yl]-amine (P-0346),
(2-Morpholin-4-yl-pyridin-3-ylmethyl)-[5-(1H-pyrrolo[2,3-b]pyridin-3-ylmethyl)-pyridin-2-yl]-amine (P-0347),
(4-Chloro-3-trifluoromethyl-benzyl)-[5-(1H-pyrrolo[2,3-b]pyridin-3-ylmethyl)-pyridin-2-yl]-amine (P-0348),
(2-Chloro-5-trifluoromethyl-benzyl)-[5-(1H-pyrrolo[2,3-b]pyridin-3-ylmethyl)-pyridin-2-yl]-amine (P-0349),
(2-Fluoro-5-trifluoromethyl-benzyl)-[5-(1H-pyrrolo[2,3-b]pyridin-3-ylmethyl)-pyridin-2-yl]-amine (P-0350),
(2,3-Dichloro-benzyl)-[5-(1H-pyrrolo[2,3-b]pyridin-3-ylmethyl)-pyridin-2-yl]-amine (P-0351),
(2-Fluoro-3-methoxy-benzyl)-[5-(1H-pyrrolo[2,3-b]pyridin-3-ylmethyl)-pyridin-2-yl]-amine (P-0352),
Dimethyl-(5-{[5-(1H-pyrrolo[2,3-b]pyridin-3-ylmethyl)-pyridin-2-ylamino]-methyl}-pyrimidin-2-yl)-amine (P-0353),
(3-Chloro-2-fluoro-benzyl)-[5-(1H-pyrrolo[2,3-b]pyridin-3-ylmethyl)-pyridin-2-yl]-amine (P-0354),
(5-Fluoro-pyridin-2-ylmethyl)-[5-(1H-pyrrolo[2,3-b]pyridin-3-ylmethyl)-pyridin-2-yl]-amine (P-0355),
(3,5-Difluoro-benzyl)-[5-(1H-pyrrolo[2,3-b]pyridin-3-ylmethyl)-pyridin-2-yl]-amine (P-0356),
(2-Prop oxy-benzyl)-[5-(1H-pyrrolo[2,3-b]pyridin-3-ylmethyl)-pyridin-2-yl]-amine (P-0357),
(2-Morpholin-4-yl-benzyl)-[5-(1H-pyrrolo[2,3-b]pyridin-3-ylmethyl)-pyridin-2-yl]-amine (P-0358),
(2-Chloro-3-methoxy-benzyl)-[5-(1H-pyrrolo[2,3-b]pyridin-3-ylmethyl)-pyridin-2-yl]-amine (P-0359),
(2-Fluoro-6-trifluoromethyl-benzyl)-[5-(1H-pyrrolo[2,3-b]pyridin-3-ylmethyl)-pyridin-2-yl]-amine (P-0360),
[2-(2-Morpholin-4-yl-ethoxy)-benzyl]-[5-(1H-pyrrolo[2,3-b]pyridin-3-ylmethyl)-pyridin-2-yl]-amine (P-0361), (2,3-Difluoro-benzyl)-[5-(1H-pyrrolo[2,3-b]pyridin-3-ylmethyl)-pyridin-2-yl]-amine (P-0362),
(2-Chloro-3-trifluoromethyl-benzyl)-[5-(1H-pyrrolo[2,3-b]pyridin-3-ylmethyl)-pyridin-2-yl]-amine (P-0363),
(2-Chloro-5-fluoro-benzyl)-[5-(1H-pyrrolo[2,3-b]pyridin-3-ylmethyl)-pyridin-2-yl]-amine (P-0364),
(2-Fluoro-3-trifluoromethyl-benzyl)-[5-(1H-pyrrolo[2,3-b]pyridin-3-ylmethyl)-pyridin-2-yl]-amine (P-0365),
(5-Fluoro-2-methoxy-benzyl)-[5-(1H-pyrrolo[2,3-b]pyridin-3-ylmethyl)-pyridin-2-yl]-amine (P-0366),
(2-Difluoromethoxy-benzyl)-[5-(1H-pyrrolo[2,3-b]pyridin-3-ylmethyl)-pyridin-2-yl]-amine (P-0367),
(2-Fluoro-4-methyl-benzyl)-[5-(1H-pyrrolo[2,3-b]pyridin-3-ylmethyl)-pyridin-2-yl]-amine (P-0368),
[2-(3-Dimethylamino-propoxy)-benzyl]-[5-(1H-pyrrolo[2,3-b]pyridin-3-ylmethyl)-pyridin-2-yl]-amine (P-0369),
(2,6-Dimethoxy-pyridin-3-ylmethyl)-[5-(1H-pyrrolo[2,3-b]pyridin-3-ylmethyl)-pyridin-2-yl]-amine (P-0370),
(2-Fluoro-5-methoxy-benzyl)-[5-(1H-pyrrolo[2,3-b]pyridin-3-ylmethyl)-pyridin-2-yl]-amine (P-0371),
(4-Fluoro-2-methyl-benzyl)-[5-(1H-pyrrolo[2,3-b]pyridin-3-ylmethyl)-pyridin-2-yl]-amine (P-0372),
(3-Chloro-5-fluoro-benzyl)-[5-(1H-pyrrolo[2,3-b]pyridin-3-ylmethyl)-pyridin-2-yl]-amine (P-0373),
(6-Cyclopentyloxy-pyridin-3-ylmethyl)-[5-(1H-pyrrolo[2,3-b]pyridin-3-ylmethyl)-pyridin-2-yl]-amine (P-0374),
(5-Fluoro-2-trifluoromethyl-benzyl)-[5-(1H-pyrrolo[2,3-b]pyridin-3-ylmethyl)-pyridin-2-yl]-amine (P-0375),
[5-(1H-Pyrrolo[2,3-b]pyridin-3-ylmethyl)-pyridin-2-yl]-[2-(2,2,2-trifluoro-ethoxy)-pyridin-3-ylmethyl]-amine (P-0376),
Propane-1-sulfonic acid (2-fluoro-3-{[5-(1H-pyrrolo[2,3-b]pyridin-3-ylmethyl)-pyridin-2-ylamino]-methyl}-phenyl)-amide (P-0377),
(2,5-Dichloro-benzyl)-[5-(1H-pyrrolo[2,3-b]pyridin-3-ylmethyl)-pyridin-2-yl]-amine (P-0380),
Pyrimidin-5-ylmethyl-[5-(1H-pyrrolo[2,3-b]pyridin-3-ylmethyl)-pyridin-2-yl]-amine (P-0381),
(5-Chloro-2-fluoro-benzyl)-[5-(1H-pyrrolo[2,3-b]pyridin-3-ylmethyl)-pyridin-2-yl]-amine (P-0382),
(2-Ethyl-benzyl)-[5-(1H-pyrrolo[2,3-b]pyridin-3-ylmethyl)-pyridin-2-yl]-amine (P-0383),
2,2-Dimethyl-N-(3-{[5-(1H-pyrrolo[2,3-b]pyridin-3-ylmethyl)-pyridin-2-ylamino]-methyl}-pyridin-2-yl)-propionamide (P-0384),
Methyl-(3-{[5-(1H-pyrrolo[2,3-b]pyridin-3-ylmethyl)-pyridin-2-ylamino]-methyl}-pyridin-2-yl)-amine (P-0385),
Methyl-(5-{[5-(1H-pyrrolo[2,3-b]pyridin-3-ylmethyl)-pyridin-2-ylamino]-methyl}-pyrimidin-2-yl)-amine (P-0386),
(2-Chloro-4-methanesulfonyl-benzyl)-[5-(1H-pyrrolo[2,3-b]pyridin-3-ylmethyl)-pyridin-2-yl]-amine (P-0387),
{5-[1-(1H-Pyrrolo[2,3-b]pyridin-3-yl)-ethyl]-pyridin-2-yl}-(4-trifluoromethyl-benzyl)-amine (P-0388),
(5-Fluoro-2-methyl-benzyl)-[5-(1H-pyrrolo[2,3-b]pyridin-3-ylmethyl)-pyridin-2-yl]-amine (P-0397),
Dimethyl-(3-{[5-(1H-pyrrolo[2,3-b]pyridin-3-ylmethyl)-pyridin-2-ylamino]-methyl}-pyridin-2-yl)-amine (P-0399),
(5-Chloro-pyridin-3-ylmethyl)-[5-(1H-pyrrolo[2,3-b]pyridin-3-ylmethyl)-pyridin-2-yl]-amine (P-0400),
(2-Methoxy-pyrimidin-5-ylmethyl)-[5-(1H-pyrrolo[2,3-b]pyridin-3-ylmethyl)-pyridin-2-yl]-amine (P-0401),
[5-(5-Chloro-1H-pyrrolo[2,3-b]pyridin-3-ylmethyl)-pyridin-2-yl]-[6-(2,2,2-trifluoro-ethoxy)-pyridin-3-ylmethyl]-amine (P-0409) and
1-(3-Fluoro-phenyl)-3-[5-(1H-pyrrolo[2,3-b]pyridin-3-ylmethyl)-pyridin-2-yl]-urea (P-0412), or
all salts, prodrugs, tautomers, or isomers thereof.

In one embodiment of the methods provided herein, the compound is:
(4-Chloro-benzyl)-[6-(1H-pyrrolo[2,3-b]pyridin-3-ylmethyl)-pyridazin-3-yl]-amine (P-0092),
(4-Morpholin-4-ylmethyl-benzyl)-[5-(1H-pyrrolo[2,3-b]pyridin-3-ylmethyl)-pyridin-2-yl]-amine (P-0093),
(2-Methoxy-ethyl)-[5-(1H-pyrrolo[2,3-b]pyridin-3-ylmethyl)-pyridin-2-yl]-amine (P-0098),
[4-Chloro-1-ethyl-5-(1H-pyrrolo[2,3-b]pyridin-3-ylmethyl)-1H-pyrazol-3-yl]-[1-(4-fluoro-phenyl)-meth-(E)-ylidene]-amine (P-0166) or
((2,2-Difluoro-benzo[1,3]dioxol-4-ylmethyl)-[5-(1H-pyrrolo[2,3-b]pyridin-3-ylmethyl)-pyridin-2-yl]-amine (P-0398); or
all salts, prodrugs, tautomers, or isomers thereof.

In one embodiment of the methods provided herein, the compound is selected from:
3-(6-tert-Butoxy-pyridin-3-ylmethyl)-1H-pyrrolo[2,3-b]pyridine (P-0020),
3-(6-Methoxy-pyridin-3-ylmethyl)-4-thiophen-3-yl-1H-pyrrolo[2,3-b]pyridine (P-0022),
(6-Isobutylamino-pyridin-3-yl)-(1H-pyrrolo[2,3-b]pyridin-3-yl)-methanol (P-0029),
[6-(Cyclopropylmethyl-amino)-pyridin-3-yl]-(1H-pyrrolo[2,3-b]pyridin-3-yl)-methanol (P-0034),
[6-(Cyclohexylmethyl-amino)-pyridin-3-yl]-(1H-pyrrolo[2,3-b]pyridin-3-yl)-methanol (P-0035),
(1H-Pyrrolo[2,3-b]pyridin-3-yl)-[6-(4-trifluoromethyl-benzylamino)-pyridin-3-yl]-methanol (P-0036),
[6-(4-Chloro-benzylamino)-pyridin-3-yl]-(1H-pyrrolo[2,3-b]pyridin-3-yl)-methanol (P-0037),
(4-Chloro-benzyl)-{5-[methoxy-(1H-pyrrolo[2,3-b]pyridin-3-yl)-methyl]-pyridin-2-yl}-amine (P-0039),
(4-Chloro-3-trifluoromethyl-benzyl)-{5-[methoxy-(1H-pyrrolo[2,3-b]pyridin-3-yl)-methyl]-pyridin-2-yl}-amine (P-0040),
(4-Chloro-benzyl)-{5-[methoxy-(5-pyridin-3-yl-1H-pyrrolo[2,3-b]pyridin-3-yl)-methyl]-pyridin-2-yl}-amine (P-0041),
[6-(4-Chloro-benzylamino)-2-methyl-pyridin-3-yl]-(1H-pyrrolo[2,3-b]pyridin-3-yl)-methanol (P-0046),
[2,6-Bis-(4-chloro-benzylamino)-pyridin-3-yl]-(1H-pyrrolo[2,3-b]pyridin-3-yl)-methanone (P-0049), and
3-(2-Ethylsulfanyl-4,6-dimethyl-pyrimidin-5-ylmethyl)-1H-pyrrolo[2,3-b]pyridine (P-0052), or
all salts, prodrugs, tautomers, or isomers thereof.

In certain embodiments of the methods provided herein, in above compounds, compounds are excluded where N (except where N is a heteroaryl ring atom), O, or S is bound to a carbon that is also bound to N (except where N is a heteroaryl ring atom), O, or S, except where the carbon forms a double bond with one of the heteroatoms, such as in an amide, carboxylic acid, and the like; or where N (except where N is a heteroaryl ring atom), O, C(S), C(O), or S(O)$_n$ (n is 0-2) is bound to an alkene carbon of an alkenyl group or bound to an alkyne carbon of an alkynyl group; accordingly, in certain embodiments compounds which include linkages such as the following are excluded from the present invention: —NR—CH$_2$—NR—, —O—CH$_2$—NR—, —S—CH$_2$—NR—, —NR—CH$_2$—O—, —O—CH$_2$—O—, —S—CH$_2$—O—, —NR—CH$_2$—S—, —O—CH$_2$—S—, —S—CH$_2$—S—, —NR—CH═CH—, —CH═CH—NR—, —NR—C≡C—, —C≡C—NR—, —O—CH═CH—, —CH═CH—O—, —O—C≡C—, —C≡C—O—, —S(O)$_{0-2}$—CH═CH—, —CH═CH—S(O)$_{0-2}$—, —S(O)$_{0-2}$—C≡C—, —C≡C—S(O)$_{0-2}$—, —C(O)—CH═CH—, —CH═CH—C(O)—, —C≡C—C(O)—, or —C(O)—C≡C—, —C(S)—CH═CH—, —CH═CH—C(S)—, —C≡C—C(S)—, or —C(S)—C≡C—.

In reference to compounds in the methods provided herein, specification of a compound or group of compounds includes pharmaceutically acceptable salts of such compound(s), prodrug(s), and all stereoisomers, unless clearly indicated to the contrary. In reference to compounds of Formula II, unless clearly indicated to the contrary, it is understood that such reference includes compounds of Formulae IIa, IIb, IIc, IId, IIe, IIf, IIg, IIh, IIi, IIj, IIk, IIm, IIn, and IIp, and all sub-embodiments thereof.

In another aspect, the invention provides methods for treating a mutant Flt3-mediated or Flt3-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal Flt3 activity (e.g. kinase activity). Invention methods involve administering to the subject suffering from or at risk of a Flt3-mediated disease or condition an effective amount of a compound of Formula II or Formula III, and all sub-embodiments thereof. In one embodiment, the Flt3 mediated disease is selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis. In another embodiment, the Flt3 mediated disease is selected from axonal degeneration, acute transverse myelitis, amyotrophic lateral sclerosis, infantile spinal muscular atrophy, juvenile spinal muscular atrophy, Creutzfeldt-Jakob disease, subacute sclerosing panencephalitis, organ rejection, bone marrow transplant rejection, non-myeloablative bone marrow transplant rejection, ankylosing spondylitis, aplastic anemia, Behcet's disease, graft-versus-host disease, Graves' disease, autoimmune hemolytic anemia, Wegener's granulomatosis, hyper IgE syndrome, idiopathic thrombocytopenia purpura, or Myasthenia gravis.

In a related aspect, compounds of Formula II or Formula III, and all sub-embodiments thereof, can be used in the preparation of a medicament for the treatment of a Flt3-mediated or a mutant Flt3-mediated disease or condition selected from the group consisting of malignancies, including, but not limited to, acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis In a further aspect, the invention provides methods for treating a Flt3-mediated or a mutant Flt3-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal Flt3 activity (e.g. kinase activity). Invention methods involve administering to the subject suffering from or at risk of a Flt3-mediated disease or condition an effective amount of compound of Formula II or Formula III, and all sub-embodiments thereof. In one embodiment, the Flt3 mediated or mutant Flt3-mediated disease is selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In a related aspect, compounds of Formula II or Formula III, and all sub-embodiments thereof, can be used in the preparation of a medicament for the treatment of a Flt3-mediated or a mutant Flt3-mediated disease or condition selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In a further aspect, the invention provides methods for treating a Flt3-mediated or a mutant Flt3-mediated disease or condition in an animal subject (e.g. a mammal such as a human, other primates, sports animals, animals of commercial interest such as cattle, farm animals such as horses, or pets such as dogs and cats), e.g., a disease or condition characterized by abnormal Flt3 activity (e.g. kinase activity). Invention methods involve administering to the subject suffering from or at risk of a Flt3-mediated or a mutant Flt3-mediated disease or condition an effective amount of compound of Formula I, Formula Ia, Formula Ib, or Formula Ig, and all sub-embodiments thereof. In one embodiment, the Flt3 mediated disease is selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In a related aspect, compounds of Formula I, Formula Ia, Formula Ib, or Formula Ig, and all sub-embodiments thereof, can be used in the preparation of a medicament for the treatment of a Flt3-mediated or a mutant Flt3-mediated disease or condition selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In a further aspect, the invention provides methods for treating, in an animal subject (e.g. a mammal such as a human, other primates, sports animals, animals of commercial interest such as cattle, farm animals such as horses, or pets such as dogs and cats), a disease or condition mediated by oncogenic Flt3, e.g., a disease or condition characterized by abnormal Flt3 activity (e.g. kinase activity). Invention methods involve administering to the subject suffering from or at risk of a disease or condition mediated by Flt3 an effective amount of compound of Formula II or Formula III, and all sub-embodiments thereof. In one embodiment, the condition mediated by Flt3 is selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In a related aspect, compounds of Formula II or Formula III, and all sub-embodiments thereof, can be used in the preparation of a medicament for the treatment of a Flt3-mediated or a mutant Flt3-mediated disease or condition selected from the group consisting of acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

In particular embodiments, the compound has an $IC_{50}$ of less than 100 nM, less than 50 nM, less than 20 nM, less than 10 nM, or less than 5 nM as determined in a generally accepted kinase activity assay. In certain embodiments, the selectivity of the compound is such that the compound is at least 2-fold, 5-fold, 10-fold, or 100-fold more active on oncogenic or mutant Flt3 than wild type Flt3. In certain embodiments, the selectivity of the compound is such that the compound is at least 2-fold, 5-fold, 10-fold, or 100-fold more active oncogenic Flt3 than wild type Flt3. In certain embodiments, the selectivity of the compound is such that the compound is at least 2-fold, 5-fold, 10-fold, or 100-fold more active on oncogenic Flt3 than wild type Flt3. In certain embodiments, the compound has in combination each pairing of activity (e.g. $IC_{50}$) and/or selectivity as specified in this paragraph.

In particular embodiments, the compound has an $IC_{50}$ of less than 100 nM, less than 50 nM, less than 20 nM, less than 10 nM, or less than 5 nM as determined in a generally accepted kinase activity assay for Flt3 kinase activity. In certain embodiments, the selectivity of the compound is such that the compound is at least 2-fold, 5-fold, 10-fold, or 100-fold more active on oncogenic Flt3 than on wild type Flt3.

In particular embodiments, the compound has an $IC_{50}$ of less than 100 nM, less than 50 nM, less than 20 nM, less than 10 nM, or less than 5 nM as determined in a generally accepted kinase activity assay for Flt3 kinase activity, and further has an $IC_{50}$ of less than 100 nM, less than 50 nM, less than 20 nM, less than 10 nM, or less than 5 nM as determined in a generally accepted kinase activity.

An additional aspect of this invention relates to compositions that include a therapeutically effective amount of a compound of Formula II or Formula III and all sub-embodiments thereof and at least one pharmaceutically acceptable carrier, excipient, and/or diluent, including combinations of any two or more compounds of Formula II or Formula III. The composition can further include one or more different pharmacologically active compounds, which can include one or more compounds of Formula I (including Formula Ia, Ib, and Ig, and all sub-embodiments thereof), Formula II or Formula III.

In one aspect, the invention provides a method of treating a cancer by administering to the subject an effective amount of a composition including a compound of Formula II or Formula III, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one aspect, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, and bone marrow and stem cell transplantation.

In one aspect, the invention provides a method of treating a cancer by administering to the subject an effective amount of a composition including a compound of Formula II or Formula III, in combination with one or more suitable chemotherapeutic agents. In one aspect, the one or more suitable chemotherapeutic agents is selected from an alkylating agent, including, but not limited to, adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, oxaliplatin, piposulfan, semustine, streptozocin, temozolomide, thiotepa, and treosulfan; an antibiotic, including, but not limited to, bleomycin, dactinomycin, daunorubicin, doxorubicin, epirubicin, idarubicin, menogaril, mitomycin, mitoxantrone, neocarzinostatin, pentostatin, and plicamycin; an antimetabolite, including, but not limited to, azacitidine, capecitabine, cladribine, clofarabine, cytarabine, decitabine, floxuridine, fludarabine, 5-fluorouracil, ftorafur, gemcitabine, hydroxyurea, mercaptopurine, methotrexate, nelarabine, pemetrexed, raltitrexed, thioguanine, and trimetrexate; an immunotherapy, including, but not limited to, alemtuzumab, bevacizumab, cetuximab, galiximab, gemtuzumab, panitumumab, pertuzumab, rituximab, tositumomab, trastuzumab, and 90 Y ibritumomab tiuxetan; a hormone or hormone antagonist, including, but not limited to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limited to, DJ-927, docetaxel, TPI 287, paclitaxel and DHA-paclitaxel; a retinoid, including, but not limited to, alitretinoin, bexarotene, fenretinide, isotretinoin, and tretinoin; an alkaloid, including, but not limited to, etoposide, homoharringtonine, teniposide, vinblastine, vincristine, vindesine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, edotecarin, exatecan, irinotecan (also active metabolite SN-38 (7-ethyl-10-hydroxy-camptothecin)), rubitecan, topotecan, and 9-aminocamptothecin; a kinase inhibitor, including, but not limited to, erlotinib, gefitinib, flavopiridol, imatinib mesylate, lapatinib, sorafenib, sunitinib malate, AEE-788, AG-013736, AMG 706, AMN107, BMS-354825, BMS-599626, UCN-01 (7-hydroxystaurosporine), vemurafenib, dabrafenib and vatalanib; a targeted signal transduction inhibitor including, but not limited to bortezomib, geldanamycin, and rapamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), aminoglutethimide, asparaginase, bryostatin-1, cilengitide, E7389, ixabepilone, procarbazine, sulindac, temsirolimus, tipifarnib. Preferably, the method of treating a cancer involves administering to the subject an effective amount of a composition of Formula II, Formula III or Formula IV in combination with a chemotherapeutic agent selected from 5-fluorouracil, carboplatin, dacarbazine, gefitinib, oxaliplatin, paclitaxel, SN-38, temozolomide, vinblastine, bevacizumab, cetuximab, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, PD98059, RDEA119(BAY 869766), TAK-733 and U0126-EtOH.

In another aspect, the invention provides a method of treating or prophylaxis of a disease or condition in a mammal, by administering to the mammal a therapeutically effective amount of a compound of Formula II or Formula III, a prodrug of such compound, or a pharmaceutically acceptable salt of such compound or prodrug. The compound can be alone or can be part of a composition.

In another aspect, the present invention also provides a method for modulating Flt3 activity by contacting a Flt3 or a mutant Flt3 with administering an effective amount of a compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III and all sub-embodiments thereof and all the compounds described herein. The compound is preferably provided at a level sufficient to modulate the activity of the Flt3 by at least 10%, more preferably at least 20%, 30%, 40%, 50%, 60%, 70%, 80%, 90%, or greater than 90%. In many embodiments, the compound will be at a concentration of about 1 µM, 100 µM, or 1 mM, or in a range of 1-100 nM, 100-500 nM, 500-1000 nM, 1-100 µM, 100-500 µM, or 500-1000 µM. In some embodiments, the contacting is carried out in vitro. In other embodiments, the contacting is carried out in vivo.

Additional aspects and embodiments will be apparent from the following Drawings and Detailed Description and from the claims.

DETAILED DESCRIPTION OF THE PREFERRED EMBODIMENTS

Figure 1:
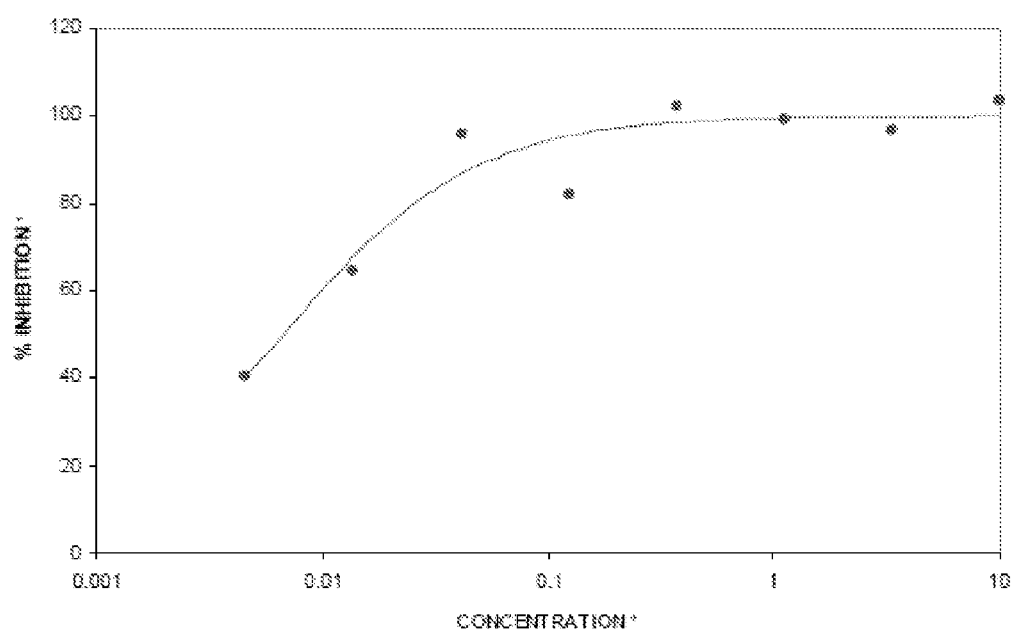
FIG. 1 demonstrates CSF stimulated pFMS in THP1 cells (ELISA) with a compound as described herein.
Figure 2:
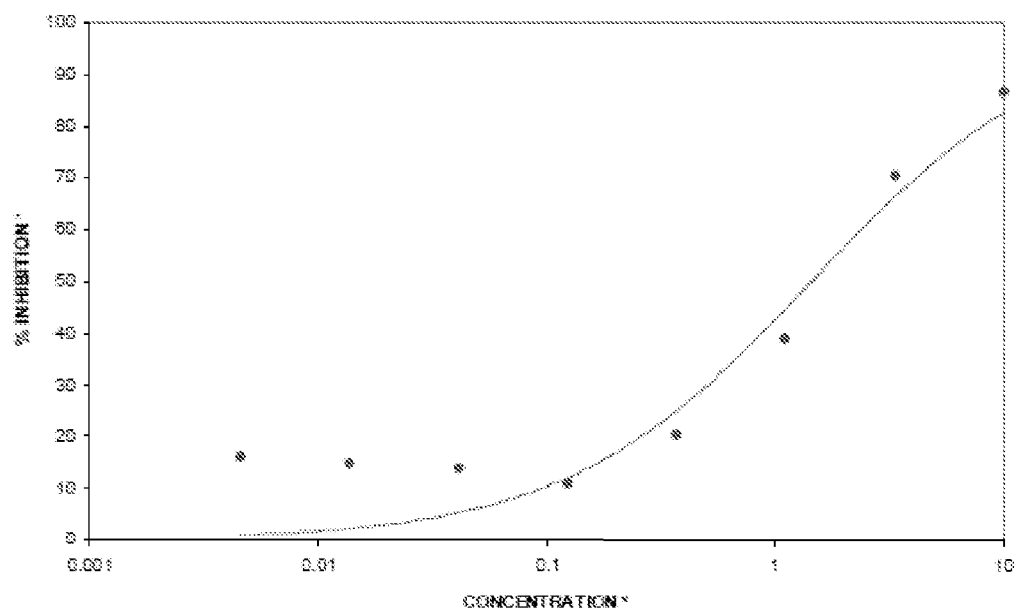
FIG. 2 demonstrates FLT-ligand stimulated pFLT3 in RS4; 11 cells with a compound as described herein.
Figure 3:
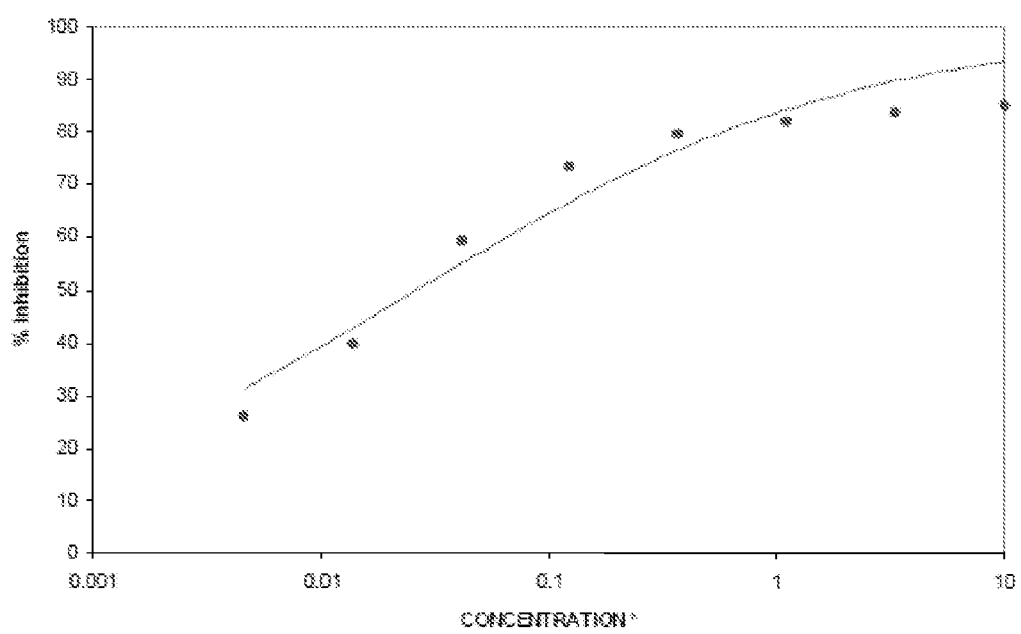
FIG. 3 demonstrates phospho-FLT3 inhibition in ITD-activated FLT3 MV-4-11 cells with a compound as described herein.

As used herein the following definitions apply:

"Halo" and "halogen" refer to all halogens, that is, chloro (Cl), fluoro (F), bromo (Br), or iodo (I).

"Hydroxyl" and "hydroxy" refer to the group —OH.

"Thiol" refers to the group —SH.

"Lower alkyl" alone or in combination means an alkane-derived radical containing from 1 to 6 carbon atoms (unless specifically defined) that includes a straight chain alkyl or branched alkyl. The straight chain or branched alkyl group is attached at any available point to produce a stable compound. In many embodiments, a lower alkyl is a straight or branched alkyl group containing from 1-6, 1-4, or 1-2, carbon atoms, such as methyl, ethyl, propyl, isopropyl, butyl, t-butyl, and the like. "Optionally substituted lower alkyl" denotes lower alkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(S)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^e$, —R$^f$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkyl" denotes a lower alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR, —NHR, —C(O)NHR, and the like, substitution of the alkyl R group is such that substitution of the alkyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkyl carbon bound to any —O—, —S—, or —N— of the moiety.

"Lower alkylene" refers to a divalent alkane-derived radical containing 1-6 carbon atoms, straight chain or branched, from which two hydrogen atoms are taken from the same carbon atom or from different carbon atoms. Examples of lower alkylene include, but are not limited to, methylene —CH$_2$—, ethylene —CH$_2$CH$_2$—, propylene —CH$_2$CH$_2$CH$_2$—, isopropylene —CH(CH$_3$)CH—, and the like. "Optionally substituted lower alkylene" denotes lower alkylene that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NHR$^a$, —NR$^a$C(O)NH$_2$, —NR$^a$C(S)NH$_2$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^e$, —R$^f$, and —R$^g$, or two substituents on any one carbon or a substituent on each of any two carbons in the alkylene chain may join to form a 3-7 membered monocyclic cycloalkyl or 5-7 membered monocyclic heterocycloalkyl wherein the monocyclic cycloalkyl or monocyclic heterocycloalkyl are optionally substituted with one or more substituents selected from the group consisting of halogen, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino.

"Lower alkenyl" alone or in combination means a straight or branched hydrocarbon containing 2-6 carbon atoms (unless specifically defined) and at least one, preferably 1-3, more preferably 1-2, most preferably one, carbon to carbon double bond. Carbon to carbon double bonds may be either contained within a straight chain or branched portion. Examples of lower alkenyl groups include ethenyl, propenyl, isopropenyl, butenyl, and the like. "Substituted lower alkenyl" denotes lower alkenyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NR$^a$C(O) NH$_2$, —NR$^a$C(S)NH$_2$, —NR$^a$C(O)NHR$^a$, —NR$^a$C(S) NHR$^a$, —NHC(O)NR$^a$R$^a$, —NHC(S)NR$^a$R$^a$, —NR$^a$C(O) NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^f$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkenyl" denotes a lower alkenyl group substituted with one or more fluoro atoms, where preferably the lower alkenyl is substituted with 1, 2, 3, 4 or 5 fluoro atoms, also 1, 2, or 3 fluoro atoms. While it is understood that substitutions are attached at any available atom to produce a stable compound, substitution of alkenyl groups are such that —F, —C(O)—, —C(S)—, —C(NH)—, —S(O)—, —S(O)$_2$—, —O—, —S—, or —N— (except where —N— is a heteroaryl ring atom), are not bound to an alkene carbon thereof. Further, where alkenyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or —N— thereof (except where —N— is a heteroaryl ring atom) are not bound to an alkene carbon of the alkenyl substituent or R group. Further, where alkenyl is a substituent of another moiety or an R group of a moiety such as —OR, —NHR, —C(O)NHR, and the like, substitution of the alkenyl R group is such that substitution of the alkenyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkenyl carbon bound to any —O—, —S—, or —N— of the moiety. An "alkenyl carbon" refers to any carbon within an alkenyl group, whether saturated or part of the carbon to carbon double bond. An "alkene carbon" refers to a carbon within an alkenyl group that is part of a carbon to carbon double bond.

"Lower alkynyl" alone or in combination means a straight or branched hydrocarbon containing 2-6 carbon atoms (unless specifically defined) containing at least one, preferably one, carbon to carbon triple bond. Examples of alkynyl groups include ethynyl, propynyl, butynyl, and the like. "Substituted lower alkynyl" denotes lower alkynyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of —F, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O) R$^a$, —OC(S)R$^a$, —C(O)R$^a$, —C(S)R$^a$, —C(O)OR$^a$, —C(S) OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC (S)NHR$^a$, —NR$^a$C(O)NH$_2$, —NR$^a$C(S)NH$_2$, —NR$^a$C(O) NHR$^a$, —NR$^a$C(S)NHR$^a$, —NHC(O)NR$^a$R$^a$, —NHC(S) NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, and —R$^g$. Further, possible substitutions include subsets of these substitutions, such as are indicated herein, for example, in the description of compounds of Formula I (including Formulae Ia, Ib, Ig and all sub-embodiments thereof), attached at any available atom to produce a stable compound. For example "fluoro substituted lower alkynyl" denotes a lower alkynyl group substituted with one or more fluoro atoms, where preferably the lower alkynyl is substituted with 1, 2, 3, 4 or 5 fluoro atoms, also 1, 2, or 3 fluoro atoms. While it is understood that substitutions are attached at any available atom to produce a stable compound, substitution of alkynyl groups are such that —F, —C(O)—, —C(S)—, —C(NH)—, —S(O)—, —S(O)$_2$—, —O—, —S—, or —N— (except where —N— is a heteroaryl ring atom), are not bound to an alkyne carbon thereof. Further, where alkynyl is a substituent of another moiety or an R group of a moiety such as —OR, —NHR, —C(O)R, and the like, substitution of the moiety is such that any —C(O)—, —C(S)—, —S(O)—, —S(O)$_2$—, —O—, —S—, or —N— thereof (except where —N— is a heteroaryl ring atom) are not bound to an alkyne carbon of the alkynyl substituent or R group. Further, where alkynyl is a substituent of another moiety or an R group of a moiety such as —OR, —NHR, —C(O)NHR, and the like, substitution of the alkynyl R group is such that substitution of the alkynyl carbon bound to any —O—, —S—, or —N— of the moiety (except where —N— is a heteroaryl ring atom) excludes substituents that would result in any —O—, —S—, or —N— of the substituent (except where —N— is a heteroaryl ring atom) being bound to the alkynyl carbon bound to any —O—, —S—, or —N— of the moiety. An "alkynyl carbon" refers to any carbon within an alkynyl group, whether saturated or part of the carbon to carbon triple bond. An "alkyne carbon" refers to a carbon within an alkynyl group that is part of a carbon to carbon triple bond.

"Cycloalkyl" refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, adamantyl, and the like. "Cycloalkylene" is a divalent cycloalkyl. A "substituted cycloalkyl" is a cycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted cycloalkylene" is a divalent substituted cycloalkyl.

"Heterocycloalkyl" refers to a saturated or unsaturated non-aromatic cycloalkyl group having from 5 to 10 atoms in which from 1 to 3 carbon atoms in the ring are replaced by heteroatoms of O, S or N, and are optionally fused with benzo or heteroaryl of 5-6 ring members. Heterocycloalkyl is also intended to include oxidized S or N, such as sulfinyl, sulfonyl and N-oxide of a tertiary ring nitrogen. Heterocycloalkyl is also intended to include compounds in which one of the ring carbons is oxo substituted, i.e. the ring carbon is a carbonyl group, such as lactones and lactams. The point of attachment of the heterocycloalkyl ring is at a carbon or nitrogen atom such that a stable ring is retained. Examples of heterocycloalkyl groups include, but are not limited to, morpholino, tetrahydrofuranyl, dihydropyridinyl, piperidinyl, pyrrolidinyl, pyrrolidonyl, piperazinyl, dihydrobenzofuryl, and dihydroindolyl. "Heterocycloalkylene" is a divalent heterocycloalkyl. A "substituted heterocycloalkyl" is a heterocycloalkyl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted heterocycloalkylene" is a divalent substituted heterocycloalkyl.

"Aryl" alone or in combination refers to a monocyclic or bicyclic ring system containing aromatic hydrocarbons such as phenyl or naphthyl, which may be optionally fused with a cycloalkyl of preferably 5-7, more preferably 5-6, ring members. "Arylene" is a divalent aryl. A "substituted aryl" is an aryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. A "substituted arylene" is a divalent substituted aryl.

"Heteroaryl" alone or in combination refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, quinoaxalyl, indolizinyl, benzo[b]thienyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, and indolyl. "Nitrogen containing heteroaryl" refers to heteroaryl wherein any heteroatoms are N. "Heteroarylene" is a divalent heteroaryl. A "substituted heteroaryl" is a heteroaryl that is independently substituted, unless indicated otherwise, with one or more, preferably 1, 2, 3, 4 or 5, also 1, 2, or 3 substituents, attached at any available atom to produce a stable compound, wherein the substituents are selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^b$R$^c$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —NHC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$, —NR$^a$R$^a$, —R$^d$, —R$^e$, —R$^f$, and —R$^g$. "Substituted heteroarylene" is a divalent substituted heteroaryl.

The variables R$^a$, R$^b$, R$^c$, —R$^d$, —R$^e$, —R$^f$ and —R$^g$ as used in the description of optional substituents for alkyl, alkylene, alkenyl, alkynyl, cycloalkyl, heterocycloalkyl, aryl and heteroaryl are defined as follows:

each R$^a$, R$^b$, and R$^c$ are independently selected from the group consisting of —R$^d$, —R$^e$, —R$^f$, and —R$^g$, or R$^b$ and R$^c$ combine with the nitrogen to which they are attached to form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, —OR$^u$, —SR$^u$, —NHR$^u$, —NR$^u$R$^u$, —R$^x$, and —R$^y$;

each —R$^d$ is independently lower alkyl, wherein lower alkyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R', and —R$^j$;

each —R$^e$ is independently lower alkenyl, wherein lower alkenyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each —R$^f$ is independently lower alkynyl, wherein lower alkynyl is optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, and —R$^j$;

each —R$^g$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^k$, —SR$^k$, —OC(O)R$^k$, —OC(S)R$^k$, —C(O)R$^k$, —C(S)R$^k$, —C(O)OR$^k$, —C(S)OR$^k$, —S(O)R$^k$, —S(O)$_2$R$^k$, —C(O)NHR$^k$, —C(S)NHR$^k$, —C(O)NR$^k$R$^k$, —C(S)NR$^k$R$^k$, —S(O)$_2$NHR$^k$, —S(O)$_2$NR$^k$R$^k$, —C(NH)NHR$^k$, —C(NH)NR$^m$R$^n$, —NHC(O)R$^k$, —NHC(S)R$^k$, —NR$^k$C(O)R$^k$, —NR$^k$C(S)R$^k$, —NHS(O)$_2$R$^k$, —NR$^k$S(O)$_2$R$^k$, —NHC(O)NHR$^k$, —NHC(S)NHR$^k$, —NR$^k$C(O)NH$_2$, —NR$^k$C(S)NH$_2$, —NR$^k$C(O)NHR$^k$, —NR$^k$C(S)NHR$^k$, —NHC(O)NR$^k$R$^k$, —NHC(S)NR$^k$R$^k$, —NR$^k$C(O)NR$^k$R$^k$, —NR$^k$C(S)NR$^k$R$^k$, —NHS(O)$_2$NHR$^k$, —NR$^k$S(O)$_2$NH$_2$, —NR$^k$S(O)$_2$NHR$^k$, —NHS(O)$_2$NR$^k$R$^k$, —NR$^k$S(O)$_2$NR$^k$R$^k$, —NHR$^k$, —NR$^k$R$^k$, —R$^h$, —R$^i$, and —R$^j$;

wherein R$^k$, R$^m$, and R$^n$ at each occurrence are independently selected from the group consisting of —R$^h$, —R$^i$, and —R$^j$, or R$^m$ and R$^n$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each —R$^h$ is independently lower alkyl optionally substituted with one or more, preferably 1, 2, 3, 4 or 5, also 1, 2, or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$'$R$^r$, —C(S)NR$'$R$^r$, —S(O)$_2$NHR$^r$, —S(O)$_2$NR$'$R$^r$, —C(NH)NHR$^r$, —C(NH)NR$^s$R$^t$, —NHC(O)R$^r$, —NHC(S)R$^r$, —NR$'$C(O)R$^r$, —NR$'$C(S)R$^r$, —NHS(O)$_2$R$^r$, —NR$'$S(O)$_2$R$^r$, —NHC(O)NHR$^r$, —NHC(S)NHR$^r$, —NR$'$C(O)NH$_2$, —NR$'$C(S)NH$_2$, —NR$'$C(O)NHR$^r$, —NR$'$C(S)NHR$^r$, —NHC(O)NR$'$R$^r$, —NHC(S)NR$'$R$^r$, —NR$'$C(O)NR$'$R$^r$, —NR$'$C(S)NR$'$R$^r$, —NHS(O)$_2$NHR$^r$, —NR$'$S(O)$_2$NH$_2$, —NR$'$S(O)$_2$NHR$^r$, —NHS(O)$_2$NR$'$R$^r$, —NR$'$S(O)$_2$NR$'$R$^r$, —NHR$^r$, —NR$'$R$^r$, —R$^i$, and —R$^j$;

wherein each —R$^i$ is independently selected from the group consisting of lower alkenyl and lower alkynyl, wherein lower alkenyl or lower alkynyl are optionally substituted with one or more, preferably 1, 2, 3, 4 or 5, also 1, 2 or 3 substituents selected from the group consisting of fluoro, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$'$R$^r$, —C(S)NR$'$R$^r$, —S(O)$_2$NHR$^r$, —S(O)$_2$NR$'$R$^r$, —C(NH)NHR$^r$, —C(NH)NR$^s$R$^t$, —NHC(O)R$^r$, —NHC(S)R$^r$, —NR$'$C(O)R$^r$, —NR$'$C(S)R$^r$, —NHS(O)$_2$R$^r$, —NR$'$S(O)$_2$R$^r$, —NHC(O)NHR$^r$, —NHC(S)NHR$^r$, —NR$'$C(O)NH$_2$, —NR$'$C(S)NH$_2$, —NR$'$C(O)NHR$^r$, —NR$'$C(S)NHR$^r$, —NHC(O)NR$'$R$^r$, —NHC(S)NR$'$R$^r$, —NR$'$C(O)NR$'$R$^r$, —NR$'$C(S)NR$'$R$^r$, —NHS(O)$_2$NHR$^r$, —NR$'$S(O)$_2$NH$_2$, —NR$'$S(O)$_2$NHR$^r$, —NHS(O)$_2$NR$'$R$^r$, —NR$'$S(O)$_2$NR$'$R$^r$, —NHR$^r$, —NR$'$R$^r$, and —R$^j$;

wherein each —R$^1$ is independently selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2 or 3 substituents selected from the group consisting of halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^r$, —SR$^r$, —OC(O)R$^r$, —OC(S)R$^r$, —C(O)R$^r$, —C(S)R$^r$, —C(O)OR$^r$, —C(S)OR$^r$, —S(O)R$^r$, —S(O)$_2$R$^r$, —C(O)NHR$^r$, —C(S)NHR$^r$, —C(O)NR$'$R$^r$, —C(S)NR$'$R$^r$, —S(O)$_2$NHR$^r$, —S(O)$_2$NR$'$R$^r$, —C(NH)NHR$^r$, —C(NH)NR$^s$R$^t$, —NHC(O)R$^r$, —NHC(S)R$^r$, —NR$'$C(O)R$^r$, —NR$'$C(S)R$^r$, —NHS(O)$_2$R$^r$, —NR$'$S(O)$_2$R$^r$, —NHC(O)NHR$^r$, —NHC(S)NHR$^r$, —NR$'$C(O)NH$_2$, —NR$'$C(O)NH$_2$, —NR$'$C(O)NHR$^r$, —NR$'$C(S)NHR$^r$, —NHC(O)NR$'$R$^r$, —NHC(S)NR$'$R$^r$, —NR$'$C(O)NR$'$R$^r$, —NR$'$C(S)NR$'$R$^r$, —NHS(O)$_2$NHR$^r$, —NR$'$S(O)$_2$NH$_2$, —NR$'$S(O)$_2$NHR$^r$, —NHS(O)$_2$NR$'$R$^r$, —NR$'$S(O)$_2$NR$'$R$^r$, —NHR$^r$, —NR$'$R$^r$, cycloalkylamino, and —R$^x$;

wherein each R$^r$, R$^s$, and R$^t$ at each occurrence are independently selected from the group consisting of lower alkyl, C$_{3-6}$ alkenyl, C$_{3-6}$ alkynyl, cycloalkyl, heterocycloalkyl, aryl and heteroaryl, wherein lower alkyl is optionally substituted with one or more, preferably 1, 2, 3, 4 or 5, also 1, 2 or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to any —O—, —S—, or —N—, of —OR$^r$, —SR$^r$, —C(O)OR$^r$, —C(S)OR$^r$, —C(O)NHR$^r$, —C(S)NHR$^r$, —C(O)NR$'$R$^r$, —C(S)NR$'$R$^r$, —S(O)$_2$NHR$^r$, —S(O)$_2$NR$'$R$^r$, —C(NH)NHR$^r$, —NR$'$C(O)R$^r$, —NR$'$C(S)R$^r$, —NR$'$S(O)$_2$R$^r$, —NR$'$C(O)NHR$^r$, —NHC(S)NHR$^r$, —NR$'$C(O)NH$_2$, —NR$'$C(S)NH$_2$, —NR$'$C(O)NHR$^r$, —NR$'$C(S)NHR$^r$, —NHC(O)NR$'$R$^r$, —NHC(S)NR$'$R$^r$, —NR$'$C(O)NR$'$R$^r$, —NR$'$C(S)NR$'$R$^r$, —NHS(O)$_2$NHR$^r$, —NR$'$S(O)$_2$NH$_2$, —NR$'$S(O)$_2$NHR$^r$, —NHS(O)$_2$NR$'$R$^r$, —NR$'$S(O)$_2$NR$'$R$^r$, —NHR$^r$, or —NR$'$R$^r$ is selected from the group consisting of fluoro and —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to any —O—, —S—, or —N—, of —OR$^r$, —SR$^r$, —C(O)OR$^r$, —C(S)OR$^r$, —C(O)NHR$^r$, —C(S)NHR$^r$, —C(O)NR$'$R$^r$, —C(S)NR$'$R$^r$, —S(O)$_2$NHR$^r$, —S(O)$_2$NR$'$R$^r$, —C(NH)NHR$^r$, —NR$'$C(O)R$^r$, —NR$'$C(S)R$^r$, —NR$'$S(O)$_2$R$^r$, —NHC(O)NHR$^r$, —NHC(S)NHR$^r$, —NR$'$C(O)NH$_2$, —NR$'$C(S)NH$_2$, —NR$'$C(O)NHR$^r$, —NR$'$C(S)NHR$^r$, —NHC(O)NR$'$R$^r$, —NHC(S)NR$'$R$^r$, —NR$'$C(O)NR$'$R$^r$, —NR$'$C(S)NR$'$R$^r$, —NHS(O)$_2$NHR$^r$, —NR$'$S(O)$_2$NH$_2$, —NR$'$S(O)$_2$NHR$^r$, —NHS(O)$_2$NR$'$R$^r$, —NR$'$S(O)$_2$NR$'$R$^r$, —NHR$^r$, or —NR$'$R$^r$ is selected from the group consisting of fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino, or R$^s$ and R$^t$ combine with the nitrogen to which they are attached form a 5-7 membered heterocycloalkyl or a 5 or 7 membered nitrogen containing heteroaryl, wherein the 5-7 membered heterocycloalkyl or 5 or 7 membered nitrogen containing heteroaryl are optionally substituted with one or more, preferably 1, 2, 3, 4 or 5, also 1, 2, or 3 substituents selected from the group consisting of halogen, —NO$_2$, —CN, —OH, —NH$_2$, OR$^u$, —SR$^u$, —NHR$^u$, —NR$^u$R$^u$, —R$^x$, and —R$^y$;

wherein each R$^u$ is independently selected from the group consisting of lower alkyl, C$_{3-6}$ alkenyl, C$_{3-6}$ alkynyl, cycloalkyl, heterocycloalkyl, aryl, and heteroaryl, wherein lower alkyl is optionally substituted with one or more, preferably 1, 2, 3, 4 or 5, also 1, 2 or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkylamino, di-alkylamino, and cycloalkylamino, provided that any substitution of the lower alkyl carbon bound to the —O— of —OR$^u$, —S— of —SR$^u$, or —N— of —NHR$^u$ is fluoro or —R$^y$, and wherein C$_{3-6}$ alkenyl or C$_{3-6}$ alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkylamino, di-alkylamino, and cycloalkylamino, provided that any substitution of the C$_{3-6}$ alkenyl or C$_{3-6}$ alkynyl carbon bound to the —O— of —OR$^u$, —S— of —SR$^u$, or —N— of —NHR$^u$ is fluoro, lower alkyl, fluoro substituted lower alkyl, or —R$^y$, and wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —R$^x$ is selected from the group consisting of lower alkyl, lower alkenyl and lower alkynyl, wherein lower alkyl is optionally substituted with one or more, preferably 1, 2, 3, 4 or 5, also 1, 2, or 3 substituents selected from the group consisting of —R$^y$, fluoro, —OH, —NH$_2$, lower alkoxy, fluoro substituted lower alkoxy, lower alkylthio, fluoro substituted lower alkylthio, mono-alkyl amino, di-alkyl amino, and cycloalkylamino, and wherein lower alkenyl or lower alkynyl are optionally substituted with one or more, preferably 1, 2, 3, 4 or 5, also 1, 2, or 3 substituents selected from the group consisting of —R$^y$, fluoro, —OH, —NH$_2$, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino;

wherein each —R$^y$ is selected from the group consisting of cycloalkyl, heterocycloalkyl, aryl, and heteroaryl, wherein cycloalkyl, heterocycloalkyl, aryl, and heteroaryl are optionally substituted with one or more, preferably 1, 2, 3, 4 or 5, also 1, 2, or 3 substituents selected from the group consisting of halogen, —OH, —NH$_2$, —NO$_2$, —CN, lower alkyl, fluoro substituted lower alkyl, lower alkoxy, fluoro substituted lower alkoxy, lower alkylthio, fluoro substituted lower alkylthio, mono-alkyl amino, di-alkyl amino, and cycloalkylamino.

"Lower alkoxy" denotes the group —OR$^z$ where R$^z$ is lower alkyl. "Substituted lower alkoxy" denotes lower alkoxy in which R$^z$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkoxy is with 1, 2, 3, 4, or 5 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that —O—, —S—, or —N— (except where N is a heteroaryl ring atom), are not bound to the alkyl carbon bound to the alkoxy —O—. Further, where alkoxy is described as a substituent of another moiety, the alkoxy oxygen is not bound to a carbon atom that is bound to an —O—, —S—, or —N— of the other moiety (except where N is a heteroaryl ring atom), or to an alkene or alkyne carbon of the other moiety.

"Lower alkylthio" denotes the group SR$^{aa}$, where R$^{aa}$ is lower alkyl. "Substituted lower alkylthio" denotes lower alkylthio in which R$^{aa}$ is lower alkyl substituted with one or more substituents as indicated herein, for example, in the description of compounds of Formula I (including Formulae Ia, Ib, Ig and all sub-embodiments thereof), including descriptions of substituted cycloalkyl, cycloheteroalkyl, aryl and heteroaryl, attached at any available atom to produce a stable compound. Preferably, substitution of lower alkylthio is with 1, 2, 3, 4, or 5 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4 or 5 fluoro atoms, also 1, 2, or 3 fluoro atoms. While it is understood that substitutions on alkylthio are attached at any available atom to produce a stable compound, substitution of alkylthio is such that —O—, —S—, or —N— (except where N is a heteroaryl ring atom), are not bound to the alkyl carbon bound to the alkylthio —S—. Further, where alkylthio is described as a substituent of another moiety, the alkylthio sulfur is not bound to a carbon atom that is bound to an —O—, —S—, or —N— of the other moiety (except where N is a heteroaryl ring atom), or to an alkene or alkyne carbon of the other moiety.

"Amino" or "amine" denotes the group NH$_2$. "Mono-alkylamino" denotes the group —NHR$^{bb}$ where R$^{bb}$ is lower alkyl. "Di-alkylamino" denotes the group NR$^{bb}$R$^{cc}$, where R$^{bb}$ and R$^{cc}$ are independently lower alkyl. "Cycloalkylamino" denotes the group —NR$^{dd}$R$^{ee}$ where R$^{dd}$ and R$^{ee}$ combine with the nitrogen to form a 5-7 membered heterocycloalkyl, where the heterocycloalkyl may contain an additional heteroatom within the ring, such as —O—, —N—, or —S—, and may also be further substituted with lower alkyl. Examples of 5-7 membered heterocycloalkyl include, but are not limited to, piperidine, piperazine, 4-methylpiperazine, morpholine, and thiomorpholine. While it is understood that when mono-alkylamino, di-alkylamino, or cycloalkylamino are substituents on other moieties that are attached at any available atom to produce a stable compound, the nitrogen of mono-alkylamino, di-alkylamino, or cycloalkylamino as substituents is not bound to a carbon atom that is bound to an —O—, —S—, or —N— of the other moiety.

As used herein, the term Flt3 mediated disease or condition refers to a disease or condition in which the biological function of Flt3 affects the development and/or course of the disease or condition, and/or in which modulation of Flt3 alters the development, course, and/or symptoms. These mutations attenuate the intrinsic tyrosine kinase activity of the receptor to different degrees and are models for the effect of modulation of Flt3 activity. A Flt3 mediated disease or condition includes a disease or condition for which Flt3 inhibition provides a therapeutic benefit, e.g. wherein treatment with Flt3 inhibitors, including compounds described herein, provides a therapeutic benefit to the subject suffering from or at risk of the disease or condition.

As used herein, the term Flt3 mediated disease or condition refers to a disease or condition in which the biological function of Flt3 affects the development and/or course of the disease or condition, and/or in which modulation of Flt3 alters the development, course, and/or symptoms.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the terms "therapeutically effective" and "effective amount" indicate that the materials or amount of material is effective to prevent, alleviate, or ameliorate one or more symptoms of a disease or medical condition, and/or to prolong the survival of the subject being treated.

Reference to particular amino acid residues in human Flt3 polypeptide is defined by the numbering corresponding to the Flt3 sequence in GenBank NP_004110.2 (SEQ ID NO. 1). Reference to particular nucleotide positions in a nucleotide sequence encoding all or a portion of Flt3 is defined by the numbering corresponding to the sequence provided in GenBank NM_44119 (SEQ ID NO. 2).

The terms "Flt3" or "FLT3" mean an enzymatically active kinase that contains a portion with greater than 90% amino acid sequence identity to amino acid residues including the ATP binding site of full-length Flt3 (e.g., human Flt3, e.g., the sequence NP_004110.2, SEQ ID NO. 1), for a maximal alignment over an equal length segment; or that contains a portion with greater than 90% amino acid sequence identity to at least 200 contiguous amino acids of native Flt3 and retains kinase activity. Preferably the sequence identity is at least 95, 97, 98, 99, or even 100%. Preferably the specified level of sequence identity is over a sequence at least 100-500, at least 200-400, or at least 300 contiguous amino acid residues in length. Unless indicated to the contrary, the term includes reference to wild-type c-Flt3, allelic variants, and mutated forms (e.g., having activating mutations).

The terms "Flt3-mediated diseases or disorders" shall include diseases associated with or implicating Flt3 activity, for example, the overactivity of Flt3, and conditions that accompany with these diseases. The term "overactivity of Flt3" refers to either 1) Flt3 expression in cells which normally do not express Flt3; 2) Flt3 expression by cells which normally do not express v; 3) increased Flt3 expression leading to unwanted cell proliferation; or 4) mutations leading to constitutive activation of Flt3. Examples of "Flt3-mediated diseases or disorders" include disorders resulting from over stimulation of Flt3 or from abnormally high amount of Flt3 activity, due to abnormally high amount of Flt3 or mutations in Flt3. It is known that overactivity of Flt3 has been implicated in the pathogenesis of a number of diseases, including inflammatory and autoimmune diseases, cell proliferative disorders, neoplastic disorders and cancers as described herein.

The term "Flt3-ITD allelic ratio" refers to the percentage of tumor DNA alleles harboring the Flt3-ITD mutation normalized to the percent blast cells in a patient sample. In one embodiment, a low Flt3-ITD allelic ratio is where less than 25% of normalized tumor DNA alleles is a Flt3-ITD allele. In certain embodiments, an intermediate Flt3-ITD allelic ratio is where between 25% and 50% of normalized tumor DNA alleles is a Flt3-ITD allele. In certain embodiments, a high Flt3-ITD allelic ratio is where greater than 50% of normalized tumor DNA alleles is a Flt3-ITD allele.

The "Flt3/ITD mutation-containing cells" include any of cells having tandem duplication mutation absent in healthy humans in a region of exons 14 to 15 in a juxtamembrane region of Flt3, that is, cells highly expressing mRNA derived from the mutation, cells having increased Flt3-derived growth signals caused by the mutation, cells highly expressing the mutant Flt3 protein, etc.

The "Flt3/ITD mutation-containing cancerous cells" include any of cancerous cells having tandem duplication mutation absent in healthy humans in a region of exons 14 to 15 in a juxtamembrane region of Flt3, that is, cancerous cells highly expressing mRNA derived from the mutation, cancerous cells having increased Flt3-derived growth signals caused by the mutation, cancerous cells highly expressing the mutant Flt3 protein, etc. The "Flt3/ITD mutation-containing leukemic cells" include any of leukemic cells having tandem duplication mutation absent in healthy humans in a region of exons 14 to 15 in a juxtamembrane region of Flt3, that is, leukemic cells highly expressing mRNA derived from the mutation, leukemic cells having increased Flt3-derived growth signals caused by the mutation, leukemic cells highly expressing the mutant Flt3 protein, etc As used herein, the terms "ligand" and "modulator" are used equivalently to refer to a compound that changes (i.e., increases or decreases) the activity of a target biomolecule, e.g., an enzyme such as a kinase or kinase. Generally a ligand or modulator will be a small molecule, where "small molecule" refers to a compound with a molecular weight of 1500 Daltons or less, or preferably 1000 Daltons or less, 800 Daltons or less, or 600 Daltons or less.

The terms "modulate", "modulation" and the like refer to the ability of a compound to increase or decrease the function and/or expression of Flt3, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Flt3, either directly or indirectly, and/or the upregulation or downregulation of the expression of Flt3, either directly or indirectly. In a preferred embodiment, the modulation is direct Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Flt3 can be demonstrated in a biochemical assay, e.g., binding assay, or a cell-based assay.

In the context of compounds binding to a target, the term "greater affinity" indicates that the compound binds more tightly than a reference compound, or than the same compound in a reference condition, i.e., with a lower dissociation constant. In particular embodiments, the greater affinity is at least 2, 3, 4, 5, 8, 10, 50, 100, 200, 400, 500, 1000, or 10,000-fold greater affinity.

Also in the context of compounds binding to a biomolecular target, the term "greater specificity" indicates that a compound binds to a specified target to a greater extent than to another biomolecule or biomolecules that may be present under relevant binding conditions, where binding to such other biomolecules produces a different biological activity than binding to the specified target. Typically, the specificity is with reference to a limited set of other biomolecules, e.g., in the case of Flt3, other tyrosine kinases or even other type of enzymes. In particular embodiments, the greater specificity is at least 2, 3, 4, 5, 8, 10, 50, 100, 200, 400, 500, or 1000-fold greater specificity.

As used herein in connection with binding compounds or ligands, the term "specific for Flt3 kinase", "specific for Flt3", and terms of like import mean that a particular compound binds to Flt3 to a statistically greater extent than to other kinases that may be present in a particular sample. Also, where biological activity other than binding is indicated, the term "specific for Flt3" indicates that a particular compound has greater biological effect associated with binding Flt3 than to other tyrosine kinases, e.g., kinase activity inhibition. Preferably, the specificity is also with respect to other biomolecules (not limited to tyrosine kinases) that may be present in a particular sample. The term "specific for Flt3 kinase", "specific for Flt3", and terms of like import mean that a particular compound binds to Flt3 to a statistically greater extent than to other kinases that may be present in a particular sample. Also, where biological activity other than binding is indicated, the term "specific for Flt3" indicates that a particular compound has greater biological effect associated with binding Flt3 than to other tyrosine kinases, e.g., kinase activity inhibition. Preferably, the specificity is also with respect to other biomolecules (not limited to tyrosine kinases) that may be present in a particular sample.

As used herein in connection with test compounds, binding compounds, and modulators (ligands), the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

The term "first line cancer therapy" refers to therapy administered to a subject as an initial regimen to reduce the number of cancer cells. First line therapy is also referred to as induction therapy, primary therapy and primary treatment. Commonly administered first-line therapy for AML is cytarabine-based therapy in which cytarabine is administered often in combination with one or more agents selected from daunorubicin, idarubicin, doxorubicin, mitoxantrone, tipifarnib, thioguanine or gemtuzumab ozogamicin. Common regimens used in cytarabine-based therapy include the "7+3" or "5+2" therapy comprising administration of cytarabine with an anthracycline such as daunorubicin or idarubicin. Another first-line therapy is clofarabine-based therapy in which clofarabine is administered, often in combination with an anthracycline such as daunorubicin, idarubicin or doxorubicin. Other first-line therapy for AML are etoposide-based therapy in which etoposide is administered, often in combination with mitoxantrone, and optionally, with cytarabine. Another first-line therapy for AML (for subtype M3, also called acute promyelocytic leukemia) is all-trans-retinoic acid (ATRA). It is recognized that what is considered "first line therapy" by those of ordinary skill in the art will continue to evolve as new anti-cancer agents are developed and tested in the clinics. A summary of the currently accepted approaches to first line treatment is described in NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/Health-Professional/page7).

The term "second line cancer therapy" refers to a cancer treatment that is administered to a subject who does not respond to first line therapy, that is, often first line therapy is administered or who has a recurrence of cancer after being in remission. In certain embodiments, second line therapy that may be administered includes a repeat of the initial successful cancer therapy, which may be any of the treatments described under "first line cancer therapy". In certain embodiments, second line therapy is the administration of gemtuzumab ozogamicin. In certain embodiments, investigational drugs may also be administered as second line therapy in a clinical trial setting. A summary of the currently accepted approaches to second line treatment is described in the NCCN Clinical Practice Guidelines in Oncology for acute myeloid leukemia and the NCI guidelines on acute myeloid leukemia treatment (see, e.g., http://www.cancer.gov/cancertopics/pdq/treatment/adultAML/HealthProfessional/page5).

The term "refractory" refers to wherein a subject fails to respond or is otherwise resistant to cancer therapy or treatment. The cancer therapy may be first-line, second-line or any subsequently administered treatment. In certain embodiments, refractory refers to a condition where a subject fails to achieve complete remission after two induction attempts. A subject may be refractory due to a cancer cell's intrinsic resistance to a particular therapy, or the subject may be refractory due to an acquired resistance that develops during the course of a particular therapy As used herein, the term "modulating" or "modulate" refers to an effect of altering a biological activity, especially a biological activity associated with a particular biomolecule such as Flt3. For example, an agonist or antagonist of a particular biomolecule modulates the activity of that biomolecule, e.g., an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the particular molecule constitutes a significantly greater proportion of the biomolecules in a composition than in a prior composition, e.g., in a cell culture. The greater proportion can be 2-fold, 5-fold, 10-fold or more greater.

I. General

In one aspect, the present invention concerns compounds of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449, and any compounds as described herein, that are useful as inhibitors of an oncogenic Flt3 or a Flt3 mutant, and the use of the compounds in treating a subject suffering from diseases that are mediated by a mutated Flt3 kinase.

FLT3 kinase is a tyrosine kinase receptor involved in the regulation and stimulation of cellular proliferation. See e.g., Gilliland et al., Blood 100: 1532-42 (2002). The FLT3 kinase is a member of the class III receptor tyrosine kinase (RTKIII) receptor family and belongs to the same subfamily of tyrosine kinases as c-kit, c-fms, and the platelet-derived growth factor .α and β receptors. See e.g., Lyman et al., FLT3 Ligand in THE CYTOKINE HANDBOOK 989 (Thomson et al., eds. 4th Ed.) (2003). The FLT3 kinase has five immunoglobulin-like domains in its extracellular region as well as an insert region of 75-100 amino acids in the middle of its cytoplasmic domain. FLT3 kinase is activated upon the binding of the FLT3 ligand, which causes receptor dimerization. Dimerization of the FLT3 kinase by FLT3 ligand activates the intracellular kinase activity as well as a cascade of downstream substrates including Stat5, Ras, phosphatidylinositol-3-kinase (PI3K), PLC γ, Erk2, Akt, MAPK, SHC, SHP2, and SHIP. See e.g., Rosnet et al., Acta Haematol. 95: 218 (1996); Hayakawa et al., Oncogene 19: 624 (2000); Mizuki et al., Blood 96: 3907 (2000); and Gilliand et al., Curr. Opin. Hematol. 9: 274-81 (2002). Both membrane-bound and soluble FLT3 ligand bind, dimerize, and subsequently activate the FLT3 kinase.

In normal cells, immature hematopoietic cells, typically CD34+ cells, placenta, gonads, and brain express FLT3 kinase. See, e.g., Rosnet, et al., Blood 82: 1110-19 (1993); Small et al., Proc. Natl. Acad. Sci. U.S.A. 91: 459-63 (1994); and Rosnet et al., Leukemia 10: 238-48 (1996). However, efficient stimulation of proliferation via FLT3 kinase typically requires other hematopoietic growth factors or interleukins. FLT3 kinase also plays a critical role in immune function through its regulation of dendritic cell proliferation and differentiation. See e.g., McKenna et al., Blood 95: 3489-97 (2000).

Numerous hematologic malignancies express FLT3 kinase, the most prominent of which is AML. See e.g., Yokota et al., Leukemia 11: 1605-09 (1997). Other FLT3 expressing malignancies include B-precursor cell acute lymphoblastic leukemias, myelodysplastic leukemias, T-cell acute lymphoblastic leukemias, and chronic myelogenous leukemias. See e.g., Rasko et al., Leukemia 9: 2058-66 (1995).

FLT3 kinase mutations associated with hematologic malignancies are activating mutations. In other words, the FLT3 kinase is constitutively activated without the need for binding and dimerization by FLT3 ligand, and therefore stimulates the cell to grow continuously.

Several studies have identified inhibitors of FLT3 kinase activity that also inhibit the kinase activity of related receptors, e.g., VEGF receptor (VEGFR), PDGF receptor (PDGFR), and kit receptor kinases. See e.g., Mendel et al., Clin. Cancer Res. 9: 327-37 (2003); O'Farrell et al., Blood 101: 3597-605 (2003); and Sun et al., J. Med. Chem. 46: 1116-19 (2003). Such compounds effectively inhibit FLT3 kinase-mediated phosphorylation, cytokine production, cellular proliferation, resulting in the induction of apoptosis. See e.g., Spiekermann et al., Blood 101: 1494-1504 (2003). Moreover, such compounds have potent antitumor activity in vitro and in vivo.

In some embodiments, the oncogenic Flt3 or Flt3 mutant is encoded by a Flt3 gene with an internal tandem duplication (ITD) mutation in the juxtamembrane as described in U.S. Pat. No. 6,846,630, which is herein incorporated by reference. In certain embodiments, the oncogenic Flt3 or Flt3 mutant encoded by Flt3 with ITD mutations has one or more mutations at residues F691, D835, Y842 or combinations thereof. In some embodiments, the oncogenic Flt3 or Flt3 mutant has one or more mutations are selected from F691L, D835V/Y, Y842C/H or combinations thereof.

In some embodiments, the subject has an Flt3 gene mutation encoding an Flt3 mutant having an amino acid substitution at residues F691, D835, Y842 or combinations thereof. In certain instances, the amino acid substitution is selected from F691L, D835V/Y, Y842C/H or combinations thereof.

In some embodiments, the invention provides a method of inhibiting an oncogenic Flt3 or a mutant Flt3. The method includes contacting the Flt3 kinase with a compound as described herein. In some embodiments, the oncogenic Flt3 or Flt3 mutant is encoded by an Flt3 gene having an ITD mutation. In some embodiments, the oncogenic Flt3 or Flt3 mutant encoded by an Flt3 gene with an ITD mutation has one or more mutations at residues F691, D835, Y842 or combinations thereof. In some embodiments, the oncogenic Flt3 or Flt3 mutant has one or more mutations are selected from F691L, D835V/Y, Y842C/H or combinations thereof.

Hematologic cancers, also known as hematologic or hematopoietic malignancies, are cancers of the blood or bone marrow; including leukemia and lymphoma. Acute myelogenous leukemia (AML) is a clonal hematopoietic stem cell leukemia that represents about 90% of all acute leukemias in adults with an incidence of 3.9 per 100,000 (See e.g., Lowenberg et al., N. Eng. J. Med. 341: 1051-62 (1999) and Lopesde Menezes, et al, Clin. Cancer Res. (2005), 11(14):5281-5291). While chemotherapy can result in complete remissions, the long term disease-free survival rate for AML is about 14% with about 7,400 deaths from AML each year in the United States. Approximately 70% of AML blasts express wild type FLT3 and about 25% to about 35% express FLT3 kinase receptor mutations which result in constitutively active FLT3. Two types of activating mutations have been identified, in AML patients: internal tandem duplications (ITDs) and point mutation in the activating loop of the kinase domain. FLT3-ITD mutations in AML patients is indicative of a poor prognosis for survival, and in patients who are in remission, FLT3-ITD mutations are the most significant factor adversely affecting relapse rate with 64% of patients having the mutation relapsing within 5 years (see Current Pharmaceutical Design (2005), 11:3449-3457. The prognostic significance of FLT3 mutations in clinical studies suggests that FLT3 plays a driving role in AML and may be necessary for the development and maintenance of the disease.

Mixed Lineage Leukemia (MLL) involve translocations of chromosome 11 band q23 (11q23) and occur in approximately 80% of infant hematological malignancies and 10% of adult acute leukemias. Although certain 11q23 translocation have been shown to be essential to immortalization of hematopoietic progenitors in vitro, a secondary genotoxic event is required to develop leukemia. There is a strong concordance between FLT3 and MLL fusion gene expression, and the most consistently overexpressed gene in MLL is FLT3. Moreover, it has been shown that activated FLT3 together with MLL fusion gene expression induces acute leukemia with a short latency period (see Ono, et al., J. of Clinical Investigation (2005), 115:919-929). Therefore, it is believed that FLT3 signally is involved in the development and maintenance of MLL (see Armstrong, et al., Cancer Cell (2003), 3:173-183).

The FLT3-ITD mutation is also present in about 3% of cases of adult myelodysplastic syndrome and some cases of acute lymphocytic leukemia (ALL) (Current Pharmaceutical Design (2005), 11:3449-3457).

FLT3 has been shown to be a client protein of Hsp90, and 17AAG, a benzoquinone ansamycin antibiotic that inhibits Hsp90 activity, has been shown to disrupts the association of Flt3 with Hsp90. The growth of leukemia cell that express either wild type FLT3 or FLT3-ITD mutations was found to be inhibited by treatment with 17"AAG (Yao, et al., Clinical Cancer Research (2003), 9:4483-4493).

The compounds as described herein are useful for the treatment or prevention of haematological malignancies, including, but not limiting to, acute myeloic leukemia (AML); mixed lineage leukemia (MLL); acute promyelocytic leukemia; acute lymphocytic leukemia, acute lymphoblastic leukemia, myeloid sarcoma; T-cell type acute lymphocytic leukemia (T-ALL); B-cell type acute lymphocytic leukemia (B-ALL); chronic myelomonocytic leukemia (CMML); myelodysplastic syndrome; myeloproliferative disorders; other proliferative disorders, including, but not limiting to, cancer; autoimmune disorders; and skin disorders, such as psoriasis and atopic dermatitis.

II. Binding Assays

The methods of the present invention can involve assays that are able to detect the binding of compounds to a target molecule. Such binding is at a statistically significant level, preferably with a confidence level of at least 90%, more preferably at least 95, 97, 98, 99% or greater confidence level that the assay signal represents binding to the target molecule, i.e., is distinguished from background. Preferably controls are used to distinguish target binding from non-specific binding. A large variety of assays indicative of binding are known for different target types and can be used for this invention.

Binding compounds can be characterized by their effect on the activity of the target molecule. Thus, a "low activity" compound has an inhibitory concentration ($IC_{50}$) or effective concentration ($EC_{50}$) of greater than 1 µM under standard conditions. By "very low activity" is meant an $IC_{50}$ or $EC_{50}$ of above 100 µM under standard conditions. By "extremely low activity" is meant an $IC_{50}$ or $EC_{50}$ of above 1 mM under standard conditions. By "moderate activity" is meant an $IC_{50}$ or $EC_{50}$ of 200 nM to 1 µM under standard conditions. By "moderately high activity" is meant an $IC_{50}$ or $EC_{50}$ of 1 nM to 200 nM. By "high activity" is meant an $IC_{50}$ or $EC_{50}$ of below 1 nM under standard conditions. The $IC_{50}$ or $EC_{50}$ is defined as the concentration of compound at which 50% of the activity of the target molecule (e.g. enzyme or other protein) activity being measured is lost or gained relative to the range of activity observed when no compound is present. Activity can be measured using methods known to those of ordinary skill in the art, e.g., by measuring any detectable product or signal produced by occurrence of an enzymatic reaction, or other activity by a protein being measured.

By "background signal" in reference to a binding assay is meant the signal that is recorded under standard conditions for the particular assay in the absence of a test compound, molecular scaffold, or ligand that binds to the target molecule. Persons of ordinary skill in the art will realize that accepted methods exist and are widely available for determining background signal.

By "standard deviation" is meant the square root of the variance. The variance is a measure of how spread out a distribution is. It is computed as the average squared deviation of each number from its mean. For example, for the numbers 1, 2, and 3, the mean is 2 and the variance is:

$$\sigma^2 = \frac{(1-2)^2 + (2-2)^2 + (3-2)^2}{3} = 0.667.$$

Surface Plasmon Resonance

Binding parameters can be measured using surface plasmon resonance, for example, with a BIAcore® chip (Biacore, Japan) coated with immobilized binding components. Surface plasmon resonance is used to characterize the microscopic association and dissociation constants of reaction between an sFv or other ligand directed against target molecules. Such methods are generally described in the following references which are incorporated herein by reference. Vely F. et al., (2000) BIAcore® analysis to test phosphopeptide-SH2 domain interactions, Methods in Molecular Biology. 121:313-21; Liparoto et al., (1999) Biosensor analysis of the interleukin-2 receptor complex, Journal of Molecular Recognition. 12:316-21; Lipschultz et al., (2000) Experimental design for analysis of complex kinetics using surface plasmon resonance, Methods. 20(3): 310-8; Malmqvist., (1999) BIACORE: an affinity biosensor system for characterization of biomolecular interactions, Biochemical Society Transactions 27:335-40; Alfthan, (1998) Surface plasmon resonance biosensors as a tool in antibody engineering, Biosensors & Bioelectronics. 13:653-63; Fivash et al., (1998) BIAcore for macromolecular interaction, Current Opinion in Biotechnology. 9:97-101; Price et al.; (1998) Summary report on the ISOBM TD-4 Workshop: analysis of 56 monoclonal antibodies against the MUC1 mucin. Tumour Biology 19 Suppl 1:1-20; Malmqvist et al, (1997) Biomolecular interaction analysis: affinity biosensor technologies for functional analysis of proteins, Current Opinion in Chemical Biology. 1:378-83; O'Shannessy et al., (1996) Interpretation of deviations from pseudo-first-order kinetic behavior in the characterization of ligand binding by biosensor technology, Analytical Biochemistry. 236:275-83; Malmborg et al., (1995) BIAcore as a tool in antibody engineering, Journal of Immunological Methods. 183:7-13; Van Regenmortel, (1994) Use of biosensors to characterize recombinant proteins, Developments in Biological Standardization. 83:143-51; and O'Shannessy, (1994) Determination of kinetic rate and equilibrium binding constants for macromolecular interactions: a critique of the surface plasmon resonance literature, Current Opinions in Biotechnology. 5:65-71.

BIAcore® uses the optical properties of surface plasmon resonance (SPR) to detect alterations in protein concentration bound to a dextran matrix lying on the surface of a gold/glass sensor chip interface, a dextran biosensor matrix. In brief, proteins are covalently bound to the dextran matrix at a known concentration and a ligand for the protein is injected through the dextran matrix. Near infrared light, directed onto the opposite side of the sensor chip surface is reflected and also induces an evanescent wave in the gold film, which in turn, causes an intensity dip in the reflected light at a particular angle known as the resonance angle. If the refractive index of the sensor chip surface is altered (e.g. by ligand binding to the bound protein) a shift occurs in the resonance angle. This angle shift can be measured and is expressed as resonance units (RUs) such that 1000 RUs is equivalent to a change in surface protein concentration of 1 $ng/mm^2$. These changes are displayed with respect to time along the y-axis of a sensorgram, which depicts the association and dissociation of any biological reaction.

High Throughput Screening (HTS) Assays

HTS typically uses automated assays to search through large numbers of compounds for a desired activity. Typically HTS assays are used to find new drugs by screening for chemicals that act on a particular enzyme or molecule. For example, if a chemical inactivates an enzyme it might prove to be effective in preventing a process in a cell which causes a disease. High throughput methods enable researchers to assay thousands of different chemicals against each target molecule very quickly using robotic handling systems and automated analysis of results.

As used herein, "high throughput screening" or "HTS" refers to the rapid in vitro screening of large numbers of compounds (libraries); generally tens to hundreds of thousands of compounds, using robotic screening assays. Ultra high-throughput Screening (uHTS) generally refers to the high-throughput screening accelerated to greater than 100,000 tests per day.

To achieve high-throughput screening, it is advantageous to house samples on a multicontainer carrier or platform. A multicontainer carrier facilitates measuring reactions of a plurality of candidate compounds simultaneously. Multi-well microplates may be used as the carrier. Such multi-well microplates, and methods for their use in numerous assays, are both known in the art and commercially available.

Screening assays may include controls for purposes of calibration and confirmation of proper manipulation of the components of the assay. Blank wells that contain all of the reactants but no member of the chemical library are usually included. As another example, a known inhibitor (or activator) of an enzyme for which modulators are sought, can be incubated with one sample of the assay, and the resulting decrease (or increase) in the enzyme activity used as a comparator or control. It will be appreciated that modulators can also be combined with the enzyme activators or inhibitors to find modulators which inhibit the enzyme activation or repression that is otherwise caused by the presence of the known the enzyme modulator.

Measuring Enzymatic and Binding Reactions During Screening Assays

Techniques for measuring the progression of enzymatic and binding reactions, e.g., in multicontainer carriers, are known in the art and include, but are not limited to, the following.

Spectrophotometric and spectrofluorometric assays are well known in the art. Examples of such assays include the use of colorimetric assays for the detection of peroxides, as described in Gordon, A. J. and Ford, R. A., (1972) *The Chemist's Companion: A Handbook Of Practical Data, Techniques, And References*, John Wiley and Sons, N.Y., Page 437.

Fluorescence spectrometry may be used to monitor the generation of reaction products. Fluorescence methodology is generally more sensitive than the absorption methodology. The use of fluorescent probes is well known to those skilled in the art. For reviews, see Bashford et al., (1987) *Spectrophotometry and Spectrofluorometry: A Practical Approach*, pp. 91-114, IRL Press Ltd.; and Bell, (1981) *Spectroscopy In Biochemistry*, Vol. I, pp. 155-194, CRC Press.

In spectrofluorometric methods, enzymes are exposed to substrates that change their intrinsic fluorescence when processed by the target enzyme. Typically, the substrate is nonfluorescent and is converted to a fluorophore through one or more reactions. As a non-limiting example, SMase activity can be detected using the Amplex® Red reagent (Molecular Probes, Eugene, Oreg.). In order to measure sphingomyelinase activity using Amplex® Red, the following reactions occur. First, SMase hydrolyzes sphingomyelin to yield ceramide and phosphorylcholine. Second, alkaline phosphatase hydrolyzes phosphorylcholine to yield choline. Third, choline is oxidized by choline oxidase to betaine. Finally, $H_2O_2$, in the presence of horseradish peroxidase, reacts with Amplex® Red to produce the fluorescent product, Resorufin, and the signal therefrom is detected using spectrofluorometry.

Fluorescence polarization (FP) is based on a decrease in the speed of molecular rotation of a fluorophore that occurs upon binding to a larger molecule, such as a receptor protein, allowing for polarized fluorescent emission by the bound ligand. FP is empirically determined by measuring the vertical and horizontal components of fluorophore emission following excitation with plane polarized light. Polarized emission is increased when the molecular rotation of a fluorophore is reduced. A fluorophore produces a larger polarized signal when it is bound to a larger molecule (i.e. a receptor), slowing molecular rotation of the fluorophore. The magnitude of the polarized signal relates quantitatively to the extent of fluorescent ligand binding. Accordingly, polarization of the "bound" signal depends on maintenance of high affinity binding.

FP is a homogeneous technology and reactions are very rapid, taking seconds to minutes to reach equilibrium. The reagents are stable, and large batches may be prepared, resulting in high reproducibility. Because of these properties, FP has proven to be highly automatable, often performed with a single incubation with a single, premixed, tracer-receptor reagent. For a review, see Owickiet al., (1997), Application of Fluorescence Polarization Assays in High-Throughput Screening, Genetic Engineering News, 17:27.

FP is particularly desirable since its readout is independent of the emission intensity (Checovich, W. J., et al., (1995) Nature 375:254-256; Dandliker, W. B., et al., (1981) Methods in Enzymology 74:3-28) and is thus insensitive to the presence of colored compounds that quench fluorescence emission. FP and FRET (see below) are well-suited for identifying compounds that block interactions between sphingolipid receptors and their ligands. See, for example, Parker et al., (2000) Development of high throughput screening assays using fluorescence polarization: nuclear receptor-ligand-binding and kinase/phosphatase assays, J Biomol Screen 5:77-88.

Fluorophores derived from sphingolipids that may be used in FP assays are commercially available. For example, Molecular Probes (Eugene, Oreg.) currently sells sphingomyelin and one ceramide fluorophores. These are, respectively, N-(4,4-difluoro-5,7-dimethyl-4-bora-3a,4a-diaza-s-indacene-3-pentanoyl)sphingosyl phosphocholine (BODIPY® FL C5-sphingomyelin); N-(4,4-difluoro-5,7-dimethyl-4-bora-3a,4a-diaza-s-indacene-3-dodecanoyl)sphingosyl phosphocholine (BODIPY® FL C12-sphingomyelin); and N-(4,4-difluoro-5,7-dimethyl-4-bora-3a,4a-diaza-s-indacene-3-pentanoyl)sphingosine (BODIPY® FL C5-ceramide). U.S. Pat. No. 4,150,949, (Immunoassay for gentamicin), discloses fluorescein-labelled gentamicins, including fluoresceinthiocarbanyl gentamicin. Additional fluorophores may be prepared using methods well known to the skilled artisan.

Exemplary normal-and-polarized fluorescence readers include the POLARION® fluorescence polarization system (Tecan AG, Hombrechtikon, Switzerland). General multi-well plate readers for other assays are available, such as the VERSAMAX® reader and the SPECTRAMAX® multiwell plate spectrophotometer (both from Molecular Devices).

Fluorescence resonance energy transfer (FRET) is another useful assay for detecting interaction and has been described. See, e.g., Heim et al., (1996) Curr. Biol. 6:178-182; Mitra et al., (1996) Gene 173:13-17; and Selvin et al., (1995) Meth. Enzymol. 246:300-345. FRET detects the transfer of energy between two fluorescent substances in close proximity, having known excitation and emission wavelengths. As an example, a protein can be expressed as a fusion protein with green fluorescent protein (GFP). When two fluorescent proteins are in proximity, such as when a protein specifically interacts with a target molecule, the resonance energy can be transferred from one excited molecule to the other. As a result, the emission spectrum of the sample shifts, which can be measured by a fluorometer, such as a fMAX multiwell fluorometer (Molecular Devices, Sunnyvale Calif.).

Scintillation proximity assay (SPA) is a particularly useful assay for detecting an interaction with the target molecule. SPA is widely used in the pharmaceutical industry and has been described (Hanselman et al., (1997) J. Lipid Res. 38:2365-2373; Kahl et al., (1996) Anal. Biochem. 243:282-283; Undenfriend et al., (1987) Anal. Biochem. 161:494-500). See also U.S. Pat. Nos. 4,626,513 and 4,568,649, and European Patent No. 0,154,734. One commercially available system uses FLASHPLATE® scintillant-coated plates (NEN Life Science Products, Boston, Mass.).

10287) The target molecule can be bound to the scintillator plates by a variety of well known means. Scintillant plates are available that are derivatized to bind to fusion proteins such as GST, His6 (SEQ ID NO: 3) or Flag fusion proteins. Where the target molecule is a protein complex or a multimer, one protein or subunit can be attached to the plate first, then the other components of the complex added later under binding conditions, resulting in a bound complex.

In a typical SPA assay, the gene products in the expression pool will have been radiolabeled and added to the wells, and allowed to interact with the solid phase, which is the immobilized target molecule and scintillant coating in the wells. The assay can be measured immediately or allowed to reach equilibrium. Either way, when a radiolabel becomes sufficiently close to the scintillant coating, it produces a signal detectable by a device such as a TOPCOUNT NXT® microplate scintillation counter (Packard BioScience Co., Meriden Conn.). If a radiolabeled expression product binds to the target molecule, the radiolabel remains in proximity to the scintillant long enough to produce a detectable signal.

In contrast, the labeled proteins that do not bind to the target molecule, or bind only briefly, will not remain near the scintillant long enough to produce a signal above background. Any time spent near the scintillant caused by random Brownian motion will also not result in a significant amount of signal. Likewise, residual unincorporated radiolabel used during the expression step may be present, but will not generate significant signal because it will be in solution rather than interacting with the target molecule. These non-binding interactions will therefore cause a certain level of background signal that can be mathematically removed. If too many signals are obtained, salt or other modifiers can be added directly to the assay plates until the desired specificity is obtained (Nichols et al., (1998) Anal. Biochem. 257:112-119).

III. Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases described assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phospho-specific antibody.

IV. Alternative Compound Forms or Derivatives (a) Isomers, Prodrugs, and Active Metabolites Compounds contemplated herein are described with reference to both generic formulae and specific compounds. In addition, the invention compounds may exist in a number of different forms or derivatives, all within the scope of the present invention. These include, for example, tautomers, stereoisomers, racemic mixtures, regioisomers, salts, prodrugs (e.g. carboxylic acid esters), solvated forms, different crystal forms or polymorphs, and active metabolites.

(b) Tautomers, Stereoisomers, Regioisomers, and Solvated Forms

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present invention. Unless specified to the contrary, all such stereoisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form.

For compounds in which synthesis involves addition of a single group at a double bond, particularly a carbon-carbon double bond, the addition may occur at either of the double bond-linked atoms. For such compounds, the present invention includes both such regioisomers.

Additionally, the formulae are intended to cover solvated as well as unsolvated forms of the identified structures. For example, the indicated structures include both hydrated and non-hydrated forms. Other examples of solvates include the structures in combination with a suitable solvent such as isopropanol, ethanol, methanol, DMSO, ethyl acetate, acetic acid, or ethanolamine.

(c) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more of advantageous handling, administration, and/or metabolic properties. For example, some prodrugs are esters of the active compound; during metabolysis, the ester group is cleaved to yield the active drug. Also, some prodrugs are activated enzymatically to yield the active compound, or a compound which, upon further chemical reaction, yields the active compound.

In this context, a common example of a prodrug is an alkyl ester of a carboxylic acid. Relative to compounds of Formula I, Formula Ia, Formula Ib, Formula Ig, Formula II, Formula IIa, Formula IIb, Formula IIc, Formula Hd, Formula IIe, Formula IIf, Formula IIg, Formula IIh, Formula IIi, Formula IIj, Formula IIk, Formula IIm, Formula IIn, Formula IIo, Formula IIp, or Formula III, further examples include, without limitation, an amide or carbamate derivative at the pyrrole nitrogen (i.e. N1) of the azaindole core.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the follow types:

Oxidative Reactions

Oxidative reactions are exemplified without limitation to reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive Reactions

Reductive reactions are exemplified without limitation to reactions such as reduction of carbonyl functionalities, reduction of alcohol functionalities and carbon-carbon double bonds, reduction of nitrogen-containing functional groups, and other reduction reactions.

Reactions without Change in the Oxidation State

Reactions without change in the state of oxidation are exemplified without limitation to reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 2004/0077595, application Ser. No. 10/656, 838, incorporated herein by reference.) Such carrier prodrugs are often advantageous for orally administered drugs. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g. stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Prodrugs may proceed from prodrug form to active form in a single step or may have one or more intermediate forms which may themselves have activity or may be inactive.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic process in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug.

Prodrugs and active metabolites may be identified using routine techniques known in the art. See, e.g., Bertolini et al., 1997, *J Med. Chem.*, 40:2011-2016; Shan et al., 1997, *J Pharm Sci* 86(7):756-757; Bagshawe, 1995, *Drug Dev. Res.*, 34:220-230; Wermuth, supra.

(d) Pharmaceutically Acceptable Salts

Compounds can be formulated as or be in the form of pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug.

Pharmaceutically acceptable salts include acid addition salts such as those containing sulfate, chloride, hydrochloride, fumarate, maleate, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid.

Pharmaceutically acceptable salts also include basic addition salts such as those containing benzathine, chloroprocaine, choline, diethanolamine, ethanolamine, t-butylamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see *Remington's Pharmaceutical Sciences*, 19$^{th}$ ed., Mack Publishing Co., Easton, Pa., Vol. 2, p. 1457, 1995. Such salts can be prepared using the appropriate corresponding bases.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent.

Thus, for example, if the particular compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

Similarly, if the particular compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as L-glycine, L-lysine, and L-arginine, ammonia, primary, secondary, and tertiary amines, and cyclic amines, such as hydroxyethylpyrrolidine, piperidine, morpholine or piperazine, and inorganic salts derived from sodium, calcium, potassium, magnesium, manganese, iron, copper, zinc, aluminum and lithium.

The pharmaceutically acceptable salt of the different compounds may be present as a complex. Examples of complexes include 8-chlorotheophylline complex (analogous to, e.g., dimenhydrinate: diphenhydramine 8-chlorotheophylline (1:1) complex; Dramamine) and various cyclodextrin inclusion complexes.

Unless specified to the contrary, specification of a compound herein includes pharmaceutically acceptable salts of such compound.

(e) Polymorphic Forms

In the case of agents that are solids, it is understood by those skilled in the art that the compounds and salts may exist in different crystal or polymorphic forms, all of which are intended to be within the scope of the present invention and specified formulae.

V. Administration

The methods and compounds will typically be used in therapy for human subjects. However, they may also be used to treat similar or identical indications in other animal subjects. In this context, the terms "subject," "animal subject," and the like refer to human and non-human vertebrates, e.g. mammals, such as non-human primates, sports and commercial animals, e.g., equines, bovines, porcines, ovines, rodents, and pets, e.g., canines and felines.

Suitable dosage forms, in part, depend upon the use or the route of administration, for example, oral, transdermal, transmucosal, inhalant, or by injection (parenteral). Such dosage forms should allow the compound to reach target cells. Other factors are well known in the art, and include considerations such as toxicity and dosage forms that retard the compound or composition from exerting its effects. Techniques and formulations generally may be found in The Science and Practice of Pharmacy, 21$^{st}$ edition, Lippincott, Williams and Wilkins, Philadelphia, Pa., 2005 (hereby incorporated by reference herein).

Compounds of the present invention (i.e. Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, and all sub-embodiments disclosed herein) can be formulated as pharmaceutically acceptable salts.

Carriers or excipients can be used to produce compositions. The carriers or excipients can be chosen to facilitate administration of the compound. Examples of carriers include calcium carbonate, calcium phosphate, various sugars such as lactose, glucose, or sucrose, or types of starch, cellulose derivatives, gelatin, vegetable oils, polyethylene glycols and physiologically compatible solvents. Examples of physiologically compatible solvents include sterile solutions of water for injection (WFI), saline solution, and dextrose.

The compounds can be administered by different routes including intravenous, intraperitoneal, subcutaneous, intramuscular, oral, transmucosal, rectal, transdermal, or inhalant. In some embodiments, oral administration is preferred. For oral administration, for example, the compounds can be formulated into conventional oral dosage forms such as capsules, tablets, and liquid preparations such as syrups, elixirs, and concentrated drops.

For inhalants, compounds of the invention may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of the invention may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratropium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

Pharmaceutical preparations for oral use can be obtained, for example, by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone). If desired, disintegrating agents may be added, such as the cross-linked polyvinylpyrrolidone, agar, or alginic acid, or a salt thereof such as sodium alginate.

Dragee cores are provided with suitable coatings. For this purpose, concentrated sugar solutions may be used, which may optionally contain, for example, gum arabic, talc, poly-vinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Alternatively, injection (parenteral administration) may be used, e.g., intramuscular, intravenous, intraperitoneal, and/or subcutaneous. For injection, the compounds of the invention are formulated in sterile liquid solutions, preferably in physiologically compatible buffers or solutions, such as saline solution, Hank's solution, or Ringer's solution. In addition, the compounds may be formulated in solid form and redissolved or suspended immediately prior to use. Lyophilized forms can also be produced.

Administration can also be by transmucosal, topical, transdermal, or inhalant means. For transmucosal, topical or transdermal administration, penetrants appropriate to the barrier to be permeated are used in the formulation. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal).

The topical compositions of this invention are formulated preferably as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount solvent (e.g. an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will, of course, be continuous rather than intermittent throughout the dosage regimen.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, preferably 0.1 and 20 mg/kg of the subject being treated. Multiple doses may be used.

The compounds of the invention may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of the present invention, or at the same time as a compound of the invention. Use in combination also includes use with a therapy or medical procedure that is administered once or infrequently, such as surgery, along with a compound of the invention administered within a short time or longer time before or after the other therapy or procedure. In some embodiments, the present invention provides for delivery of compounds of the invention and one or more other drug therapeutics delivered by a different route of administration or by the same route of administration. The use in combination for any route of administration includes delivery of compounds of the invention and one or more other drug therapeutics delivered by the same route of administration together in any formulation, including formulations where the two compounds are chemically linked in such a way that they maintain their therapeutic activity when administered. In one aspect, the other drug therapy may be co-administered with one or more compounds of the invention. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of compounds of the invention and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

In certain embodiments, the patient is 60 years or older and relapsed after a first line cancer therapy. In certain embodiments, the patient is 18 years or older and is relapsed or refractory after a second line cancer therapy. In certain embodiments, the patient is 60 years or older and is primary refractory to a first line cancer therapy. In certain embodiments, the patient is 70 years or older and is previously untreated. In certain embodiments, the patient is 70 years or older and is ineligible and/or unlikely to benefit from cancer therapy.

In certain embodiments, the therapeutically effective amount used in the methods provided herein is at least 10 mg per day. In certain embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500 mg per dosage. In other embodiments, the therapeutically effective amount is 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day or more. In certain embodiments, the compound is administered continuously.

In certain embodiments, provided herein is a method for treating a diseases or condition mediated by Flt3 or oncogenic Flt3 by administering to a mammal having a disease or condition at least 10, 50, 90, 100, 135, 150, 200, 250, 300, 350, 400, 450, 500, 600, 700, 800, 900, 1000, 1200, 1300, 1400, 1500, 1600, 1700, 1800, 1900, 2000, 2200, 2500, 3000, 3500, 4000, 4500, 5000 mg per day of a compound of any of formulas I, Ia, Ib, Ig, IIa to IIk, IIm to IIp and III or any of the compounds described herein or a pharmaceutically acceptable salt or solvate thereof, and wherein the compound is administered on an empty stomach.

In certain embodiments, the disease or condition in the methods provided herein is cancer. In certain embodiments, the disease or condition in the methods provided herein is a solid tumor. In yet another embodiment, the disease or condition in the methods provided herein is a blood-borne tumor. In yet another embodiment, the disease or condition is leukemia. In certain embodiments, the leukemia is acute myeloid leukemia. In certain embodiments, the leukemia is acute lymphocytic leukemia. In still another embodiment, the leukemia is a refractory or drug resistant leukemia.

In certain embodiments, the drug resistant leukemia is drug resistant acute myeloid leukemia. In certain embodiments, the mammal having the drug resistant acute myeloid leukemia has an activating FLT3 mutation. In still another embodiment, the drug resistant acute myeloid leukemia has a FLT3 internal tandem duplication (ITD) mutation.

Each method provided herein may further comprise administering a second therapeutic agent. In certain embodiments, the second therapeutic agent is an anticancer agent. In certain embodiments, the second therapeutic agent is a protein kinase inhibitor. In certain embodiments, a tyrosine kinase inhibitor; and in yet another embodiment, a second FLT3 kinase inhibitor, including, but not limiting to, Sunitinib, Cediranib, XL-184 free base (Cabozantinib, Ponatinib (AP24534), PHA-665752, Dovitinib (TKI258, CHIR-258), AC220 (Quizartinib), TG101209, KW-2449, AEE788 (NVP-AEE788), MP-470 (Amuvatinib), TSU-68 (SU6668, Orantinib, ENMD-2076, Vatalanib dihydrochloride (PTK787) and Tandutinib (MLN518).

VII. Manipulation of Flt3

Techniques for the manipulation of nucleic acids, such as, e.g., subcloning, labeling probes (e.g. random-primer labeling using Klenow polymerase, nick translation, amplification), sequencing, hybridization and the like are well disclosed in the scientific and patent literature, see, e.g., Sambrook, ed., Molecular Cloning: a Laboratory Manual (2nd ed.), Vols. 1-3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Nucleic acid sequences can be amplified as necessary for further use using amplification methods, such as PCR, isothermal methods, rolling circle methods, etc., are well known to the skilled artisan. See, e.g., Saiki, "Amplification of Genomic DNA" in PCR Protocols, Innis et al., Eds., Academic Press, San Diego, Calif. 1990, pp 13-20; Wharam et al., Nucleic Acids Res. 2001 Jun. 1; 29(11):E54-E54; Hafner et al., Biotechniques 2001 April; 30(4):852-6, 858, 860 passim; Zhong et al., Biotechniques 2001 April; 30(4): 852-6, 858, 860 passim.

Nucleic acids, vectors, capsids, polypeptides, and the like can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, e.g. fluid or gel precipitin reactions, immunodiffusion, immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g. SDS-PAGE), nucleic acid or target or signal amplification methods, radiolabeling, scintillation counting, and affinity chromatography.

Obtaining and manipulating nucleic acids used to practice the methods of the invention can be performed by cloning from genomic samples, and, if desired, screening and recloning inserts isolated or amplified from, e.g., genomic clones or cDNA clones. Sources of nucleic acid used in the methods of the invention include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

The nucleic acids used to practice the methods of the invention can be operatively linked to a promoter. A promoter can be one motif or an array of nucleic acid control sequences which direct transcription of a nucleic acid. A promoter can include necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. A "constitutive" promoter is a promoter which is active under most environmental and developmental conditions. An "inducible" promoter is a promoter which is under environmental or developmental regulation. A "tissue specific" promoter is active in certain tissue types of an organism, but not in other tissue types from the same organism. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The nucleic acids used to practice the methods of the invention can also be provided in expression vectors and cloning vehicles, e.g., sequences encoding the polypeptides used to practice the methods of the invention. Expression vectors and cloning vehicles used to practice the methods of the invention can comprise viral particles, baculovirus, phage, plasmids, phagemids, cosmids, fosmids, bacterial artificial chromosomes, viral DNA (e.g. vaccinia, adenovirus, foul pox virus, pseudorabies and derivatives of SV40), P1-based artificial chromosomes, yeast plasmids, yeast artificial chromosomes, and any other vectors specific for specific hosts of interest (such as bacillus, Aspergillus and yeast). Vectors used to practice the methods of the invention can include chromosomal, non-chromosomal and synthetic DNA sequences. Large numbers of suitable vectors are known to those of skill in the art, and are commercially available.

The nucleic acids used to practice the methods of the invention can be cloned, if desired, into any of a variety of vectors using routine molecular biological methods; methods for cloning in vitro amplified nucleic acids are disclosed, e.g., U.S. Pat. No. 5,426,039. To facilitate cloning of amplified sequences, restriction enzyme sites can be "built into" a PCR primer pair. Vectors may be introduced into a genome or into the cytoplasm or a nucleus of a cell and expressed by a variety of conventional techniques, well described in the scientific and patent literature. See, e.g., Roberts (1987) Nature 328:731; Schneider (1995) Protein Expr. Purif. 6435: 10; Sambrook, Tijssen or Ausubel. The vectors can be isolated from natural sources, obtained from such sources as ATCC or GenBank libraries, or prepared by synthetic or recombinant methods. For example, the nucleic acids used to practice the methods of the invention can be expressed in expression cassettes, vectors or viruses which are stably or transiently expressed in cells (e.g. episomal expression systems). Selection markers can be incorporated into expression cassettes and vectors to confer a selectable phenotype on transformed cells and sequences. For example, selection markers can code for episomal maintenance and replication such that integration into the host genome is not required.

In one aspect, the nucleic acids used to practice the methods of the invention are administered in vivo for in situ expression of the peptides or polypeptides used to practice the methods of the invention. The nucleic acids can be administered as "naked DNA" (see, e.g., U.S. Pat. No. 5,580,859) or in the form of an expression vector, e.g., a recombinant virus. The nucleic acids can be administered by any route, including peri- or intra-tumorally, as described below. Vectors administered in vivo can be derived from viral genomes, including recombinantly modified enveloped or non-enveloped DNA and RNA viruses, preferably selected from baculoviridiae, parvoviridiae, picornoviridiae, herpesveridiae, poxyiridae, adenoviridiae, or picornnaviridiae. Chimeric vectors may also be employed which exploit advantageous merits of each of the parent vector properties (See e.g., Feng (1997) Nature Biotechnology 15:866-870). Such viral genomes may be modified by recombinant DNA techniques to include the nucleic acids used to practice the methods of the invention; and may be further engineered to be replication deficient, conditionally replicating or replication competent. In alternative aspects, vectors are derived from the adenoviral (e.g. replication incompetent vectors derived from the human adenovirus genome, see, e.g., U.S. Pat. Nos. 6,096,718; 6,110,458; 6,113,913; 5,631,236); adeno-associated viral and retroviral genomes. Retroviral vectors can include those based upon murine leukemia virus (MuLV), gibbon ape leukemia virus (GaLV), Simian Immuno deficiency virus (SIV), human immuno deficiency virus (HIV), and combinations thereof; see, e.g., U.S. Pat. Nos. 6,117,681; 6,107,478; 5,658,775; 5,449,614; Buchscher (1992) J. Virol. 66:2731-2739; Johann (1992) J Virol. 66:1635-1640). Adeno-associated virus (AAV)-based vectors can be used to transduce cells with target nucleic acids, e.g., in the in vitro production of nucleic acids and peptides, and in vivo and ex vivo gene therapy procedures; see, e.g., U.S. Pat. Nos. 6,110,456; 5,474,935; Okada (1996) Gene Ther. 3:957-964.

The present invention also relates to use of fusion proteins, and nucleic acids encoding them. A polypeptide used to practice the methods of the invention can be fused to a heterologous peptide or polypeptide, such as N-terminal identification peptides which impart desired characteristics, such as increased stability or simplified purification. Peptides and polypeptides used to practice the methods of the invention can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues (SEQ ID NO: 3) followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. In one aspect, a nucleic acid encoding a polypeptide used to practice the methods of the invention is assembled in appropriate phase with a leader sequence capable of directing secretion of the translated polypeptide or fragment thereof. Technology pertaining to vectors encoding fusion proteins and application of fusion proteins are well disclosed in the scientific and patent literature, see e.g., Kroll (1993) DNA Cell. Biol. 12:441-53.

The nucleic acids and polypeptides used to practice the methods of the invention can be bound to a solid support, e.g., for use in screening and diagnostic methods. Solid supports can include, e.g., membranes (e.g. nitrocellulose or nylon), a microtiter dish (e.g. PVC, polypropylene, or polystyrene), a test tube (glass or plastic), a dip stick (e.g. glass, PVC, polypropylene, polystyrene, latex and the like), a microfuge tube, or a glass, silica, plastic, metallic or polymer bead or other substrate such as paper. One solid support uses a metal (e.g. cobalt or nickel)-comprising column which binds with specificity to a histidine tag engineered onto a peptide.

Adhesion of molecules to a solid support can be direct (i.e., the molecule contacts the solid support) or indirect (a "linker" is bound to the support and the molecule of interest binds to this linker). Molecules can be immobilized either covalently (e.g. utilizing single reactive thiol groups of cysteine residues (see, e.g., Colliuod (1993) Bioconjugate Chem. 4:528-536) or non-covalently but specifically (e.g. via immobilized antibodies (see, e.g., Schuhmann (1991) Adv. Mater. 3:388-391; Lu (1995) Anal. Chem. 67:83-87; the biotin/strepavidin system (see, e.g., Iwane (1997) Biophys. Biochem. Res. Comm 230:76-80); metal chelating, e.g., Langmuir-Blodgett films (see, e.g., Ng (1995) Langmuir 11:4048-55); metal-chelating self-assembled monolayers (see, e.g., Sigal (1996) Anal. Chem. 68:490-497) for binding of polyhistidine fusions.

Indirect binding can be achieved using a variety of linkers which are commercially available. The reactive ends can be any of a variety of functionalities including, but not limited to: amino reacting ends such as N-hydroxysuccinimide (NHS) active esters, imidoesters, aldehydes, epoxides, sulfonyl halides, isocyanate, isothiocyanate, and nitroaryl halides; and thiol reacting ends such as pyridyl disulfides, maleimides, thiophthalimides, and active halogens. The heterobifunctional crosslinking reagents have two different reactive ends, e.g., an amino-reactive end and a thiol-reactive end, while homobifunctional reagents have two similar reactive ends, e.g., bismaleimidohexane (BMH) which permits the cross-linking of sulfhydryl-containing compounds. The spacer can be of varying length and be aliphatic or aromatic. Examples of commercially available homobifunctional cross-linking reagents include, but are not limited to, the imidoesters such as dimethyl adipimidate dihydrochloride (DMA); dimethyl pimelimidate dihydrochloride (DMP); and dimethyl suberimidate dihydrochloride (DMS). Heterobifunctional reagents include commercially available active halogen-NHS active esters coupling agents such as N-succinimidyl bromoacetate and N-succinimidyl (4-iodoacetyl)aminobenzoate (SIAB) and the sulfosuccinimidyl derivatives such as sulfosuccinimidyl(4-iodoacetyl) aminobenzoate (sulfo-SIAB) (Pierce). Another group of coupling agents is the heterobifunctional and thiol cleavable agents such as N-succinimidyl 3-(2-pyridyldithio)propionate (SPDP) (Pierce Chemicals, Rockford, Ill.).

Antibodies can also be used for binding polypeptides and peptides used to practice the methods of the invention to a solid support. This can be done directly by binding peptide-specific antibodies to the column or it can be done by creating fusion protein chimeras comprising motif-containing peptides linked to, e.g., a known epitope (e.g. a tag (e.g. FLAG, myc) or an appropriate immunoglobulin constant domain sequence (an "immunoadhesin," see, e.g., Capon (1989) Nature377:525-531 (1989).

Nucleic acids or polypeptides used to practice the methods of the invention can be immobilized to or applied to an array. Arrays can be used to screen for or monitor libraries of compositions (e.g. small molecules, antibodies, nucleic acids, etc.) for their ability to bind to or modulate the activity of a nucleic acid or a polypeptide used to practice the methods of the invention. For example, in one aspect of the invention, a monitored parameter is transcript expression of a gene comprising a nucleic acid used to practice the methods of the invention. One or more, or all the transcripts of a cell can be measured by hybridization of a sample comprising transcripts of the cell, or nucleic acids representative of or complementary to transcripts of a cell, by hybridization to immobilized nucleic acids on an array, or "biochip." By using an "array" of nucleic acids on a microchip, some or all of the transcripts of a cell can be simultaneously quantified. Alternatively, arrays comprising genomic nucleic acid can also be used to determine the genotype of a newly engineered strain made by the methods of the invention. Polypeptide arrays" can also be used to simultaneously quantify a plurality of proteins.

The terms "array" or "microarray" or "biochip" or "chip" as used herein is a plurality of target elements, each target element comprising a defined amount of one or more polypeptides (including antibodies) or nucleic acids immobilized onto a defined area of a substrate surface. In practicing the methods of the invention, any known array and/or method of making and using arrays can be incorporated in whole or in part, or variations thereof, as disclosed, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent application Nos. 20010018642; 20010019827; 20010016322; 20010014449; 20010014448; 20010012537; 20010008765.

Host Cells and Transformed Cells

The invention also provides a transformed cell comprising a nucleic acid sequence used to practice the methods of the invention, e.g., a sequence encoding a polypeptide used to practice the methods of the invention, or a vector used to practice the methods of the invention. The host cell may be any of the host cells familiar to those skilled in the art, including prokaryotic cells, eukaryotic cells, such as bacterial cells, fungal cells, yeast cells, mammalian cells, insect cells, or plant cells. Exemplary bacterial cells include *E. coli, Streptomyces, Bacillus subtilis, Salmonella typhimurium* and various species within the genera *Pseudomonas, Streptomyces*, and *Staphylococcus*. Exemplary insect cells include *Drosophila* S2 and *Spodoptera* Sf9. Exemplary animal cells include CHO, COS or Bowes melanoma or any mouse or human cell line. The selection of an appropriate host is within the abilities of those skilled in the art.

Vectors may be introduced into the host cells using any of a variety of techniques, including transformation, transfection, transduction, viral infection, gene guns, or Ti-mediated gene transfer. Particular methods include calcium phosphate transfection, DEAE-Dextran mediated transfection, lipofection, or electroporation.

Engineered host cells can be cultured in conventional nutrient media modified as appropriate for activating promoters, selecting transformants or amplifying the genes used to practice the methods of the invention. Following transformation of a suitable host strain and growth of the host strain to an appropriate cell density, the selected promoter may be induced by appropriate means (e.g. temperature shift or chemical induction) and the cells may be cultured for an additional period to allow them to produce the desired polypeptide or fragment thereof.

Cells can be harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts and other cell lines capable of expressing proteins from a compatible vector, such as the C127, 3T3, CHO, HeLa and BHK cell lines.

The constructs in host cells can be used in a conventional manner to produce the gene product encoded by the recombinant sequence. Depending upon the host employed in a recombinant production procedure, the polypeptides produced by host cells containing the vector may be glycosylated or may be non-glycosylated. Polypeptides used to practice the methods of the invention may or may not also include an initial methionine amino acid residue.

Cell-free translation systems can also be employed to produce a polypeptide used to practice the methods of the invention. Cell-free translation systems can use mRNAs transcribed from a DNA construct comprising a promoter operably linked to a nucleic acid encoding the polypeptide or fragment thereof. In some aspects, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The expression vectors can contain one or more selectable marker genes to provide a phenotypic trait for selection of transformed host cells such as dihydrofolate reductase or neomycin resistance for eukaryotic cell culture, or such as tetracycline or ampicillin resistance in E. coli.

For transient expression in mammalian cells, cDNA encoding a polypeptide of interest may be incorporated into a mammalian expression vector, e.g. pcDNA1, which is available commercially from Invitrogen Corporation (San Diego, Calif., U.S.A.; catalogue number V490-20). This is a multifunctional 4.2 kb plasmid vector designed for cDNA expression in eukaryotic systems, and cDNA analysis in prokaryotes, incorporated on the vector are the CMV promoter and enhancer, splice segment and polyadenylation signal, an SV40 and Polyoma virus origin of replication, and M13 origin to rescue single strand DNA for sequencing and mutagenesis, Sp6 and T7 RNA promoters for the production of sense and anti-sense RNA transcripts and a Col E1-like high copy plasmid origin. A polylinker is located appropriately downstream of the CMV promoter (and 3' of the T7 promoter).

The cDNA insert may be first released from the above phagemid incorporated at appropriate restriction sites in the pcDNAI polylinker. Sequencing across the junctions may be performed to confirm proper insert orientation in pcDNAI. The resulting plasmid may then be introduced for transient expression into a selected mammalian cell host, for example, the monkey-derived, fibroblast like cells of the COS-1 lineage (available from the American Type Culture Collection, Rockville, Md. as ATCC CRL 1650).

For transient expression of the protein-encoding DNA, for example, COS-1 cells may be transfected with approximately 8 µg DNA per $10^6$ COS cells, by DEAE-mediated DNA transfection and treated with chloroquine according to the procedures described by Sambrook et al, Molecular Cloning: A Laboratory Manual, 1989, Cold Spring Harbor Laboratory Press, Cold Spring Harbor N.Y., pp. 16.30-16.37. An exemplary method is as follows. Briefly, COS-1 cells are plated at a density of $5 \times 10^6$ cells/dish and then grown for 24 hours in FBS-supplemented DMEM/F12 medium. Medium is then removed and cells are washed in PBS and then in medium. A transfection solution containing DEAE dextran (0.4 mg/ml), 100 µM chloroquine, 10% NuSerum, DNA (0.4 mg/ml) in DMEM/F12 medium is then applied on the cells 10 ml volume. After incubation for 3 hours at 37° C., cells are washed in PBS and medium as just described and then shocked for 1 minute with 10% DMSO in DMEM/F12 medium. Cells are allowed to grow for 2-3 days in 10% FBS-supplemented medium, and at the end of incubation dishes are placed on ice, washed with ice cold PBS and then removed by scraping. Cells are then harvested by centrifugation at 1000 rpm for 10 minutes and the cellular pellet is frozen in liquid nitrogen, for subsequent use in protein expression. Northern blot analysis of a thawed aliquot of frozen cells may be used to confirm expression of receptor-encoding cDNA in cells under storage.

In a like manner, stably transfected cell lines can also prepared, for example, using two different cell types as host: CHO K1 and CHO Pro5. To construct these cell lines, cDNA coding for the relevant protein may be incorporated into the mammalian expression vector pRC/CMV (Invitrogen), which enables stable expression. Insertion at this site places the cDNA under the expression control of the cytomegalovirus promoter and upstream of the polyadenylation site and terminator of the bovine growth hormone gene, and into a vector background comprising the neomycin resistance gene (driven by the SV40 early promoter) as selectable marker.

An exemplary protocol to introduce plasmids constructed as described above is as follows. The host CHO cells are first seeded at a density of $5 \times 10^5$ in 10% FBS-supplemented MEM medium. After growth for 24 hours, fresh medium is added to the plates and three hours later, the cells are transfected using the calcium phosphate-DNA co-precipitation procedure (Sambrook et al, supra). Briefly, 3 µg of DNA is mixed and incubated with buffered calcium solution for 10 minutes at room temperature. An equal volume of buffered phosphate solution is added and the suspension is incubated for 15 minutes at room temperature. Next, the incubated suspension is applied to the cells for 4 hours, removed and cells were shocked with medium containing 15% glycerol. Three minutes later, cells are washed with medium and incubated for 24 hours at normal growth conditions. Cells resistant to neomycin are selected in 10% FBS-supplemented alpha-MEM medium containing G418 (1 mg/ml). Individual colonies of G418-resistant cells are isolated about 2-3 weeks later, clonally selected and then propagated for assay purposes.

EXAMPLES

Examples related to the present invention are described below. In most cases, alternative techniques can be used. The examples are intended to be illustrative and are not limiting or restrictive to the scope of the invention. Compound A as used herein and noted the Figures refers to any of compounds P-001 to P-0499 as described herein or a compound listed in Table 1.

Example 1

Synthesis

The synthesis of the compounds described herein was described in PCT Patent publication Nos.: WO 2008/064255; WO 2008/064265; and US Patent Application Publication No.: US 2009/0076046. A person of skill in the art is readily capable of preparing all the compounds described herein and those encompassed by the generic formulas I, Ia, Ib, Ig, IIa to IIk, IIm to IIp and III using the procedures described in the above-mentioned patent applications.

Example 2

Binding Assays

Binding assays can be performed in a variety of ways, including a variety of ways known in the art. For example, as indicated above, binding assays can be performed using fluorescence resonance energy transfer (FRET) format, or using an AlphaScreen.

Alternatively, any method which can measure binding of a ligand to the ATP-binding site can be used. For example, a fluorescent ligand can be used. When bound Flt3, the emitted fluorescence is polarized. Once displaced by inhibitor binding, the polarization decreases.

Determination of $IC_{50}$ for compounds by competitive binding assays. (Note that $K_I$ is the dissociation constant for inhibitor binding; $K_D$ is the dissociation constant for substrate binding.)

For this system, the $IC_{50}$, inhibitor binding constant and substrate binding constant can be interrelated according to the following Formula:

$$K_I = \frac{IC50}{1 + [L^*]/K_D}.$$

When using radiolabeled substrate, the $IC_{50} \sim K_I$ when there is a small amount of labeled substrate.

Example 3

Cell-Based Assays of Flt3-ITD Kinase Activity

The FLT3 inhibitors may also be assessed using MV-4-11 cells are a human biphenotypic B-myelomonocytic leukemia derived cell line that harbor an activated FLT3 allele with an internal tandem duplication (ITD) which is frequently observed in human acute myelocytic leukemia. MV-4-11 cells (ATCC catalog #CRL-9591). This cell line proliferation is dependent on the FLT3-ITD activity Inhibitors of FLT3 kinase activity reduce or eliminate the FLT3-ITD oncogenic signaling, resulting in reduced cell proliferation. This inhibition is measured as a function of compound concentration to assess $IC_{50}$ values. MV-4-11 cells were seeded at $1\times10^4$ cells per well of a 96 well cell culture plate in 50 µl of cell culture medium of IMDM (Invitrogen catalog #12440) supplemented with 10% FBS (Sigma catalog #12306C). Compounds were dissolved in DMSO at a concentration of 1 mM and were serially diluted 1:3 for a total of eight points and added to the cells to final concentrations of 10, 3.3, 1.1, 0.37, 0.12, 0.041, 0.014 and 0.0046 µM in 100 µl cell culture medium (final concentration 0.2% DMSO). Cells were also treated with staurosporine as a positive control. The cells were incubated at 37° C., 5% $CO_2$ for three days. CellTiter-Glo Buffer (Promega Cell Viability Assay catalog #G7573) and substrate were equilibrated to room temperature, and enzyme/substrate Recombinant Firefly Luciferase/Beetle Luciferin was reconstituted. The cell plates were equilibrated to room temperature for 30 minutes, then lysed by addition of an equivalent volume of the Celltiter-Glo Reagent. The plate was mixed for 2 minutes on a plate shaker to lyse the cells, then incubated for 10 minutes at room temperature. The plates were read on a Victor Wallac II using Luminescence protocol modified to read 0.1 s per well. The luminescence reading assesses the ATP content, which correlates directly with cell number such that the reading as a function of compound concentration was used to determine the $IC_{50}$ value.

This cell based assay was also used to assess inhibition of FLT3-ITD phosphorylation in MV-4-11 cells. Samples were prepared with compounds as described for the growth inhibition assay only MV-4-11 cells were seeded at $2\times10^6$ cells per well in a 96 Well Flat Clear Bottom Black Polystyrene Poly-D-Lysine Coated Microplate (Corning #3667). Cells were incubated for 1 hour at 37° C. with the compounds as described above, and then the culture medium was removed by aspiration and the cells were lysed by addition of 30 µl lysis buffer (25 mM Tris HCl pH 7.5, 150 mM NaCl, 5 mM EDTA, 1% Triton X100, 5 mM NaF, 1 mM NaVanadate, 10 mM Beta-glycerophosphate, no EDTA (Boehringer-Roche catatalog #1873580) and placed on ice for 30 minutes. A 15 µl aliquot of the lysate was taken and assayed according to Cell Signaling Technology ELISA protocol (catalog #7206) PathScan® Phospho-FLT3 (Tyr591) Sandwich ELISA Kit by diluting the aliquot with 85 µl dilution buffer in the assay plate, incubating for 2 hours at room temperature and washing the plate 4 times with wash buffer. Detection antibody (100 µl) was added to the plate and samples incubated for 1 hour at room temperature, then washed 4 times with wash buffer. HRP anti-rabbit antibody (100 µl) was added and samples incubated for 30 minutes at room temperature, then washed 4 times with wash buffer. Stabilized chromogen (100 µl) was added and samples incubated for 15-25 minutes at room temperature, then washed 4 times with wash buffer. Stop solution (100 µl) was added and the samples read on a Wallac Victor reader at 450 nm. The absorbance was plotted against the compound concentration and the $IC_{50}$ concentration was determined.

Example 4

Exemplary Flt3 Biochemical Assay Protocol

In order to determine the effect of compounds on FLT3 catalytic activity, kinase assays using recombinant enzymes and AlphaScreen™ technology has been established. When the kinases are catalytically active, they phosphorylates a biotinylated peptide substrate on tyrosine residues. Using AlphaScreen™ technology, the ability of the compounds to affect the catalytic activity of the kinases can be measured quantitatively. The peptide substrate is immobilized by the AlphaScreen™ Streptavidin Donor beads and, upon phosphorylation by a tyrosine kinase, can bind to AlphaScreen™ Anti-Phosphotyrosine (PY20) Acceptor beads. Upon excitation of these beads with laser light at 680 nm, singlet oxygen is produced. This singlet oxygen is rapidly quenched, unless the AlphaScreen™ Anti-Phosphotyrosine (PY20) Acceptor beads are in close proximity, in which case a proximity signal can be measured at 580 nm. In the presence of catalytic activity, there is a very strong proximity signal. Selective kinase inhibitors affect a decrease in this proximity signal through a decrease in tyrosine phosphorylation of the peptide substrate.

| Assay | Assay Buffer | Stop/Detection Buffer |
|---|---|---|
| FLT3 | 25 mM Hepes pH 7.5<br>5 mM MnCl$_2$<br>5 mM MgCl$_2$<br>0.01% Tween-20<br>1 mM DTT | 25 mM Hepes pH 7.5<br>5 mM MnCl$_2$<br>5 mM MgCl$_2$<br>0.01% Tween-20<br>0.3% BSA<br>1 mM DTT<br>100 mM EDTA |

Recombinant Enzymes

| Enzyme | Commercial Source |
|---|---|
| FLT3 | Invitrogen #PV3182 |

Substrate
Poly (Glu4-Tyr) (SEQ ID NO: 4) Peptide, biotin conjugate
[Biotin-GG(EEEEY)$_{10}$EE] (SEQ ID NO: 5)
UBI/Millipore #12-440
Final concentration=30 nM
Adenosine Triphosphate (ATP)
Sigma #A-3377
Final concentration for IC50 determination=100 μM
Detection Reagent
AlphaScreen™ Phosphotyrosine (PY20) Assay Kit
Perkin-Elmer #6760601 M
Final concentration=10 μg/ml
 Protocol
  IC50
  Dilute compounds in DMSO to 20× final concentration.
  Add 1 μl of compound to each well of 384 well white reaction plate (Corning #3705).
  Mix enzyme and Poly (Glu4-Tyr) (SEQ ID NO: 4) Peptide substrate at 1.33× final concentration in assay buffer.
  Mix ATP at 5× final concentration in assay buffer.
  Add 15 μL enzyme/substrate mixture to the reaction plate.
  Add 4 μL of ATP to the reaction plate. Centrifuge 1 minute, shake to mix, and incubate as follows:

| Assay | Reaction temperature | Reaction time |
|---|---|---|
| FLT3 | Room temperature | 60 minutes |

Mix Streptavidin Donor beads at 6× final concentration in Stop/Detection buffer.
  Add 5 μL Streptavidin Donor beads to the reaction plate. Centrifuge 1 minute, shake to mix, and incubate at room temperature for 20 minutes.
  Mix Anti-Phosphotyrosine (PY20) Acceptor beads at 6× final concentration in Stop/Detection buffer.
  Add 5 μL Anti-Phosphotyrosine (PY20) beads to the reaction plate.
  Centrifuge 1 minute, shake to mix, and incubate at room temperature for 60 minutes.
  Read plate on Wallac EnVision™ 2103 Multilabel Reader.

The following Table provides Flt3 biochemical assay data of certain compounds.

| Compound No. | FLT3 IC50 (μM) |
|---|---|
| P-0233 | <0.01 |
| P-0187 | <0.01 |
| P-0234 | <0.01 |
| P-0449 | <0.01 |
| P-0181 | <0.1 |
| P-0195 | <0.1 |
| P-0429 | <0.1 |
| P-0432 | <0.1 |
| P-0232 | <0.1 |
| P-0332 | <0.1 |
| P-0282 | <0.1 |
| P-0283 | <0.1 |
| P-0370 | <0.1 |
| P-0372 | <0.1 |
| P-0442 | <0.1 |
| P-0399 | <0.1 |
| P-0326 | <0.1 |
| P-0383 | <1 |
| P-0433 | <1 |
| P-0428 | <1 |
| P-0284 | <1 |
| P-0324 | <1 |
| P-0427 | <1 |
| P-0408 | <1 |
| P-0380 | <1 |
| P-0385 | <1 |
| P-0415 | <1 |
| P-0330 | <1 |
| P-0391 | <10 |
| P-0333 | <10 |

Compounds P-0001, P-0002, P-0003, P-0004, P-0005, P-0006, P-0007, P-0008, P-0009, P-0010, P-0011, P-0012, P-0013, P-0014, P-0015, P-0016, P-0017, P-0018, P-0020, P-0022, P-0024, P-0025, P-0026, P-0027, P-0028, P-0029, P-0030, P-0031, P-0032, P-0033, P-0035, P-0036, P-0037, P-0038, P-0039, P-0040, P-0041, P-0046, P-0049, P-0052, P-0053, P-0054, P-0055, P-0056, P-0057, P-0058, P-0059, P-0060, P-0061, P-0062, P-0063, P-0064, P-0065, P-0066, P-0069, P-0071, P-0072, P-0073, P-0074, P-0075, P-0078, P-0082, P-0092, P-0093, P-0094, P-0095, P-0096, P-0097, P-0098, P-0099, P-0100, P-0101, P-0102, P-0103, P-0104, P-0105, P-0107, P-0108, P-0109, P-0111, P-0112, P-0113, P-0114, P-0115, P-0116, P-0118, P-0120, P-0121, P-0122, P-0123, P-0125, P-0126, P-0127, P-0128, P-0129, P-0131, P-0132, P-0138, P-0143, P-0144, P-0145, P-0148, P-0154, P-0156, P-0157, P-0159, P-0161, P-0163, P-0170, P-0171, P-0173, P-0174, P-0176, P-0177, P-0179, P-0180, P-0181, P-0182, P-0186, P-0187, P-0188, P-0190, P-0192, P-0193, P-0194, P-0195, P-0197, P-0199, P-0201, P-0203, P-0205, P-0206, P-0208, P-0211, P-0212, P-0213, P-0214, P-0215, P-0216, P-0217, P-0218, P-0219, P-0221, P-0222, P-0224, P-0225, P-0226, P-0228, P-0234, P-0237, P-0239, P-0240, P-0242, P-0243, P-0244, P-0245, P-0246, P-0252, P-0253, P-0255, P-0257, P-0258, P-0259, P-0260, P-0262, P-0263, P-0264, P-0265, P-0266, P-0267, P-0268, P-0269, P-0270, P-0271, P-0272, P-0273, P-0274, P-0275, P-0276, P-0277, P-0278, P-0279, P-0280, P-0281, P-0282, P-0283, P-0284, P-0285, P-0286, P-0287, P-0288, P-0289, P-0290, P-0291, P-0294, P-0297, P-0298, P-0301, P-0302, P-0303, P-0305, P-0306, P-0307, P-0308, P-0309, P-0311, P-0312, P-0313, P-0314, P-0316, P-0319, P-0320, P-0321, P-0322, P-0323, P-0324, P-0325, P-0326, P-0327, P-0328, P-0329, P-0330, P-0331, P-0332, P-0334, P-0336, P-0337, P-0338, P-0339, P-0340, P-0341, P-0342, P-0343, P-0344, P-0345, P-0346, P-0347, P-0348, P-0350, P-0351, P-0352, P-0354, P-0355, P-0356, P-0357, P-0358, P-0359, P-0361, P-0362, P-0363, P-0365, P-0366, P-0367, P-0368, P-0369, P-0370, P-0371, P-0372, P-0373, P-0375, P-0376, P-0377, P-0378, P-0379, P-0382, P-0383, P-0385, P-0387, P-0390, P-0392, P-0393, P-0394, P-0395, P-0396, P-0402, P-0404, P-0406, P-0407, P-0408, P-0409, and P-0412 had $IC_{50}$ of less than 1 µM in the Flt3 assays described above in Example 3.

In Vivo Model System Testing

For in vivo testing, a suitable animal model system can be selected for use. For example, for multiple sclerosis, the rodent experimental allergic encephalomyelitis (EAE) is commonly used. This system is well-known, and is described, for example, in Steinman, 1996, Cell 85:299-302 and Secor et al., 2000, J. Exp. Med. 5:813-821, which are incorporated herein by reference in their entireties.

Similarly, other model systems can be selected and used in the present invention.

Example 5

Inhibition of the Proliferation of the Human FLT3-ITD+AML Cell Lines

Compounds of Formula I, Formula Ia, Formula Ib, Formula Ig, Formula II, Formula IIa, Formula IIb, Formula IIe, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449, and any compounds as described herein were found to inhibited the proliferation of the human FLT3-ITD+AML cell lines MV4; 11 and Molm14 with a 50% inhibitory concentration ($IC_{50}$) in the submicromolar range (~0.1-0.25 uM). The compounds as described herein inhibited phosphorylation of FLT3-ITD with a dose response similar to the growth inhibition range.

Example 6

Inhibition of FLT3-ITD Mutant Isoforms

Compounds of Formula I, Formula Ia, Formula Ib, Formula Ig, Formula II, Formula IIa, Formula IIb, Formula IIe, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449, and any compounds as described herein were found to inhibit the proliferation of BaF3 cells transformed with FLT3-ITD and AC220-resistant FLT3-ITD mutant isoforms F691L, D835V/Y, and Y842C/H. The compounds as described herein inhibited the proliferation of Ba/F3/FLT3-ITD cells at submicromolar concentrations. Encouragingly, The compounds as described herein retained activity against cells expressing the clinically-relevant F691L gatekeeper mutation at a similar concentration, although all other AC220-resistant mutations evaluated conferred substantial cross-resistance to The compounds as described herein.

Example 7

FLT3 Inhibitor for AML Therapy

A modified plasma inhibitory assay was performed by incubating Molm14 cells in either normal donor or AML patient plasma spiked with increasing concentrations of compounds of Formula I, Formula Ia, Formula Ib, Formula Ig, Formula II, Formula IIa, Formula IIb, Formula IIe, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449, and any compounds as described herein as well as unmanipulated, steady-state plasma samples from the solid tumor. Using phospho-specific flow cytometry to evaluate FLT3 signaling through the downstream protein ribosomal S6, we observed near-maximal reductions in phospho-S6 in both normal and AML patient plasma containing ≥10 uM the compounds as described herein as well as plasma samples obtained from the solid tumor trial.

Example 8

Phospho-FMS and Phospho-FLT3 ELISA Assays

To evaluate the ability of compounds as described herein to inhibit FMS or FLT3 catalytic activity in cells, ELISA assays were established using the THP-1, RS4; 11 and MV-4-11 cell lines, respectively. THP-1 are human acute monocytic leukemia cells that express FMS, and RS4; 11 cells are human B cell precursor leukemia cells that express normal wild type FLT31-2. Stimulation of THP-1 cells with CSF-1 activates FMS, and results in receptor autophosphorylation. Similarly, treatment of RS4; 11 cells with FLT3 Ligand stimulates catalytic activation and autophosphorylation of FLT3. MV-4-11 cells are a human biphenotypic B-myelomonocytic leukemia derived cell line that harbor an activated FLT3 allele with an internal tandem duplication 3.

For the ELISA assays, the cells are deprived of serum and additional growth factor overnight to minimize receptor phosphorylation. The cells are subsequently incubated with either DMSO or a compound as described herein for one hour and then stimulated with either the FMS ligand CSF-1 or FLT3 Ligand for 5 minutes in case of THP-1 and RS4; 11 cells respectively. MV-4-11 cells did not require stimulation. The cells were subsequently disrupted with lysis buffer containing protease and phosphatase inhibitors.

To examine FMS phosphorylation, the CSF-1-stimulated THP-1 lysates are added to an ELISA plate coated with an anti-FMS capture antibody. Phosphorylation of bound FMS is detected using a horseradish-peroxidase-(HRP)-labeled anti-phosphotyrosine antibody. This format allows detection at all FMS phosphorylation sites.

To examine FLT3 phosphorylation, the RS4; 11 or MV-4-11 lysates are added to an ELISA plate coated with an anti-Phospho-FLT3 (Tyr591) Antibody. Bound FLT3 is detected using a FLT3 mouse monoclonal antibody followed by an HRP-labeled anti mouse IgG secondary antibody. This format allows detection of phosphorylation at tyrosine 591 of FLT3, a known autophosphorylation site4.

For both ELISA protocols, the samples are incubated with 3, 3', 5, 5'-tetramethylbenzidine (TMB) substrate to generate a colorimetric signal. The HRP-TMB reaction is stopped with sulfuric acid, and the resulting absorbance signal is measured at a 450 nm wavelength on a Tecan SafireII reader Treatment of THP-1, RS4; 11 or MV-4-11 cells with FMS or FLT3 inhibitors, respectively, will decrease the ELISA signals compared to DMSO vehicle.

Materials and Methods
1. Cell Lines

| Cell line | Commercial source |
|---|---|
| THP | 1 ATCC #TIB |
| RS4; 11 | ATCC #CRL-1873 |
| MV-4-11 | ATCC #CRL-9591 |

2. Cell Culture Media

Both THP-1 and RS4; 11 were cultured in RPMI media supplemented with 10% FBS; MV-4-11 cells in IMDM supplemented with 10% FBS:

| Reagent | Commercial Source |
|---|---|
| RPMI | Invitrogen #11875 |
| IMDM | Invitrogen #21056-023 |
| 10% FBS | Sigma #12306C |

3. Recombinant Cytokines
Human CSF-1 (Protein ID: hCSF-1_J6131_1603)
Human FLT-3 Ligand (R&D Systems, catalog #308-FK)
4. Culture Plates
96 Well Flat Clear Bottom Black Polystyrene Poly-D-Lysine Coated Microplates (Corning #3667)
Corning® 96 Well Clear V-Bottom Polypropylene Not Treated Microplate, 25 per Bag, without Lids, Nonsterile (Product #3363)
5. ELISA Kits

| Reagent | Commerical Source |
|---|---|
| Human Phospho-M-CSFR DuoSet IC ELISA kit | R&D Systems #DYC3268E |
| PathScan ® Phospho-FLT3 (Tyr591) Sandwich ELISA Kit | Cell Signaling Technology #7206 |

6. Protocol
Cells are plated in Corning® T150 cell culture flasks at a density of 1×106 cells/mL in the absence of FBS or exogenous growth factor. The cells are incubated overnight at 37° C. in 5% CO2.
A 200 μL volume of cells is transferred to every well of a 96 Well Flat Clear Bottom Black Polystyrene Poly-D-Lysine Coated Microplate (Corning #3667). The plate is centrifuged at 1000 rpm for 5 minutes at room temperature, and incubated @ 37° C. for one hour.
A 1 μL amount of DMSO or a Flt3 inhibitor compound as described herein is transferred to a Corning® 96 Well Clear VBottom Polypropylene Microplate (#3363) and diluted 1:250 with cell culture media (without FBS or exogenous growth factor).
The mediate is gently aspirated from the cells, and replaced with 100 μL diluted DMSO or a Flt3 inhibitor compound as described herein. The final dilution of DMSO/Flt3 inhibitor is 1:250, so that the final DMSO concentration is 0.4%. The cells are incubated with DMSO/Flt3 inhibitor for one hour at 37° C. in 5% CO2.
Growth factor (CSF-1 or FLT3 Ligand) is diluted in cell culture media (without FBS) to a concentration that is 6× the final stimulation concentration. CSF-1 is diluted to 3.6 μg/mL, and FLT3 Ligand is diluted to 1.8 μg/mL.
A 20 μL volume of CSF-1 or FLT3 Ligand is added to the THP-1 and RS4; 11 cells, respectively. The cells are mixed gently, and incubated at room temperature for 5 minutes. The final concentrations of CSF-1 and FLT3 Ligand are 600 ng/mL and 300 ng/ml, respectively.
The stimulation media is aspirated, and the cells are lysed as directed in the ELISA kit protocols. The plates are incubated on ice for 30 minutes to allow the cells to lyse completely.
A 100 μL volume of lysate is removed to the ELISA plates; the CSF-1-stimulated THP-1 lysates are added to the Human Phospho-M-CSFR ELISA plate, and the FLT3 Ligandstimulated RS4; 11 lysates are added to the Phospho-FLT3 (Tyr591) ELISA plate. The rest of the assay proceeds as directed in the commercial ELISA kit protocols The Phospho-FMS and Phospho-FLT3 ELISA assays using CSF-1- and FLT3-Ligand stimulated cells yield data of sufficient quality to determine that a compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449 or a compound as described herein is a potent inhibitor of FMS phosphorylation, but does not significantly block autophosphorylation of wild type ligand stimulated FLT3. A compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449 or a compound as described herein is however a potent inhibitor of the mutated FLT3 enzyme that is activated by an internal tandem duplication (ITD) which is frequently observed in AML.

Example 9

Inhibition of ITD-FLT3 Driven Human AML (MV-4-11) Xenografts in Nude Mice

Mice with human xenografts of the ITD-FLT3 driven AML cell line MV-4-11 with a compound as described herein, e.g. compound A were treated. MV-4-11 cells are a human biphenotypic B-myelomonocytic leukemia derived cell line that harbor an activated FLT3 allele with an internal tandem duplication.

In order to test use of compounds of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449 or a compound as described herein to inhibit human myeloid leukemias (AML) that harbor a mutated FLT3 allele animals that harbored xenografts with human AML tumors were dosed. When compared by inhibition of FLT3 phosphorylation compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449 or a compound as described herein potently inhibits the activated ITD-FLT3 allele in cells (IC50 0.026 uM) in contrast to the wild type ligand stimulated FLT3 (IC50 1.4 uM). Therefore, compounds as described herein can be specifically useful in inhibiting ITD-FLT3 driven tumors and have little side effect on normal non-mutated FLT3 functioning in any other tissues. The efficacy of compounds as described herein to inhibit tumor growth of human AML ITD-FLT3 driven cells as xenografts in nude mice were determined.

Method

In order to test the ability of the compounds as described herein to inhibit ITD-FLT3 AML tumors in vivo the human MV-4-11 tumor cell line was injected subcutaneously in nude mice. Once the xenograft tumors reached 125 mm, 3 animals were treated daily by oral gavage dosing of a compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof, compounds P-0001-P-0449 or a compound as described herein.

Protocol

MV-4-11 cells were purchased from ATCC and expanded to 0.5 l at a density of 0.5×10E6/ml. Cells were washed three times with PBS after which the cells were resuspended in to the final density of 50×10E6 cells/ml in PBS before inoculation.

Result

Figure 4:
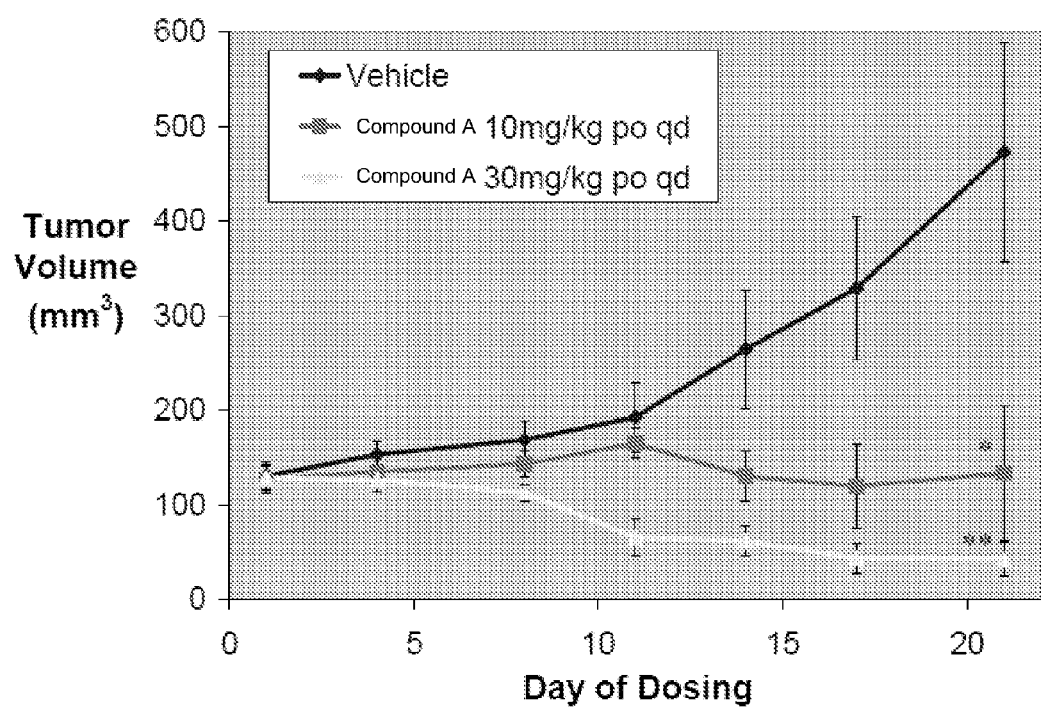
FIG. 4 demonstrates a daily dosing for 21 days with a compound as described herein significantly inhibited in a dose dependent manner MV-4-11 tumor growth as compared to Vehicle controls. Averages of calculated tumor volumes are depicted +/−SE. T-test significance as compared to Vehicle *p<0.05, **p<0.005.

A compound of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof and compounds P-0001-P-0449 potently inhibited the growth of the mutated ITD-FLT3 driven human AML cell line xenografts in nude mice. At a daily oral dose of 30 mg/kg of the compound, the average size of tumor had significantly regressed from the initial size at start of dosing. In four out of eight animals the tumor was macroscopically undetectable in this dose group. The effect of 10 mg/kg daily dosing of the compound resulted in tumor stasis and significantly different from Vehicle controls. FIG. 4 shows at daily doses of 10 and 30 mg/kg a compound in Table 1 inhibited significantly the human AML MV4-11 tumor growth as compared to vehicle. A oral dose of 10 mg/kg ($p<0.05$) showed tumor stasis as compared to Day 1 of dosing. At a daily dose of 30 mg/kg a Flt3 inhibitor compound as described herein resulted in tumor regression as compared to Day 1 ($p<0.005$). In four out of eight animals of the 30 mg/kg dose group the tumors could not be detected on day 21. Therefore, compounds of Formula I, Formula Ia, Formula Ib, Formula Ig, Formula II, Formula IIa, Formula IIb, Formula IIc, Formula IId, Formula IIe, Formula IIf, Formula IIg, Formula IIh, Formula IIi, Formula IIj, Formula IIk, Formula IIm, Formula IIn, Formula IIo, Formula IIp, or Formula III, all sub-embodiments thereof and compounds P-0001-P-0449 are effective in treating ITD-Flt3 driven tumors.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. For example, variations can be made to provide additional compounds of Formulae I, II or III, and all sub-embodiments thereof, and/or various methods of administration can be used. Thus, such additional embodiments are within the scope of the present invention and the following claims.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A method for treating a subject suffering from acute myeloid leukemia (AML), said method comprising administering to the subject an effective amount of a compound having the formula:

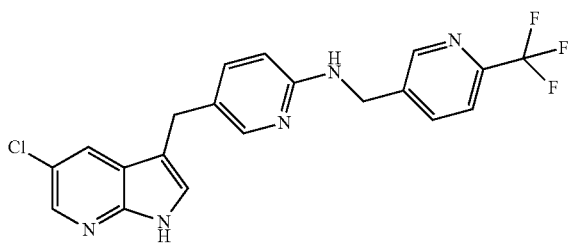 [SMILES: FC(F)(F)c1ccc(CNc2ccc(Cc3c[nH]c4ncc(Cl)cc34)cn2)cn1]

or a pharmaceutically acceptable salt, tautomer or isomer thereof, wherein the subject has an FMS-like tyrosine kinase (Flt3) gene with an internal tandem duplication (ITD) mutation.

2. The method of claim 1, wherein the Flt3 gene further comprises an amino acid substitution at residues F691, D835, Y842 or combinations thereof.

3. The method of claim 2, wherein the amino acid substitution is selected from F691L, D835V/Y, Y842C/H and combinations thereof.

4. The method of claim 3, wherein the amino acid substitution comprises F691L.

5. The method of claim 1, wherein the administration is oral.

6. The method of claim 1, wherein the effective amount is 0.1 mg/kg to 20 mg/kg.

* * * * *

SEQUENCE LISTING

```
<160> NUMBER OF SEQ ID NOS: 5

<210> SEQ ID NO 1
<211> LENGTH: 993
<212> TYPE: PRT
<213> ORGANISM: Homo sapiens

<400> SEQUENCE: 1
```

```
Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
                35                  40                  45

Lys Ser Ser Ser Tyr Pro Met Val Ser Glu Ser Pro Glu Asp Leu Gly
            50                  55                  60

Cys Ala Leu Arg Pro Gln Ser Ser Gly Thr Val Tyr Glu Ala Ala Ala
65                      70                  75                  80

Val Glu Val Asp Val Ser Ala Ser Ile Thr Leu Gln Val Leu Val Asp
                    85                  90                  95

Ala Pro Gly Asn Ile Ser Cys Leu Trp Val Phe Lys His Ser Ser Leu
                100                 105                 110

Asn Cys Gln Pro His Phe Asp Leu Gln Asn Arg Gly Val Val Ser Met
            115                 120                 125

Val Ile Leu Lys Met Thr Glu Thr Gln Ala Gly Glu Tyr Leu Leu Phe
        130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
        210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
            275                 280                 285

Asn Lys Ala Leu Glu Glu Gly Asn Tyr Phe Glu Met Ser Thr Tyr Ser
            290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
            355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415
```

```
Ile Phe His Ala Glu Asn Asp Asp Ala Gln Phe Thr Lys Met Phe Thr
                420                 425                 430

Leu Asn Ile Arg Arg Lys Pro Gln Val Leu Ala Glu Ala Ser Ala Ser
            435                 440                 445

Gln Ala Ser Cys Phe Ser Asp Gly Tyr Pro Leu Pro Ser Trp Thr Trp
        450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
        595                 600                 605

Asn Leu Glu Phe Gly Lys Val Leu Gly Ser Gly Ala Phe Gly Lys Val
610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
        675                 680                 685

Leu Ile Phe Glu Tyr Cys Cys Tyr Gly Asp Leu Leu Asn Tyr Leu Arg
690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
```

```
                  835                 840                 845
Arg Leu Pro Val Lys Trp Met Ala Pro Glu Ser Leu Phe Glu Gly Ile
            850                 855                 860
Tyr Thr Ile Lys Ser Asp Val Trp Ser Tyr Gly Ile Leu Leu Trp Glu
865                 870                 875                 880
Ile Phe Ser Leu Gly Val Asn Pro Tyr Pro Gly Ile Pro Val Asp Ala
                885                 890                 895
Asn Phe Tyr Lys Leu Ile Gln Asn Gly Phe Lys Met Asp Gln Pro Phe
            900                 905                 910
Tyr Ala Thr Glu Glu Ile Tyr Ile Ile Met Gln Ser Cys Trp Ala Phe
915                 920                 925
Asp Ser Arg Lys Arg Pro Ser Phe Pro Asn Leu Thr Ser Phe Leu Gly
            930                 935                 940
Cys Gln Leu Ala Asp Ala Glu Glu Ala Met Tyr Gln Asn Val Asp Gly
945                 950                 955                 960
Arg Val Ser Glu Cys Pro His Thr Tyr Gln Asn Arg Arg Pro Phe Ser
                965                 970                 975
Arg Glu Met Asp Leu Gly Leu Leu Ser Pro Gln Ala Gln Val Glu Asp
            980                 985                 990
Ser

<210> SEQ ID NO 2
<211> LENGTH: 3848
<212> TYPE: DNA
<213> ORGANISM: Homo sapiens

<400> SEQUENCE: 2
acctgcagcg cgaggcgcgc cgctccaggc ggcatcgcag ggctgggccg gcgcggcctg      60
gggaccccgg gctccggagg ccatgccggc gttggcgcgc gacggcggcc agctgccgct     120
gctcgttgtt ttttctgcaa tgatatttgg gactattaca aatcaagatc tgcctgtgat     180
caagtgtgtt ttaatcaatc ataagaacaa tgattcatca gtggggaagt catcatcata     240
tcccatggta tcagaatccc cggaagacct cgggtgtgcg ttgagacccc agagctcagg     300
gacagtgtac gaagctgccg ctgtggaagt ggatgtatct gcttccatca cactgcaagt     360
gctggtcgac gccccaggga acatttcctg tctctgggtc tttaagcaca gctccctgaa     420
ttgccagcca cattttgatt tacaaaacag aggagttgtt tccatggtca ttttgaaaat     480
gacagaaacc caagctggag aatacctact ttttattcag agtgaagcta ccaattacac     540
aatattgttt acagtgagta taagaaatac cctgctttac acattaagaa gaccttactt     600
tagaaaaatg gaaaccagg acgccctggt ctgcatatct gagagcgttc cagagccgat     660
cgtggaatgg gtgctttgcg attcacaggg ggaaagctgt aaagaagaa gtccagctgt     720 tgttaaaaag gaggaaaaag tgcttcatga attatttggg acggacataa ggtgctgtgc     780
cagaaatgaa ctgggcaggg aatgcaccag gctgttcaca atagatctaa atcaaactcc     840
tcagaccaca ttgccacaat tatttcttaa gtaggggaa cccttatgga taaggtgcaa     900
agctgttcat gtgaaccatg gattcgggct cacctgggaa ttagaaaaca aagcactcga     960
ggagggcaac tactttgaga tgagtaccta ttcaacaaac agaactatga tacgattct     1020 gtttgctttt gtatcatcag tggcaagaaa cgacaccgga tactacactt gttcctcttc     1080
aaagcatccc agtcaatcag ctttggttac catcgtagaa aagggattta taaatgctac     1140
caattcaagt gaagattatg aaattgacca atatgaagag ttttgttttt ctgtcaggtt     1200
```

```
taaagcctac ccacaaatca gatgtacgtg gaccttctct cgaaaatcat ttccttgtga    1260
gcaaaagggt cttgataacg gatacagcat atccaagttt tgcaatcata agcaccagcc    1320
aggagaatat atattccatg cagaaaatga tgatgcccaa tttaccaaaa tgttcacgct    1380
gaatataaga aggaaacctc aagtgctcgc agaagcatcg gcaagtcagg cgtcctgttt    1440
ctcggatgga tacccattac catcttggac ctggaagaag tgttcagaca agtctcccaa    1500
ctgcacagaa gagatcacag aaggagtctg aatagaaag gctaacagaa aagtgtttgg    1560
acagtgggtg tcgagcagta ctctaaacat gagtgaagcc ataaaagggt tcctggtcaa    1620
gtgctgtgca tacaattccc ttggcacatc ttgtgagacg atccttttaa actctccagg    1680 cccttccct ttcatccaag acaacatctc attctatgca acaattggtg tttgtctcct    1740
cttcattgtc gttttaaccc tgctaatttg tcacaagtac aaaaagcaat ttaggtatga    1800
aagccagcta cagatggtac aggtgaccgg ctcctcagat aatgagtact tctacgttga    1860
tttcagagaa tatgaatatg atctcaaatg ggagtttcca agagaaaatt tagagtttgg    1920
gaaggtacta ggatcaggtg cttttggaaa agtgatgaac gcaacagctt atggaattag    1980
caaaacagga gtctcaatcc aggttgccgt caaaatgctg aaagaaaaag cagacagctc    2040
tgaaagagag gcactcatgt cagaactcaa gatgatgacc cagctgggaa gccacgagaa    2100
tattgtgaac ctgctggggg cgtgcacact gtcaggacca atttacttga ttttgaata    2160 ctgttgctat ggtgatcttc tcaactatct aagaagtaaa agagaaaat ttcacaggac    2220 ttggacagag attttcaagg aacacaattt cagtttttac cccactttcc aatcacatcc    2280
aaattccagc atgcctggtt caagagaagt tcagatacac ccggactcgg atcaaatctc    2340
agggcttcat gggaattcat ttcactctga agatgaaatt gaatatgaaa accaaaaaag    2400
gctggaagaa gaggaggact tgaatgtgct tacatttgaa gatcttcttt gctttgcata    2460
tcaagttgcc aaaggaatgg aatttctgga atttaagtcg tgtgttcaca gagacctggc    2520
cgccaggaac gtgcttgtca cccacgggaa agtggtgaag atatgtgact ttggattggc    2580
tcgagatatc atgagtgatt ccaactatgt tgtcaggggc aatgcccgtc tgcctgtaaa    2640
atggatggcc cccgaaagcc tgtttgaagg catctacacc attaagagtg atgtctggtc    2700
atatggaata ttactgtggg aaatcttctc acttggtgtg aatccttacc ctggcattcc    2760
ggttgatgct aacttctaca aactgattca aaatggattt aaaatggatc agccatttta    2820
tgctacagaa gaaatataca ttataatgca atcctgctgg gcttttgact caaggaaacg    2880
gccatccttc cctaatttga cttcgttttt aggatgtcag ctggcagatg cagaagaagc    2940
gatgtatcag aatgtggatg gccgtgtttc ggaatgtcct cacacctacc aaaacaggcg    3000
acctttcagc agagagatgg atttggggct actctctccg caggctcagg tcgaagattc    3060
gtagaggaac aatttagttt taaggacttc atccctccac ctatccctaa caggctgtag    3120
attaccaaaa caagattaat ttcatcacta aaagaaaatc tattatcaac tgctgcttca    3180
ccagactttt ctctagaagc tgtctgcgtt tactcttgtt ttcaaaggga cttttgtaaa    3240
atcaaatcat cctgtcacaa ggcaggagga gctgataatg aactttattg gagcattgat    3300
ctgcatccaa ggccttctca ggctggcttg agtgaattgt gtacctgaag tacagtatat    3360
tcttgtaaat acataaaaca aaagcatttt gctaaggaga agctaatatg attttttaag    3420
```

```
tctatgtttt aaaataatat gtaaattttt cagctattta gtgatatatt ttatgggtgg    3480
gaataaaatt tctactacag aattgcccat tattgaatta tttacatggt ataattaggg    3540
caagtcttaa ctggagttca cgaacccect gaaattgtgc acccatagcc acctacacat    3600
tccttccaga gcacgtgtgc ttttacccca agatacaagg aatgtgtagg cagctatggt    3660
tgtcacagcc taagatttct gcaacaacag gggttgtatt gggggaagtt tataatgaat    3720
aggtgttcta ccataaagag taatacatca cctagacact ttggcggcct tcccagactc    3780
agggccagtc agaagtaaca tggaggatta gtattttcaa taaagttact cttgtcccca    3840
caaaaaaa                                                              3848

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Glu Glu Glu Tyr
1               5

<210> SEQ ID NO 5
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term Biotin

<400> SEQUENCE: 5

Gly Gly Glu Glu Glu Glu Tyr Glu Glu Glu Glu Tyr Glu Glu Glu Glu
1               5                   10                  15

Tyr Glu Glu Glu Glu Tyr Glu Glu Glu Glu Tyr Glu Glu Glu Glu Tyr
            20                  25                  30

Glu Glu Glu Glu Tyr Glu Glu Glu Glu Tyr Glu Glu Glu Glu Tyr Glu
        35                  40                  45

Glu Glu Glu Tyr Glu Glu
    50
```